US011793196B2

(12) United States Patent
Curtis et al.

(10) Patent No.: US 11,793,196 B2
(45) Date of Patent: Oct. 24, 2023

(54) FUSION PROTEINS, RECOMBINANT BACTERIA, AND EXOSPORIUM FRAGMENTS FOR PEST CONTROL AND PLANT HEALTH

(71) Applicant: Bayer CropScience LP, St. Louis, MO (US)

(72) Inventors: Damian Curtis, Davis, CA (US); Kevin Bugg, Apex, NC (US)

(73) Assignee: Bayer CropScience LP, St. Louis, MO (US)

( * ) Notice: Subject to any disclaimer, the term of this patent is extended or adjusted under 35 U.S.C. 154(b) by 332 days.

(21) Appl. No.: 16/822,279

(22) Filed: Mar. 18, 2020

(65) Prior Publication Data

US 2020/0296960 A1 Sep. 24, 2020

Related U.S. Application Data

(60) Provisional application No. 62/820,773, filed on Mar. 19, 2019.

(51) Int. Cl.

*A01N 37/46* (2006.01)
*C07K 14/32* (2006.01)
*C12N 9/64* (2006.01)

(52) U.S. Cl.

CPC .............. *A01N 37/46* (2013.01); *C07K 14/32* (2013.01); *C12N 9/6424* (2013.01); *C07K 2319/00* (2013.01); *C07K 2319/035* (2013.01)

(58) Field of Classification Search

CPC ................................ A01N 37/46; C07K 14/32
See application file for complete search history.

(56) References Cited

U.S. PATENT DOCUMENTS

| | | | |
|---|---|---|---|
| 9,132,175 | B2 | 9/2015 | Stewart et al. |
| 9,573,980 | B2 | 2/2017 | Thompson et al. |
| 9,826,743 | B2 | 11/2017 | Curtis et al. |
| 9,845,342 | B2 | 12/2017 | Thompson et al. |
| 2014/0370569 | A1 | 12/2014 | Kueppers et al. |
| 2017/0347664 | A1 | 12/2017 | Thompson et al. |
| 2020/0216828 | A1 | 7/2020 | Thompson et al. |

FOREIGN PATENT DOCUMENTS

| | | | |
|---|---|---|---|
| RU | 2644199 | C2 | 2/2018 |
| WO | 2014145964 | A1 | 9/2014 |
| WO | 2016/044661 | A1 | 3/2016 |
| WO | 2016044529 | A1 | 3/2016 |
| WO | 2016044533 | A1 | 3/2016 |
| WO | 2016044542 | A1 | 3/2016 |
| WO | 2016044548 | A1 | 3/2016 |
| WO | 2016044563 | A1 | 3/2016 |
| WO | 2016044575 | A1 | 3/2016 |
| WO | 2017/161181 | A1 | 9/2017 |
| WO | 2019060574 | A1 | 3/2019 |

OTHER PUBLICATIONS

Takekawa, S et al. "Proteases Involved in Generation of Beta- and Alpha-Amylases from a Large Amylase Precursor in Bacillus Polymyxa." Journal of Bacteriology 173.21 (1991): 6820-6825. Web. (Year: 1991).*

Geng, Ce et al. "A Novel Serine Protease, Sep1, from Bacillus Firmus DS-1 has Nematicidal Activity and Degrades Multiple Intestinal-Associated Nematode Proteins." Scientific Reports 6.1 (2016): 25012-. Web. (Year: 2016).*

Dunne, C., et al., "Overproduction of an Inducible Extracellular Serine Protease Improves Biological Control of Pythium ultimum by Stenotrophomonas maltophilia Strain W81," Microbiology, 2000, vol. 146, pp. 2069-2078.

Geng, C., et al., "A Novel Serine Protease, Sep1, from Bacillus firmus DS-1 has Nematicidal Activity and Degrades Multiple Intestinal-Associated Nematode Proteins," Scientific Reports, Apr. 27, 2016, vol. 6, No. 25012, pp. 1-12.

Yen, Y-H., et al., "An Antifungal Protease Produced by Pseudomonas aeruginosa M-1001 with Shrimp and Crab Shell Powder as a Carbon Source," Enzyme and Microbial Technology, 2006, vol. 29, pp. 311-317.

Database UniProt [Online], Apr. 16, 2014, "SubName: Full= Intracellular serine protease {ECO:0000313 | EWG10090.1};"XP55707253, retrieved from EBI accession No. UNIPROT:W &KRH1 Database accession No. W7KRH1 sequence & Ce Geng et al: A Novel Serine Protease, Sep1, from Bacillus firmus DS-1 has Nematicidal Activity and Degrades Multiple Intestinal-Associated Nematode Proteins, Scientific Reports, Apr. 27, 2016, vol. 6, No. 1, XP55707229, DOI: 10.1038/srep25012.

Database UniProt [Online], Nov. 7, 2018, "SubName: Full= Intracellular serine protease {ECO:0000313 | EMBL: SUV04921.1}; EC=3.4.21.-{ECO:0000313 | EMBL:SUV04921.1};",XP55707259, retrieved from EBI accession No. UNIPROT: A0A380XNG8 Database accession No. A0A380XNG8 sequence.

International Search Report and Written Opinion on the International Searching Authority, PCT International Patent Application No. PCT/US2020/023255, dated Jul. 1, 2020, 13 pages.

(Continued)

*Primary Examiner* — Louise W Humphrey
*Assistant Examiner* — John Paul Selwanes
(74) *Attorney, Agent, or Firm* — Michelle L. Samonek

(57) ABSTRACT

The present invention relates to a fusion protein having a targeting sequence, exosporium protein, or exosporium protein fragment that targets the fusion protein to the exosporium of a recombinant *Bacillus cereus* family member and an enzyme having serine protease activity, wherein the enzyme having serine protease activity is from *Bacillus firmus* or is a variant of such enzyme. The present invention also provides a recombinant *Bacillus cereus* family member that expresses such fusion protein and exosporium fragments derived from such recombinant *Bacillus cereus* family member. Methods of using such recombinant *Bacillus cereus* family members or exosporium fragments derived therefrom for nematode control are also provided.

15 Claims, 6 Drawing Sheets

Specification includes a Sequence Listing.

(56) References Cited

OTHER PUBLICATIONS

Park, T.J. et al., "Spore display using Bacillus thuringiensis exosporium protein InhA", J Microbiol Biotechnol, 2009, vol. 19, N. 5, pp. 495-501.

McPherson, S.A. et al., "ExsB, an unusually highly phosphorylated protein required for the stable attachment of the exosporium of Bacillus anthracis", Mol Microbiol, 2010, vol. 76, No. 6, pp. 1527-1538.

Colman, P. M., "Effects of amino acid sequence changes on antibody-antigen interactions", Research in Immunology, 1994, vol. 145, No. 1, pp. 33-36.

* cited by examiner

FIG. 1A

| | SEQ ID NO. | 20-35 %Identity | 25-35 %Identity |
|---|---|---|---|
| MSNNNYSNGLNPDESLSAS**AFDPNLVGPTLPPIPP**FTLPTG | 1 | 100% | 100% |
| MSEKYIIILHGT**ALEPNLIGPTLPPIPP**FTFPNG | 3 | 81.3% | 90.9% |
| MVKVVEGNGGKSKIKSPLNSNF**KILSDLVGPTFPPVPT**GMTGIT | 5 | 50.0% | 72.7% |
| MKQNDKLWLDKG**IIGPENIGPTFPVLPP**IHIPTG | 7 | 43.8% | 54.5% |
| MDEFLSSA**ALNPGSVGPTLPPMQP**FQFRTG | 9 | 62.5% | 72.7% |
| MFDKNEIQKINGILQAN**ALNPNLIGPTLPPIPP**FTLPTG | 11 | 81.3% | 90.9% |
| MFDKNEMKKTNEVLQAN**ALDPNIIGPTLPPIPP**FTLPTG | 13 | 81.3% | 81.8% |
| MSRKDKFNRSRMSRKDRFNSPKIKSEI**SISPDLVGPTFPPIPS**FTLPTG | 15 | 62.5% | 81.8% |
| MNEEYSILHGP**ALEPNLIGPTLPSIPP**FTFPTG | 17 | 75.0% | 81.8% |
| MKNRDNNRKQNSLSSNF**RIPPELIGPTFPPVPT**GFTGIG | 19 | 50.0% | 63.6% |
| MSDKHQMKKISEVLQAH**ALDPNLIGPPLPPITP**FTFPTG | 21 | 75.0% | 72.7% |
| MDEFLSFA**ALNPGSIGPTLPPVPP**FQFPTG | 23 | 62.5% | 72.7% |
| MDEFLSST**ALNPCSIGPTLPPMQP**FQFPTG | 25 | 56.2% | 63.6% |
| MKERDRQNSLNSNF**RISPNLIGPTFPPVPT**GFTGIG | 27 | 56.2% | 63.6% |
| VFDKNEIQKINGILQAN**ALNPNLIGPTLPPIPP**FTLPTG | 29 | 81.3% | 90.9% |
| MDEFLYFA**ALNPGSIGPTLPPVQP**FQFPTG | 31 | 56.2% | 63.6% |
| **MDSKNIGPTFPPLPS**INFPTG | 33 | 43.8% | 54.5% |
| **MIGPENIGPTFPILPP**IYIPTG | 35 | 43.8% | 54.5% |
| MSNNNIPSPFFFN**NFNPELIGPTFPPIPP**LTLPTG | 43 | 68.8% | 81.8% |
| MFSEKKRKDLIPDNFLSAP**ALDPNLIGPTFPPIPS**FTLPTG | 45 | 75.0% | 72.7% |
| MTRKDKFNRSRISRRDRFNSPKIKSEI**LISPDLVGPTFPPIPS**FTLPTG | 47 | 62.5% | 81.8% |
| MSRKDRFNSPKIKSEI**SISPDLVGPTFPPIPS**FTLPTG | 49 | 62.5% | 81.8% |
| MKERDNKGKQHSLNSNF**RIPPELIGPTFPPVPT**GFTGIG | 51 | 50.0% | 63.6% |
| MRERDNKRQQHSLNPNF**RISPELIGPTFPPVPT**GFTGIG | 53 | 50.0% | 63.6% |
| MKNRDNKGKQQSNF**RIPPELIGPTFPPVPT**GFTGIG | 55 | 50.0% | 63.6% |
| MKFSKKSTVDSSIVGKRVVSKVNILRFYDARSCQDKDVDGFVDVGELFTIFRKLNMEGSVQFKAHNSI GKTYYITINEVYVFVTVLLQYSTLIGGSYVFDKNEIQKINGILQAN**ALNPNLIGPTLPPIPP**FTLPTG | 57 | 81.3% | 90.9% |

FIG. 1B

| | SEQ ID NO. | 20-35 %Identity | 25-35 %Identity |
|---|---|---|---|
| MSNNNYSNGLNPDESLSAS**AFDPNLVGPTLPPIPP**FTLPTG | 1 | 100% | 100% |
| MKERDKQNSLNSNF**RISPNLIGPTFPPVPT**GFTGIG | 59 | 56.2% | 63.6% |
| MMENKKGSKHNEFLSAK**AFNPNLVGPTLPPVPS**FTLPTG | 61 | 81.3% | 81.8% |
| MSNNNYSDGLNPDEFLSAS**AFDPNLVGPTLPPIPP**FTLPTG | 63 | 100% | 100% |
| MDEFLSSA**AINPNLVGPTLPPVPP**FTLPTG | 65 | 81.3% | 90.9% |
| MFDKNKILQAN**AFNSNLIGPTLPPIPP**FTLPTG | 67 | 81.3% | 90.9% |
| MSDENEKKYSNELAQADFISAA**AFDPSLVGPTLPPTPP**FTLPTG | 69 | 87.5% | 90.9% |
| MSRKDRFNSPKIKSEI**SISPDLVGPTFPPIPS**FTLPTG | 71 | 62.5% | 81.8% |
| MDEFLSSA**ALNPGSVGPTLPPMQP**FQFSTG | 73 | 62.5% | 72.7% |
| MFLGGGYMERKNKWYGLNSNVNLSAS**SFDPNLVGPTLPPISP**ISVPTG | 75 | 87.5% | 90.9% |
| MDELLSST**LINPDLLGPTLPAIPP**FTLPTG | 77 | 62.5% | 81.8% |
| MKNRDNNRKQNSLSSNF**RIPPELIGPTFPPVPT**GFTGIG | 79 | 50.0% | 63.6% |
| MVKVVEGNSGKSKIKSSLNSNF**KLSSGLVGPTFPPVPT**GMTGIT | 81 | 50.0% | 72.7% |
| MEGNGGKSKIKSPLNSNF**KILSDLVGPTFPPVPT**GMTGIT | 83 | 50.0% | 72.7% |
| MKQNDKLWLDKG**IIGPENIGPTFPVLPP**IHIPTG | 85 | 43.8% | 54.5% |
| MNSNEKLSLNKG**MVRPENIGPTFPVLPP**IYIPTG | 87 | 43.8% | 54.5% |
| MKRNDNLSLNKG**MIGPENIGPTFPILPP**IYIPTG | 89 | 43.8% | 54.5% |
| MDSFVDVGEIFTIFRKLNMEGSLQFKVHNS MGKTYYITINEVYVYVTVLLQYSTLIGGSYVFDKNEIQKINGILQAN**ALNPNLIGPTLPPIPP**FTLPTG | 91 | 81.3% | 90.9% |
| MKFSKKSTVDSSIVGKRVVSKVNILRFYDARSWQDKDVDGFVDVGELFTIFRKLNMEGSVQFKAHNSI GKTYYITINEVYVFVTVLLQYSTLIGGSYVFDKNEIQKINGILQAN**ALNPNLIGPTLPPIPP**FTLPTG | 93 | 81.3% | 90.9% |

SEQUENCE LISTING

```
<160> NUMBER OF SEQ ID NOS: 213

<210> SEQ ID NO 1
<211> LENGTH: 41
<212> TYPE: PRT
<213> ORGANISM: Bacillus anthracis

<400> SEQUENCE: 1

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40


<210> SEQ ID NO 2
<211> LENGTH: 332
<212> TYPE: PRT
<213> ORGANISM: Bacillus anthracis

<400> SEQUENCE: 2

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
```

```
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60

Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly Leu Pro Ala Gly Leu Tyr Ala Phe Asn Ser Gly Gly
        195                 200                 205

Ile Ser Leu Asp Leu Gly Ile Asn Asp Pro Val Pro Phe Asn Thr Val
    210                 215                 220

Gly Ser Gln Phe Phe Thr Gly Thr Ala Ile Ser Gln Leu Asp Ala Asp
225                 230                 235                 240

Thr Phe Val Ile Ser Glu Thr Gly Phe Tyr Lys Ile Thr Val Ile Ala
                245                 250                 255

Asn Thr Ala Thr Ala Ser Val Leu Gly Gly Leu Thr Ile Gln Val Asn
            260                 265                 270

Gly Val Pro Val Pro Gly Thr Gly Ser Ser Leu Ile Ser Leu Gly Ala
        275                 280                 285

Pro Phe Thr Ile Val Ile Gln Ala Ile Thr Gln Ile Thr Thr Thr Pro
    290                 295                 300

Ser Leu Val Glu Val Ile Val Thr Gly Leu Gly Leu Ser Leu Ala Leu
305                 310                 315                 320

Gly Thr Ser Ala Ser Ile Ile Ile Glu Lys Val Ala
                325                 330


<210> SEQ ID NO 3
<211> LENGTH: 33
<212> TYPE: PRT
<213> ORGANISM: Bacillus anthracis

<400> SEQUENCE: 3

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly


<210> SEQ ID NO 4
<211> LENGTH: 209
<212> TYPE: PRT
```

<213> ORGANISM: Bacillus anthracis

<400> SEQUENCE: 4

```
Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Leu Gly Ile Leu Pro Val Phe
65                  70                  75                  80

Gly Thr Ile Thr Thr Asp Val Gly Ile Gly Phe Ser Val Ile Val Asn
                85                  90                  95

Thr Asn Ile Asn Phe Thr Leu Pro Gly Pro Val Ser Gly Thr Thr Leu
            100                 105                 110

Asn Pro Val Asp Asn Ser Ile Ile Ile Asn Thr Thr Gly Val Tyr Ser
        115                 120                 125

Val Ser Phe Ser Ile Val Phe Val Ile Gln Ala Ile Ser Ser Ser Ile
    130                 135                 140

Leu Asn Leu Thr Ile Asn Asp Ser Ile Gln Phe Ala Ile Glu Ser Arg
145                 150                 155                 160

Ile Gly Gly Gly Pro Gly Val Arg Ala Thr Ser Ala Arg Thr Asp Leu
                165                 170                 175

Leu Ser Leu Asn Gln Gly Asp Val Leu Arg Val Arg Ile Arg Glu Ala
            180                 185                 190

Thr Gly Asp Ile Ile Tyr Ser Asn Ala Ser Leu Val Val Ser Lys Val
        195                 200                 205

Asp
```

<210> SEQ ID NO 5
<211> LENGTH: 44
<212> TYPE: PRT
<213> ORGANISM: Bacillus anthracis

<400> SEQUENCE: 5

```
Met Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr
        35                  40
```

<210> SEQ ID NO 6
<211> LENGTH: 647
<212> TYPE: PRT
<213> ORGANISM: Bacillus anthracis

<400> SEQUENCE: 6

```
Val Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr Gly Ser Thr Gly
        35                  40                  45
```

-continued

```
Ala Thr Gly Asn Thr Gly Pro Thr Gly Glu Thr Gly Ala Thr Gly Ser
    50                  55                  60

Ala Gly Ile Thr Gly Ser Thr Gly Pro Thr Gly Asn Thr Gly Gly Thr
65                  70                  75                  80

Gly Ser Thr Gly Pro Thr Gly Asn Thr Gly Ala Thr Gly Ser Thr Gly
                85                  90                  95

Val Thr Gly Ser Thr Gly Val Thr Gly Ser Thr Gly Val Thr Gly Ser
            100                 105                 110

Thr Gly Val Thr Gly Ser Thr Gly Pro Thr Gly Glu Thr Gly Gly Thr
        115                 120                 125

Gly Ser Thr Gly Val Thr Gly Ser Thr Gly Ala Thr Gly Ser Thr Gly
    130                 135                 140

Val Thr Gly Asn Thr Gly Pro Thr Gly Ser Thr Gly Ala Thr Gly Asn
145                 150                 155                 160

Thr Gly Ser Ile Gly Glu Thr Gly Gly Thr Gly Ser Met Gly Pro Thr
                165                 170                 175

Gly Glu Thr Gly Val Thr Gly Ser Thr Gly Gly Thr Gly Ser Thr Gly
            180                 185                 190

Val Thr Gly Asn Thr Gly Pro Thr Gly Ser Thr Gly Val Thr Gly Ser
        195                 200                 205

Thr Gly Val Thr Gly Ser Thr Gly Pro Thr Gly Ser Thr Gly Val Thr
    210                 215                 220

Gly Ser Thr Gly Pro Thr Gly Ser Thr Gly Val Thr Gly Ser Thr Gly
225                 230                 235                 240

Val Thr Gly Asn Met Gly Pro Thr Gly Ser Thr Gly Val Thr Gly Asn
                245                 250                 255

Thr Gly Ser Thr Gly Thr Thr Gly Ala Thr Gly Glu Thr Gly Pro Met
            260                 265                 270

Gly Ser Thr Gly Ala Thr Gly Thr Thr Gly Pro Thr Gly Glu Thr Gly
        275                 280                 285

Glu Thr Gly Glu Thr Gly Gly Thr Gly Ser Thr Gly Pro Thr Gly Asn
    290                 295                 300

Thr Gly Ala Thr Gly Ser Thr Gly Val Thr Gly Ser Thr Gly Val Thr
305                 310                 315                 320

Gly Ser Thr Gly Val Thr Gly Glu Thr Gly Pro Thr Gly Ser Thr Gly
                325                 330                 335

Ala Thr Gly Asn Thr Gly Pro Thr Gly Glu Thr Gly Gly Thr Gly Ser
            340                 345                 350

Thr Gly Ala Thr Gly Ser Thr Gly Val Thr Gly Asn Thr Gly Pro Thr
        355                 360                 365

Gly Ser Thr Gly Val Thr Gly Asn Thr Gly Ala Thr Gly Glu Thr Gly
    370                 375                 380

Pro Thr Gly Asn Thr Gly Ala Thr Gly Asn Thr Gly Pro Thr Gly Glu
385                 390                 395                 400

Thr Gly Val Thr Gly Ser Thr Gly Pro Thr Gly Glu Thr Gly Val Thr
                405                 410                 415

Gly Ser Thr Gly Pro Thr Gly Asn Thr Gly Ala Thr Gly Glu Thr Gly
            420                 425                 430

Ala Thr Gly Ser Thr Gly Val Thr Gly Asn Thr Gly Ser Thr Gly Glu
        435                 440                 445

Thr Gly Pro Thr Gly Ser Thr Gly Pro Thr Gly Ser Thr Gly Ala Thr
    450                 455                 460

Gly Val Thr Gly Asn Thr Gly Pro Thr Gly Ser Thr Gly Ala Thr Gly
```

```
465                 470                 475                 480

Ala Thr Gly Ser Thr Gly Pro Thr Gly Ser Thr Gly Thr Thr Gly Asn
                485                 490                 495

Thr Gly Val Thr Gly Asp Thr Gly Pro Thr Gly Ala Thr Gly Val Ser
            500                 505                 510

Thr Thr Ala Thr Tyr Ala Phe Ala Asn Asn Thr Ser Gly Ser Val Ile
        515                 520                 525

Ser Val Leu Leu Gly Gly Thr Asn Ile Pro Leu Pro Asn Asn Gln Asn
    530                 535                 540

Ile Gly Pro Gly Ile Thr Val Ser Gly Gly Asn Thr Val Phe Thr Val
545                 550                 555                 560

Ala Asn Ala Gly Asn Tyr Tyr Ile Ala Tyr Thr Ile Asn Leu Thr Ala
                565                 570                 575

Gly Leu Leu Val Ser Ser Arg Ile Thr Val Asn Gly Ser Pro Leu Ala
            580                 585                 590

Gly Thr Ile Asn Ser Pro Thr Val Ala Thr Gly Ser Phe Ser Ala Thr
        595                 600                 605

Ile Ile Ala Ser Leu Pro Ala Gly Ala Ala Val Ser Leu Gln Leu Phe
    610                 615                 620

Gly Val Val Ala Leu Ala Thr Leu Ser Thr Ala Thr Pro Gly Ala Thr
625                 630                 635                 640

Leu Thr Ile Ile Arg Leu Ser
                645


<210> SEQ ID NO 7
<211> LENGTH: 34
<212> TYPE: PRT
<213> ORGANISM: Bacillus anthracis

<400> SEQUENCE: 7

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly


<210> SEQ ID NO 8
<211> LENGTH: 366
<212> TYPE: PRT
<213> ORGANISM: Bacillus anthracis

<400> SEQUENCE: 8

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
        35                  40                  45

Gly Pro Thr Gly Thr Thr Gly Ala Thr Gly Ala Thr Gly Ile Thr Gly
    50                  55                  60

Val Thr Gly Ala Thr Gly Ile Thr Gly Val Thr Gly Ala Thr Gly Ile
65                  70                  75                  80

Thr Gly Val Thr Gly Ala Thr Gly Ile Thr Gly Val Thr Gly Pro Thr
                85                  90                  95

Gly Ile Thr Gly Ala Thr Gly Pro Thr Gly Ile Thr Gly Ala Thr Gly
            100                 105                 110
```

```
Pro Ala Gly Ile Thr Gly Val Thr Gly Pro Thr Gly Ile Thr Gly Ala
        115                 120                 125

Thr Gly Pro Thr Gly Thr Thr Gly Val Thr Gly Pro Thr Gly Asp Thr
    130                 135                 140

Gly Leu Ala Gly Ala Thr Gly Pro Thr Gly Ala Thr Gly Leu Ala Gly
145                 150                 155                 160

Ala Thr Gly Pro Thr Gly Asp Thr Gly Ala Thr Gly Pro Thr Gly Ala
                165                 170                 175

Thr Gly Leu Ala Gly Ala Thr Gly Pro Thr Gly Ala Thr Gly Leu Thr
            180                 185                 190

Gly Ala Thr Gly Ala Thr Gly Ala Thr Gly Gly Gly Ala Ile Ile Pro
        195                 200                 205

Phe Ala Ser Gly Thr Thr Pro Ala Leu Leu Val Asn Ala Val Leu Ala
    210                 215                 220

Asn Thr Gly Thr Leu Leu Gly Phe Gly Phe Ser Gln Pro Gly Ile Ala
225                 230                 235                 240

Pro Gly Val Gly Gly Thr Leu Thr Ile Leu Pro Gly Val Val Gly Asp
                245                 250                 255

Tyr Ala Phe Val Ala Pro Arg Asp Gly Ile Ile Thr Ser Leu Ala Gly
            260                 265                 270

Phe Phe Ser Ala Thr Ala Ala Leu Ala Pro Leu Thr Pro Val Gln Ile
        275                 280                 285

Gln Met Gln Ile Phe Ile Ala Pro Ala Ala Ser Asn Thr Phe Thr Pro
    290                 295                 300

Val Ala Pro Pro Leu Leu Leu Thr Pro Ala Leu Pro Ala Ile Ala Ile
305                 310                 315                 320

Gly Thr Thr Ala Thr Gly Ile Gln Ala Tyr Asn Val Pro Val Val Ala
                325                 330                 335

Gly Asp Lys Ile Leu Val Tyr Val Ser Leu Thr Gly Ala Ser Pro Ile
            340                 345                 350

Ala Ala Val Ala Gly Phe Val Ser Ala Gly Leu Asn Ile Val
        355                 360                 365


<210> SEQ ID NO 9
<211> LENGTH: 30
<212> TYPE: PRT
<213> ORGANISM: Bacillus anthracis

<400> SEQUENCE: 9

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly
            20                  25                  30


<210> SEQ ID NO 10
<211> LENGTH: 77
<212> TYPE: PRT
<213> ORGANISM: Bacillus anthracis

<400> SEQUENCE: 10

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly Pro Thr
            20                  25                  30

Gly Ser Thr Gly Ala Lys Gly Ala Ile Gly Asn Thr Glu Pro Tyr Trp
        35                  40                  45
```

```
His Thr Gly Pro Pro Gly Ile Val Leu Leu Thr Tyr Asp Phe Lys Ser
    50                  55                  60

Leu Ile Ile Ser Phe Ala Phe Arg Ile Leu Pro Ile Ser
65                  70                  75


<210> SEQ ID NO 11
<211> LENGTH: 39
<212> TYPE: PRT
<213> ORGANISM: Bacillus weihenstephensis

<400> SEQUENCE: 11

Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35


<210> SEQ ID NO 12
<211> LENGTH: 299
<212> TYPE: PRT
<213> ORGANISM: Bacillus weihenstephensis

<400> SEQUENCE: 12

Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly Pro Thr Gly Val Thr Gly Pro Thr Gly
        35                  40                  45

Val Thr Gly Pro Thr Gly Val Thr Gly Pro Thr Gly Val Thr Gly Pro
    50                  55                  60

Thr Gly Val Thr Gly Pro Thr Gly Val Thr Gly Pro Thr Gly Val Thr
65                  70                  75                  80

Gly Pro Thr Gly Val Thr Gly Pro Thr Gly Val Thr Gly Pro Thr Gly
                85                  90                  95

Val Thr Gly Pro Thr Gly Val Thr Gly Pro Thr Gly Val Thr Gly Pro
            100                 105                 110

Thr Gly Val Thr Gly Pro Thr Gly Val Thr Gly Pro Thr Gly Glu Thr
        115                 120                 125

Gly Pro Thr Gly Gly Thr Glu Gly Cys Leu Cys Asp Cys Cys Val Leu
    130                 135                 140

Pro Met Gln Ser Val Leu Gln Gln Leu Ile Gly Glu Thr Val Ile Leu
145                 150                 155                 160

Gly Thr Ile Ala Asp Thr Pro Asn Thr Pro Pro Leu Phe Phe Leu Phe
                165                 170                 175

Thr Ile Thr Ser Val Asn Asp Phe Leu Val Thr Val Thr Asp Gly Thr
            180                 185                 190

Thr Thr Phe Val Val Asn Ile Ser Asp Val Thr Gly Val Gly Phe Leu
        195                 200                 205

Pro Pro Gly Pro Pro Ile Thr Leu Leu Pro Pro Thr Asp Val Gly Cys
    210                 215                 220

Glu Cys Glu Cys Arg Glu Arg Pro Ile Arg Gln Leu Leu Asp Ala Phe
225                 230                 235                 240

Ile Gly Ser Thr Val Ser Leu Leu Ala Ser Asn Gly Ser Ile Ala Ala
                245                 250                 255
```

```
Asp Phe Ser Val Glu Gln Thr Gly Leu Gly Ile Val Leu Gly Thr Leu
            260                 265                 270

Pro Ile Asn Pro Thr Thr Thr Val Arg Phe Ala Ile Ser Thr Cys Lys
        275                 280                 285

Ile Thr Ala Val Asn Ile Thr Pro Ile Thr Met
    290                 295


<210> SEQ ID NO 13
<211> LENGTH: 39
<212> TYPE: PRT
<213> ORGANISM: Bacillus weihenstephensis

<400> SEQUENCE: 13

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly
        35


<210> SEQ ID NO 14
<211> LENGTH: 289
<212> TYPE: PRT
<213> ORGANISM: Bacillus weihenstephensis

<400> SEQUENCE: 14

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly Pro Thr Gly Pro Thr Gly Pro Thr Gly
        35                  40                  45

Pro Thr Gly Pro Thr Gly Pro Thr Gly Pro Thr Gly Pro Thr Gly Pro
    50                  55                  60

Thr Gly Pro Thr Gly Pro Thr Gly Pro Thr Gly Pro Thr Gly Leu Thr
65                  70                  75                  80

Gly Pro Thr Gly Pro Thr Gly Leu Thr Gly Pro Thr Gly Leu Thr Gly
                85                  90                  95

Pro Thr Gly Pro Thr Gly Leu Thr Gly Gln Thr Gly Ser Thr Gly Pro
            100                 105                 110

Thr Gly Ala Thr Glu Gly Cys Leu Cys Asp Cys Cys Val Phe Pro Met
        115                 120                 125

Gln Glu Val Leu Arg Gln Leu Val Gly Gln Thr Val Ile Leu Ala Thr
    130                 135                 140

Ile Ala Asp Ala Pro Asn Val Ala Pro Arg Phe Phe Leu Phe Asn Ile
145                 150                 155                 160

Thr Ser Val Asn Asp Phe Leu Val Thr Val Thr Asp Pro Val Ser Asn
                165                 170                 175

Thr Thr Phe Val Val Asn Ile Ser Asp Val Ile Gly Val Gly Phe Ser
            180                 185                 190

Leu Thr Val Pro Pro Leu Thr Leu Leu Pro Pro Ala Asp Leu Gly Cys
        195                 200                 205

Glu Cys Asp Cys Arg Glu Arg Pro Ile Arg Glu Leu Leu Asp Thr Leu
    210                 215                 220

Ile Gly Ser Thr Val Asn Leu Leu Val Ser Asn Gly Ser Ile Ala Thr
225                 230                 235                 240
```

```
Gly Phe Asn Val Glu Gln Thr Ala Leu Gly Ile Val Ile Gly Thr Leu
                245                 250                 255

Pro Ile Pro Ile Asn Pro Pro Pro Pro Thr Leu Phe Arg Phe Ala Ile
            260                 265                 270

Ser Thr Cys Lys Ile Thr Ala Val Asp Ile Thr Pro Thr Pro Thr Ala
        275                 280                 285

Thr


<210> SEQ ID NO 15
<211> LENGTH: 49
<212> TYPE: PRT
<213> ORGANISM: Bacillus cereus

<400> SEQUENCE: 15

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly


<210> SEQ ID NO 16
<211> LENGTH: 189
<212> TYPE: PRT
<213> ORGANISM: Bacillus cereus

<400> SEQUENCE: 16

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly Ile Thr Gly Pro Thr Phe Asn Ile Asn Phe Arg Ala Glu Lys Asn
    50                  55                  60

Val Ala Gln Ser Phe Thr Pro Pro Ala Asp Ile Gln Val Ser Tyr Gly
65                  70                  75                  80

Asn Ile Ile Phe Asn Asn Gly Gly Gly Tyr Ser Ser Val Thr Asn Thr
                85                  90                  95

Phe Thr Ala Pro Ile Asn Gly Ile Tyr Leu Phe Ser Ala Ser Ile Gly
            100                 105                 110

Phe Asn Pro Thr Leu Gly Thr Thr Ser Thr Leu Arg Ile Thr Ile Arg
        115                 120                 125

Lys Asn Leu Val Ser Val Ala Ser Gln Thr Gly Thr Ile Thr Thr Gly
    130                 135                 140

Gly Thr Pro Gln Leu Glu Ile Thr Thr Ile Ile Asp Leu Leu Ala Ser
145                 150                 155                 160

Gln Thr Ile Asp Ile Gln Phe Ser Ala Ala Glu Ser Gly Thr Leu Thr
                165                 170                 175

Val Gly Ser Ser Asn Phe Phe Ser Gly Ala Leu Leu Pro
            180                 185


<210> SEQ ID NO 17
<211> LENGTH: 33
<212> TYPE: PRT
```

<213> ORGANISM: Bacillus cereus

<400> SEQUENCE: 17

Met Asn Glu Glu Tyr Ser Ile Leu His Gly Pro Ala Leu Glu Pro Asn
1               5                   10                  15

Leu Ile Gly Pro Thr Leu Pro Ser Ile Pro Pro Phe Thr Phe Pro Thr
            20                  25                  30

Gly

<210> SEQ ID NO 18
<211> LENGTH: 84
<212> TYPE: PRT
<213> ORGANISM: Bacillus cereus

<400> SEQUENCE: 18

Met Asn Glu Glu Tyr Ser Ile Leu His Gly Pro Ala Leu Glu Pro Asn
1               5                   10                  15

Leu Ile Gly Pro Thr Leu Pro Ser Ile Pro Pro Phe Thr Phe Pro Thr
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Pro Thr Gly Ile Gly Ile Thr
65                  70                  75                  80

Gly Pro Thr Gly

<210> SEQ ID NO 19
<211> LENGTH: 39
<212> TYPE: PRT
<213> ORGANISM: Bacillus cereus

<400> SEQUENCE: 19

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
        35

<210> SEQ ID NO 20
<211> LENGTH: 1056
<212> TYPE: PRT
<213> ORGANISM: Bacillus cereus

<400> SEQUENCE: 20

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Leu Gln Gly Pro Met Gly Glu
    50                  55                  60

Met Gly Pro Thr Gly Pro Gln Gly Val Gln Gly Ile Gln Gly Ser Val
65                  70                  75                  80

Gly Pro Ile Gly Ala Thr Gly Pro Glu Gly Gln Gln Gly Pro Gln Gly
                85                  90                  95

```
Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
                165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
        195                 200                 205

Gly Pro Ser Gly Gly Pro Pro Gly Pro Thr Gly Pro Thr Gly Ala Thr
    210                 215                 220

Gly Pro Gly Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Ser Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
                325                 330                 335

Gly Ala Thr Gly Asp Gln Gly Pro Gln Gly Ile Gln Gly Val Pro Gly
            340                 345                 350

Pro Ser Gly Glu Thr Gly Pro Gln Gly Val Gln Gly Ile Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gln Gly Ala Thr Gly Ile Gln Gly
        435                 440                 445

Ile Gln Gly Glu Ile Gly Ala Thr Gly Pro Glu Gly Pro Gln Gly Val
    450                 455                 460

Gln Gly Ala Gln Gly Ala Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495

Val Gln Gly Pro Gln Gly Ile Gln Gly Ile Gln Gly Pro Thr Gly Ala
            500                 505                 510
```

```
Thr Gly Asp Met Gly Ala Thr Gly Ala Thr Gly Glu Gly Thr Thr Gly
        515                 520                 525

Pro Thr Gly Val Thr Gly Pro Thr Gly Val Thr Gly Pro Ser Gly Gly
    530                 535                 540

Pro Ala Gly Pro Thr Gly Pro Thr Gly Pro Ser Gly Pro Ala Gly Val
545                 550                 555                 560

Thr Gly Pro Ser Gly Gly Pro Pro Gly Pro Thr Gly Ala Thr Gly Ala
                565                 570                 575

Thr Gly Val Thr Gly Asp Thr Gly Ala Thr Gly Ser Thr Gly Val Thr
            580                 585                 590

Gly Ala Thr Gly Glu Thr Gly Ala Thr Gly Val Thr Gly Leu Gln Gly
        595                 600                 605

Pro Gln Gly Ile Gln Gly Val Gln Gly Glu Ile Gly Pro Thr Gly Pro
    610                 615                 620

Gln Gly Val Gln Gly Pro Gln Gly Ile Gln Gly Val Thr Gly Ala Thr
625                 630                 635                 640

Gly Asp Gln Gly Pro Gln Gly Ile Gln Gly Pro Gln Gly Asp Ile Gly
                645                 650                 655

Pro Thr Gly Pro Gln Gly Ile Gln Gly Pro Gln Gly Ser Gln Gly Ile
            660                 665                 670

Gln Gly Ala Thr Gly Gly Thr Gly Ala Gln Gly Pro Gln Gly Ile Gln
        675                 680                 685

Gly Pro Gln Gly Asp Ile Gly Leu Thr Gly Ser Gln Gly Pro Thr Gly
    690                 695                 700

Ile Gln Gly Ile Gln Gly Glu Ile Gly Pro Thr Gly Pro Glu Gly Pro
705                 710                 715                 720

Glu Gly Leu Gln Gly Pro Gln Gly Ile Gln Gly Ile Gln Gly Pro Val
                725                 730                 735

Gly Ala Thr Gly Pro Glu Gly Pro Gln Gly Ile Gln Gly Ile Gln Gly
            740                 745                 750

Val Gln Gly Ala Thr Gly Pro Gln Gly Pro Gln Gly Ile Gln Gly Ile
        755                 760                 765

Gln Gly Val Gln Gly Ile Thr Gly Ala Thr Gly Ala Gln Gly Ala Thr
    770                 775                 780

Gly Ile Gln Gly Ile Gln Gly Glu Ile Gly Ala Thr Gly Pro Glu Gly
785                 790                 795                 800

Pro Gln Gly Val Gln Gly Ile Gln Gly Ala Ile Gly Pro Thr Gly Pro
                805                 810                 815

Met Gly Ala Gln Gly Val Gln Gly Ile Gln Gly Ile Gln Gly Ala Thr
            820                 825                 830

Gly Ala Gln Gly Val Gln Gly Pro Gln Gly Ile Gln Gly Val Gln Gly
        835                 840                 845

Pro Thr Gly Ala Thr Gly Glu Thr Gly Ala Thr Gly Ala Thr Gly Glu
    850                 855                 860

Gly Thr Thr Gly Pro Thr Gly Val Thr Gly Pro Thr Gly Val Thr Gly
865                 870                 875                 880

Pro Ser Gly Gly Pro Ala Gly Pro Thr Gly Pro Thr Gly Pro Ser Gly
                885                 890                 895

Pro Ala Gly Val Thr Gly Pro Ser Gly Gly Pro Pro Gly Pro Thr Gly
            900                 905                 910

Ala Thr Gly Ala Thr Gly Val Thr Gly Asp Thr Gly Ala Thr Gly Ser
        915                 920                 925

Thr Gly Val Thr Gly Ala Thr Gly Ala Thr Gly Ala Thr Gly Val Thr
```

```
    930                 935                 940

Gly Leu Gln Gly Pro Gln Gly Ile Gln Gly Val Gln Gly Glu Ile Gly
945                 950                 955                 960

Pro Thr Gly Pro Gln Gly Ile Gln Gly Pro Gln Gly Ile Gln Gly Val
                965                 970                 975

Thr Gly Ala Thr Gly Ala Gln Gly Pro Gln Gly Ile Gln Gly Pro Gln
            980                 985                 990

Gly Asp Ile Gly Pro Thr Gly Ser  Gln Gly Ile Gln Gly  Pro Gln Gly
        995                 1000                1005

Pro Gln  Gly Ile Gln Gly Ala  Thr Gly Ala Thr Gly  Ala Gln Gly
    1010                1015                1020

Pro Gln  Gly Ile Gln Gly Pro  Gln Gly Glu Ile Gly  Pro Thr Gly
    1025                1030                1035

Pro Gln  Gly Pro Gln Gly Ile  Gln Gly Pro Gln Gly  Ile Gln Gly
    1040                1045                1050

Pro Thr  Gly
    1055


<210> SEQ ID NO 21
<211> LENGTH: 39
<212> TYPE: PRT
<213> ORGANISM: Bacillus weihenstephensis

<400> SEQUENCE: 21

Met Ser Asp Lys His Gln Met Lys Lys Ile Ser Glu Val Leu Gln Ala
1               5                   10                  15

His Ala Leu Asp Pro Asn Leu Ile Gly Pro Pro Leu Pro Pro Ile Thr
            20                  25                  30

Pro Phe Thr Phe Pro Thr Gly
        35


<210> SEQ ID NO 22
<211> LENGTH: 365
<212> TYPE: PRT
<213> ORGANISM: Bacillus weihenstephensis

<400> SEQUENCE: 22

Met Ser Asp Lys His Gln Met Lys Lys Ile Ser Glu Val Leu Gln Ala
1               5                   10                  15

His Ala Leu Asp Pro Asn Leu Ile Gly Pro Pro Leu Pro Pro Ile Thr
            20                  25                  30

Pro Phe Thr Phe Pro Thr Gly Ser Thr Gly Pro Thr Gly Ser Thr Gly
        35                  40                  45

Ser Thr Gly Pro Thr Gly Ser Thr Gly Asn Thr Gly Pro Thr Gly Pro
    50                  55                  60

Thr Gly Pro Pro Val Gly Thr Asn Leu Asp Thr Ile Tyr Val Thr Asn
65                  70                  75                  80

Asp Ile Ser Asn Asn Val Ser Ala Ile Asp Gly Asn Thr Asn Thr Val
                85                  90                  95

Leu Thr Thr Ile Pro Val Gly Thr Asn Pro Val Gly Val Gly Val Asn
            100                 105                 110

Ser Ser Thr Asn Leu Ile Tyr Val Val Asn Asn Gly Ser Asp Asn Ile
        115                 120                 125

Ser Val Ile Asn Gly Ser Thr Asn Thr Val Val Ala Thr Ile Pro Val
    130                 135                 140

Gly Thr Gln Pro Phe Gly Val Gly Val Asn Pro Ser Thr Asn Leu Ile
```

```
145                 150                 155                 160

Tyr Val Ala Asn Arg Thr Ser Asn Asn Val Ser Val Ile Lys Gly Gly
                165                 170                 175

Thr Asn Thr Val Leu Thr Thr Ile Pro Val Gly Thr Asn Pro Val Gly
            180                 185                 190

Val Gly Val Asn Ser Ser Thr Asn Leu Ile Tyr Val Thr Asn Glu Ile
        195                 200                 205

Pro Asn Ser Val Ser Val Ile Lys Gly Gly Thr Asn Thr Val Val Ala
    210                 215                 220

Thr Ile Pro Val Gly Leu Phe Pro Phe Gly Val Gly Val Asn Ser Leu
225                 230                 235                 240

Thr Asn Leu Ile Tyr Val Val Asn Asn Ser Pro His Asn Val Ser Val
                245                 250                 255

Ile Asp Gly Asn Thr Asn Thr Val Leu Thr Thr Ile Ser Val Gly Thr
            260                 265                 270

Ser Pro Val Gly Val Gly Val Asn Leu Ser Thr Asn Leu Ile Tyr Val
        275                 280                 285

Ala Asn Glu Val Pro Asn Asn Ile Ser Val Ile Asn Gly Asn Thr Asn
    290                 295                 300

Thr Val Leu Thr Thr Ile Pro Val Gly Thr Thr Pro Phe Glu Val Gly
305                 310                 315                 320

Val Asn Ser Ser Thr Asn Leu Ile Tyr Val Ser Asn Leu Asn Ser Asn
                325                 330                 335

Asn Val Ser Val Ile Asn Gly Ser Ala Asn Thr Val Ile Ala Thr Val
            340                 345                 350

Pro Val Gly Ser Val Pro Arg Gly Ile Gly Val Lys Pro
        355                 360                 365


<210> SEQ ID NO 23
<211> LENGTH: 30
<212> TYPE: PRT
<213> ORGANISM: Bacillus weihenstephensis

<400> SEQUENCE: 23

Met Asp Glu Phe Leu Ser Phe Ala Ala Leu Asn Pro Gly Ser Ile Gly
1               5                   10                  15

Pro Thr Leu Pro Pro Val Pro Pro Phe Gln Phe Pro Thr Gly
            20                  25                  30


<210> SEQ ID NO 24
<211> LENGTH: 160
<212> TYPE: PRT
<213> ORGANISM: Bacillus weihenstephensis

<400> SEQUENCE: 24

Met Asp Glu Phe Leu Ser Phe Ala Ala Leu Asn Pro Gly Ser Ile Gly
1               5                   10                  15

Pro Thr Leu Pro Pro Val Pro Pro Phe Gln Phe Pro Thr Gly Pro Thr
            20                  25                  30

Gly Ser Thr Gly Ser Thr Gly Pro Thr Gly Ser Thr Gly Ser Thr Gly
        35                  40                  45

Pro Thr Gly Phe Asn Leu Pro Ala Gly Pro Ala Ser Ile Thr Leu Thr
    50                  55                  60

Ser Asn Glu Thr Thr Ala Cys Val Ser Thr Gln Gly Asn Asn Thr Leu
65                  70                  75                  80

Phe Phe Ser Gly Gln Val Leu Val Asn Gly Ser Pro Thr Pro Gly Val
```

```
                85                  90                  95

Val Val Ser Phe Ser Phe Ser Asn Pro Ser Leu Ala Phe Met Val Pro
            100                 105                 110

Leu Ala Val Ile Thr Asn Ala Ser Gly Asn Phe Thr Ala Val Phe Leu
        115                 120                 125

Ala Ala Asn Gly Pro Gly Thr Val Thr Val Thr Ala Ser Leu Leu Asp
    130                 135                 140

Ser Pro Gly Thr Met Ala Ser Val Thr Ile Thr Ile Val Asn Cys Pro
145                 150                 155                 160


<210> SEQ ID NO 25
<211> LENGTH: 30
<212> TYPE: PRT
<213> ORGANISM: Bacillus weihenstephensis

<400> SEQUENCE: 25

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly
            20                  25                  30


<210> SEQ ID NO 26
<211> LENGTH: 69
<212> TYPE: PRT
<213> ORGANISM: Bacillus weihenstephensis

<400> SEQUENCE: 26

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly Pro Thr
            20                  25                  30

Gly Ser Thr Gly Thr Thr Gly Pro Thr Gly Ser Ile Gly Pro Thr Gly
        35                  40                  45

Asn Thr Gly Leu Thr Gly Asn Thr Gly Pro Thr Gly Ile Thr Gly Pro
    50                  55                  60

Thr Gly Asp Thr Gly
65


<210> SEQ ID NO 27
<211> LENGTH: 36
<212> TYPE: PRT
<213> ORGANISM: Bacillus weihenstephensis

<400> SEQUENCE: 27

Met Lys Glu Arg Asp Arg Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly
        35


<210> SEQ ID NO 28
<211> LENGTH: 934
<212> TYPE: PRT
<213> ORGANISM: Bacillus weihenstephensis

<400> SEQUENCE: 28

Met Lys Glu Arg Asp Arg Gln Asn Ser Leu Asn Ser Asn Phe Arg Ile
1               5                   10                  15
```

```
Ser Pro Asn Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Phe Gln Gly Pro Met Gly Glu Met Gly Pro
    50                  55                  60

Thr Gly Pro Gln Gly Val Gln Gly Ile Gln Gly Pro Ala Gly Gln Met
65                  70                  75                  80

Gly Ala Thr Gly Pro Glu Gly Gln Gln Gly Pro Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ile Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Val Pro Gly Ala Thr Gly Ser
145                 150                 155                 160

Gln Gly Ile Gln Gly Ala Gln Gly Ile Gln Gly Pro Gln Gly Pro Ser
                165                 170                 175

Gly Asn Thr Gly Ala Thr Gly Val Thr Gly Gln Gly Ile Ser Gly Pro
            180                 185                 190

Thr Gly Ile Thr Gly Pro Thr Gly Ile Thr Gly Pro Ser Gly Gly Pro
        195                 200                 205

Pro Gly Pro Thr Gly Ala Thr Gly Ala Thr Gly Pro Gly Gly Gly Pro
    210                 215                 220

Ser Gly Ser Thr Gly Ala Thr Gly Ala Thr Gly Asn Thr Gly Val Thr
225                 230                 235                 240

Gly Ser Ala Gly Val Thr Gly Asn Thr Gly Ser Thr Gly Ser Thr Gly
                245                 250                 255

Glu Thr Gly Ala Gln Gly Leu Gln Gly Ile Gln Gly Val Gln Gly Pro
            260                 265                 270

Ile Gly Pro Thr Gly Pro Glu Gly Pro Gln Gly Ile Gln Gly Ile Pro
        275                 280                 285

Gly Pro Thr Gly Val Thr Gly Glu Gln Gly Ile Gln Gly Val Gln Gly
    290                 295                 300

Ile Gln Gly Ile Thr Gly Ala Thr Gly Asp Gln Gly Pro Gln Gly Ile
305                 310                 315                 320

Gln Gly Ala Ile Gly Pro Gln Gly Ile Thr Gly Ala Thr Gly Asp Gln
                325                 330                 335

Gly Pro Gln Gly Ile Gln Gly Val Pro Gly Pro Thr Gly Asp Thr Gly
            340                 345                 350

Ser Gln Gly Val Gln Gly Ile Gln Gly Pro Met Gly Asp Ile Gly Pro
        355                 360                 365

Thr Gly Pro Glu Gly Pro Glu Gly Leu Gln Gly Pro Gln Gly Ile Gln
    370                 375                 380

Gly Val Pro Gly Pro Ala Gly Ala Thr Gly Pro Glu Gly Pro Gln Gly
385                 390                 395                 400

Ile Gln Gly Ile Gln Gly Pro Ile Gly Val Thr Gly Pro Glu Gly Pro
                405                 410                 415

Gln Gly Ile Gln Gly Ile Gln Gly Ile Gln Gly Ile Thr Gly Ala Thr
            420                 425                 430

Gly Ala Gln Gly Ala Thr Gly Val Gln Gly Val Gln Gly Asn Ile Gly
```

```
        435                 440                 445

Ala Thr Gly Pro Glu Gly Pro Gln Gly Val Gln Gly Thr Gln Gly Asp
    450                 455                 460

Ile Gly Pro Thr Gly Pro Met Gly Pro Gln Gly Val Gln Gly Ile Gln
465                 470                 475                 480

Gly Ile Gln Gly Pro Thr Gly Ala Gln Gly Val Gln Gly Pro Gln Gly
                485                 490                 495

Ile Gln Gly Ile Gln Gly Pro Thr Gly Val Thr Gly Asp Thr Gly Thr
            500                 505                 510

Thr Gly Ala Thr Gly Glu Gly Thr Thr Gly Ala Thr Gly Val Thr Gly
        515                 520                 525

Pro Ser Gly Val Thr Gly Pro Ser Gly Gly Pro Ala Gly Pro Thr Gly
    530                 535                 540

Pro Thr Gly Pro Ser Gly Pro Thr Gly Leu Thr Gly Pro Ser Gly Gly
545                 550                 555                 560

Pro Pro Gly Pro Thr Gly Ala Thr Gly Val Thr Gly Gly Val Gly Asp
                565                 570                 575

Thr Gly Ala Thr Gly Ser Thr Gly Val Thr Gly Ala Thr Gly Val Thr
            580                 585                 590

Gly Ala Thr Gly Ala Thr Gly Leu Gln Gly Pro Gln Gly Ile Gln Gly
        595                 600                 605

Val Gln Gly Asp Ile Gly Pro Thr Gly Pro Gln Gly Val Gln Gly Pro
    610                 615                 620

Gln Gly Ile Gln Gly Ile Thr Gly Ala Thr Gly Asp Gln Gly Pro Gln
625                 630                 635                 640

Gly Ile Gln Gly Pro Gln Gly Ile Gln Gly Pro Thr Gly Pro Gln Gly
                645                 650                 655

Ile Gln Gly Gly Gln Gly Pro Gln Gly Ile Gln Gly Ala Thr Gly Ala
            660                 665                 670

Thr Gly Ala Gln Gly Pro Gln Gly Ile Gln Gly Ile Gln Gly Val Gln
        675                 680                 685

Gly Pro Thr Gly Pro Gln Gly Pro Thr Gly Ile Gln Gly Val Gln Gly
    690                 695                 700

Glu Ile Gly Pro Thr Gly Pro Gln Gly Val Gln Gly Leu Gln Gly Pro
705                 710                 715                 720

Gln Gly Pro Thr Gly Asp Thr Gly Pro Thr Gly Pro Gln Gly Pro Gln
                725                 730                 735

Gly Ile Gln Gly Pro Thr Gly Ala Thr Gly Ala Thr Gly Ser Gln Gly
            740                 745                 750

Ile Gln Gly Pro Thr Gly Ala Thr Gly Ala Thr Gly Ser Gln Gly Ile
        755                 760                 765

Gln Gly Pro Thr Gly Ala Thr Gly Ala Thr Gly Ala Thr Gly Ala Thr
    770                 775                 780

Gly Ala Thr Gly Ala Thr Gly Ala Thr Gly Val Thr Gly Val Ser Thr
785                 790                 795                 800

Thr Ala Thr Tyr Ser Phe Ala Asn Asn Thr Ser Gly Ser Ala Ile Ser
                805                 810                 815

Val Leu Leu Gly Gly Thr Asn Ile Pro Leu Pro Asn Asn Gln Asn Ile
            820                 825                 830

Gly Pro Gly Ile Thr Val Ser Gly Gly Asn Thr Val Phe Thr Val Thr
        835                 840                 845

Asn Ala Gly Asn Tyr Tyr Ile Ala Tyr Thr Ile Asn Ile Thr Ala Ala
    850                 855                 860
```

```
Leu Leu Val Ser Ser Arg Ile Thr Val Asn Gly Ser Pro Leu Ala Gly
865                 870                 875                 880

Thr Ile Asn Ser Pro Ala Val Ala Thr Gly Ser Phe Asn Ala Thr Ile
                885                 890                 895

Ile Ser Asn Leu Ala Ala Gly Ser Ala Ile Ser Leu Gln Leu Phe Gly
            900                 905                 910

Leu Leu Ala Val Ala Thr Leu Ser Thr Thr Thr Pro Gly Ala Thr Leu
        915                 920                 925

Thr Ile Ile Arg Leu Ser
    930


<210> SEQ ID NO 29
<211> LENGTH: 39
<212> TYPE: PRT
<213> ORGANISM: Bacillus mycoides

<400> SEQUENCE: 29

Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35


<210> SEQ ID NO 30
<211> LENGTH: 287
<212> TYPE: PRT
<213> ORGANISM: Bacillus mycoides

<400> SEQUENCE: 30

Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly Pro Thr Gly Gly Thr Gly Pro Thr Gly
        35                  40                  45

Val Thr Gly Pro Thr Gly Val Thr Gly Pro Thr Gly Val Thr Gly Pro
    50                  55                  60

Thr Gly Val Thr Gly Pro Thr Gly Val Thr Gly Pro Thr Gly Val Thr
65                  70                  75                  80

Gly Pro Thr Gly Val Thr Gly Pro Thr Gly Val Thr Gly Pro Thr Gly
                85                  90                  95

Val Thr Gly Pro Thr Gly Val Thr Gly Pro Thr Gly Val Thr Gly Pro
            100                 105                 110

Thr Gly Val Thr Gly Pro Thr Gly Gly Thr Glu Gly Cys Leu Cys Asp
        115                 120                 125

Cys Cys Val Leu Pro Met Gln Ser Val Leu Gln Gln Leu Ile Gly Glu
    130                 135                 140

Thr Val Ile Leu Gly Thr Ile Ala Asp Thr Pro Asn Thr Pro Pro Leu
145                 150                 155                 160

Phe Phe Leu Phe Thr Ile Thr Ser Val Asn Asp Phe Leu Val Thr Val
                165                 170                 175

Thr Asp Gly Thr Thr Thr Phe Val Val Asn Ile Ser Asp Val Thr Gly
            180                 185                 190

Val Gly Phe Leu Pro Pro Gly Pro Pro Ile Thr Leu Leu Pro Pro Thr
        195                 200                 205
```

```
Asp Val Gly Cys Glu Cys Glu Cys Arg Glu Arg Pro Ile Arg Gln Leu
    210                 215                 220

Leu Asp Ala Phe Ile Gly Ser Thr Val Ser Leu Leu Ala Ser Asn Gly
225                 230                 235                 240

Ser Ile Ala Ala Asp Phe Ser Val Glu Gln Thr Gly Leu Gly Ile Val
                245                 250                 255

Leu Gly Thr Leu Pro Ile Asn Pro Thr Thr Thr Val Arg Phe Ala Ile
            260                 265                 270

Ser Thr Cys Lys Ile Thr Ala Val Asn Ile Thr Pro Ile Thr Met
        275                 280                 285


<210> SEQ ID NO 31
<211> LENGTH: 30
<212> TYPE: PRT
<213> ORGANISM: Bacillus mycoides

<400> SEQUENCE: 31

Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly
            20                  25                  30


<210> SEQ ID NO 32
<211> LENGTH: 190
<212> TYPE: PRT
<213> ORGANISM: Bacillus mycoides

<400> SEQUENCE: 32

Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly Pro Thr
            20                  25                  30

Gly Ser Thr Gly Ala Thr Gly Ser Thr Gly Ser Thr Gly Ser Thr Gly
        35                  40                  45

Pro Thr Gly Ser Thr Gly Ser Thr Gly Ser Thr Gly Ser Thr Gly Pro
    50                  55                  60

Thr Gly Pro Thr Gly Pro Thr Gly Ser Thr Gly Pro Thr Gly Pro Thr
65                  70                  75                  80

Gly Phe Asn Leu Pro Ala Gly Pro Ala Ser Ile Thr Leu Thr Ser Asn
                85                  90                  95

Glu Thr Thr Ala Cys Val Ser Thr Gln Gly Asn Asn Thr Leu Phe Phe
            100                 105                 110

Ser Gly Gln Val Leu Val Asn Gly Ser Pro Thr Pro Gly Val Val Val
        115                 120                 125

Ser Phe Ser Phe Ser Asn Pro Ser Leu Ala Phe Met Val Pro Leu Ala
    130                 135                 140

Val Ile Thr Asn Ala Ser Gly Asn Phe Thr Ala Val Phe Leu Ala Ala
145                 150                 155                 160

Asn Gly Pro Gly Thr Val Thr Val Thr Ala Ser Leu Leu Asp Ser Pro
                165                 170                 175

Gly Thr Met Ala Ser Val Thr Ile Thr Ile Val Asn Cys Pro
            180                 185                 190


<210> SEQ ID NO 33
<211> LENGTH: 21
<212> TYPE: PRT
<213> ORGANISM: Bacillus mycoides
```

<400> SEQUENCE: 33

```
Met Asp Ser Lys Asn Ile Gly Pro Thr Phe Pro Pro Leu Pro Ser Ile
1               5                   10                  15

Asn Phe Pro Thr Gly
            20
```

<210> SEQ ID NO 34
<211> LENGTH: 335
<212> TYPE: PRT
<213> ORGANISM: Bacillus mycoides

<400> SEQUENCE: 34

```
Met Asp Ser Lys Asn Ile Gly Pro Thr Phe Pro Pro Leu Pro Ser Ile
1               5                   10                  15

Asn Phe Pro Thr Gly Val Thr Gly Glu Thr Gly Ala Thr Gly Glu Thr
            20                  25                  30

Gly Ala Thr Gly Ala Thr Gly Glu Thr Gly Ala Thr Gly Glu Thr Gly
        35                  40                  45

Glu Thr Gly Ala Thr Gly Ala Thr Gly Ala Thr Gly Ala Thr Gly Glu
    50                  55                  60

Thr Gly Ala Thr Gly Ala Thr Gly Ala Thr Gly Ala Ala Gly Ala Thr
65                  70                  75                  80

Gly Glu Thr Gly Ala Thr Gly Glu Thr Gly Ala Thr Gly Glu Thr Gly
                85                  90                  95

Ala Thr Gly Glu Thr Gly Ala Thr Gly Val Thr Gly Glu Thr Gly Ala
            100                 105                 110

Thr Gly Glu Thr Gly Ala Ala Gly Glu Thr Gly Ile Thr Gly Val Thr
        115                 120                 125

Gly Pro Thr Gly Glu Thr Gly Ala Thr Gly Glu Thr Gly Ala Thr Gly
    130                 135                 140

Ala Thr Gly Ile Thr Gly Ala Thr Gly Ile Thr Gly Val Ala Gly Ala
145                 150                 155                 160

Thr Gly Glu Thr Gly Ala Ala Gly Glu Thr Gly Pro Thr Gly Ala Thr
                165                 170                 175

Gly Ala Ile Gly Ala Ile Gly Ala Thr Gly Ala Thr Gly Ile Thr Gly
            180                 185                 190

Val Thr Gly Ala Thr Gly Glu Thr Gly Ala Ala Gly Ala Thr Gly Ile
        195                 200                 205

Thr Gly Val Thr Gly Ala Thr Gly Glu Thr Gly Ala Ala Gly Ala Thr
    210                 215                 220

Gly Ile Thr Gly Ala Thr Gly Ile Thr Gly Val Ala Gly Ala Thr Gly
225                 230                 235                 240

Ile Thr Gly Pro Thr Gly Ile Pro Gly Thr Ile Pro Thr Thr Asn Leu
                245                 250                 255

Leu Tyr Phe Thr Phe Ser Asp Gly Glu Lys Leu Ile Tyr Thr Asn Ala
            260                 265                 270

Asp Gly Ile Ala Gln Tyr Gly Thr Thr Gln Ile Leu Ser Pro Ser Glu
        275                 280                 285

Val Ser Tyr Ile Asn Leu Phe Ile Asn Gly Ile Leu Gln Pro Gln Pro
    290                 295                 300

Phe Tyr Glu Val Thr Ala Gly Gln Leu Thr Leu Leu Asp Asp Glu Pro
305                 310                 315                 320

Pro Ser Gln Gly Ser Ser Ile Ile Leu Gln Phe Ile Ile Ile Asn
                325                 330                 335
```

<210> SEQ ID NO 35
<211> LENGTH: 22
<212> TYPE: PRT
<213> ORGANISM: Bacillus thuringiensis

<400> SEQUENCE: 35

```
Met Ile Gly Pro Glu Asn Ile Gly Pro Thr Phe Pro Ile Leu Pro Pro
1               5                   10                  15

Ile Tyr Ile Pro Thr Gly
            20
```

<210> SEQ ID NO 36
<211> LENGTH: 234
<212> TYPE: PRT
<213> ORGANISM: Bacillus thuringiensis

<400> SEQUENCE: 36

```
Met Ile Gly Pro Glu Asn Ile Gly Pro Thr Phe Pro Ile Leu Pro Pro
1               5                   10                  15

Ile Tyr Ile Pro Thr Gly Glu Thr Gly Pro Thr Gly Ile Thr Gly Ala
            20                  25                  30

Thr Gly Glu Thr Gly Pro Thr Gly Ile Thr Gly Pro Thr Gly Ile Thr
        35                  40                  45

Gly Ala Thr Gly Glu Thr Gly Ser Thr Gly Ile Thr Gly Ala Thr Gly
    50                  55                  60

Glu Thr Gly Ser Thr Gly Ile Thr Gly Pro Ile Gly Ile Thr Gly Ala
65                  70                  75                  80

Thr Gly Glu Thr Gly Pro Ile Gly Ile Thr Gly Ala Thr Gly Glu Thr
                85                  90                  95

Gly Pro Thr Gly Ile Thr Gly Ser Thr Gly Ile Thr Gly Leu Thr Gly
            100                 105                 110

Val Thr Gly Leu Thr Gly Glu Thr Gly Pro Ile Gly Ile Thr Gly Pro
        115                 120                 125

Thr Gly Ile Thr Gly Pro Thr Gly Val Thr Gly Ala Thr Gly Pro Thr
    130                 135                 140

Gly Gly Ile Gly Pro Ile Thr Thr Thr Asn Leu Leu Tyr Tyr Thr Phe
145                 150                 155                 160

Ala Asp Gly Glu Lys Leu Ile Tyr Thr Asp Thr Asp Gly Ile Pro Gln
                165                 170                 175

Tyr Gly Thr Thr Asn Ile Leu Ser Pro Ser Glu Val Ser Tyr Ile Asn
            180                 185                 190

Leu Phe Val Asn Gly Ile Leu Gln Pro Gln Pro Leu Tyr Glu Val Ser
        195                 200                 205

Thr Gly Lys Leu Thr Leu Leu Asp Thr Gln Pro Pro Ser Gln Gly Ser
    210                 215                 220

Ser Ile Ile Leu Gln Phe Ile Ile Ile Asn
225                 230
```

<210> SEQ ID NO 37
<211> LENGTH: 299
<212> TYPE: DNA
<213> ORGANISM: Bacillus cereus

<400> SEQUENCE: 37

```
tttcttaatc ctttaccctt tacttttgta aaagttgata cacttccatc cggctctgta      60

atttctaatt catcaataaa tggtcttcgc aaaaagcctg taattttatc ataaacaatt     120
```

aaacgagtga gcctaaaagc agctaacgcg aaaataaaaa ataaaagcca gcttgtaaac 180
agcataattc caccttccct tatcctcttt cgcctattta aaaaaaggtc ttgagattgt 240
gaccaaatct cctcaactcc aatatcttat taatgtaaat acaaacaaga agataagga 299

<210> SEQ ID NO 38
<211> LENGTH: 58
<212> TYPE: DNA
<213> ORGANISM: Bacillus cereus

<400> SEQUENCE: 38
accaaatctc ctcaactcca atatcttatt aatgtaaata caaacaagaa gataagga 58

<210> SEQ ID NO 39
<211> LENGTH: 300
<212> TYPE: DNA
<213> ORGANISM: Bacillus anthracis

<400> SEQUENCE: 39
accacctacc gacgatccaa tctgtacatt cctagctgta ccaaatgcaa gattaatatc 60
gactaacact tgtcttactg ttgatttaag ttgcttctgt gcgattcaat gcttgcgtga 120
tgttacgatt taaaactaaa taatgagcta agcatggatt gggtggcaga attatctgcc 180
acccaatcca tgcttaacga gtattattat gtaaatttct taaaattggg aacttgtcta 240
gaacatagaa cctgtccttt tcattaactg aaagtagaaa cagataaagg agtgaaaaac 300

<210> SEQ ID NO 40
<211> LENGTH: 58
<212> TYPE: DNA
<213> ORGANISM: Bacillus anthracis

<400> SEQUENCE: 40
acatagaacc tgtccttttc attaactgaa agtagaaaca gataaaggag tgaaaaac 58

<210> SEQ ID NO 41
<211> LENGTH: 300
<212> TYPE: DNA
<213> ORGANISM: Bacillus anthracis

<400> SEQUENCE: 41
tagaagaaga acgccgacta ctttatgtcg caattacacg ggcgaaagaa gaactttaca 60
tttcctctcc gcaatttttt agaggaaaaa aattagatat atctcgtttt ttatacactg 120
tgcgaaaaga tttacctgaa aagacatcca ctaaataagg atgtcttttt ttatattgta 180
ttatgtacat ccctactata taaattccct gcttttatcg taagaattaa cgtaatatca 240
accatatccc gttcatattg tagtagtgta tgtcagaact cacgagaagg agtgaacata 300

<210> SEQ ID NO 42
<211> LENGTH: 63
<212> TYPE: DNA
<213> ORGANISM: Bacillus anthracis

<400> SEQUENCE: 42
tcaaccatat cccgttcata ttgtagtagt gtatgtcaga actcacgaga aggagtgaac 60
ata 63

<210> SEQ ID NO 43
<211> LENGTH: 35
<212> TYPE: PRT

<213> ORGANISM: Bacillus cereus

<400> SEQUENCE: 43

Met Ser Asn Asn Asn Ile Pro Ser Pro Phe Phe Phe Asn Asn Phe Asn
1 5 10 15

Pro Glu Leu Ile Gly Pro Thr Phe Pro Pro Ile Pro Pro Leu Thr Leu
20 25 30

Pro Thr Gly
35

<210> SEQ ID NO 44
<211> LENGTH: 222
<212> TYPE: PRT
<213> ORGANISM: Bacillus cereus

<400> SEQUENCE: 44

Met Ser Asn Asn Asn Ile Pro Ser Pro Phe Phe Phe Asn Asn Phe Asn
1 5 10 15

Pro Glu Leu Ile Gly Pro Thr Phe Pro Pro Ile Pro Pro Leu Thr Leu
20 25 30

Pro Thr Gly Pro Thr Gly Ser Thr Gly Ala Thr Gly Ala Thr Gly Pro
35 40 45

Thr Gly Ala Thr Gly Pro Thr Gly Ala Thr Gly Pro Thr Gly Ala Thr
50 55 60

Gly Ala Thr Gly Ser Thr Gly Ala Thr Gly Pro Thr Gly Ala Thr Gly
65 70 75 80

Thr Phe Ser Ser Ala Asn Ala Ser Ile Val Thr Pro Ala Pro Gln Thr
85 90 95

Val Asn Asn Leu Ala Pro Ile Gln Phe Thr Ala Pro Val Leu Ile Ser
100 105 110

Lys Asn Val Thr Phe Asn Gly Ile Asp Thr Phe Thr Ile Gln Ile Pro
115 120 125

Gly Asn Tyr Phe Phe Ile Gly Ala Val Met Thr Ser Asn Asn Gln Ala
130 135 140

Gly Pro Val Ala Val Gly Val Gly Phe Asn Gly Ile Pro Val Pro Ser
145 150 155 160

Leu Asp Gly Ala Asn Tyr Gly Thr Pro Thr Gly Gln Glu Val Val Cys
165 170 175

Phe Gly Phe Ser Gly Gln Ile Pro Ala Gly Thr Thr Ile Asn Leu Tyr
180 185 190

Asn Ile Ser Asp Lys Thr Ile Ser Ile Gly Gly Ala Thr Ala Ala Gly
195 200 205

Ser Ser Ile Val Ala Ala Arg Leu Ser Phe Phe Arg Ile Ser
210 215 220

<210> SEQ ID NO 45
<211> LENGTH: 41
<212> TYPE: PRT
<213> ORGANISM: Bacillus cereus

<400> SEQUENCE: 45

Met Phe Ser Glu Lys Lys Arg Lys Asp Leu Ile Pro Asp Asn Phe Leu
1 5 10 15

Ser Ala Pro Ala Leu Asp Pro Asn Leu Ile Gly Pro Thr Phe Pro Pro
20 25 30

Ile Pro Ser Phe Thr Leu Pro Thr Gly
35 40

<210> SEQ ID NO 46
<211> LENGTH: 293
<212> TYPE: PRT
<213> ORGANISM: Bacillus cereus

<400> SEQUENCE: 46

```
Met Phe Ser Glu Lys Lys Arg Lys Asp Leu Ile Pro Asp Asn Phe Leu
1               5                   10                  15

Ser Ala Pro Ala Leu Asp Pro Asn Leu Ile Gly Pro Thr Phe Pro Pro
            20                  25                  30

Ile Pro Ser Phe Thr Leu Pro Thr Gly Ser Thr Gly Pro Thr Gly Pro
        35                  40                  45

Thr Gly Asp Thr Gly Pro Thr Gly Pro Thr Ala Thr Ile Cys Ile Arg
    50                  55                  60

Thr Asp Pro Asp Asn Gly Cys Ser Val Ala Glu Gly Ser Gly Thr Val
65                  70                  75                  80

Ala Ser Gly Phe Ala Ser His Ala Glu Ala Cys Asn Thr Gln Ala Ile
                85                  90                  95

Gly Asp Cys Ser His Ala Glu Gly Gln Phe Ala Thr Ala Ser Gly Thr
            100                 105                 110

Ala Ser His Ala Glu Gly Phe Gln Thr Thr Ala Ser Gly Phe Ala Ser
        115                 120                 125

His Thr Glu Gly Ser Gly Thr Thr Ala Asp Ala Asn Phe Ser His Thr
    130                 135                 140

Glu Gly Ile Asn Thr Ile Val Asp Val Leu His Pro Gly Ser His Ile
145                 150                 155                 160

Met Gly Lys Asn Gly Thr Thr Arg Ser Ser Phe Ser Trp His Leu Ala
                165                 170                 175

Asn Gly Leu Ala Val Gly Pro Ser Leu Asn Ser Ala Val Ile Glu Gly
            180                 185                 190

Val Thr Gly Asn Leu Tyr Leu Asp Gly Val Val Ile Ser Pro Asn Ala
        195                 200                 205

Ala Asp Tyr Ala Glu Met Phe Glu Thr Ile Asp Gly Asn Leu Ile Asp
    210                 215                 220

Val Gly Tyr Phe Val Thr Leu Tyr Gly Glu Lys Ile Arg Lys Ala Asn
225                 230                 235                 240

Ala Asn Asp Asp Tyr Ile Leu Gly Val Val Ser Ala Thr Pro Ala Met
                245                 250                 255

Ile Ala Asp Ala Ser Asp Leu Arg Trp His Asn Leu Phe Val Arg Asp
            260                 265                 270

Glu Trp Gly Arg Thr Gln Tyr His Glu Val Val Val Pro Glu Lys Lys
        275                 280                 285

Met Ala Met Glu Glu
    290
```

<210> SEQ ID NO 47
<211> LENGTH: 49
<212> TYPE: PRT
<213> ORGANISM: Bacillus cereus

<400> SEQUENCE: 47

```
Met Thr Arg Lys Asp Lys Phe Asn Arg Ser Arg Ile Ser Arg Arg Asp
1               5                   10                  15

Arg Phe Asn Ser Pro Lys Ile Lys Ser Glu Ile Leu Ile Ser Pro Asp
            20                  25                  30
```

```
Leu Val Gly Pro Thr Phe Pro Pro Ile Pro Ser Phe Thr Leu Pro Thr
        35                  40                  45

Gly


<210> SEQ ID NO 48
<211> LENGTH: 83
<212> TYPE: PRT
<213> ORGANISM: Bacillus cereus

<400> SEQUENCE: 48

Met Thr Arg Lys Asp Lys Phe Asn Arg Ser Arg Ile Ser Arg Arg Asp
1               5                   10                  15

Arg Phe Asn Ser Pro Lys Ile Lys Ser Glu Ile Leu Ile Ser Pro Asp
            20                  25                  30

Leu Val Gly Pro Thr Phe Pro Pro Ile Pro Ser Phe Thr Leu Pro Thr
        35                  40                  45

Gly Val Thr Gly Pro Thr Gly Asn Thr Gly Pro Thr Gly Ile Thr Gly
    50                  55                  60

Pro Thr Gly Asp Thr Gly Pro Thr Gly Asp Thr Gly Pro Thr Gly Ile
65                  70                  75                  80

Thr Gly Pro


<210> SEQ ID NO 49
<211> LENGTH: 38
<212> TYPE: PRT
<213> ORGANISM: Bacillus cereus

<400> SEQUENCE: 49

Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Pro Ile Pro Ser
            20                  25                  30

Phe Thr Leu Pro Thr Gly
        35


<210> SEQ ID NO 50
<211> LENGTH: 163
<212> TYPE: PRT
<213> ORGANISM: Bacillus cereus

<400> SEQUENCE: 50

Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Pro Ile Pro Ser
            20                  25                  30

Phe Thr Leu Pro Thr Gly Ile Thr Gly Pro Thr Gly Asn Thr Gly Pro
        35                  40                  45

Thr Gly Asp Thr Gly Pro Thr Gly Pro Thr Phe Asn Ile Asn Phe Arg
    50                  55                  60

Ala Glu Lys Asn Gly Ala Gln Ser Phe Thr Pro Pro Ala Asp Ile Gln
65                  70                  75                  80

Val Ser Tyr Gly Asn Ile Ile Phe Asn Asn Gly Gly Gly Tyr Ser Ser
                85                  90                  95

Val Thr Asn Thr Phe Thr Ala Pro Ile Asn Gly Ile Tyr Leu Phe Ser
            100                 105                 110

Ala Asn Ile Gly Phe Asn Pro Thr Leu Gly Thr Thr Ser Thr Leu Arg
        115                 120                 125
```

```
Ile Thr Ile Arg Lys Asn Leu Val Ser Val Ala Ser Gln Thr Ile Asp
    130                 135                 140

Ile Gln Phe Ser Ala Ala Glu Ser Gly Thr Leu Thr Val Gly Ser Ser
145                 150                 155                 160

Asn Phe Phe


<210> SEQ ID NO 51
<211> LENGTH: 39
<212> TYPE: PRT
<213> ORGANISM: Bacillus cereus

<400> SEQUENCE: 51

Met Lys Glu Arg Asp Asn Lys Gly Lys Gln His Ser Leu Asn Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
        35


<210> SEQ ID NO 52
<211> LENGTH: 323
<212> TYPE: PRT
<213> ORGANISM: Bacillus cereus

<400> SEQUENCE: 52

Met Lys Glu Arg Asp Asn Lys Gly Lys Gln His Ser Leu Asn Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Phe Gln Gly Pro Met Gly Glu
    50                  55                  60

Met Gly Pro Thr Gly Pro Gln Gly Val Gln Gly Ile Gln Gly Pro Ala
65                  70                  75                  80

Gly Gln Met Gly Ala Thr Gly Pro Glu Gly Gln Gln Gly Pro Glu Gly
                85                  90                  95

Leu Arg Gly Pro Val Gly Ala Thr Gly Ala Thr Gly Leu Gln Gly Val
            100                 105                 110

Gln Gly Ile Gln Gly Pro Ile Gly Ser Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Pro Gln Gly Ile Gln Gly Val Gln Gly Leu Pro Gly Ala
145                 150                 155                 160

Thr Gly Pro Gln Gly Val Gln Gly Val Gln Gly Val Ile Gly Pro Gln
                165                 170                 175

Gly Pro Ser Gly Ser Thr Gly Gly Thr Gly Ala Thr Gly Gln Gly Val
            180                 185                 190

Thr Gly Pro Thr Gly Ile Thr Gly Ser Thr Gly Val Thr Gly Pro Ser
        195                 200                 205

Gly Gly Pro Pro Gly Pro Thr Gly Pro Thr Gly Ala Thr Gly Pro Gly
    210                 215                 220

Gly Gly Pro Ser Gly Ser Thr Gly Val Thr Gly Ser Thr Gly Asn Thr
225                 230                 235                 240
```

```
Gly Ala Thr Gly Ser Pro Gly Val Thr Gly Ala Thr Gly Pro Thr Gly
                245                 250                 255

Ser Thr Gly Ala Thr Gly Ile Gln Gly Ser Gln Gly Ile Gln Gly Ile
            260                 265                 270

Gln Gly Ile Gln Gly Pro Leu Gly Pro Thr Gly Pro Glu Gly Pro Gln
        275                 280                 285

Gly Ile Gln Gly Ile Pro Gly Pro Thr Gly Ile Thr Gly Glu Gln Gly
    290                 295                 300

Ile Gln Gly Val Gln Gly Ile Gln Gly Ile Thr Gly Ala Thr Gly Asp
305                 310                 315                 320

Gln Gly Thr


<210> SEQ ID NO 53
<211> LENGTH: 39
<212> TYPE: PRT
<213> ORGANISM: Bacillus cereus

<400> SEQUENCE: 53

Met Arg Glu Arg Asp Asn Lys Arg Gln Gln His Ser Leu Asn Pro Asn
1               5                   10                  15

Phe Arg Ile Ser Pro Glu Leu Ile Gly Pro Thr Phe Pro Pro Val Pro
            20                  25                  30

Thr Gly Phe Thr Gly Ile Gly
        35


<210> SEQ ID NO 54
<211> LENGTH: 436
<212> TYPE: PRT
<213> ORGANISM: Bacillus cereus

<400> SEQUENCE: 54

Met Arg Glu Arg Asp Asn Lys Arg Gln Gln His Ser Leu Asn Pro Asn
1               5                   10                  15

Phe Arg Ile Ser Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Phe Gln Gly Pro Met Gly Glu
    50                  55                  60

Met Gly Pro Thr Gly Pro Gln Gly Val Gln Gly Ile Gln Gly Pro Val
65                  70                  75                  80

Gly Pro Ile Gly Ala Thr Gly Pro Glu Gly Gln Gln Gly Pro Gln Gly
                85                  90                  95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125

Gly Val Gln Gly Ile Gln Gly Leu Gln Gly Pro Ile Gly Ala Thr Gly
    130                 135                 140

Pro Glu Gly Pro Gln Gly Ile Gln Gly Val Gln Gly Leu Pro Gly Ala
145                 150                 155                 160

Thr Gly Ser Gln Gly Ile Gln Gly Val Gln Gly Ile Gln Gly Pro Gln
                165                 170                 175

Gly Pro Ser Gly Asn Thr Gly Ala Thr Gly Ala Thr Gly Gln Gly Ile
            180                 185                 190

Thr Gly Pro Thr Gly Ile Thr Gly Pro Thr Gly Ile Thr Gly Pro Ser
```

```
        195                 200                 205

Gly Gly Pro Pro Gly Pro Thr Gly Pro Thr Gly Ala Thr Gly Pro Gly
    210                 215                 220

Gly Gly Pro Ser Gly Ser Thr Gly Ala Thr Gly Ala Thr Gly Asn Thr
225                 230                 235                 240

Gly Ala Thr Gly Asn Thr Gly Ile Thr Gly Ala Thr Gly Ser Thr Gly
                245                 250                 255

Pro Thr Gly Ser Thr Gly Ala Gln Gly Leu Gln Gly Ile Gln Gly Ile
            260                 265                 270

Gln Gly Pro Ile Gly Pro Thr Gly Pro Glu Gly Pro Gln Gly Ile Gln
        275                 280                 285

Gly Ile Pro Gly Pro Thr Gly Val Thr Gly Glu Gln Gly Ile Gln Gly
    290                 295                 300

Val Gln Gly Ile Gln Gly Ile Thr Gly Ala Thr Gly Asp Gln Gly Pro
305                 310                 315                 320

Gln Gly Ile Gln Gly Val Ile Gly Ala Gln Gly Val Thr Gly Ala Thr
                325                 330                 335

Gly Asp Gln Gly Pro Gln Gly Ile Gln Gly Val Pro Gly Pro Ser Gly
            340                 345                 350

Ala Thr Gly Pro Gln Gly Val Gln Gly Ile Gln Gly Pro Met Gly Asp
        355                 360                 365

Ile Gly Pro Thr Gly Pro Glu Gly Pro Glu Gly Leu Gln Gly Pro Gln
    370                 375                 380

Gly Ile Gln Gly Val Pro Gly Pro Val Gly Ala Thr Gly Pro Glu Gly
385                 390                 395                 400

Pro Gln Gly Ile Gln Gly Ile Gln Gly Val Gln Gly Ala Thr Gly Pro
                405                 410                 415

Gln Gly Pro Gln Gly Ile Gln Gly Ile Gln Gly Val Gln Gly Ile Thr
            420                 425                 430

Gly Ala Thr Gly
        435


<210> SEQ ID NO 55
<211> LENGTH: 36
<212> TYPE: PRT
<213> ORGANISM: Bacillus thuringiensis

<400> SEQUENCE: 55

Met Lys Asn Arg Asp Asn Lys Gly Lys Gln Gln Ser Asn Phe Arg Ile
1               5                   10                  15

Pro Pro Glu Leu Ile Gly Pro Thr Phe Pro Pro Val Pro Thr Gly Phe
            20                  25                  30

Thr Gly Ile Gly
        35


<210> SEQ ID NO 56
<211> LENGTH: 470
<212> TYPE: PRT
<213> ORGANISM: Bacillus thuringiensis

<400> SEQUENCE: 56

Met Lys Asn Arg Asp Asn Lys Gly Lys Gln Gln Ser Asn Phe Arg Ile
1               5                   10                  15

Pro Pro Glu Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
```

```
        35                  40                  45

Pro Gln Gly Pro Arg Gly Phe Gln Gly Pro Met Gly Glu Met Gly Pro
    50                  55                  60

Thr Gly Pro Gln Gly Val Gln Gly Ile Gln Gly Pro Val Gly Pro Ile
65                  70                  75                  80

Gly Ala Thr Gly Pro Glu Gly Gln Gln Gly Ala Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ile Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Leu Pro Gly Ala Thr Gly Pro
145                 150                 155                 160

Gln Gly Ile Gln Gly Ala Gln Gly Ile Gln Gly Thr Gln Gly Pro Ser
                165                 170                 175

Gly Asn Thr Gly Ala Thr Gly Ala Thr Gly Gln Gly Leu Thr Gly Pro
            180                 185                 190

Thr Gly Ile Thr Gly Pro Thr Gly Ile Thr Gly Pro Ser Gly Gly Pro
        195                 200                 205

Pro Gly Pro Thr Gly Pro Thr Gly Ala Thr Gly Pro Gly Gly Gly Pro
    210                 215                 220

Ser Gly Ser Thr Gly Ala Thr Gly Ala Thr Gly Asp Thr Gly Ala Thr
225                 230                 235                 240

Gly Ser Thr Gly Val Thr Gly Ala Thr Gly Ala Gln Gly Pro Gln Gly
                245                 250                 255

Val Gln Gly Ile Gln Gly Pro Thr Gly Ala Thr Gly Ala Thr Gly Ala
            260                 265                 270

Thr Gly Pro Gln Gly Ile Gln Gly Pro Gln Gly Ile Gln Gly Pro Thr
        275                 280                 285

Gly Ala Thr Gly Ala Thr Gly Ser Gln Gly Pro Thr Gly Asn Thr Gly
    290                 295                 300

Pro Thr Gly Ser Gln Gly Ile Gln Gly Pro Thr Gly Pro Thr Gly Ala
305                 310                 315                 320

Gly Ala Thr Gly Ala Thr Gly Ala Thr Gly Ala Thr Gly Val Ser Thr
                325                 330                 335

Thr Ala Thr Tyr Ala Phe Ala Asn Asn Thr Ser Gly Ser Ile Ile Ser
            340                 345                 350

Val Leu Leu Gly Gly Thr Asn Ile Pro Leu Pro Asn Asn Gln Asn Ile
        355                 360                 365

Gly Pro Gly Ile Thr Val Ser Gly Gly Asn Thr Val Phe Thr Val Ala
    370                 375                 380

Asn Ala Gly Asn Tyr Tyr Ile Ala Tyr Thr Ile Asn Leu Thr Ala Gly
385                 390                 395                 400

Leu Leu Val Ser Ser Arg Ile Thr Val Asn Gly Ser Pro Leu Ala Gly
                405                 410                 415

Thr Ile Asn Ser Pro Ala Val Ala Ala Gly Ser Phe Ser Ala Thr Ile
            420                 425                 430

Ile Ala Asn Leu Pro Ala Gly Ala Ala Val Ser Leu Gln Leu Phe Gly
        435                 440                 445

Val Ile Ala Leu Ala Thr Leu Ser Thr Ala Thr Pro Gly Ala Thr Leu
    450                 455                 460
```

```
Thr Ile Ile Arg Leu Ser
465                 470


<210> SEQ ID NO 57
<211> LENGTH: 136
<212> TYPE: PRT
<213> ORGANISM: Bacillus mycoides

<400> SEQUENCE: 57

Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Cys Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly
    130                 135


<210> SEQ ID NO 58
<211> LENGTH: 384
<212> TYPE: PRT
<213> ORGANISM: Bacillus mycoides

<400> SEQUENCE: 58

Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Cys Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly Pro Thr Gly Gly Thr Gly Pro Thr
    130                 135                 140

Gly Val Thr Gly Pro Thr Gly Val Thr Gly Pro Thr Gly Val Thr Gly
145                 150                 155                 160

Pro Thr Gly Val Thr Gly Pro Thr Gly Val Thr Gly Pro Thr Gly Val
                165                 170                 175
```

```
Thr Gly Pro Thr Gly Val Thr Gly Pro Thr Gly Val Thr Gly Pro Thr
            180                 185                 190

Gly Val Thr Gly Pro Thr Gly Val Thr Gly Pro Thr Gly Val Thr Gly
        195                 200                 205

Pro Thr Gly Val Thr Gly Pro Thr Gly Gly Thr Glu Gly Cys Leu Cys
    210                 215                 220

Asp Cys Cys Val Leu Pro Met Gln Ser Val Leu Gln Gln Leu Ile Gly
225                 230                 235                 240

Glu Thr Val Ile Leu Gly Thr Ile Ala Asp Thr Pro Asn Thr Pro Pro
                245                 250                 255

Leu Phe Phe Leu Phe Thr Ile Thr Ser Val Asn Asp Phe Leu Val Thr
            260                 265                 270

Val Thr Asp Gly Thr Thr Thr Phe Val Val Asn Ile Ser Asp Val Thr
        275                 280                 285

Gly Val Gly Phe Leu Pro Pro Gly Pro Pro Ile Thr Leu Leu Pro Pro
    290                 295                 300

Thr Asp Val Gly Cys Glu Cys Glu Cys Arg Glu Arg Pro Ile Arg Gln
305                 310                 315                 320

Leu Leu Asp Ala Phe Ile Gly Ser Thr Val Ser Leu Leu Ala Ser Asn
                325                 330                 335

Gly Ser Ile Ala Ala Asp Phe Ser Val Glu Gln Thr Gly Leu Gly Ile
            340                 345                 350

Val Leu Gly Thr Leu Pro Ile Asn Pro Thr Thr Thr Val Arg Phe Ala
        355                 360                 365

Ile Ser Thr Cys Lys Ile Thr Ala Val Asn Ile Thr Pro Ile Thr Met
    370                 375                 380


<210> SEQ ID NO 59
<211> LENGTH: 36
<212> TYPE: PRT
<213> ORGANISM: Bacillus cereus

<400> SEQUENCE: 59

Met Lys Glu Arg Asp Lys Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly
        35


<210> SEQ ID NO 60
<211> LENGTH: 1321
<212> TYPE: PRT
<213> ORGANISM: Bacillus cereus

<400> SEQUENCE: 60

Met Lys Glu Arg Asp Lys Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Leu Gln Gly Pro Met Gly Glu Met Gly Pro
    50                  55                  60

Thr Gly Pro Gln Gly Val Gln Gly Ile Gln Gly Pro Val Gly Ser Ile
65                  70                  75                  80
```

```
Gly Ala Thr Gly Pro Glu Gly Gln Gln Gly Pro Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ala Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Leu Pro Gly Ala Thr Gly Pro
145                 150                 155                 160

Gln Gly Ile Gln Gly Ala Gln Gly Met Gln Gly Leu Gln Gly Pro Ser
                165                 170                 175

Gly Asn Thr Gly Ala Thr Gly Ala Thr Gly Gln Gly Ile Thr Gly Pro
            180                 185                 190

Thr Gly Val Thr Gly Pro Thr Gly Ile Thr Gly Pro Ser Gly Gly Pro
        195                 200                 205

Pro Gly Pro Thr Gly Pro Thr Gly Ala Thr Gly Pro Gly Gly Gly Pro
    210                 215                 220

Ser Gly Ser Thr Gly Ala Thr Gly Ala Thr Gly Asn Thr Gly Ala Thr
225                 230                 235                 240

Gly Ser Thr Gly Val Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Pro Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Ala Ile Gly Pro Gln Gly Ala Thr
                325                 330                 335

Gly Ala Thr Gly Asp Gln Gly Pro Gln Gly Ile Gln Gly Val Pro Gly
            340                 345                 350

Pro Ser Gly Ala Thr Gly Pro Gln Gly Val Gln Gly Leu Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gln Gly Ala Thr Gly Ile Gln Gly
        435                 440                 445

Ile Gln Gly Glu Ile Gly Ala Thr Gly Pro Glu Gly Pro Gln Gly Val
    450                 455                 460

Gln Gly Ala Gln Gly Gly Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495
```

```
Val Gln Gly Pro Gln Gly Ile Gln Gly Ile Gln Gly Ile Gln Gly Ile
            500                 505                 510

Gln Gly Pro Thr Gly Ala Thr Gly Asp Thr Gly Ala Thr Gly Ala Thr
        515                 520                 525

Gly Glu Gly Thr Thr Gly Pro Thr Gly Val Thr Gly Pro Thr Gly Pro
    530                 535                 540

Ser Gly Gly Pro Ala Gly Pro Thr Gly Pro Thr Gly Pro Ser Gly Pro
545                 550                 555                 560

Ala Gly Val Thr Gly Pro Ser Gly Gly Pro Pro Gly Pro Thr Gly Ala
                565                 570                 575

Thr Gly Ala Thr Gly Val Thr Gly Asp Thr Gly Ala Thr Gly Ser Thr
            580                 585                 590

Gly Val Thr Gly Ala Thr Gly Glu Thr Gly Ala Thr Gly Val Thr Gly
        595                 600                 605

Leu Gln Gly Pro Gln Gly Ile Gln Gly Val Gln Gly Glu Ile Gly Pro
    610                 615                 620

Thr Gly Pro Gln Gly Val Gln Gly Pro Gln Gly Ile Gln Gly Val Thr
625                 630                 635                 640

Gly Ala Thr Gly Asp Gln Gly Pro Gln Gly Val Gln Gly Pro Gln Gly
                645                 650                 655

Asp Ile Gly Pro Thr Gly Pro Gln Gly Ile Gln Gly Pro Gln Gly Ser
            660                 665                 670

Gln Gly Ile Gln Gly Ala Thr Gly Gly Thr Gly Ala Gln Gly Pro Gln
        675                 680                 685

Gly Ile Gln Gly Pro Gln Gly Asp Val Gly Pro Thr Gly Pro Gln Gly
    690                 695                 700

Pro Thr Gly Ile Gln Gly Ile Gln Gly Glu Ile Gly Pro Thr Gly Pro
705                 710                 715                 720

Glu Gly Pro Glu Gly Leu Gln Gly Pro Gln Gly Ile Gln Gly Val Gln
                725                 730                 735

Gly Pro Val Gly Ala Thr Gly Pro Glu Gly Pro Gln Gly Ile Gln Gly
            740                 745                 750

Ile Gln Gly Val Gln Gly Ala Thr Gly Ser Gln Gly Pro Gln Gly Ile
        755                 760                 765

Gln Gly Ile Gln Gly Val Gln Gly Ile Thr Gly Ala Thr Gly Ala Gln
    770                 775                 780

Gly Ala Thr Gly Ile Gln Gly Ile Gln Gly Glu Ile Gly Ala Thr Gly
785                 790                 795                 800

Pro Glu Gly Pro Gln Gly Val Gln Gly Val Gln Gly Glu Ile Gly Pro
                805                 810                 815

Thr Gly Pro Met Gly Pro Gln Gly Val Gln Gly Val Gln Gly Ile Gln
            820                 825                 830

Gly Ala Thr Gly Ala Gln Gly Val Gln Gly Pro Gln Gly Ile Gln Gly
        835                 840                 845

Ile Gln Gly Pro Thr Gly Ala Thr Gly Glu Thr Gly Ala Thr Gly Ala
    850                 855                 860

Thr Gly Glu Gly Thr Thr Gly Pro Thr Gly Val Thr Gly Pro Thr Gly
865                 870                 875                 880

Val Thr Gly Pro Ser Gly Gly Pro Ala Gly Pro Thr Gly Pro Thr Gly
                885                 890                 895

Pro Ser Gly Pro Ala Gly Val Thr Gly Pro Ser Gly Gly Pro Pro Gly
            900                 905                 910

Pro Thr Gly Ala Thr Gly Ala Thr Gly Ala Thr Gly Val Thr Gly Asp
```

-continued

```
        915                 920                 925

Thr Gly Ala Thr Gly Ser Thr Gly Val Thr Gly Ala Thr Gly Glu Thr
    930                 935                 940

Gly Ala Thr Gly Val Thr Gly Leu Gln Gly Pro Gln Gly Ile Gln Gly
945                 950                 955                 960

Val Gln Gly Glu Ile Gly Pro Thr Gly Pro Gln Gly Ile Gln Gly Pro
                965                 970                 975

Gln Gly Ile Gln Gly Val Thr Gly Ala Thr Gly Ala Gln Gly Pro Gln
            980                 985                 990

Gly Ile Gln Gly Pro Gln Gly Asp  Ile Gly Pro Thr Gly  Pro Gln Gly
        995                 1000                1005

Ile Gln  Gly Pro Gln Gly Pro  Gln Gly Ile Gln Gly  Ala Thr Gly
    1010                1015                1020

Ala Thr  Gly Ala Gln Gly Pro  Gln Gly Ile Gln Gly  Pro Gln Gly
    1025                1030                1035

Glu Ile  Gly Pro Thr Gly Pro  Gln Gly Pro Gln Gly  Ile Gln Gly
    1040                1045                1050

Pro Gln  Gly Ile Gln Gly Pro  Thr Gly Ala Thr Gly  Ala Thr Gly
    1055                1060                1065

Ala Thr  Gly Leu Gln Gly Ile  Gln Gly Pro Gln Gly  Ile Gln Gly
    1070                1075                1080

Pro Gln  Gly Ile Gln Gly Pro  Thr Gly Ala Thr Gly  Ala Thr Gly
    1085                1090                1095

Ala Thr  Gly Leu Gln Gly Ile  Gln Gly Pro Gln Gly  Ile Gln Gly
    1100                1105                1110

Pro Gln  Gly Ile Gln Gly Pro  Thr Gly Ala Thr Gly  Ala Thr Gly
    1115                1120                1125

Ala Thr  Gly Leu Gln Gly Ile  Gln Gly Pro Gln Gly  Ile Gln Gly
    1130                1135                1140

Pro Gln  Gly Ile Gln Gly Pro  Thr Gly Ala Thr Gly  Ala Thr Gly
    1145                1150                1155

Ala Thr  Gly Ser Gln Gly Pro  Thr Gly Asp Thr Gly  Pro Thr Gly
    1160                1165                1170

Ala Gly  Ala Thr Gly Ala Thr  Gly Ala Thr Gly Val  Ser Thr Thr
    1175                1180                1185

Ala Thr  Tyr Ala Phe Ala Asn  Asn Thr Ser Gly Thr  Ala Ile Ser
    1190                1195                1200

Val Leu  Leu Gly Gly Thr Asn  Ile Pro Leu Pro Asn  Asn Gln Asn
    1205                1210                1215

Ile Gly  Pro Gly Ile Thr Val  Ser Gly Gly Asn Thr  Val Phe Thr
    1220                1225                1230

Val Ala  Ser Ala Gly Asn Tyr  Tyr Ile Ala Tyr Thr  Ile Asn Leu
    1235                1240                1245

Thr Ala  Gly Leu Leu Val Ser  Ser Arg Ile Thr Val  Asn Gly Ser
    1250                1255                1260

Pro Leu  Ala Gly Thr Ile Asn  Ala Pro Thr Val Ala  Thr Gly Ser
    1265                1270                1275

Phe Ser  Ala Thr Ile Ile Ala  Asn Leu Pro Ala Gly  Ala Ala Ile
    1280                1285                1290

Ser Leu  Gln Leu Phe Gly Leu  Val Ala Ile Ala Thr  Leu Ser Thr
    1295                1300                1305

Thr Thr  Pro Gly Ala Thr Leu  Thr Ile Ile Arg Leu  Ser
    1310                1315                1320
```

<210> SEQ ID NO 61
<211> LENGTH: 39
<212> TYPE: PRT
<213> ORGANISM: Bacillus cereus

<400> SEQUENCE: 61

```
Met Met Glu Asn Lys Lys Gly Ser Lys His Asn Glu Phe Leu Ser Ala
1               5                   10                  15

Lys Ala Phe Asn Pro Asn Leu Val Gly Pro Thr Leu Pro Pro Val Pro
            20                  25                  30

Ser Phe Thr Leu Pro Thr Gly
        35
```

<210> SEQ ID NO 62
<211> LENGTH: 309
<212> TYPE: PRT
<213> ORGANISM: Bacillus cereus

<400> SEQUENCE: 62

```
Met Met Glu Asn Lys Lys Gly Ser Lys His Asn Glu Phe Leu Ser Ala
1               5                   10                  15

Lys Ala Phe Asn Pro Asn Leu Val Gly Pro Thr Leu Pro Pro Val Pro
            20                  25                  30

Ser Phe Thr Leu Pro Thr Gly Pro Thr Gly Ala Thr Gly Ala Thr Gly
        35                  40                  45

Val Thr Gly Ala Thr Gly Ala Thr Gly Ala Thr Gly Ala Thr Gly Val
    50                  55                  60

Thr Gly Ala Thr Gly Ala Thr Gly Val Thr Gly Ala Thr Gly Ala Thr
65                  70                  75                  80

Gly Val Thr Gly Ala Thr Gly Ala Thr Gly Ala Thr Gly Ala Thr Gly
                85                  90                  95

Val Thr Gly Ala Thr Gly Ala Thr Gly Val Thr Gly Ala Thr Gly Ala
            100                 105                 110

Thr Gly Val Thr Gly Ala Thr Gly Ala Thr Gly Val Thr Gly Val Thr
        115                 120                 125

Gly Ala Thr Gly Ala Thr Gly Ala Thr Gly Val Thr Gly Pro Thr Gly
    130                 135                 140

Ala Thr Gly Ala Thr Gly Ala Thr Gly Val Thr Gly Pro Thr Gly Ala
145                 150                 155                 160

Thr Gly Ala Thr Gly Ala Thr Gly Gly Leu Ala Val Ala Ser Ala Ser
                165                 170                 175

Ala Met Thr Ser Thr Ala Gln Thr Val Asp Asn Leu Val Ala Val Gln
            180                 185                 190

Phe Thr Ala Pro Val Leu Glu Leu Asp Ser Val Ile Phe Asn Gly Thr
        195                 200                 205

Asp Thr Phe Thr Val Leu Val Pro Gly Asn Tyr Tyr Cys Ile Gly Ser
    210                 215                 220

Leu Met Pro Ala Glu Thr Gln Thr Gly Pro Phe Ala Val Gly Ile Gly
225                 230                 235                 240

Leu Asn Gly Ile Pro Val Pro Ala Leu Asp Gly Ala Asn Tyr Ala Gln
                245                 250                 255

Ser Ala Gly Gln Glu Val Val Gly Phe Gly Leu Thr Gly Gln Ile Pro
            260                 265                 270

Ala Gly Thr Thr Ile Ser Leu Phe Asn Leu Ser Gly His Thr Ile Ser
        275                 280                 285
```

```
Ile Gly Gly Thr Ile Ser Gly Ala Thr Ser Val Ala Ala Arg Leu Leu
    290                 295                 300

Leu Phe Arg Ile Ser
305


<210> SEQ ID NO 63
<211> LENGTH: 41
<212> TYPE: PRT
<213> ORGANISM: Bacillus weihenstephanensis

<400> SEQUENCE: 63

Met Ser Asn Asn Asn Tyr Ser Asp Gly Leu Asn Pro Asp Glu Phe Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40


<210> SEQ ID NO 64
<211> LENGTH: 292
<212> TYPE: PRT
<213> ORGANISM: Bacillus weihenstephanensis

<400> SEQUENCE: 64

Met Ser Asn Asn Asn Tyr Ser Asp Gly Leu Asn Pro Asp Glu Phe Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Thr Gly Pro
        35                  40                  45

Thr Gly Pro Thr Gly Pro Thr Val Pro Thr Gly Pro Thr Gly Pro Thr
    50                  55                  60

Gly Pro Thr Gly Pro Thr Gly Pro Thr Gly Asp Thr Gly Thr Thr Gly
65                  70                  75                  80

Ala Thr Gly Asp Thr Gly Ala Thr Gly Asp Thr Gly Ala Thr Gly Pro
                85                  90                  95

Thr Gly Pro Thr Gly Asp Thr Gly Ala Thr Gly Pro Thr Gly Pro Thr
            100                 105                 110

Gly Asp Thr Gly Ala Thr Gly Pro Thr Gly Pro Thr Gly Asp Thr Gly
        115                 120                 125

Ala Thr Gly Pro Thr Gly Pro Thr Gly Asp Thr Gly Ala Thr Gly Ala
    130                 135                 140

Thr Gly Pro Thr Gly Pro Thr Gly Pro Thr Gly Pro Ser Gly Leu Gly
145                 150                 155                 160

Leu Pro Ala Gly Leu Tyr Ala Phe Asn Ser Ala Thr Ile Ser Leu Ala
                165                 170                 175

Leu Gly Ile Asn Asp Pro Val Pro Phe Asn Thr Val Gly Ser Gln Phe
            180                 185                 190

Gly Thr Ala Ile Ser Gln Leu Asp Ala Asp Thr Phe Ile Ile Ser Glu
        195                 200                 205

Thr Gly Phe Tyr Lys Ile Thr Val Ile Ala Tyr Thr Ala Ala Val Ser
    210                 215                 220

Ile Leu Gly Ser Leu Ala Ile Gln Val Asn Gly Val Asn Ile Pro Gly
225                 230                 235                 240

Ala Gly Thr Ser Leu Ile Ser Leu Gly Ala Pro Leu Val Ile Gln Ala
                245                 250                 255
```

```
Ile Thr Gln Ile Thr Ile Thr Pro Ser Met Val Glu Ala Val Val Thr
            260                 265                 270

Gly Leu Gly Leu Ser Leu Ala Leu Gly Thr Ser Ala Ser Ile Ile Ile
        275                 280                 285

Glu Lys Ile Ala
    290


<210> SEQ ID NO 65
<211> LENGTH: 30
<212> TYPE: PRT
<213> ORGANISM: Bacillus thuringiensis

<400> SEQUENCE: 65

Met Asp Glu Phe Leu Ser Ser Ala Ala Ile Asn Pro Asn Leu Val Gly
1               5                   10                  15

Pro Thr Leu Pro Pro Val Pro Pro Phe Thr Leu Pro Thr Gly
            20                  25                  30


<210> SEQ ID NO 66
<211> LENGTH: 233
<212> TYPE: PRT
<213> ORGANISM: Bacillus thuringiensis

<400> SEQUENCE: 66

Met Asp Glu Phe Leu Ser Ser Ala Ala Ile Asn Pro Asn Leu Val Gly
1               5                   10                  15

Pro Thr Leu Pro Pro Val Pro Pro Phe Thr Leu Pro Thr Gly Pro Thr
            20                  25                  30

Gly Ser Thr Gly Pro Thr Gly Thr Thr Gly Pro Thr Gly Pro Thr Gly
        35                  40                  45

Thr Thr Gly Thr Thr Gly Thr Thr Gly Pro Thr Gly Pro Thr Gly Thr
    50                  55                  60

Thr Gly Pro Thr Gly Pro Thr Gly Thr Thr Gly Thr Thr Gly Pro Thr
65                  70                  75                  80

Gly Thr Thr Gly Thr Leu Ser Val Ala Tyr Gly His Phe Trp Gln Thr
                85                  90                  95

Asp Ile Ile Thr Val Pro Phe Glu Ser Pro Phe Ser Phe Asp Gln Ala
            100                 105                 110

Gly Pro Met Val Gly Gly Ile Ser Leu Leu Asn Pro Thr Thr Ile Ser
        115                 120                 125

Ile Thr Gln Pro Gly Asp Tyr Arg Val Ser Phe Ile Ser Ser Ile Asn
    130                 135                 140

Leu Thr Val Ala Leu Val Phe Pro Tyr Ser Pro Thr Ile Ser Ile Leu
145                 150                 155                 160

Leu Asn Asn Ser Leu Ile Pro Asn Phe Lys Ala Thr Phe Gly Leu Leu
                165                 170                 175

Ile Gln Asp Leu Glu Asp Val Asp Cys Asp Gln Leu Thr Gly Glu Thr
            180                 185                 190

Ile Leu Ser Ile Pro Ala Asn Ser Thr Leu Gln Leu Ile Asn Asn Ser
        195                 200                 205

Phe Val Gly Asn Arg Asp Ile Arg Thr Cys Asp Asn Gly Ile Asn Ala
    210                 215                 220

Leu Glu Leu Thr Ile Ile Lys Leu Asn
225                 230


<210> SEQ ID NO 67
```

<211> LENGTH: 33
<212> TYPE: PRT
<213> ORGANISM: Bacillus cereus

<400> SEQUENCE: 67

Met Phe Asp Lys Asn Lys Ile Leu Gln Ala Asn Ala Phe Asn Ser Asn
1 5 10 15

Leu Ile Gly Pro Thr Leu Pro Pro Ile Pro Pro Phe Thr Leu Pro Thr
20 25 30

Gly

<210> SEQ ID NO 68
<211> LENGTH: 295
<212> TYPE: PRT
<213> ORGANISM: Bacillus cereus

<400> SEQUENCE: 68

Met Phe Asp Lys Asn Lys Ile Leu Gln Ala Asn Ala Phe Asn Ser Asn
1 5 10 15

Leu Ile Gly Pro Thr Leu Pro Pro Ile Pro Pro Phe Thr Leu Pro Thr
20 25 30

Gly Pro Thr Gly Gly Thr Gly Pro Thr Gly Val Thr Gly Pro Thr Gly
35 40 45

Val Thr Gly Pro Ile Gly Val Thr Gly Pro Thr Gly Val Thr Gly Pro
50 55 60

Thr Gly Val Thr Gly Pro Thr Gly Ile Thr Gly Pro Thr Gly Val Thr
65 70 75 80

Gly Pro Thr Gly Val Thr Gly Pro Thr Gly Val Thr Gly Pro Thr Gly
85 90 95

Val Thr Gly Pro Thr Gly Val Thr Gly Pro Thr Gly Val Thr Gly Pro
100 105 110

Thr Gly Val Thr Gly Pro Thr Gly Val Thr Gly Pro Thr Gly Val Thr
115 120 125

Gly Pro Thr Gly Ser Thr Glu Ser Cys Leu Cys Asp Cys Cys Val Leu
130 135 140

Pro Met Gln Asn Val Leu Gln Gln Leu Ile Gly Glu Thr Val Leu Leu
145 150 155 160

Gly Thr Ile Ala Asp Ala Pro Asn Thr Pro Pro Leu Phe Phe Leu Phe
165 170 175

Thr Ile Thr Ser Val Asn Asp Phe Leu Val Thr Val Thr Asp Gly Ser
180 185 190

Thr Ser Tyr Val Val Asn Ile Ser Asp Val Thr Gly Val Gly Phe Leu
195 200 205

Pro Pro Gly Pro Ser Ile Thr Leu Leu Pro Pro Val Asp Ile Gly Cys
210 215 220

Glu Cys Asp Cys Arg Glu Arg Pro Ile Arg Glu Leu Leu Asp Thr Leu
225 230 235 240

Ile Gly Ser Thr Val Asn Leu Leu Ala Ser Thr Gly Ser Ile Ala Ala
245 250 255

Asp Phe Asn Val Glu Gln Thr Gly Leu Gly Ile Val Leu Gly Thr Leu
260 265 270

Pro Ile Asn Pro Thr Thr Ile Val Arg Phe Ala Ile Ser Thr Cys Lys
275 280 285

Ile Thr Ala Val Asn Ile Leu
290 295

<210> SEQ ID NO 69
<211> LENGTH: 44
<212> TYPE: PRT
<213> ORGANISM: Bacillus cereus

<400> SEQUENCE: 69

```
Met Ser Asp Glu Asn Glu Lys Lys Tyr Ser Asn Glu Leu Ala Gln Ala
1               5                   10                  15

Asp Phe Ile Ser Ala Ala Ala Phe Asp Pro Ser Leu Val Gly Pro Thr
            20                  25                  30

Leu Pro Pro Thr Pro Pro Phe Thr Leu Pro Thr Gly
        35                  40
```

<210> SEQ ID NO 70
<211> LENGTH: 639
<212> TYPE: PRT
<213> ORGANISM: Bacillus cereus

<400> SEQUENCE: 70

```
Met Ser Asp Glu Asn Glu Lys Lys Tyr Ser Asn Glu Leu Ala Gln Ala
1               5                   10                  15

Asp Phe Ile Ser Ala Ala Ala Phe Asp Pro Ser Leu Val Gly Pro Thr
            20                  25                  30

Leu Pro Pro Thr Pro Pro Phe Thr Leu Pro Thr Gly Pro Thr Gly Ala
        35                  40                  45

Thr Gly Pro Thr Gly Ala Thr Gly Pro Thr Gly Ala Thr Gly Ser Thr
    50                  55                  60

Gly Val Thr Gly Pro Thr Gly Val Thr Gly Pro Thr Gly Ala Thr Gly
65                  70                  75                  80

Pro Thr Gly Ala Thr Gly Ser Thr Gly Val Thr Gly Pro Thr Gly Ala
                85                  90                  95

Thr Gly Pro Ser Gly Ala Thr Gly Ser Thr Gly Thr Thr Gly Pro Thr
            100                 105                 110

Gly Asp Thr Gly Pro Thr Gly Ile Thr Gly Pro Thr Gly Val Thr Gly
        115                 120                 125

Pro Thr Gly Ala Thr Gly Pro Thr Gly Ala Thr Gly Pro Thr Gly Ala
    130                 135                 140

Thr Gly Ser Thr Gly Val Thr Gly Pro Thr Gly Val Thr Gly Pro Thr
145                 150                 155                 160

Gly Ala Thr Gly Pro Thr Gly Ala Thr Gly Ser Thr Gly Val Thr Gly
                165                 170                 175

Pro Thr Gly Ile Thr Gly Pro Thr Gly Ala Thr Gly Thr Thr Gly Ser
            180                 185                 190

Thr Gly Pro Thr Gly Val Thr Gly Pro Thr Gly Ala Thr Gly Pro Thr
        195                 200                 205

Gly Ala Thr Gly Pro Thr Gly Ala Thr Gly Ser Thr Gly Val Thr Gly
    210                 215                 220

Pro Thr Gly Ile Thr Gly Pro Thr Gly Ala Thr Gly Thr Thr Gly Ser
225                 230                 235                 240

Thr Gly Pro Thr Gly Val Thr Gly Pro Thr Gly Ala Thr Gly Pro Thr
                245                 250                 255

Gly Ala Thr Gly Pro Thr Gly Ala Thr Gly Ser Thr Gly Val Thr Gly
            260                 265                 270

Pro Thr Gly Val Thr Gly Pro Thr Gly Ala Thr Gly Pro Thr Gly Ala
        275                 280                 285
```

```
Thr Gly Ser Thr Gly Val Thr Gly Pro Thr Gly Ala Thr Gly Pro Thr
    290                 295                 300

Gly Ala Thr Gly Ser Thr Gly Val Thr Gly Pro Thr Gly Val Thr Gly
305                 310                 315                 320

Pro Thr Gly Ala Thr Gly Ser Thr Gly Ala Thr Gly Pro Thr Gly Ala
                325                 330                 335

Thr Gly Ser Thr Gly Val Thr Gly Pro Thr Gly Ala Thr Gly Pro Thr
            340                 345                 350

Gly Ala Thr Gly Pro Thr Gly Ala Thr Gly Ser Thr Gly Val Thr Gly
        355                 360                 365

Pro Thr Gly Ile Thr Gly Pro Thr Gly Ala Thr Gly Thr Thr Gly Ser
    370                 375                 380

Thr Gly Pro Thr Gly Val Thr Gly Pro Thr Gly Val Thr Gly Pro Thr
385                 390                 395                 400

Gly Val Thr Gly Pro Thr Gly Ala Thr Gly Pro Thr Gly Ala Thr Gly
                405                 410                 415

Ser Thr Gly Val Thr Gly Pro Thr Gly Ile Thr Gly Pro Thr Gly Ala
            420                 425                 430

Thr Gly Thr Thr Gly Ser Thr Gly Pro Thr Gly Val Thr Gly Pro Thr
        435                 440                 445

Gly Val Thr Gly Pro Thr Gly Ala Thr Gly Pro Thr Gly Val Thr Gly
    450                 455                 460

Pro Thr Gly Ala Thr Gly Pro Thr Gly Ala Thr Gly Ala Thr Ala Thr
465                 470                 475                 480

Thr Ser Thr Lys Ala Ile Leu Phe Gly Gly Thr Asn Ala Gly Phe Gln
                485                 490                 495

Arg Ile Ala Gly Ser Pro Gly Ala Asp Ser Gln Thr Leu Pro Tyr Val
            500                 505                 510

Thr Ala Gly Ala Gly Ser Val Val Ala Phe Ser Ala Ser Ile Asn Val
        515                 520                 525

Asn Asn Leu Gly Thr Gly Val Tyr Leu Leu Arg Val Cys Asp Asn Val
    530                 535                 540

Pro Thr Asn Leu Ala Ser Pro Gly Ala Gly Gln Ile Val Ser Thr Ile
545                 550                 555                 560

Thr Leu Thr Leu Thr Ala Asn Ile Thr Gly Thr Ile Val Phe Ser Ile
                565                 570                 575

Lys Pro Thr Asp Ile Gly Ala Gln Pro Val Lys Val Phe Asn Pro Asn
            580                 585                 590

Pro Val Val Ala Pro Ala Thr Val Thr Trp Thr Ser Thr Ile Pro Gly
        595                 600                 605

Asn Pro Val Ala Arg Thr Asp Ala Ile Ser Leu Phe Ile Thr Pro Gly
    610                 615                 620

Ile Thr Gln Ser Ala Val Tyr Ser Val Phe Ile Ser Thr Ala Val
625                 630                 635


<210> SEQ ID NO 71
<211> LENGTH: 38
<212> TYPE: PRT
<213> ORGANISM: Bacillus cereus

<400> SEQUENCE: 71

Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Pro Ile Pro Ser
            20                  25                  30
```

```
Phe Thr Leu Pro Thr Gly
        35


<210> SEQ ID NO 72
<211> LENGTH: 163
<212> TYPE: PRT
<213> ORGANISM: Bacillus cereus

<400> SEQUENCE: 72

Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Pro Ile Pro Ser
            20                  25                  30

Phe Thr Leu Pro Thr Gly Ile Thr Gly Pro Thr Gly Asn Thr Gly Ala
        35                  40                  45

Thr Gly Asp Thr Gly Pro Thr Gly Pro Thr Phe Asn Ile Asn Phe Arg
    50                  55                  60

Ala Glu Lys Asn Gly Ala Gln Ser Phe Thr Pro Pro Ala Asp Ile Gln
65                  70                  75                  80

Val Ser Tyr Gly Asn Ile Ile Phe Asn Asn Gly Gly Gly Tyr Ser Ser
                85                  90                  95

Val Thr Asn Thr Phe Thr Ala Pro Ile Asn Gly Ile Tyr Leu Phe Ser
            100                 105                 110

Ala Asn Ile Gly Phe Asn Pro Thr Leu Gly Thr Thr Ser Thr Leu Arg
        115                 120                 125

Ile Thr Ile Arg Lys Asn Leu Val Ser Val Ala Ser Gln Thr Ile Asp
    130                 135                 140

Ile Gln Phe Ser Ala Ala Glu Ser Gly Thr Leu Thr Val Gly Ser Ser
145                 150                 155                 160

Asn Phe Phe


<210> SEQ ID NO 73
<211> LENGTH: 30
<212> TYPE: PRT
<213> ORGANISM: Bacillus cereus

<400> SEQUENCE: 73

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Ser Thr Gly
            20                  25                  30


<210> SEQ ID NO 74
<211> LENGTH: 77
<212> TYPE: PRT
<213> ORGANISM: Bacillus cereus

<400> SEQUENCE: 74

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Ser Thr Gly Pro Thr
            20                  25                  30

Gly Ser Thr Gly Ala Thr Gly Ala Thr Gly Asn Thr Glu Pro Tyr Trp
        35                  40                  45

His Thr Gly Pro Pro Gly Ile Val Leu Leu Thr Tyr Asp Phe Lys Ser
    50                  55                  60

Leu Ile Ile Ser Phe Ala Phe Gln Ile Leu Pro Ile Ser
```

65 70 75

<210> SEQ ID NO 75
<211> LENGTH: 48
<212> TYPE: PRT
<213> ORGANISM: Bacillus weihenstephanensis

<400> SEQUENCE: 75

Met Phe Leu Gly Gly Gly Tyr Met Glu Arg Lys Asn Lys Trp Tyr Gly
1 5 10 15

Leu Asn Ser Asn Val Asn Leu Ser Ala Ser Ser Phe Asp Pro Asn Leu
20 25 30

Val Gly Pro Thr Leu Pro Pro Ile Ser Pro Ile Ser Val Pro Thr Gly
35 40 45

<210> SEQ ID NO 76
<211> LENGTH: 247
<212> TYPE: PRT
<213> ORGANISM: Bacillus weihenstephanensis

<400> SEQUENCE: 76

Met Phe Leu Gly Gly Gly Tyr Met Glu Arg Lys Asn Lys Trp Tyr Gly
1 5 10 15

Leu Asn Ser Asn Val Asn Leu Ser Ala Ser Ser Phe Asp Pro Asn Leu
20 25 30

Val Gly Pro Thr Leu Pro Pro Ile Ser Pro Ile Ser Val Pro Thr Gly
35 40 45

Pro Thr Gly Glu Thr Gly Ile Thr Gly Pro Thr Gly Pro Thr Gly Pro
50 55 60

Thr Gly Pro Thr Gly Val Thr Gly Ile Thr Gly Pro Thr Gly Pro Thr
65 70 75 80

Gly Ala Thr Gly Ile Thr Gly Pro Thr Gly Pro Thr Gly Glu Thr Gly
85 90 95

Ile Thr Gly Pro Thr Gly Pro Gly Pro Thr Val Ser Leu Lys Phe Leu
100 105 110

Tyr Val Ala Asn Phe Asn Glu Asn Thr Val Glu Ile Tyr Asp Ile Phe
115 120 125

Asn Pro Ile Phe Pro Val Arg Ile Gly Glu Phe Asn Gly Gly Asn Leu
130 135 140

Ala Asn Pro Ala Gly Leu Ala Ile Thr Gly Thr Thr Leu Tyr Val Thr
145 150 155 160

Asn Asn Gly Asp Asn Thr Val Glu Ile Tyr Asp Ile Leu Asn Pro Ile
165 170 175

Ala Pro Val His Val Gly Glu Phe Asn Gly Gly Asn Leu Ser Glu Pro
180 185 190

Asp Gly Leu Ala Ile Thr Gly Thr Thr Leu Tyr Val Ala Asn Phe Asn
195 200 205

Asp Asn Thr Val Glu Ile Tyr Asp Ile Leu Asn Pro Ile Ala Pro Val
210 215 220

Arg Val Gly Glu Phe Asn Ala Gly Asn Leu Ser Ser Pro Ala Gly Leu
225 230 235 240

Ile Ile Phe Ser Leu Phe Gly
245

<210> SEQ ID NO 77
<211> LENGTH: 30
<212> TYPE: PRT

<213> ORGANISM: Bacillus cereus

<400> SEQUENCE: 77

```
Met Asp Glu Leu Leu Ser Ser Thr Leu Ile Asn Pro Asp Leu Leu Gly
1               5                   10                  15

Pro Thr Leu Pro Ala Ile Pro Pro Phe Thr Leu Pro Thr Gly
            20                  25                  30
```

<210> SEQ ID NO 78
<211> LENGTH: 536
<212> TYPE: PRT
<213> ORGANISM: Bacillus cereus

<400> SEQUENCE: 78

```
Met Asp Glu Leu Leu Ser Ser Thr Leu Ile Asn Pro Asp Leu Leu Gly
1               5                   10                  15

Pro Thr Leu Pro Ala Ile Pro Pro Phe Thr Leu Pro Thr Gly Pro Thr
            20                  25                  30

Gly Ser Thr Gly Pro Thr Gly Pro Thr Gly Ser Thr Gly Pro Thr Gly
        35                  40                  45

Pro Thr Gly Ser Thr Gly Pro Thr Gly Pro Thr Gly Ser Thr Gly Leu
    50                  55                  60

Thr Gly Leu Thr Gly Pro Thr Gly Pro Thr Gly Pro Thr Gly Pro Thr
65                  70                  75                  80

Gly Pro Thr Gly Pro Thr Gly Ser Thr Gly Leu Thr Gly Pro Thr Gly
                85                  90                  95

Pro Asn Ser Asp Thr Gly Pro Thr Gly Pro Thr Gly Pro Thr Gly Pro
            100                 105                 110

Ser Asp Gly Pro Thr Gly Pro Thr Gly Ala Thr Gly Pro Thr Gly Pro
        115                 120                 125

Pro Asp Gly Pro Thr Gly Asp Thr Gly Pro Thr Gly Ser Thr Gly Pro
    130                 135                 140

Thr Gly Asp Thr Gly Pro Thr Gly Ser Thr Gly Pro Thr Gly Asp Thr
145                 150                 155                 160

Gly Pro Thr Gly Ser Thr Gly Pro Thr Gly Asp Thr Gly Pro Thr Gly
                165                 170                 175

Ser Thr Gly Pro Thr Gly Asp Thr Gly Pro Thr Gly Ser Thr Gly Pro
            180                 185                 190

Thr Gly Asp Thr Gly Pro Thr Gly Ser Thr Gly Pro Thr Gly Pro Gly
        195                 200                 205

Cys Ile Glu Pro Leu Pro Thr Phe Thr Gln Ile Val Tyr Val Asn Lys
    210                 215                 220

Ala Gly Asn Asp Ala Thr Ala Asp Gly Ser Glu Cys Ala Pro Phe Leu
225                 230                 235                 240

Thr Val Thr Ala Ala Met Ala Ser Ile Thr Asp Ala Ile Ala Pro Phe
                245                 250                 255

Pro Asp Pro Leu Asn Ile Thr Lys Arg Tyr Ala Ile Ser Ile Gly Pro
            260                 265                 270

Gly Asn Tyr Ile Glu Pro Leu Ile His Leu Lys Ala Asn Val Gln Leu
        275                 280                 285

Val Gly Thr Ser Thr Leu Leu Thr Arg Leu Gln Ile Pro Phe Asp Ile
    290                 295                 300

Asn Asp Pro Ser Trp Phe Asp Leu Asn Phe Ser Gln Asp Pro Arg Ser
305                 310                 315                 320

Gly Phe Val Asn Leu Thr Leu Leu Ser Gly Pro Leu Asp Phe Asn Phe
```

```
                325                 330                 335

Gln Thr Ala Gln Ser Val Ser Gly Lys Leu Phe Phe Val Ser Val Asn
            340                 345                 350

Ile Thr Pro Thr Pro Ile Phe Thr Ala Leu Ser Thr Ser Val Asn Gln
        355                 360                 365

Val Asn Ile Arg Asp Ser Met Leu Ser Gly Gly Tyr Thr Gln Asn Gly
    370                 375                 380

Ile Asn Met Ala Met Phe Ala Ser Phe Val Ser Ser Gly Asn Ile Thr
385                 390                 395                 400

Ile Asn Ser Gln Ala Thr Thr Asp Thr Gln Val Asn Leu Val Gly Gly
                405                 410                 415

Gly Ile Asn Gly Asn Val Ile Ile Asn Val Leu Pro Gly His Ile Pro
            420                 425                 430

Ile Asp Pro Leu Asn Leu Thr Ser Phe Ala Ile Thr Glu Asn Ile Phe
        435                 440                 445

Asn Pro Ser Pro Asn Ser Gly Asn Leu Phe Val Asn Gly Ala Asn Asn
    450                 455                 460

Val Ile Thr Arg Val Arg Ala Thr Val Asp Ser Leu Pro Ile Arg Ser
465                 470                 475                 480

Arg Ile Asn Leu Ile Gly Thr Ser Thr Ser Leu Ile Arg Val Asp Asp
                485                 490                 495

Ala Phe Asp Leu Ala Tyr Thr Pro Ile Asn Pro Ala Asn Trp Ala Pro
            500                 505                 510

Leu Pro Pro Thr Thr Val Gln Glu Ala Leu Asp Arg Ile Ala Ala Leu
        515                 520                 525

Met Ala Ile Thr Ile Gly Thr Pro
    530                 535


<210> SEQ ID NO 79
<211> LENGTH: 39
<212> TYPE: PRT
<213> ORGANISM: Bacillus cereus

<400> SEQUENCE: 79

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
        35


<210> SEQ ID NO 80
<211> LENGTH: 1309
<212> TYPE: PRT
<213> ORGANISM: Bacillus cereus

<400> SEQUENCE: 80

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Leu Gln Gly Pro Met Gly Glu
    50                  55                  60

Met Gly Pro Thr Gly Pro Gln Gly Val Gln Gly Ile Gln Gly Ser Val
```

-continued

```
65                  70                  75                  80

Gly Pro Ile Gly Ala Thr Gly Pro Glu Gly Gln Gln Gly Pro Gln Gly
                85                  90                  95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
                165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
        195                 200                 205

Gly Pro Ser Gly Gly Pro Pro Gly Pro Thr Gly Pro Thr Gly Ala Thr
    210                 215                 220

Gly Pro Gly Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Ser Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
                325                 330                 335

Gly Ala Thr Gly Asp Gln Gly Pro Gln Gly Ile Gln Gly Val Pro Gly
            340                 345                 350

Pro Ser Gly Glu Thr Gly Pro Gln Gly Val Gln Gly Ile Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gln Gly Ala Thr Gly Ile Gln Gly
        435                 440                 445

Ile Gln Gly Glu Ile Gly Ala Thr Gly Pro Glu Gly Pro Gln Gly Val
    450                 455                 460

Gln Gly Ala Gln Gly Ala Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495
```

```
Val Gln Gly Pro Gln Gly Ile Gln Gly Ile Gln Gly Pro Thr Gly Ala
            500                 505                 510

Thr Gly Asp Met Gly Ala Thr Gly Ala Thr Gly Glu Gly Thr Thr Gly
        515                 520                 525

Pro Thr Gly Val Thr Gly Pro Thr Gly Val Thr Gly Pro Ser Gly Gly
    530                 535                 540

Pro Ala Gly Pro Thr Gly Pro Thr Gly Pro Ser Gly Pro Ala Gly Val
545                 550                 555                 560

Thr Gly Pro Ser Gly Gly Pro Pro Gly Pro Thr Gly Ala Thr Gly Ala
                565                 570                 575

Thr Gly Val Thr Gly Asp Thr Gly Ala Thr Gly Ser Thr Gly Val Thr
            580                 585                 590

Gly Ala Thr Gly Glu Thr Gly Ala Thr Gly Val Thr Gly Leu Gln Gly
        595                 600                 605

Pro Gln Gly Ile Gln Gly Val Gln Gly Glu Ile Gly Pro Thr Gly Pro
    610                 615                 620

Gln Gly Val Gln Gly Pro Gln Gly Ile Gln Gly Val Thr Gly Ala Thr
625                 630                 635                 640

Gly Asp Gln Gly Pro Gln Gly Ile Gln Gly Pro Gln Gly Asp Ile Gly
                645                 650                 655

Pro Thr Gly Pro Gln Gly Ile Gln Gly Pro Gln Gly Ser Gln Gly Ile
            660                 665                 670

Gln Gly Ala Thr Gly Gly Thr Gly Ala Gln Gly Pro Gln Gly Ile Gln
        675                 680                 685

Gly Pro Gln Gly Asp Ile Gly Pro Thr Gly Ser Gln Gly Pro Thr Gly
    690                 695                 700

Ile Gln Gly Ile Gln Gly Glu Ile Gly Pro Thr Gly Pro Arg Arg Pro
705                 710                 715                 720

Glu Gly Cys Arg Gly Arg Lys Arg Ile Gln Gly Val Gln Gly Pro Val
                725                 730                 735

Gly Ala Thr Gly Pro Glu Gly Pro Gln Gly Ile Gln Gly Ile Gln Gly
            740                 745                 750

Val Gln Gly Ala Thr Gly Pro Gln Gly Pro Gln Gly Ile Gln Gly Ile
        755                 760                 765

Gln Gly Val Gln Gly Ile Thr Gly Ala Thr Gly Ala Gln Gly Ala Thr
    770                 775                 780

Gly Ile Gln Gly Ile Gln Gly Glu Ile Gly Ala Thr Gly Pro Glu Gly
785                 790                 795                 800

Pro Gln Gly Val Gln Gly Ile Gln Gly Ala Ile Gly Pro Thr Gly Pro
                805                 810                 815

Met Gly Ala Gln Gly Val Gln Gly Ile Gln Gly Ile Gln Gly Ala Thr
            820                 825                 830

Gly Ala Gln Gly Val Gln Gly Pro Gln Gly Ile Gln Gly Val Gln Gly
        835                 840                 845

Pro Thr Gly Ala Thr Gly Asp Thr Gly Ala Thr Gly Ala Thr Gly Glu
    850                 855                 860

Gly Thr Thr Gly Pro Thr Gly Val Thr Gly Pro Thr Gly Val Thr Gly
865                 870                 875                 880

Pro Ser Gly Gly Pro Ala Gly Pro Thr Gly Pro Thr Gly Pro Ser Gly
                885                 890                 895

Pro Ala Gly Val Thr Gly Pro Ser Gly Gly Pro Pro Gly Pro Thr Gly
            900                 905                 910
```

```
Ala Thr Gly Ala Thr Gly Val Thr Gly Asp Thr Gly Ala Thr Gly Ser
        915                 920                 925

Thr Gly Val Thr Gly Ala Thr Gly Ala Thr Gly Val Thr Gly Leu Gln
    930                 935                 940

Gly Pro Gln Gly Ile Gln Gly Val Gln Gly Glu Ile Gly Pro Thr Gly
945                 950                 955                 960

Pro Gln Gly Ile Gln Gly Pro Gln Gly Ile Gln Gly Val Thr Gly Ala
                965                 970                 975

Thr Gly Ala Gln Gly Pro Gln Gly Ile Gln Gly Pro Gln Gly Asp Ile
            980                 985                 990

Gly Pro Thr Gly Ser Gln Gly Ile  Gln Gly Pro Gln Gly  Pro Gln Gly
        995                 1000                 1005

Ile Gln  Gly Ala Thr Gly Ala  Thr Gly Ala Gln Gly  Pro Gln Gly
    1010                 1015                 1020

Ile Gln  Gly Pro Gln Gly Glu  Ile Gly Pro Thr Gly  Pro Gln Gly
    1025                 1030                 1035

Pro Gln  Gly Ile Gln Gly Pro  Gln Gly Ile Gln Gly  Pro Thr Gly
    1040                 1045                 1050

Ala Thr  Gly Ala Thr Gly Ala  Thr Gly Pro Gln Gly  Ile Gln Gly
    1055                 1060                 1065

Pro Gln  Gly Ile Gln Gly Pro  Gln Gly Ile Gln Gly  Pro Thr Gly
    1070                 1075                 1080

Val Thr  Gly Ala Thr Gly Ala  Thr Gly Pro Gln Gly  Ile Gln Gly
    1085                 1090                 1095

Pro Gln  Gly Ile Gln Gly Pro  Gln Gly Ile Gln Gly  Pro Thr Gly
    1100                 1105                 1110

Ala Thr  Gly Ala Thr Gly Ala  Thr Gly Pro Gln Gly  Ile Gln Gly
    1115                 1120                 1125

Pro Gln  Gly Ile Gln Gly Pro  Gln Gly Ile Gln Gly  Pro Thr Gly
    1130                 1135                 1140

Ala Thr  Gly Ala Thr Gly Ser  Gln Gly Pro Thr Gly  Asp Thr Gly
    1145                 1150                 1155

Pro Thr  Gly Ala Gly Ala Thr  Gly Ala Thr Gly Ala  Thr Gly Val
    1160                 1165                 1170

Ser Thr  Thr Ala Thr Tyr Ala  Phe Ala Asn Asn Thr  Ser Gly Thr
    1175                 1180                 1185

Ala Ile  Ser Val Leu Leu Gly  Gly Thr Asn Val Pro  Leu Pro Asn
    1190                 1195                 1200

Asn Gln  Asn Ile Gly Pro Gly  Ile Thr Val Ser Gly  Gly Asn Thr
    1205                 1210                 1215

Val Phe  Thr Val Ala Asn Ala  Gly Asn Tyr Tyr Ile  Ala Tyr Thr
    1220                 1225                 1230

Ile Asn  Leu Thr Ala Gly Leu  Leu Val Ser Ser Arg  Ile Thr Val
    1235                 1240                 1245

Asn Gly  Ser Pro Leu Ala Gly  Thr Ile Asn Ala Pro  Thr Val Ala
    1250                 1255                 1260

Thr Gly  Ser Phe Ser Ala Thr  Ile Ile Ala Asn Leu  Pro Ala Gly
    1265                 1270                 1275

Ala Ala  Val Ser Leu Gln Leu  Phe Gly Val Val Ala  Val Ala Thr
    1280                 1285                 1290

Leu Ser  Thr Ala Thr Pro Gly  Ala Thr Leu Thr Ile  Ile Arg Leu
    1295                 1300                 1305

Ser
```

<210> SEQ ID NO 81
<211> LENGTH: 44
<212> TYPE: PRT
<213> ORGANISM: Bacillus cereus

<400> SEQUENCE: 81

```
Met Val Lys Val Val Glu Gly Asn Ser Gly Lys Ser Lys Ile Lys Ser
1               5                   10                  15

Ser Leu Asn Ser Asn Phe Lys Leu Ser Ser Gly Leu Val Gly Pro Thr
            20                  25                  30

Phe Pro Pro Val Pro Thr Gly Met Thr Gly Ile Thr
        35                  40
```

<210> SEQ ID NO 82
<211> LENGTH: 815
<212> TYPE: PRT
<213> ORGANISM: Bacillus cereus

<400> SEQUENCE: 82

```
Met Val Lys Val Val Glu Gly Asn Ser Gly Lys Ser Lys Ile Lys Ser
1               5                   10                  15

Ser Leu Asn Ser Asn Phe Lys Leu Ser Ser Gly Leu Val Gly Pro Thr
            20                  25                  30

Phe Pro Pro Val Pro Thr Gly Met Thr Gly Ile Thr Gly Ser Thr Gly
        35                  40                  45

Ala Thr Gly Asn Thr Gly Pro Thr Gly Glu Thr Gly Ala Thr Gly Ser
    50                  55                  60

Thr Gly Val Thr Gly Asn Thr Gly Pro Thr Gly Glu Thr Gly Val Thr
65                  70                  75                  80

Gly Ser Thr Gly Pro Thr Gly Glu Thr Gly Ser Thr Gly Asn Thr Gly
                85                  90                  95

Ala Thr Gly Glu Thr Gly Pro Thr Gly Ser Thr Gly Ala Thr Gly Ser
            100                 105                 110

Thr Gly Val Thr Gly Ser Thr Gly Pro Thr Gly Asn Thr Gly Pro Thr
        115                 120                 125

Gly Glu Thr Gly Val Thr Gly Ser Thr Gly Pro Thr Gly Asn Thr Gly
    130                 135                 140

Ala Thr Gly Glu Thr Gly Pro Thr Gly Ser Thr Gly Pro Thr Gly Glu
145                 150                 155                 160

Thr Gly Val Thr Gly Ser Thr Gly Val Thr Gly Pro Thr Gly Ala Thr
                165                 170                 175

Gly Asn Thr Gly Ala Thr Gly Ser Thr Gly Val Thr Gly Asn Thr Gly
            180                 185                 190

Pro Thr Gly Glu Thr Gly Val Thr Gly Ser Thr Gly Pro Thr Gly Asn
        195                 200                 205

Thr Gly Ala Thr Gly Asn Thr Gly Pro Thr Gly Glu Thr Gly Ser Thr
    210                 215                 220

Gly Val Thr Gly Ser Thr Gly Ala Thr Gly Ser Thr Gly Val Thr Gly
225                 230                 235                 240

Pro Thr Gly Val Thr Gly Pro Thr Gly Glu Thr Gly Val Thr Gly Ser
                245                 250                 255

Thr Gly Pro Thr Gly Asn Thr Gly Ala Thr Gly Asn Thr Gly Pro Thr
            260                 265                 270

Gly Glu Thr Gly Val Thr Gly Ser Thr Gly Pro Thr Gly Asn Thr Gly
        275                 280                 285
```

```
Ala Thr Gly Asn Thr Gly Ala Thr Gly Glu Thr Gly Ser Thr Gly Val
    290                 295                 300

Thr Gly Ser Thr Gly Val Thr Gly Ser Thr Gly Ala Thr Gly Ser Thr
305                 310                 315                 320

Gly Val Thr Gly Asn Thr Gly Ala Thr Gly Ser Thr Gly Ala Thr Gly
                325                 330                 335

Asn Thr Gly Pro Thr Gly Ala Thr Gly Ser Thr Gly Val Thr Gly Asn
            340                 345                 350

Thr Gly Pro Thr Gly Glu Thr Gly Pro Thr Gly Ser Thr Gly Pro Thr
        355                 360                 365

Gly Asn Thr Gly Ala Thr Gly Asn Thr Gly Ala Thr Gly Ala Thr Gly
    370                 375                 380

Ala Thr Gly Ala Thr Gly Ser Thr Gly Pro Thr Gly Asn Thr Gly Ala
385                 390                 395                 400

Thr Gly Asn Thr Gly Pro Thr Gly Val Thr Gly Ser Thr Gly Pro Thr
                405                 410                 415

Gly Ser Thr Gly Glu Thr Gly Glu Thr Gly Pro Thr Gly Glu Thr Gly
            420                 425                 430

Val Thr Gly Ser Thr Gly Pro Thr Gly Pro Thr Gly Ala Thr Gly Asn
        435                 440                 445

Thr Gly Pro Thr Gly Glu Thr Gly Ala Thr Gly Ser Thr Gly Glu Thr
    450                 455                 460

Gly Glu Thr Gly Pro Thr Gly Glu Thr Gly Val Thr Gly Ser Thr Gly
465                 470                 475                 480

Pro Thr Gly Asn Thr Gly Ala Thr Gly Asn Thr Gly Pro Thr Gly Glu
                485                 490                 495

Thr Gly Val Thr Gly Ser Thr Gly Pro Thr Gly Asn Thr Gly Ala Thr
            500                 505                 510

Gly Asn Thr Gly Pro Thr Gly Glu Thr Gly Glu Thr Gly Val Thr Gly
        515                 520                 525

Ser Thr Gly Val Thr Gly Asn Thr Gly Ala Thr Gly Ser Thr Gly Ala
    530                 535                 540

Thr Gly Asn Thr Gly Pro Thr Gly Glu Thr Gly Ala Thr Gly Pro Thr
545                 550                 555                 560

Gly Ala Thr Gly Val Thr Gly Ser Thr Gly Pro Thr Gly Asn Thr Gly
                565                 570                 575

Pro Thr Gly Glu Thr Gly Ser Thr Gly Ser Thr Gly Ala Thr Gly Ser
            580                 585                 590

Thr Gly Val Thr Gly Asn Thr Gly Ala Thr Gly Glu Thr Gly Pro Thr
        595                 600                 605

Gly Ser Thr Gly Ala Thr Gly Asn Thr Gly Ala Thr Gly Glu Thr Gly
    610                 615                 620

Pro Thr Gly Ala Thr Gly Val Thr Gly Pro Thr Gly Ser Thr Gly Val
625                 630                 635                 640

Thr Gly Ser Thr Gly Pro Thr Gly Ser Thr Gly Ala Thr Gly Ala Thr
                645                 650                 655

Gly Ser Thr Gly Pro Thr Gly Ser Thr Gly Thr Thr Gly Asp Thr Gly
            660                 665                 670

Pro Thr Gly Ala Thr Gly Val Ser Thr Thr Ala Thr Tyr Ala Phe Ala
        675                 680                 685

Asn Asn Thr Ser Gly Ser Val Ile Ser Val Leu Leu Gly Gly Thr Asn
    690                 695                 700
```

```
Ile Pro Leu Pro Asn Asn Gln Asn Ile Gly Pro Gly Ile Thr Val Ser
705                 710                 715                 720

Gly Gly Asn Thr Val Phe Thr Val Ala Asn Ala Gly Asn Tyr Tyr Ile
                725                 730                 735

Ala Tyr Thr Ile Asn Leu Thr Ala Gly Leu Leu Val Ser Ser Arg Ile
            740                 745                 750

Thr Val Asn Gly Ser Pro Leu Ala Gly Thr Ile Asn Ser Pro Thr Val
        755                 760                 765

Ala Thr Gly Ser Phe Asn Ala Thr Ile Ile Ala Ser Leu Pro Ala Gly
    770                 775                 780

Ala Ala Val Ser Leu Gln Leu Phe Gly Val Val Ala Leu Ala Thr Leu
785                 790                 795                 800

Ser Thr Ala Thr Pro Gly Ala Thr Leu Thr Ile Ile Arg Leu Ser
                805                 810                 815


<210> SEQ ID NO 83
<211> LENGTH: 40
<212> TYPE: PRT
<213> ORGANISM: Bacillus anthracis

<400> SEQUENCE: 83

Met Glu Gly Asn Gly Gly Lys Ser Lys Ile Lys Ser Pro Leu Asn Ser
1               5                   10                  15

Asn Phe Lys Ile Leu Ser Asp Leu Val Gly Pro Thr Phe Pro Pro Val
            20                  25                  30

Pro Thr Gly Met Thr Gly Ile Thr
        35                  40


<210> SEQ ID NO 84
<211> LENGTH: 469
<212> TYPE: PRT
<213> ORGANISM: Bacillus anthracis

<400> SEQUENCE: 84

Met Glu Gly Asn Gly Gly Lys Ser Lys Ile Lys Ser Pro Leu Asn Ser
1               5                   10                  15

Asn Phe Lys Ile Leu Ser Asp Leu Val Gly Pro Thr Phe Pro Pro Val
            20                  25                  30

Pro Thr Gly Met Thr Gly Ile Thr Gly Ser Thr Gly Ala Thr Gly Asn
        35                  40                  45

Thr Gly Pro Thr Gly Glu Thr Gly Ala Thr Gly Ser Ala Gly Ile Thr
    50                  55                  60

Gly Ser Thr Gly Pro Thr Gly Asn Thr Gly Gly Thr Gly Ser Thr Gly
65                  70                  75                  80

Ser Thr Gly Asn Thr Gly Ala Thr Gly Ser Thr Gly Val Thr Gly Ser
                85                  90                  95

Thr Gly Val Thr Gly Ser Thr Gly Val Thr Gly Ser Thr Gly Val Thr
            100                 105                 110

Gly Ser Thr Gly Pro Thr Gly Glu Thr Gly Gly Thr Gly Ser Thr Gly
        115                 120                 125

Val Thr Gly Ser Thr Gly Ala Thr Gly Ser Thr Gly Val Thr Gly Ser
    130                 135                 140

Thr Gly Val Thr Gly Glu Thr Gly Pro Thr Gly Ser Thr Gly Ala Thr
145                 150                 155                 160

Gly Asn Thr Gly Pro Thr Gly Glu Thr Gly Gly Thr Gly Ser Thr Gly
                165                 170                 175
```

```
Ala Thr Gly Ser Thr Gly Val Thr Gly Asn Thr Gly Pro Thr Gly Ser
            180                 185                 190

Thr Gly Val Thr Gly Asn Thr Gly Ala Thr Gly Glu Thr Gly Pro Thr
        195                 200                 205

Gly Asn Thr Gly Ala Thr Gly Asn Thr Gly Pro Thr Gly Glu Thr Gly
    210                 215                 220

Val Thr Gly Ser Thr Gly Pro Thr Gly Glu Thr Gly Val Thr Gly Ser
225                 230                 235                 240

Thr Gly Pro Thr Gly Asn Thr Gly Ala Thr Gly Glu Thr Gly Ala Thr
                245                 250                 255

Gly Ser Thr Gly Val Thr Gly Asn Thr Gly Ser Thr Gly Glu Thr Gly
            260                 265                 270

Pro Thr Gly Ser Thr Gly Pro Thr Gly Ser Thr Gly Ala Thr Gly Val
        275                 280                 285

Thr Gly Asn Thr Gly Pro Thr Gly Ser Thr Gly Ala Thr Gly Ala Thr
    290                 295                 300

Gly Ser Thr Gly Pro Thr Gly Ser Thr Gly Thr Thr Gly Asn Thr Gly
305                 310                 315                 320

Val Thr Gly Asp Thr Gly Pro Thr Gly Ala Thr Gly Val Ser Thr Thr
                325                 330                 335

Ala Thr Tyr Ala Phe Ala Asn Asn Thr Ser Gly Ser Val Ile Ser Val
            340                 345                 350

Leu Leu Gly Gly Thr Asn Ile Pro Leu Pro Asn Asn Gln Asn Ile Gly
        355                 360                 365

Pro Gly Ile Thr Val Ser Gly Gly Asn Thr Val Phe Thr Val Ala Asn
    370                 375                 380

Ala Gly Asn Tyr Tyr Ile Ala Tyr Thr Ile Asn Leu Thr Ala Gly Leu
385                 390                 395                 400

Leu Val Ser Ser Arg Ile Thr Val Asn Gly Ser Pro Leu Ala Gly Thr
                405                 410                 415

Ile Asn Ser Pro Thr Val Ala Thr Gly Ser Phe Ser Ala Thr Ile Ile
            420                 425                 430

Ala Ser Leu Pro Ala Gly Ala Ala Val Ser Leu Gln Leu Phe Gly Val
        435                 440                 445

Val Ala Leu Ala Thr Leu Ser Thr Ala Thr Pro Gly Ala Thr Leu Thr
    450                 455                 460

Ile Ile Arg Leu Ser
465
```

<210> SEQ ID NO 85
<211> LENGTH: 34
<212> TYPE: PRT
<213> ORGANISM: Bacillus thuringiensis

<400> SEQUENCE: 85

```
Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly
```

<210> SEQ ID NO 86
<211> LENGTH: 285
<212> TYPE: PRT
<213> ORGANISM: Bacillus thuringiensis

<400> SEQUENCE: 86

```
Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
        35                  40                  45

Gly Pro Thr Gly Thr Thr Gly Ala Thr Gly Ala Thr Gly Ile Thr Gly
    50                  55                  60

Val Thr Gly Ala Thr Gly Ile Thr Gly Val Thr Gly Ala Thr Gly Ile
65                  70                  75                  80

Thr Gly Ala Thr Gly Pro Thr Gly Ile Thr Gly Ala Thr Gly Pro Ala
                85                  90                  95

Gly Ile Thr Gly Ala Thr Gly Pro Ala Gly Ile Thr Gly Ala Thr Gly
            100                 105                 110

Pro Ala Gly Ile Thr Gly Ala Thr Gly Pro Thr Gly Ile Thr Gly Ala
        115                 120                 125

Thr Gly Pro Thr Gly Ile Thr Gly Ala Thr Gly Pro Thr Gly Ile Thr
    130                 135                 140

Gly Ala Thr Gly Pro Ala Gly Ile Thr Gly Ala Thr Gly Pro Thr Gly
145                 150                 155                 160

Thr Thr Gly Val Thr Gly Ala Thr Gly Ile Thr Gly Val Thr Gly Ala
                165                 170                 175

Thr Gly Ile Thr Gly Ala Thr Gly Pro Thr Gly Thr Thr Gly Val Thr
            180                 185                 190

Gly Pro Thr Gly Val Ile Gly Pro Ile Thr Thr Thr Asn Leu Leu Phe
        195                 200                 205

Tyr Thr Phe Ala Asp Gly Glu Lys Leu Ile Tyr Thr Asp Ser Asp Gly
    210                 215                 220

Leu Ala Gln Tyr Gly Thr Thr His Ile Leu Ser Pro Asp Glu Val Ser
225                 230                 235                 240

Tyr Ile Asn Leu Phe Ile Asn Gly Ile Leu Gln Pro Gln Pro Leu Tyr
                245                 250                 255

Gln Val Ser Thr Gly Gln Leu Thr Leu Leu Asp Asn Gln Pro Pro Ser
            260                 265                 270

Gln Gly Ser Ser Ile Ile Leu Gln Phe Ile Ile Ile Asn
        275                 280                 285
```

<210> SEQ ID NO 87
<211> LENGTH: 34
<212> TYPE: PRT
<213> ORGANISM: Bacillus cereus

<400> SEQUENCE: 87

```
Met Asn Ser Asn Glu Lys Leu Ser Leu Asn Lys Gly Met Val Arg Pro
1               5                   10                  15

Glu Asn Ile Gly Pro Thr Phe Pro Val Leu Pro Pro Ile Tyr Ile Pro
            20                  25                  30

Thr Gly
```

<210> SEQ ID NO 88
<211> LENGTH: 258
<212> TYPE: PRT
<213> ORGANISM: Bacillus cereus

<400> SEQUENCE: 88

```
Met Asn Ser Asn Glu Lys Leu Ser Leu Asn Lys Gly Met Val Arg Pro
1               5                   10                  15

Glu Asn Ile Gly Pro Thr Phe Pro Val Leu Pro Pro Ile Tyr Ile Pro
            20                  25                  30

Thr Gly Ala Thr Gly Ala Thr Gly Ala Thr Gly Ala Thr Gly Ala Thr
        35                  40                  45

Gly Ala Thr Gly Ala Thr Gly Ala Thr Gly Ala Thr Gly Ala Thr Gly
    50                  55                  60

Ala Thr Gly Ala Thr Gly Ala Thr Gly Ala Thr Gly Val Thr Gly Ala
65                  70                  75                  80

Thr Gly Ala Thr Gly Ala Thr Gly Val Thr Gly Ala Thr Gly Ala Thr
                85                  90                  95

Gly Val Thr Gly Ala Thr Gly Val Thr Gly Ala Thr Gly Ala Thr Gly
            100                 105                 110

Val Thr Gly Ala Thr Gly Val Thr Gly Ala Thr Gly Ala Thr Gly Ala
        115                 120                 125

Thr Gly Val Thr Gly Ala Thr Gly Ala Thr Gly Ala Thr Gly Ala Thr
    130                 135                 140

Gly Val Thr Gly Ala Thr Gly Val Thr Gly Val Thr Gly Val Thr Gly
145                 150                 155                 160

Ala Thr Gly Ala Thr Gly Pro Thr Gly Val Ile Gly Pro Ile Thr Thr
                165                 170                 175

Thr Asn Leu Leu Phe Tyr Thr Phe Ser Asp Gly Glu Lys Leu Ile Tyr
            180                 185                 190

Thr Asp Ser Asp Gly Leu Ala Gln Tyr Gly Thr Thr His Ile Leu Ser
        195                 200                 205

Pro Asp Glu Val Ser Tyr Ile Asn Leu Phe Ile Asn Gly Ile Leu Gln
    210                 215                 220

Pro Gln Pro Leu Tyr Gln Val Ser Thr Gly Gln Leu Thr Leu Leu Asp
225                 230                 235                 240

Asn Gln Pro Pro Ser Gln Gly Ser Ser Ile Ile Leu Gln Phe Ile Ile
                245                 250                 255

Ile Asn


<210> SEQ ID NO 89
<211> LENGTH: 34
<212> TYPE: PRT
<213> ORGANISM: Bacillus cereus

<400> SEQUENCE: 89

Met Lys Arg Asn Asp Asn Leu Ser Leu Asn Lys Gly Met Ile Gly Pro
1               5                   10                  15

Glu Asn Ile Gly Pro Thr Phe Pro Ile Leu Pro Pro Ile Tyr Ile Pro
            20                  25                  30

Thr Gly


<210> SEQ ID NO 90
<211> LENGTH: 279
<212> TYPE: PRT
<213> ORGANISM: Bacillus cereus

<400> SEQUENCE: 90

Met Lys Arg Asn Asp Asn Leu Ser Leu Asn Lys Gly Met Ile Gly Pro
1               5                   10                  15

Glu Asn Ile Gly Pro Thr Phe Pro Ile Leu Pro Pro Ile Tyr Ile Pro
```

```
            20                  25                  30

Thr Gly Ala Thr Gly Pro Thr Gly Ile Thr Gly Pro Thr Gly Glu Thr
        35                  40                  45

Gly Pro Thr Gly Ile Thr Gly Pro Thr Gly Val Thr Gly Pro Thr Gly
    50                  55                  60

Ile Thr Gly Pro Thr Gly Ala Thr Gly Pro Thr Gly Ile Thr Gly Pro
65                  70                  75                  80

Thr Gly Ala Thr Gly Pro Thr Gly Ile Thr Gly Pro Thr Gly Ala Thr
                85                  90                  95

Gly Pro Thr Gly Glu Thr Gly Pro Thr Gly Ile Thr Gly Pro Thr Gly
            100                 105                 110

Ala Thr Gly Pro Thr Gly Ile Thr Gly Pro Thr Gly Ala Thr Gly Pro
        115                 120                 125

Thr Gly Glu Thr Gly Pro Thr Gly Glu Thr Gly Pro Thr Gly Val Thr
    130                 135                 140

Gly Pro Thr Gly Ile Thr Gly Pro Thr Gly Ala Thr Gly Pro Thr Gly
145                 150                 155                 160

Ile Thr Gly Pro Thr Gly Ala Thr Gly Pro Thr Gly Glu Thr Gly Pro
                165                 170                 175

Thr Gly Ile Thr Gly Pro Thr Gly Ala Thr Gly Pro Thr Gly Gly Ile
            180                 185                 190

Gly Pro Ile Thr Thr Thr Asn Leu Leu Tyr Tyr Thr Phe Ala Asp Gly
        195                 200                 205

Glu Lys Leu Ile Tyr Thr Asp Ala Asp Gly Ile Pro Gln Tyr Gly Thr
    210                 215                 220

Thr Asn Ile Leu Ser Pro Ser Glu Val Ser Tyr Ile Asn Leu Phe Val
225                 230                 235                 240

Asn Gly Ile Leu Gln Pro Gln Pro Leu Tyr Glu Val Ser Thr Gly Lys
                245                 250                 255

Leu Thr Leu Leu Asp Thr Gln Pro Pro Ser Gln Gly Ser Ser Ile Ile
            260                 265                 270

Leu Gln Phe Ile Ile Ile Asn
        275
```

```
<210> SEQ ID NO 91
<211> LENGTH: 99
<212> TYPE: PRT
<213> ORGANISM: Bacillus cereus

<400> SEQUENCE: 91

Met Asp Ser Phe Val Asp Val Gly Glu Ile Phe Thr Ile Phe Arg Lys
1               5                   10                  15

Leu Asn Met Glu Gly Ser Leu Gln Phe Lys Val His Asn Ser Met Gly
            20                  25                  30

Lys Thr Tyr Tyr Ile Thr Ile Asn Glu Val Tyr Val Tyr Val Thr Val
        35                  40                  45

Leu Leu Gln Tyr Ser Thr Leu Ile Gly Gly Ser Tyr Val Phe Asp Lys
    50                  55                  60

Asn Glu Ile Gln Lys Ile Asn Gly Ile Leu Gln Ala Asn Ala Leu Asn
65                  70                  75                  80

Pro Asn Leu Ile Gly Pro Thr Leu Pro Pro Ile Pro Pro Phe Thr Leu
                85                  90                  95

Pro Thr Gly
```

<210> SEQ ID NO 92
<211> LENGTH: 145
<212> TYPE: PRT
<213> ORGANISM: Bacillus cereus

<400> SEQUENCE: 92

```
Met Asp Ser Phe Val Asp Val Gly Glu Ile Phe Thr Ile Phe Arg Lys
1               5                   10                  15

Leu Asn Met Glu Gly Ser Leu Gln Phe Lys Val His Asn Ser Met Gly
            20                  25                  30

Lys Thr Tyr Tyr Ile Thr Ile Asn Glu Val Tyr Val Tyr Val Thr Val
        35                  40                  45

Leu Leu Gln Tyr Ser Thr Leu Ile Gly Gly Ser Tyr Val Phe Asp Lys
    50                  55                  60

Asn Glu Ile Gln Lys Ile Asn Gly Ile Leu Gln Ala Asn Ala Leu Asn
65                  70                  75                  80

Pro Asn Leu Ile Gly Pro Thr Leu Pro Pro Ile Pro Pro Phe Thr Leu
                85                  90                  95

Pro Thr Gly Pro Thr Gly Val Thr Gly Pro Thr Gly Gly Thr Gly Pro
            100                 105                 110

Thr Gly Val Thr Gly Pro Thr Gly Val Thr Gly Pro Thr Gly Val Thr
        115                 120                 125

Gly Val Thr Gly Pro Thr Gly Val Thr Gly Pro Thr Gly Val Thr Gly
    130                 135                 140

Pro
145
```

<210> SEQ ID NO 93
<211> LENGTH: 136
<212> TYPE: PRT
<213> ORGANISM: Bacillus weihenstephanensis

<400> SEQUENCE: 93

```
Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Trp Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly
    130                 135
```

<210> SEQ ID NO 94
<211> LENGTH: 142
<212> TYPE: PRT
<213> ORGANISM: Bacillus weihenstephanensis

<400> SEQUENCE: 94

```
Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Trp Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly Pro Thr Gly Gly Thr Gly
    130                 135                 140
```

<210> SEQ ID NO 95
<211> LENGTH: 196
<212> TYPE: PRT
<213> ORGANISM: Bacillus anthracis

<400> SEQUENCE: 95

```
Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60

Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly
        195
```

<210> SEQ ID NO 96
<211> LENGTH: 17
<212> TYPE: PRT

<213> ORGANISM: Bacillus anthracis

<400> SEQUENCE: 96

Met Ala Phe Asp Pro Asn Leu Val Gly Pro Thr Leu Pro Pro Ile Pro
1 5 10 15

Pro

<210> SEQ ID NO 97
<211> LENGTH: 17
<212> TYPE: PRT
<213> ORGANISM: Bacillus anthracis

<400> SEQUENCE: 97

Met Ala Leu Glu Pro Asn Leu Ile Gly Pro Thr Leu Pro Pro Ile Pro
1 5 10 15

Pro

<210> SEQ ID NO 98
<211> LENGTH: 17
<212> TYPE: PRT
<213> ORGANISM: Bacillus weihenstephanensis

<400> SEQUENCE: 98

Met Ala Leu Asn Pro Asn Leu Ile Gly Pro Thr Leu Pro Pro Ile Pro
1 5 10 15

Pro

<210> SEQ ID NO 99
<211> LENGTH: 17
<212> TYPE: PRT
<213> ORGANISM: Bacillus weihenstephanensis

<400> SEQUENCE: 99

Met Ala Leu Asp Pro Asn Ile Ile Gly Pro Thr Leu Pro Pro Ile Pro
1 5 10 15

Pro

<210> SEQ ID NO 100
<211> LENGTH: 17
<212> TYPE: PRT
<213> ORGANISM: Bacillus cereus

<400> SEQUENCE: 100

Met Ala Leu Glu Pro Asn Leu Ile Gly Pro Thr Leu Pro Ser Ile Pro
1 5 10 15

Pro

<210> SEQ ID NO 101
<211> LENGTH: 17
<212> TYPE: PRT
<213> ORGANISM: Bacillus weihenstephanensis

<400> SEQUENCE: 101

Met Ala Leu Asp Pro Asn Leu Ile Gly Pro Pro Leu Pro Pro Ile Thr
1 5 10 15

Pro

<210> SEQ ID NO 102
<211> LENGTH: 17
<212> TYPE: PRT
<213> ORGANISM: Bacillus weihenstephanensis

<400> SEQUENCE: 102

Met Ala Leu Asn Pro Gly Ser Ile Gly Pro Thr Leu Pro Pro Val Pro
1 5 10 15

Pro

<210> SEQ ID NO 103
<211> LENGTH: 17
<212> TYPE: PRT
<213> ORGANISM: Bacillus weihenstephanensis

<400> SEQUENCE: 103

Met Ala Leu Asn Pro Cys Ser Ile Gly Pro Thr Leu Pro Pro Met Gln
1 5 10 15

Pro

<210> SEQ ID NO 104
<211> LENGTH: 17
<212> TYPE: PRT
<213> ORGANISM: Bacillus mycoides

<400> SEQUENCE: 104

Met Ala Leu Asn Pro Gly Ser Ile Gly Pro Thr Leu Pro Pro Val Gln
1 5 10 15

Pro

<210> SEQ ID NO 105
<211> LENGTH: 17
<212> TYPE: PRT
<213> ORGANISM: Bacillus anthracis

<400> SEQUENCE: 105

Met Ala Leu Asn Pro Gly Ser Val Gly Pro Thr Leu Pro Pro Met Gln
1 5 10 15

Pro

<210> SEQ ID NO 106
<211> LENGTH: 17
<212> TYPE: PRT
<213> ORGANISM: Bacillus cereus

<400> SEQUENCE: 106

Met Ala Leu Asp Pro Asn Leu Ile Gly Pro Thr Phe Pro Pro Ile Pro
1 5 10 15

Ser

<210> SEQ ID NO 107
<211> LENGTH: 18
<212> TYPE: PRT
<213> ORGANISM: Bacillus thuringiensis

<400> SEQUENCE: 107

Met Ala Ala Ile Asn Pro Asn Leu Val Gly Pro Thr Leu Pro Pro Val
1 5 10 15

Pro Pro

<210> SEQ ID NO 108
<211> LENGTH: 799
<212> TYPE: PRT
<213> ORGANISM: Bacillus mycoides

<400> SEQUENCE: 108

```
Met Lys Arg Lys Thr Pro Phe Lys Val Phe Ser Ser Leu Ala Ile Thr
1               5                   10                  15

Thr Met Leu Gly Cys Thr Phe Ala Leu Gly Thr Ser Val Ala Tyr Ala
            20                  25                  30

Glu Thr Thr Ser Gln Ser Lys Gly Ser Ile Ser Thr Thr Pro Ile Asp
        35                  40                  45

Asn Asn Leu Ile Gln Glu Glu Arg Leu Ala Glu Ala Leu Lys Glu Arg
    50                  55                  60

Gly Thr Ile Asp Gln Ser Ala Ser Lys Glu Glu Thr Gln Lys Ala Val
65                  70                  75                  80

Glu Gln Tyr Ile Glu Lys Lys Lys Gly Asp Gln Pro Asn Lys Glu Ile
                85                  90                  95

Leu Pro Asp Asp Pro Ala Lys Glu Ala Ser Asp Phe Val Lys Lys Val
            100                 105                 110

Lys Glu Lys Lys Met Glu Glu Lys Glu Lys Val Lys Lys Ser Val Glu
        115                 120                 125

Asn Ala Ser Ser Glu Gln Thr Pro Ser Gln Asn Lys Lys Gln Leu Asn
    130                 135                 140

Gly Lys Val Pro Thr Ser Pro Ala Lys Gln Ala Pro Tyr Asn Gly Ala
145                 150                 155                 160

Val Arg Thr Asp Lys Val Leu Val Leu Leu Val Glu Phe Ser Asp Tyr
                165                 170                 175

Lys His Asn Asn Ile Glu Gln Ser Pro Gly Tyr Met Tyr Ala Asn Asp
            180                 185                 190

Phe Ser Arg Glu His Tyr Gln Lys Met Leu Phe Gly Asn Glu Pro Phe
        195                 200                 205

Thr Leu Phe Asp Gly Ser Lys Val Lys Thr Phe Lys Gln Tyr Tyr Glu
    210                 215                 220

Glu Gln Ser Gly Gly Ser Tyr Thr Thr Asp Gly Tyr Val Thr Glu Trp
225                 230                 235                 240

Leu Thr Val Pro Gly Lys Ala Ala Asp Tyr Gly Ala Asp Gly Lys Thr
                245                 250                 255

Gly His Asp Asn Lys Gly Pro Lys Gly Ala Arg Asp Leu Val Lys Glu
            260                 265                 270

Ala Leu Lys Ala Ala Ala Glu Lys Gly Leu Asp Leu Ser Gln Phe Asp
        275                 280                 285

Gln Phe Asp Arg Tyr Asp Thr Asn Gly Asp Gly Asn Gln Asn Glu Pro
    290                 295                 300

Asp Gly Val Ile Asp His Leu Met Val Ile His Ala Gly Val Gly Gln
305                 310                 315                 320

Glu Ala Gly Gly Gly Lys Leu Gly Asp Asp Ala Ile Trp Ser His Arg
                325                 330                 335

Ser Lys Leu Ala Gln Asp Pro Val Ala Ile Glu Gly Thr Lys Ser Lys
            340                 345                 350

Val Ser Tyr Trp Asp Gly Lys Val Ala Ala His Asp Tyr Thr Ile Glu
        355                 360                 365

Pro Glu Asp Gly Ala Val Gly Val Phe Ala His Glu Phe Gly His Asp
    370                 375                 380

Leu Gly Leu Pro Asp Glu Tyr Asp Thr Asn Tyr Thr Gly Ala Gly Ser
385                 390                 395                 400

Pro Val Glu Ala Trp Ser Leu Met Ser Gly Gly Ser Trp Thr Gly Arg
                405                 410                 415
```

```
Ile Ala Gly Thr Glu Pro Thr Ser Phe Ser Pro Gln Asn Lys Asp Phe
            420                 425                 430

Leu Gln Lys Asn Met Asp Gly Asn Trp Ala Lys Ile Val Glu Val Asp
        435                 440                 445

Tyr Asp Lys Ile Lys Arg Gly Val Gly Phe Pro Thr Tyr Ile Asp Gln
    450                 455                 460

Ser Val Thr Lys Ser Asn Arg Pro Gly Leu Val Arg Val Asn Leu Pro
465                 470                 475                 480

Glu Lys Ser Val Glu Thr Ile Lys Thr Gly Phe Gly Lys His Ala Tyr
                485                 490                 495

Tyr Ser Thr Arg Gly Asp Asp Met His Thr Thr Leu Glu Thr Pro Leu
            500                 505                 510

Phe Asp Leu Thr Lys Ala Ala Asn Ala Lys Phe Asp Tyr Lys Ala Asn
        515                 520                 525

Tyr Glu Leu Glu Ala Glu Cys Asp Phe Ile Glu Val His Ala Val Thr
    530                 535                 540

Glu Asp Gly Thr Lys Thr Leu Ile Asp Lys Leu Gly Asp Lys Val Val
545                 550                 555                 560

Lys Gly Asp Gln Asp Thr Thr Glu Gly Lys Trp Ile Asp Lys Ser Tyr
                565                 570                 575

Asp Leu Ser Gln Phe Lys Gly Lys Lys Val Lys Leu Gln Phe Asp Tyr
            580                 585                 590

Ile Thr Asp Pro Ala Leu Thr Tyr Lys Gly Phe Ala Met Asp Asn Val
        595                 600                 605

Asn Val Thr Val Asp Gly Lys Val Val Phe Ser Asp Asp Ala Glu Gly
    610                 615                 620

Gln Ala Lys Met Lys Leu Asn Gly Phe Val Val Ser Asp Gly Thr Glu
625                 630                 635                 640

Lys Lys Pro His Tyr Tyr Tyr Leu Glu Trp Arg Asn Tyr Ala Gly Ser
                645                 650                 655

Asp Glu Gly Leu Lys Val Gly Arg Gly Pro Val Tyr Asn Thr Gly Leu
            660                 665                 670

Val Val Trp Tyr Ala Asp Asp Ser Phe Lys Asp Asn Trp Val Gly Arg
        675                 680                 685

His Pro Gly Glu Gly Phe Leu Gly Val Val Asp Ser His Pro Glu Ala
    690                 695                 700

Val Val Gly Asn Leu Asn Gly Lys Pro Val Tyr Gly Asn Thr Gly Leu
705                 710                 715                 720

Gln Ile Ala Asp Ala Ala Phe Ser Leu Asp Gln Thr Pro Ala Trp Asn
                725                 730                 735

Val Asn Ser Phe Thr Arg Gly Gln Phe Asn Tyr Pro Gly Leu Pro Gly
            740                 745                 750

Val Ala Thr Phe Asp Asp Ser Lys Val Tyr Ser Asn Thr Gln Ile Pro
        755                 760                 765

Asp Ala Gly Arg Lys Val Pro Gln Leu Gly Leu Lys Phe Gln Val Val
    770                 775                 780

Gly Gln Ala Asp Asp Lys Ser Ala Gly Ala Ile Trp Ile Arg Arg
785                 790                 795
```

```
<210> SEQ ID NO 109
<211> LENGTH: 152
<212> TYPE: PRT
<213> ORGANISM: Bacillus anthracis
```

```
<400> SEQUENCE: 109

Met Ser Cys Asn Glu Asn Lys His His Gly Ser Ser His Cys Val Val
1               5                   10                  15

Asp Val Val Lys Phe Ile Asn Glu Leu Gln Asp Cys Ser Thr Thr Thr
            20                  25                  30

Cys Gly Ser Gly Cys Glu Ile Pro Phe Leu Gly Ala His Asn Thr Ala
        35                  40                  45

Ser Val Ala Asn Thr Arg Pro Phe Ile Leu Tyr Thr Lys Ala Gly Ala
    50                  55                  60

Pro Phe Glu Ala Phe Ala Pro Ser Ala Asn Leu Thr Ser Cys Arg Ser
65                  70                  75                  80

Pro Ile Phe Arg Val Glu Ser Val Asp Asp Asp Ser Cys Ala Val Leu
                85                  90                  95

Arg Val Leu Ser Val Val Leu Gly Asp Ser Ser Pro Val Pro Pro Thr
            100                 105                 110

Asp Asp Pro Ile Cys Thr Phe Leu Ala Val Pro Asn Ala Arg Leu Val
        115                 120                 125

Ser Thr Ser Thr Cys Ile Thr Val Asp Leu Ser Cys Phe Cys Ala Ile
    130                 135                 140

Gln Cys Leu Arg Asp Val Thr Ile
145                 150


<210> SEQ ID NO 110
<211> LENGTH: 167
<212> TYPE: PRT
<213> ORGANISM: Bacillus anthracis

<400> SEQUENCE: 110

Met Phe Ser Ser Asp Cys Glu Phe Thr Lys Ile Asp Cys Glu Ala Lys
1               5                   10                  15

Pro Ala Ser Thr Leu Pro Ala Phe Gly Phe Ala Phe Asn Ala Ser Ala
            20                  25                  30

Pro Gln Phe Ala Ser Leu Phe Thr Pro Leu Leu Leu Pro Ser Val Ser
        35                  40                  45

Pro Asn Pro Asn Ile Thr Val Pro Val Ile Asn Asp Thr Val Ser Val
    50                  55                  60

Gly Asp Gly Ile Arg Ile Leu Arg Ala Gly Ile Tyr Gln Ile Ser Tyr
65                  70                  75                  80

Thr Leu Thr Ile Ser Leu Asp Asn Ser Pro Val Ala Pro Glu Ala Gly
                85                  90                  95

Arg Phe Phe Leu Ser Leu Gly Thr Pro Ala Asn Ile Ile Pro Gly Ser
            100                 105                 110

Gly Thr Ala Val Arg Ser Asn Val Ile Gly Thr Gly Glu Val Asp Val
        115                 120                 125

Ser Ser Gly Val Ile Leu Ile Asn Leu Asn Pro Gly Asp Leu Ile Arg
    130                 135                 140

Ile Val Pro Val Glu Leu Ile Gly Thr Val Asp Ile Arg Ala Ala Ala
145                 150                 155                 160

Leu Thr Val Ala Gln Ile Ser
                165


<210> SEQ ID NO 111
<211> LENGTH: 156
<212> TYPE: PRT
<213> ORGANISM: Bacillus anthracis
```

<400> SEQUENCE: 111

```
Met Ser Cys Asn Cys Asn Glu Asp His His His His Asp Cys Asp Phe
1               5                   10                  15

Asn Cys Val Ser Asn Val Val Arg Phe Ile His Glu Leu Gln Glu Cys
            20                  25                  30

Ala Thr Thr Thr Cys Gly Ser Gly Cys Glu Val Pro Phe Leu Gly Ala
        35                  40                  45

His Asn Ser Ala Ser Val Ala Asn Thr Arg Pro Phe Ile Leu Tyr Thr
    50                  55                  60

Lys Ala Gly Ala Pro Phe Glu Ala Phe Ala Pro Ser Ala Asn Leu Thr
65                  70                  75                  80

Ser Cys Arg Ser Pro Ile Phe Arg Val Glu Ser Ile Asp Asp Asp Asp
                85                  90                  95

Cys Ala Val Leu Arg Val Leu Ser Val Val Leu Gly Asp Thr Ser Pro
            100                 105                 110

Val Pro Pro Thr Asp Asp Pro Ile Cys Thr Phe Leu Ala Val Pro Asn
        115                 120                 125

Ala Arg Leu Ile Ser Thr Asn Thr Cys Leu Thr Val Asp Leu Ser Cys
    130                 135                 140

Phe Cys Ala Ile Gln Cys Leu Arg Asp Val Thr Ile
145                 150                 155
```

<210> SEQ ID NO 112
<211> LENGTH: 182
<212> TYPE: PRT
<213> ORGANISM: Bacillus anthracis

<400> SEQUENCE: 112

```
Met Glu Val Gly Gly Thr Ser Val Lys Asn Lys Asn Lys Ser Ser Thr
1               5                   10                  15

Val Gly Lys Pro Leu Leu Tyr Ile Ala Gln Val Ser Leu Glu Leu Ala
            20                  25                  30

Ala Pro Lys Thr Lys Arg Ile Ile Leu Thr Asn Phe Glu Asn Glu Asp
        35                  40                  45

Arg Lys Glu Glu Ser Asn Arg Asn Glu Asn Val Val Ser Ser Ala Val
    50                  55                  60

Glu Glu Val Ile Glu Gln Glu Glu Gln Gln Gln Glu Gln Glu Gln Glu
65                  70                  75                  80

Gln Glu Glu Gln Val Glu Glu Lys Thr Glu Glu Glu Glu Gln Val Gln
                85                  90                  95

Glu Gln Gln Glu Pro Val Arg Thr Val Pro Tyr Asn Lys Ser Phe Lys
            100                 105                 110

Asp Met Asn Asn Glu Glu Lys Ile His Phe Leu Leu Asn Arg Pro His
        115                 120                 125

Tyr Ile Pro Lys Val Arg Cys Arg Ile Lys Thr Ala Thr Ile Ser Tyr
    130                 135                 140

Val Gly Ser Ile Ile Ser Tyr Arg Asn Gly Ile Val Ala Ile Met Pro
145                 150                 155                 160

Pro Asn Ser Met Arg Asp Ile Arg Leu Ser Ile Glu Glu Ile Lys Ser
                165                 170                 175

Ile Asp Met Ala Gly Phe
            180
```

<210> SEQ ID NO 113
<211> LENGTH: 174

<212> TYPE: PRT
<213> ORGANISM: Bacillus anthracis

<400> SEQUENCE: 113

```
Met Lys Glu Arg Ser Glu Asn Met Arg Ser Ser Ser Arg Lys Leu Thr
1               5                   10                  15

Asn Phe Asn Cys Arg Ala Gln Ala Pro Ser Thr Leu Pro Ala Leu Gly
            20                  25                  30

Phe Ala Phe Asn Ala Thr Ser Pro Gln Phe Ala Thr Leu Phe Thr Pro
        35                  40                  45

Leu Leu Leu Pro Ser Thr Gly Pro Asn Pro Asn Ile Thr Val Pro Val
    50                  55                  60

Ile Asn Asp Thr Ile Ser Thr Gly Thr Gly Ile Arg Ile Gln Val Ala
65                  70                  75                  80

Gly Ile Tyr Gln Ile Ser Tyr Thr Leu Thr Ile Ser Leu Asp Asn Val
                85                  90                  95

Pro Val Thr Pro Glu Ala Ala Arg Phe Phe Leu Thr Leu Asn Ser Ser
            100                 105                 110

Thr Asn Ile Ile Ala Gly Ser Gly Thr Ala Val Arg Ser Asn Ile Ile
        115                 120                 125

Gly Thr Gly Glu Val Asp Val Ser Ser Gly Val Ile Leu Ile Asn Leu
    130                 135                 140

Asn Pro Gly Asp Leu Ile Gln Ile Val Pro Val Glu Val Ile Gly Thr
145                 150                 155                 160

Val Asp Ile Arg Ser Ala Ala Leu Thr Val Ala Gln Ile Arg
                165                 170
```

<210> SEQ ID NO 114
<211> LENGTH: 796
<212> TYPE: PRT
<213> ORGANISM: Bacillus thuringiensis

<400> SEQUENCE: 114

```
Met Ser Lys Lys Pro Phe Lys Val Leu Ser Ser Ile Ala Leu Thr Ala
1               5                   10                  15

Val Leu Gly Leu Ser Phe Gly Ala Gly Thr Gln Ser Ala Tyr Ala Glu
            20                  25                  30

Thr Pro Val Asn Lys Thr Ala Thr Ser Pro Val Asp Asp His Leu Ile
        35                  40                  45

Pro Glu Glu Arg Leu Ala Asp Ala Leu Lys Lys Arg Gly Val Ile Asp
    50                  55                  60

Ser Lys Ala Ser Glu Thr Glu Thr Lys Lys Ala Val Glu Lys Tyr Val
65                  70                  75                  80

Glu Asn Lys Lys Gly Glu Asn Pro Gly Lys Glu Ala Ala Asn Gly Asp
                85                  90                  95

Gln Leu Thr Lys Asp Ala Ser Asp Phe Leu Lys Lys Val Lys Asp Ala
            100                 105                 110

Lys Ala Asp Thr Lys Glu Lys Leu Asn Gln Pro Ala Thr Gly Thr Pro
        115                 120                 125

Ala Ala Thr Gly Pro Val Lys Gly Gly Leu Asn Gly Lys Val Pro Thr
    130                 135                 140

Ser Pro Ala Lys Gln Lys Asp Tyr Asn Gly Glu Val Arg Lys Asp Lys
145                 150                 155                 160

Val Leu Val Leu Leu Val Glu Tyr Ala Asp Phe Lys His Asn Asn Ile
                165                 170                 175
```

```
Asp Lys Glu Pro Gly Tyr Met Tyr Ser Asn Asp Phe Asn Lys Glu His
            180                 185                 190

Tyr Glu Lys Met Leu Phe Gly Asn Glu Pro Phe Thr Leu Asp Asp Gly
        195                 200                 205

Ser Lys Ile Glu Thr Phe Lys Gln Tyr Tyr Glu Glu Gln Ser Gly Gly
    210                 215                 220

Ser Tyr Thr Val Asp Gly Thr Val Thr Lys Trp Leu Thr Val Pro Gly
225                 230                 235                 240

Lys Ala Ala Asp Tyr Gly Ala Asp Ala Pro Gly Gly Gly His Asp Asn
                245                 250                 255

Lys Gly Pro Lys Gly Pro Arg Asp Leu Val Lys Asp Ala Leu Lys Ala
            260                 265                 270

Ala Val Asp Ser Gly Ile Asp Leu Ser Glu Phe Asp Gln Phe Asp Gln
        275                 280                 285

Tyr Asp Val Asn Gly Asp Gly Asn Lys Asn Gln Pro Asp Gly Leu Ile
    290                 295                 300

Asp His Leu Met Ile Ile His Ala Gly Val Gly Gln Glu Ala Gly Gly
305                 310                 315                 320

Gly Lys Leu Gly Asp Asp Ala Ile Trp Ser His Arg Trp Thr Val Gly
                325                 330                 335

Pro Lys Pro Phe Pro Ile Glu Gly Thr Gln Ala Lys Val Pro Tyr Trp
            340                 345                 350

Gly Gly Lys Met Ala Ala Phe Asp Tyr Thr Ile Glu Pro Glu Asp Gly
        355                 360                 365

Ala Val Gly Val Phe Ala His Glu Tyr Gly His Asp Leu Gly Leu Pro
    370                 375                 380

Asp Glu Tyr Asp Thr Gln Tyr Ser Gly Gln Gly Glu Pro Ile Glu Ala
385                 390                 395                 400

Trp Ser Ile Met Ser Gly Gly Ser Trp Ala Gly Lys Ile Ala Gly Thr
                405                 410                 415

Thr Pro Thr Ser Phe Ser Pro Gln Asn Lys Glu Phe Phe Gln Lys Thr
            420                 425                 430

Ile Gly Gly Asn Trp Ala Asn Ile Val Glu Val Asp Tyr Glu Lys Leu
        435                 440                 445

Asn Lys Gly Ile Gly Leu Ala Thr Tyr Leu Asp Gln Ser Val Thr Lys
    450                 455                 460

Ser Ala Arg Pro Gly Met Ile Arg Val Asn Leu Pro Asp Lys Asp Val
465                 470                 475                 480

Lys Thr Ile Glu Pro Ala Phe Gly Lys Gln Tyr Tyr Tyr Ser Thr Lys
                485                 490                 495

Gly Asp Asp Leu His Thr Lys Met Glu Thr Pro Leu Phe Asp Leu Thr
            500                 505                 510

Asn Ala Thr Ser Ala Lys Phe Asp Phe Lys Ser Leu Tyr Glu Ile Glu
        515                 520                 525

Ala Gly Tyr Asp Phe Leu Glu Val His Ala Val Thr Glu Asp Gly Lys
    530                 535                 540

Gln Thr Leu Ile Glu Arg Leu Gly Glu Lys Ala Asn Ser Gly Asn Ala
545                 550                 555                 560

Asp Ser Thr Asn Gly Lys Trp Ile Asp Lys Ser Tyr Asp Leu Ser Gln
                565                 570                 575

Phe Lys Gly Lys Lys Val Lys Leu Thr Phe Asp Tyr Ile Thr Asp Gly
            580                 585                 590

Gly Leu Ala Leu Asn Gly Phe Ala Leu Asp Asn Ala Ser Leu Thr Val
```

```
        595                 600                 605

Asp Gly Lys Val Val Phe Ser Asp Asp Ala Glu Gly Thr Pro Gln Leu
    610                 615                 620

Lys Leu Asp Gly Phe Val Val Ser Asn Gly Thr Glu Lys Lys Lys His
625                 630                 635                 640

Asn Tyr Tyr Val Glu Trp Arg Asn Tyr Ala Gly Ala Asp Asn Ala Leu
                645                 650                 655

Lys Phe Ala Arg Gly Pro Val Phe Asn Thr Gly Met Val Val Trp Tyr
            660                 665                 670

Ala Asp Ser Ala Tyr Thr Asp Asn Trp Val Gly Val His Pro Gly His
        675                 680                 685

Gly Phe Leu Gly Val Val Asp Ser His Pro Glu Ala Ile Val Gly Thr
    690                 695                 700

Leu Asn Gly Lys Pro Thr Val Lys Ser Ser Thr Arg Phe Gln Ile Ala
705                 710                 715                 720

Asp Ala Ala Phe Ser Phe Asp Lys Thr Pro Ala Trp Lys Val Val Ser
                725                 730                 735

Pro Thr Arg Gly Thr Phe Thr Tyr Asp Gly Leu Ala Gly Val Pro Lys
            740                 745                 750

Phe Asp Asp Ser Lys Thr Tyr Ile Asn Gln Gln Ile Pro Asp Ala Gly
        755                 760                 765

Arg Ile Leu Pro Lys Leu Gly Leu Lys Phe Glu Val Val Gly Gln Ala
    770                 775                 780

Asp Asp Asn Ser Ala Gly Ala Val Arg Leu Tyr Arg
785                 790                 795


<210> SEQ ID NO 115
<211> LENGTH: 430
<212> TYPE: PRT
<213> ORGANISM: Bacillus cereus

<400> SEQUENCE: 115

Met Lys His Asn Asp Cys Phe Asp His Asn Asn Cys Asn Pro Ile Val
1               5                   10                  15

Phe Ser Ala Asp Cys Cys Lys Asn Pro Gln Ser Val Pro Ile Thr Arg
            20                  25                  30

Glu Gln Leu Ser Gln Leu Ile Thr Leu Leu Asn Ser Leu Val Ser Ala
        35                  40                  45

Ile Ser Ala Phe Phe Ala Asn Pro Ser Asn Ala Asn Arg Leu Val Leu
    50                  55                  60

Leu Asp Leu Phe Asn Gln Phe Leu Ile Phe Leu Asn Ser Leu Leu Pro
65                  70                  75                  80

Ser Pro Glu Val Asn Phe Leu Lys Gln Leu Thr Gln Ser Ile Ile Val
                85                  90                  95

Leu Leu Gln Ser Pro Ala Pro Asn Leu Gly Gln Leu Ser Thr Leu Leu
            100                 105                 110

Gln Gln Phe Tyr Ser Ala Leu Ala Gln Phe Phe Phe Ala Leu Asp Leu
        115                 120                 125

Ile Pro Ile Ser Cys Asn Ser Asn Val Asp Ser Ala Thr Leu Gln Leu
    130                 135                 140

Leu Phe Asn Leu Leu Ile Gln Leu Ile Asn Ala Thr Pro Gly Ala Thr
145                 150                 155                 160

Gly Pro Thr Gly Pro Thr Gly Pro Thr Gly Pro Thr Gly Pro Ala Gly
                165                 170                 175
```

```
Thr Gly Ala Gly Pro Thr Gly Ala Thr Gly Ala Thr Gly Ala Thr Gly
            180                 185                 190

Pro Thr Gly Ala Thr Gly Pro Ala Gly Thr Gly Gly Ala Thr Gly Ala
        195                 200                 205

Thr Gly Ala Thr Gly Val Thr Gly Ala Thr Gly Ala Thr Gly Ala Thr
    210                 215                 220

Gly Pro Thr Gly Pro Thr Gly Ala Thr Gly Pro Thr Gly Ala Thr Gly
225                 230                 235                 240

Ala Thr Gly Ala Thr Gly Pro Thr Gly Ala Thr Gly Pro Thr Gly Ala
                245                 250                 255

Thr Gly Leu Thr Gly Ala Thr Gly Ala Ala Gly Gly Gly Ala Ile Ile
            260                 265                 270

Pro Phe Ala Ser Gly Thr Thr Pro Ser Ala Leu Val Asn Ala Leu Val
        275                 280                 285

Ala Asn Thr Gly Thr Leu Leu Gly Phe Gly Phe Ser Gln Pro Gly Val
    290                 295                 300

Ala Leu Thr Gly Gly Thr Ser Ile Thr Leu Ala Leu Gly Val Gly Asp
305                 310                 315                 320

Tyr Ala Phe Val Ala Pro Arg Ala Gly Thr Ile Thr Ser Leu Ala Gly
                325                 330                 335

Phe Phe Ser Ala Thr Ala Ala Leu Ala Pro Ile Ser Pro Val Gln Val
            340                 345                 350

Gln Ile Gln Ile Leu Thr Ala Pro Ala Ala Ser Asn Thr Phe Thr Val
        355                 360                 365

Gln Gly Ala Pro Leu Leu Leu Thr Pro Ala Phe Ala Ala Ile Ala Ile
    370                 375                 380

Gly Ser Thr Ala Ser Gly Ile Ile Ala Glu Ala Ile Pro Val Ala Ala
385                 390                 395                 400

Gly Asp Lys Ile Leu Leu Tyr Val Ser Leu Thr Ala Ala Ser Pro Ile
                405                 410                 415

Ala Ala Val Ala Gly Phe Val Ser Ala Gly Ile Asn Ile Val
            420                 425                 430


<210> SEQ ID NO 116
<211> LENGTH: 437
<212> TYPE: PRT
<213> ORGANISM: Bacillus cereus

<400> SEQUENCE: 116

Met Lys His Asn Asp Cys Phe Gly His Asn Asn Cys Asn Asn Pro Ile
1               5                   10                  15

Val Phe Thr Pro Asp Cys Cys Asn Asn Pro Gln Thr Val Pro Ile Thr
            20                  25                  30

Ser Glu Gln Leu Gly Arg Leu Ile Thr Leu Leu Asn Ser Leu Ile Ala
        35                  40                  45

Ala Ile Ala Ala Phe Phe Ala Asn Pro Ser Asp Ala Asn Arg Leu Ala
    50                  55                  60

Leu Leu Asn Leu Phe Thr Gln Leu Leu Asn Leu Leu Asn Glu Leu Ala
65                  70                  75                  80

Pro Ser Pro Glu Gly Asn Phe Leu Lys Gln Leu Ile Gln Ser Ile Ile
                85                  90                  95

Asn Leu Leu Gln Ser Pro Asn Pro Asn Leu Gly Gln Leu Leu Ser Leu
            100                 105                 110

Leu Gln Gln Phe Tyr Ser Ala Leu Ala Pro Phe Phe Phe Ser Leu Ile
        115                 120                 125
```

```
Leu Asp Pro Ala Ser Leu Gln Leu Leu Leu Asn Leu Leu Ala Gln Leu
    130                 135                 140

Ile Gly Val Thr Pro Gly Gly Gly Ala Thr Gly Pro Thr Gly Pro Thr
145                 150                 155                 160

Gly Pro Gly Gly Gly Ala Thr Gly Pro Thr Gly Pro Thr Gly Pro Gly
                165                 170                 175

Gly Gly Ala Thr Gly Pro Thr Gly Ala Thr Gly Pro Thr Gly Asp Thr
            180                 185                 190

Gly Leu Ala Gly Ala Thr Gly Ala Thr Gly Pro Thr Gly Asp Thr Gly
        195                 200                 205

Val Ala Gly Pro Ala Gly Pro Thr Gly Pro Thr Gly Asp Thr Gly Leu
    210                 215                 220

Ala Gly Ala Thr Gly Pro Thr Gly Pro Thr Gly Asp Thr Gly Leu Ala
225                 230                 235                 240

Gly Ala Thr Gly Pro Thr Gly Ala Thr Gly Leu Ala Gly Ala Thr Gly
                245                 250                 255

Pro Thr Gly Ala Thr Gly Leu Thr Gly Ala Thr Gly Ala Thr Gly Ala
            260                 265                 270

Ala Gly Gly Gly Ala Ile Ile Pro Phe Ala Ser Gly Thr Thr Pro Ala
        275                 280                 285

Ala Leu Val Asn Ala Leu Ile Ala Asn Thr Gly Thr Leu Leu Gly Phe
    290                 295                 300

Gly Phe Ser Gln Pro Gly Ile Gly Leu Ala Gly Gly Thr Ser Ile Thr
305                 310                 315                 320

Leu Ala Leu Gly Val Gly Asp Tyr Ala Phe Val Ala Pro Arg Asp Gly
                325                 330                 335

Val Ile Thr Ser Leu Ala Gly Phe Phe Ser Ala Thr Ala Ala Leu Ser
            340                 345                 350

Pro Leu Ser Pro Val Gln Val Gln Ile Gln Ile Leu Thr Ala Pro Ala
        355                 360                 365

Ala Ser Asn Thr Phe Thr Val Gln Gly Ala Pro Leu Leu Leu Thr Pro
    370                 375                 380

Ala Phe Ala Ala Ile Ala Ile Gly Ser Thr Ala Ser Gly Ile Ile Pro
385                 390                 395                 400

Glu Ala Ile Pro Val Val Ala Gly Asp Lys Ile Leu Leu Tyr Val Ser
                405                 410                 415

Leu Thr Ala Ala Ser Pro Ile Ala Ala Val Ala Gly Phe Val Ser Ala
            420                 425                 430

Gly Ile Asn Ile Val
        435


<210> SEQ ID NO 117
<211> LENGTH: 119
<212> TYPE: PRT
<213> ORGANISM: Bacillus anthracis

<400> SEQUENCE: 117

Met Leu Phe Thr Ser Trp Leu Leu Phe Phe Ile Phe Ala Leu Ala Ala
1               5                   10                  15

Phe Arg Leu Thr Arg Leu Ile Val Tyr Asp Lys Ile Thr Gly Phe Leu
            20                  25                  30

Arg Arg Pro Phe Ile Asp Glu Leu Glu Ile Thr Glu Pro Asp Gly Ser
        35                  40                  45

Val Ser Thr Phe Thr Lys Val Lys Gly Lys Gly Leu Arg Lys Trp Ile
```

```
    50                  55                  60

Gly Glu Leu Leu Ser Cys Tyr Trp Cys Thr Gly Val Trp Val Ser Ala
65                  70                  75                  80

Phe Leu Leu Val Leu Tyr Asn Trp Ile Pro Ile Val Ala Glu Pro Leu
                85                  90                  95

Leu Ala Leu Leu Ala Ile Ala Gly Ala Ala Ala Ile Ile Glu Thr Ile
            100                 105                 110

Thr Gly Tyr Phe Met Gly Glu
        115


<210> SEQ ID NO 118
<211> LENGTH: 61
<212> TYPE: PRT
<213> ORGANISM: Bacillus anthracis

<400> SEQUENCE: 118

Met Phe Ala Val Ser Asn Asn Pro Arg Gln Asn Ser Tyr Asp Leu Gln
1               5                   10                  15

Gln Trp Tyr His Met Gln Gln Gln His Gln Ala Gln Gln Gln Ala Tyr
            20                  25                  30

Gln Glu Gln Leu Gln Gln Gln Gly Phe Val Lys Lys Lys Gly Cys Asn
        35                  40                  45

Cys Gly Lys Lys Lys Ser Thr Ile Lys His Tyr Glu Glu
    50                  55                  60


<210> SEQ ID NO 119
<211> LENGTH: 481
<212> TYPE: PRT
<213> ORGANISM: Bacillus anthracis

<400> SEQUENCE: 119

Met Ser Arg Tyr Asp Asp Ser Gln Asn Lys Phe Ser Lys Pro Cys Phe
1               5                   10                  15

Pro Ser Ser Ala Gly Arg Ile Pro Asn Thr Pro Ser Ile Pro Val Thr
            20                  25                  30

Lys Ala Gln Leu Arg Thr Phe Arg Ala Ile Ile Ile Asp Leu Thr Lys
        35                  40                  45

Ile Ile Pro Lys Leu Phe Ala Asn Pro Ser Pro Gln Asn Ile Glu Asp
    50                  55                  60

Leu Ile Asp Thr Leu Asn Leu Leu Ser Lys Phe Ile Cys Ser Leu Asp
65                  70                  75                  80

Ala Ala Ser Ser Leu Lys Ala Gln Gly Leu Ala Ile Ile Lys Asn Leu
                85                  90                  95

Ile Thr Ile Leu Lys Asn Pro Thr Phe Val Ala Ser Ala Val Phe Ile
            100                 105                 110

Glu Leu Gln Asn Leu Ile Asn Tyr Leu Leu Ser Ile Thr Lys Leu Phe
        115                 120                 125

Arg Ile Asp Pro Cys Thr Leu Gln Glu Leu Leu Lys Leu Ile Ala Ala
    130                 135                 140

Leu Gln Thr Ala Leu Val Asn Ser Ala Ser Phe Ile Gln Gly Pro Thr
145                 150                 155                 160

Gly Pro Thr Gly Pro Thr Gly Pro Thr Gly Pro Ala Gly Ala Thr Gly
                165                 170                 175

Ala Thr Gly Pro Gln Gly Val Gln Gly Pro Ala Gly Ala Thr Gly Ala
            180                 185                 190

Thr Gly Pro Gln Gly Val Gln Gly Pro Ala Gly Ala Thr Gly Ala Thr
```

```
        195                 200                 205

Gly Pro Gln Gly Ala Gln Gly Pro Ala Gly Ala Thr Gly Ala Thr Gly
    210                 215                 220

Pro Gln Gly Ala Gln Gly Pro Ala Gly Ala Thr Gly Ala Thr Gly Pro
225                 230                 235                 240

Gln Gly Ile Gln Gly Pro Ala Gly Ala Thr Gly Ala Thr Gly Pro Gln
                245                 250                 255

Gly Val Gln Gly Pro Thr Gly Ala Thr Gly Ile Gly Val Thr Gly Pro
            260                 265                 270

Thr Gly Pro Ser Gly Gly Pro Ala Gly Ala Thr Gly Pro Gln Gly Pro
        275                 280                 285

Gln Gly Asn Thr Gly Ala Thr Gly Pro Gln Gly Ile Gln Gly Pro Ala
    290                 295                 300

Gly Ala Thr Gly Ala Thr Gly Pro Gln Gly Ala Gln Gly Pro Ala Gly
305                 310                 315                 320

Ala Thr Gly Ala Thr Gly Pro Gln Gly Val Gln Gly Pro Thr Gly Ala
                325                 330                 335

Thr Gly Ile Gly Val Thr Gly Pro Thr Gly Pro Ser Gly Pro Ser Phe
            340                 345                 350

Pro Val Ala Thr Ile Val Val Thr Asn Asn Ile Gln Gln Thr Val Leu
        355                 360                 365

Gln Phe Asn Asn Phe Ile Phe Asn Thr Ala Ile Asn Val Asn Asn Ile
    370                 375                 380

Ile Phe Asn Gly Thr Asp Thr Val Thr Val Ile Asn Ala Gly Ile Tyr
385                 390                 395                 400

Val Ile Ser Val Ser Ile Ser Thr Thr Ala Pro Gly Cys Ala Pro Leu
                405                 410                 415

Gly Val Gly Ile Ser Ile Asn Gly Ala Val Ala Thr Asp Asn Phe Ser
            420                 425                 430

Ser Asn Leu Ile Gly Asp Ser Leu Ser Phe Thr Thr Ile Glu Thr Leu
        435                 440                 445

Thr Ala Gly Ala Asn Ile Ser Val Gln Ser Thr Leu Asn Glu Ile Thr
    450                 455                 460

Ile Pro Ala Thr Gly Asn Thr Asn Ile Arg Leu Thr Val Phe Arg Ile
465                 470                 475                 480

Ala


<210> SEQ ID NO 120
<211> LENGTH: 275
<212> TYPE: PRT
<213> ORGANISM: Bacillus thuringiensis

<400> SEQUENCE: 120

Met Lys Met Lys Arg Gly Ile Thr Thr Leu Leu Ser Val Ala Val Leu
1               5                   10                  15

Ser Thr Ser Leu Val Ala Cys Ser Gly Ile Thr Glu Lys Thr Val Ala
            20                  25                  30

Lys Glu Glu Lys Val Lys Leu Thr Asp Gln Gln Leu Met Ala Asp Leu
        35                  40                  45

Trp Tyr Gln Thr Ala Gly Glu Met Lys Ala Leu Tyr Tyr Gln Gly Tyr
    50                  55                  60

Asn Ile Gly Gln Leu Lys Leu Asp Ala Val Leu Ala Lys Gly Thr Glu
65                  70                  75                  80

Lys Lys Pro Ala Ile Val Leu Asp Leu Asp Glu Thr Val Leu Asp Asn
```

```
                85                  90                  95

Ser Pro His Gln Ala Met Ser Val Lys Thr Gly Lys Gly Tyr Pro Tyr
            100                 105                 110

Lys Trp Asp Asp Trp Ile Asn Lys Ala Glu Ala Glu Ala Leu Pro Gly
        115                 120                 125

Ala Ile Asp Phe Leu Lys Tyr Thr Glu Ser Lys Gly Val Asp Ile Tyr
    130                 135                 140

Tyr Ile Ser Asn Arg Lys Thr Asn Gln Leu Asp Ala Thr Ile Lys Asn
145                 150                 155                 160

Leu Glu Arg Val Gly Ala Pro Gln Ala Thr Lys Glu His Ile Leu Leu
                165                 170                 175

Gln Asp Pro Lys Glu Lys Gly Lys Glu Lys Arg Arg Glu Leu Val Ser
            180                 185                 190

Gln Thr His Asp Ile Val Leu Phe Phe Gly Asp Asn Leu Ser Asp Phe
        195                 200                 205

Thr Gly Phe Asp Gly Lys Ser Val Lys Asp Arg Asn Gln Ala Val Ala
    210                 215                 220

Asp Ser Lys Ala Gln Phe Gly Glu Lys Phe Ile Ile Phe Pro Asn Pro
225                 230                 235                 240

Met Tyr Gly Asp Trp Glu Gly Ala Leu Tyr Asp Tyr Asp Phe Lys Lys
                245                 250                 255

Ser Asp Ala Glu Lys Asp Lys Ile Arg Arg Asp Asn Leu Lys Ser Phe
            260                 265                 270

Asp Thr Lys
        275


<210> SEQ ID NO 121
<211> LENGTH: 795
<212> TYPE: PRT
<213> ORGANISM: Bacillus thuringiensis

<400> SEQUENCE: 121

Met Lys Lys Lys Lys Lys Leu Lys Pro Leu Ala Val Leu Thr Thr Ala
1               5                   10                  15

Ala Val Leu Ser Ser Thr Phe Ala Phe Gly Gly His Ala Ala Tyr Ala
            20                  25                  30

Glu Thr Pro Thr Ser Ser Leu Pro Ile Asp Glu His Leu Ile Pro Glu
        35                  40                  45

Glu Arg Leu Ala Glu Ala Leu Lys Gln Arg Gly Val Ile Asp Gln Ser
    50                  55                  60

Ala Ser Gln Ala Glu Thr Ser Lys Ala Val Glu Lys Tyr Val Glu Lys
65                  70                  75                  80

Lys Lys Gly Glu Asn Pro Gly Lys Glu Ile Leu Thr Gly Asp Ser Leu
                85                  90                  95

Thr Gln Glu Ala Ser Asp Phe Met Lys Lys Val Lys Asp Ala Lys Met
            100                 105                 110

Arg Glu Asn Glu Gln Ala Gln Gln Pro Glu Val Gly Pro Val Ala Gly
        115                 120                 125

Gln Gly Ala Ala Leu Asn Pro Gly Lys Leu Asn Gly Lys Val Pro Thr
    130                 135                 140

Thr Ser Ala Lys Gln Glu Glu Tyr Asn Gly Ala Val Arg Lys Asp Lys
145                 150                 155                 160

Val Leu Val Leu Leu Val Glu Phe Ser Asp Phe Lys His Asn Asn Ile
                165                 170                 175
```

```
Asp Gln Glu Pro Gly Tyr Met Tyr Ser Lys Asp Phe Asn Arg Glu His
            180                 185                 190

Tyr Gln Lys Met Leu Phe Gly Asp Glu Pro Phe Thr Leu Phe Asp Gly
        195                 200                 205

Ser Lys Ile Asn Thr Phe Lys Gln Tyr Tyr Glu Glu Gln Ser Gly Gly
    210                 215                 220

Ser Tyr Thr Val Asp Gly Thr Val Thr Glu Trp Leu Thr Val Pro Gly
225                 230                 235                 240

Lys Ala Ser Asp Tyr Gly Ala Asp Ala Gly Thr Gly His Asp Asn Lys
                245                 250                 255

Gly Pro Leu Gly Pro Lys Asp Leu Val Lys Glu Ala Leu Lys Ala Ala
            260                 265                 270

Val Ala Lys Gly Ile Asn Leu Ala Asp Phe Asp Gln Tyr Asp Gln Tyr
        275                 280                 285

Asp Gln Asn Gly Asn Gly Asn Lys Asn Glu Pro Asp Gly Ile Ile Asp
    290                 295                 300

His Leu Met Val Val His Ala Gly Val Gly Gln Glu Ala Gly Gly Gly
305                 310                 315                 320

Lys Leu Lys Asp Asp Ala Ile Trp Ser His Arg Ser Lys Leu Gly Ser
                325                 330                 335

Lys Pro Tyr Ala Ile Asp Gly Thr Lys Ser Ser Val Ser Asn Trp Gly
            340                 345                 350

Gly Lys Met Ala Ala Tyr Asp Tyr Thr Ile Glu Pro Glu Asp Gly Ala
        355                 360                 365

Val Gly Val Phe Ala His Glu Tyr Gly His Asp Leu Gly Leu Pro Asp
    370                 375                 380

Glu Tyr Asp Thr Lys Tyr Ser Gly Gln Gly Glu Pro Val Glu Ser Trp
385                 390                 395                 400

Ser Ile Met Ser Gly Gly Ser Trp Ala Gly Lys Ile Ala Gly Thr Glu
                405                 410                 415

Pro Thr Ser Phe Ser Pro Gln Asn Lys Glu Phe Phe Gln Lys Asn Met
            420                 425                 430

Lys Gly Asn Trp Ala Asn Ile Leu Glu Val Asp Tyr Asp Lys Leu Ser
        435                 440                 445

Lys Gly Ile Gly Val Ala Thr Tyr Val Asp Gln Ser Thr Thr Lys Ser
    450                 455                 460

Lys Arg Pro Gly Ile Val Arg Val Asn Leu Pro Asp Lys Asp Ile Lys
465                 470                 475                 480

Asn Ile Glu Ser Ala Phe Gly Lys Lys Phe Tyr Tyr Ser Thr Lys Gly
                485                 490                 495

Asn Asp Ile His Thr Thr Leu Glu Thr Pro Val Phe Asp Leu Thr Asn
            500                 505                 510

Ala Lys Asp Ala Lys Phe Asp Tyr Lys Ala Phe Tyr Glu Leu Glu Ala
        515                 520                 525

Lys Tyr Asp Phe Leu Asp Val Tyr Ala Ile Ala Glu Asp Gly Thr Lys
    530                 535                 540

Thr Arg Ile Asp Arg Met Gly Glu Lys Asp Ile Lys Gly Gly Ala Asp
545                 550                 555                 560

Thr Thr Asp Gly Lys Trp Val Asp Lys Ser Tyr Asp Leu Ser Gln Phe
                565                 570                 575

Lys Gly Lys Lys Val Lys Leu Gln Phe Glu Tyr Leu Thr Asp Ile Ala
            580                 585                 590

Val Ala Tyr Lys Gly Phe Ala Leu Asp Asn Ala Ala Leu Thr Val Asp
```

```
        595                 600                 605

Gly Lys Val Val Phe Ser Asp Asp Ala Glu Gly Gln Pro Ala Met Thr
    610                 615                 620

Leu Lys Gly Phe Thr Val Ser Asn Gly Phe Glu Gln Lys Lys His Asn
625                 630                 635                 640

Tyr Tyr Val Glu Trp Arg Asn Tyr Ala Gly Ser Asp Thr Ala Leu Gln
                645                 650                 655

Tyr Ala Arg Gly Pro Val Phe Asn Thr Gly Met Val Val Trp Tyr Ala
            660                 665                 670

Asp Gln Ser Phe Thr Asp Asn Trp Val Gly Val His Pro Gly Glu Gly
        675                 680                 685

Phe Leu Gly Val Val Asp Ser His Pro Glu Ala Ile Val Gly Thr Leu
    690                 695                 700

Asn Gly Gln Pro Thr Val Lys Ser Ser Thr Arg Tyr Gln Ile Ala Asp
705                 710                 715                 720

Ala Ala Phe Ser Phe Asp Gln Thr Pro Ala Trp Lys Val Asn Ser Pro
                725                 730                 735

Thr Arg Gly Ile Phe Asp Tyr Lys Gly Leu Pro Gly Val Ala Lys Phe
            740                 745                 750

Asp Asp Ser Lys Gln Tyr Ile Asn Ser Val Ile Pro Asp Ala Gly Arg
        755                 760                 765

Lys Leu Pro Lys Leu Gly Leu Lys Phe Glu Val Val Gly Gln Ala Glu
    770                 775                 780

Asp Lys Ser Ala Gly Ala Val Trp Leu His Arg
785                 790                 795


<210> SEQ ID NO 122
<211> LENGTH: 798
<212> TYPE: PRT
<213> ORGANISM: Bacillus mycoides

<400> SEQUENCE: 122

Lys Arg Lys Thr Pro Phe Lys Val Phe Ser Ser Leu Ala Ile Thr Thr
1               5                   10                  15

Met Leu Gly Cys Thr Phe Ala Leu Gly Thr Ser Val Ala Tyr Ala Glu
            20                  25                  30

Thr Thr Ser Gln Ser Lys Gly Ser Ile Ser Thr Thr Pro Ile Asp Asn
        35                  40                  45

Asn Leu Ile Gln Glu Glu Arg Leu Ala Glu Ala Leu Lys Glu Arg Gly
    50                  55                  60

Thr Ile Asp Gln Ser Ala Ser Lys Glu Glu Thr Gln Lys Ala Val Glu
65                  70                  75                  80

Gln Tyr Ile Glu Lys Lys Lys Gly Asp Gln Pro Asn Lys Glu Ile Leu
                85                  90                  95

Pro Asp Asp Pro Ala Lys Glu Ala Ser Asp Phe Val Lys Lys Val Lys
            100                 105                 110

Glu Lys Lys Met Glu Glu Lys Glu Lys Val Lys Lys Ser Val Glu Asn
        115                 120                 125

Ala Ser Ser Glu Gln Thr Pro Ser Gln Asn Lys Lys Gln Leu Asn Gly
    130                 135                 140

Lys Val Pro Thr Ser Pro Ala Lys Gln Ala Pro Tyr Asn Gly Ala Val
145                 150                 155                 160

Arg Thr Asp Lys Val Leu Val Leu Leu Val Glu Phe Ser Asp Tyr Lys
                165                 170                 175
```

```
His Asn Asn Ile Glu Gln Ser Pro Gly Tyr Met Tyr Ala Asn Asp Phe
            180                 185                 190

Ser Arg Glu His Tyr Gln Lys Met Leu Phe Gly Asn Glu Pro Phe Thr
        195                 200                 205

Leu Phe Asp Gly Ser Lys Val Lys Thr Phe Lys Gln Tyr Tyr Glu Glu
    210                 215                 220

Gln Ser Gly Gly Ser Tyr Thr Thr Asp Gly Tyr Val Thr Glu Trp Leu
225                 230                 235                 240

Thr Val Pro Gly Lys Ala Ala Asp Tyr Gly Ala Asp Gly Lys Thr Gly
                245                 250                 255

His Asp Asn Lys Gly Pro Lys Gly Ala Arg Asp Leu Val Lys Glu Ala
            260                 265                 270

Leu Lys Ala Ala Ala Glu Lys Gly Leu Asp Leu Ser Gln Phe Asp Gln
        275                 280                 285

Phe Asp Arg Tyr Asp Thr Asn Gly Asp Gly Asn Gln Asn Glu Pro Asp
    290                 295                 300

Gly Val Ile Asp His Leu Met Val Ile His Ala Gly Val Gly Gln Glu
305                 310                 315                 320

Ala Gly Gly Gly Lys Leu Gly Asp Asp Ala Ile Trp Ser His Arg Ser
                325                 330                 335

Lys Leu Ala Gln Asp Pro Val Ala Ile Glu Gly Thr Lys Ser Lys Val
            340                 345                 350

Ser Tyr Trp Asp Gly Lys Val Ala Ala His Asp Tyr Thr Ile Glu Pro
        355                 360                 365

Glu Asp Gly Ala Val Gly Val Phe Ala His Glu Phe Gly His Asp Leu
    370                 375                 380

Gly Leu Pro Asp Glu Tyr Asp Thr Asn Tyr Thr Gly Ala Gly Ser Pro
385                 390                 395                 400

Val Glu Ala Trp Ser Leu Met Ser Gly Gly Ser Trp Thr Gly Arg Ile
                405                 410                 415

Ala Gly Thr Glu Pro Thr Ser Phe Ser Pro Gln Asn Lys Asp Phe Leu
            420                 425                 430

Gln Lys Asn Met Asp Gly Asn Trp Ala Lys Ile Val Glu Val Asp Tyr
        435                 440                 445

Asp Lys Ile Lys Arg Gly Val Gly Phe Pro Thr Tyr Ile Asp Gln Ser
    450                 455                 460

Val Thr Lys Ser Asn Arg Pro Gly Leu Val Arg Val Asn Leu Pro Glu
465                 470                 475                 480

Lys Ser Val Glu Thr Ile Lys Thr Gly Phe Gly Lys His Ala Tyr Tyr
                485                 490                 495

Ser Thr Arg Gly Asp Asp Met His Thr Thr Leu Glu Thr Pro Leu Phe
            500                 505                 510

Asp Leu Thr Lys Ala Ala Asn Ala Lys Phe Asp Tyr Lys Ala Asn Tyr
        515                 520                 525

Glu Leu Glu Ala Glu Cys Asp Phe Ile Glu Val His Ala Val Thr Glu
    530                 535                 540

Asp Gly Thr Lys Thr Leu Ile Asp Lys Leu Gly Asp Lys Val Val Lys
545                 550                 555                 560

Gly Asp Gln Asp Thr Thr Glu Gly Lys Trp Ile Asp Lys Ser Tyr Asp
                565                 570                 575

Leu Ser Gln Phe Lys Gly Lys Lys Val Lys Leu Gln Phe Asp Tyr Ile
            580                 585                 590

Thr Asp Pro Ala Leu Thr Tyr Lys Gly Phe Ala Met Asp Asn Val Asn
```

```
        595                 600                 605

Val Thr Val Asp Gly Lys Val Val Phe Ser Asp Asp Ala Glu Gly Gln
    610                 615                 620

Ala Lys Met Lys Leu Asn Gly Phe Val Val Ser Asp Gly Thr Glu Lys
625                 630                 635                 640

Lys Pro His Tyr Tyr Tyr Leu Glu Trp Arg Asn Tyr Ala Gly Ser Asp
                645                 650                 655

Glu Gly Leu Lys Val Gly Arg Gly Pro Val Tyr Asn Thr Gly Leu Val
            660                 665                 670

Val Trp Tyr Ala Asp Asp Ser Phe Lys Asp Asn Trp Val Gly Arg His
        675                 680                 685

Pro Gly Glu Gly Phe Leu Gly Val Val Asp Ser His Pro Glu Ala Val
    690                 695                 700

Val Gly Asn Leu Asn Gly Lys Pro Val Tyr Gly Asn Thr Gly Leu Gln
705                 710                 715                 720

Ile Ala Asp Ala Ala Phe Ser Leu Asp Gln Thr Pro Ala Trp Asn Val
                725                 730                 735

Asn Ser Phe Thr Arg Gly Gln Phe Asn Tyr Pro Gly Leu Pro Gly Val
            740                 745                 750

Ala Thr Phe Asp Asp Ser Lys Val Tyr Ser Asn Thr Gln Ile Pro Asp
        755                 760                 765

Ala Gly Arg Lys Val Pro Gln Leu Gly Leu Lys Phe Gln Val Val Gly
    770                 775                 780

Gln Ala Asp Asp Lys Ser Ala Gly Ala Ile Trp Ile Arg Arg
785                 790                 795
```

<210> SEQ ID NO 123
<211> LENGTH: 300
<212> TYPE: DNA
<213> ORGANISM: Bacillus cereus

<400> SEQUENCE: 123

```
taactcaatc ttaagagaaa ttgaggagcg cgcaccactt cgtcgtacaa caacgcaaga     60

agaagttggg gatacagcag tattcttatt cagtgattta gcacgcggcg taacaggaga    120

aaacattcac gttgattcag ggtatcatat cttaggataa atataatatt aattttaaag    180

gacaatctct acatgttgag attgtccttt ttatttgttc ttagaaagaa cgatttttaa    240

cgaaagttct taccacgtta tgaatataag tataatagta cacgatttat tcagctacgt    300
```

<210> SEQ ID NO 124
<211> LENGTH: 172
<212> TYPE: DNA
<213> ORGANISM: Bacillus cereus

<400> SEQUENCE: 124

```
acgttgattc agggtatcat atcttaggat aaatataata ttaattttaa aggacaatct     60

ctacatgttg agattgtcct ttttatttgt tcttagaaag aacgattttt aacgaaagtt    120

cttaccacgt tatgaatata agtataatag tacacgattt attcagctac gt            172
```

<210> SEQ ID NO 125
<211> LENGTH: 291
<212> TYPE: DNA
<213> ORGANISM: Bacillus cereus

<400> SEQUENCE: 125

```
cataaaaatc tacttttctt gtcaaagagt atgcttatat gcgtgctctt tttatttggt     60
```

```
tttctttcat ttctaaataa cattttcaac tctattcata ctattctttc aactttaggt    120

tacaaactat ttctgtaagc gtagtgtttc ttttgtacta taggcagtta gttttatcca    180

taacagtaca cctctgcact attcactata aattttcata tattatattg tgcttgtcca    240

aaacatgtgg ttattactca cgcgatctaa atgaaagaaa ggagtgaaaa t             291


<210> SEQ ID NO 126
<211> LENGTH: 94
<212> TYPE: DNA
<213> ORGANISM: Bacillus cereus

<400> SEQUENCE: 126

actattcact ataaattttc atatattata ttgtgcttgt ccaaaacatg tggttattac     60

tcacgcgatc taaatgaaag aaaggagtga aaat                                 94


<210> SEQ ID NO 127
<211> LENGTH: 300
<212> TYPE: DNA
<213> ORGANISM: Bacillus thuringiensis

<400> SEQUENCE: 127

aatacatgat aatgaaatcc gattttgtgt tttatatagt gaattatcaa atattgtgta     60

gatgaaacaa agataaaatc cccattaaac tccctctatg gaaattataa attgttcgat    120

aaaaactttc aatattttca gaaaacattg ttgaattgtg atatattcgt atgctaacta    180

tgaaattttt acaaatatat taaaaacatt acataatatg actaaatatt gaaaaaatat    240

tgaattttta ataaaattta atttgtaata catattattt attaggggag gaaataaggg    300


<210> SEQ ID NO 128
<211> LENGTH: 48
<212> TYPE: DNA
<213> ORGANISM: Bacillus thuringiensis

<400> SEQUENCE: 128

aaaatttaat ttgtaataca tattatttat taggggagga aataaggg                  48


<210> SEQ ID NO 129
<211> LENGTH: 300
<212> TYPE: DNA
<213> ORGANISM: Bacillus mycoides

<400> SEQUENCE: 129

aattgtgcat attgtctttt aaattttcta tctaagttat ttaatatata ataaataact     60

ctttttgtg agttttttg atacgaggta aataatcagt acagggtctg accagaggac    120

tggagggcat gattctataa gggaatattt actattccat gattatagaa ctatgtcttt    180

tttattgtat atagaagggg ggataggtct atattataga acttatatat attgtgcatt    240

ccatattatc aattatctaa attttaagtc ttgttacaat taataaggga ggaaatagta    300


<210> SEQ ID NO 130
<211> LENGTH: 80
<212> TYPE: DNA
<213> ORGANISM: Bacillus mycoides

<400> SEQUENCE: 130

acttatatat attgtgcatt ccatattatc aattatctaa attttaagtc ttgttacaat     60

taataaggga ggaaatagta                                                 80
```

<210> SEQ ID NO 131
<211> LENGTH: 141
<212> TYPE: DNA
<213> ORGANISM: Bacillus thuringiensis

<400> SEQUENCE: 131
aatgacgttt tcaagtttga ttatcattca tgtttcctat tttaagagaa acatataact 60
caactacttt tttcaatggc atcttttata gtacttagaa taggaaaaca ctcaactata 120
agaaaagtaa ggaggaaata a 141

<210> SEQ ID NO 132
<211> LENGTH: 79
<212> TYPE: DNA
<213> ORGANISM: Bacillus thuringiensis

<400> SEQUENCE: 132
actacttttt tcaatggcat cttttatagt acttagaata ggaaaacact caactataag 60
aaaagtaagg aggaaataa 79

<210> SEQ ID NO 133
<211> LENGTH: 300
<212> TYPE: DNA
<213> ORGANISM: Bacillus cereus

<400> SEQUENCE: 133
atatgctaat gcttagtttt tatactcaag ttaaaatgtg cttttggacc taagagataa 60
acgtggaaaa ataaaataaa ctcttaagtt taggtgttta atctaagcag tcaattatta 120
aaaacatata attaatatgt gagtcatgaa cataattaaa taatgttttc aagtttaatt 180
atcgttcatg tttcctattt taagcagaac aaataactca attacttttt tcgattggat 240 ctttttaac tcttataata ggaaaacact caactataaa aataagtaag gaggaaataa 300

<210> SEQ ID NO 134
<211> LENGTH: 167
<212> TYPE: DNA
<213> ORGANISM: Bacillus cereus

<400> SEQUENCE: 134
aatatgtgag tcatgaacat aattaaataa tgttttcaag tttaattatc gttcatgttt 60
cctattttaa gcagaacaaa taactcaatt actttttcg attggatctt ttttaactct 120
tataatagga aaacactcaa ctataaaaat aagtaaggag gaaataa 167

<210> SEQ ID NO 135
<211> LENGTH: 300
<212> TYPE: DNA
<213> ORGANISM: Bacillus thuringiensis

<400> SEQUENCE: 135
tataaaataa aagggcgtgt atttgctact gatgcagtat tgtgtgcgcc taaaaatgga 60
atttcacaac cagatccaca tgttgttgta gaacaatctt gtaattcatt gatgaatttt 120
acaacgtcaa ctacacaatg agaagagcca tggtgtttat tttcgttaca actcattaat 180
gtcactcctt atcttcttgt ttgtatttac attaataaga tattggagtt gaggagattt 240
ggtcacaatc tcaagacctt ttttttaaat aggcgaaaga ggataaggga aggtggaatt 300

<210> SEQ ID NO 136
<211> LENGTH: 106

<212> TYPE: DNA
<213> ORGANISM: Bacillus thuringiensis

<400> SEQUENCE: 136
tcttgtttgt atttacatta ataagatatt ggagttgagg agatttggtc acaatctcaa 60 gaccttttt ttaaataggc gaaagaggat aagggaaggt ggaatt 106

<210> SEQ ID NO 137
<211> LENGTH: 300
<212> TYPE: DNA
<213> ORGANISM: Bacillus thuringiensis

<400> SEQUENCE: 137
atcaactttt acaaaagtaa agggtaaagg attaagaaag tggattggcg aattattaag 60
ctgttattgg tgtacaggtg tatgggttag tgctttttta ttagttttat ataattggat 120
tccgatcgtt gcagagccgt tacttgcatt attagctatt gcaggagcag cagcaatcat 180
tgaaacgatt acaggatatt ttatgggaga ataatatatt ttcataatac gagaaaaagc 240
ggagtttaaa agaatgaggg aacggaaata aagagttgtt catatagtaa atagacagaa 300

<210> SEQ ID NO 138
<211> LENGTH: 39
<212> TYPE: DNA
<213> ORGANISM: Bacillus thuringiensis

<400> SEQUENCE: 138
acggaaataa agagttgttc atatagtaaa tagacagaa 39

<210> SEQ ID NO 139
<211> LENGTH: 300
<212> TYPE: DNA
<213> ORGANISM: Bacillus anthracis

<400> SEQUENCE: 139
tgaagtatct agagctaatt tacgcaaagg aatctcagga caacactttc gcaacaccta 60
tattttaaat ttaataaaaa aagagactcc ggagtcagaa attataaagc tagctgggtt 120
caaatcaaaa atttcactaa aacgatatta tcaatacgca gaaaatggaa aaaacgcctt 180
atcataaggc gttttttcca tttttttcttc aaacaaacga ttttactatg accatttaac 240
taatttttgc atctactatg atgagtttca ttcacattct cattagaaag gagagattta 300

<210> SEQ ID NO 140
<211> LENGTH: 70
<212> TYPE: DNA
<213> ORGANISM: Bacillus anthracis

<400> SEQUENCE: 140
accatttaac taatttttgc atctactatg atgagtttca ttcacattct cattagaaag 60
gagagattta 70

<210> SEQ ID NO 141
<211> LENGTH: 300
<212> TYPE: DNA
<213> ORGANISM: Bacillus cereus

<400> SEQUENCE: 141
gactatgttt attcaggata aaatatagca ctacactctc tcctcttatt atgtagcatc 60
tctctaatcc atcatttgtt tcatttagtt aaaattgtaa ataaaatcac atgatttgtc 120

```
aattataatt gtcatttcga caattaaact tgtcaaaata attctcatca ttttttctca    180

tctttctaat ataggacata ctactatata tacaaaagac aatatgcaaa tgttcataca    240

aaaaatatta tttttcgata tataatatta actgattttc taacatcaag gagggtacat    300


<210> SEQ ID NO 142
<211> LENGTH: 84
<212> TYPE: DNA
<213> ORGANISM: Bacillus cereus

<400> SEQUENCE: 142

agacaatatg caaatgttca tacaaaaaat attatttttc gatatataat attaactgat     60

tttctaacat caaggagggt acat                                             84


<210> SEQ ID NO 143
<211> LENGTH: 300
<212> TYPE: DNA
<213> ORGANISM: Bacillus thuringiensis

<400> SEQUENCE: 143

atagtgagta atatggtaat ccatagatta aatagtatag aaaatattta attcttattt     60

ttattaaaaa agcatgaatc ccagatttac tgggttttga ttgtaactaa gaacatataa    120

aagttcactg ttatttatag gagagtctgt ttgtttttat atcttatgta tttcaccctg    180

cataaaaaaa tatttctcaa cattttattt gttgaaaaat attgaatatt cgtattataa    240

cgaatattat gttgttatcg gcaaaaaacg ataatttgca gacactgggg aggaaataca    300


<210> SEQ ID NO 144
<211> LENGTH: 139
<212> TYPE: DNA
<213> ORGANISM: Bacillus thuringiensis

<400> SEQUENCE: 144

tcttatgtat ttcaccctgc ataaaaaaat atttctcaac attttatttg ttgaaaaata     60

ttgaatattc gtattataac gaatattatg ttgttatcgg caaaaaacga taatttgcag    120

acactgggga ggaaataca                                                  139


<210> SEQ ID NO 145
<211> LENGTH: 300
<212> TYPE: DNA
<213> ORGANISM: Bacillus cereus

<400> SEQUENCE: 145

cttcgtcagc aataagtgtg agcggagaat tggttgatct tggctttaca attggagcat     60

tgacgaaaga ctctttaacg tggtcgcata acggagtaga atatatgctc gtgtctaaag    120

gtttagagcc gaaggagcta ttaatggttg ctcgttcagt tacagagaag caagtgaagt    180

aaacttctta gacgtggtga tatatgtgca ccacgtcttt tcttagtttg aagggtggat    240

ttcataaaag aagcatataa aagaataagc ttcgcatatc gtgtataagg aagtgtattt    300


<210> SEQ ID NO 146
<211> LENGTH: 44
<212> TYPE: DNA
<213> ORGANISM: Bacillus cereus

<400> SEQUENCE: 146

ataaaagaat aagcttcgca tatcgtgtat aaggaagtgt attt                       44
```

<210> SEQ ID NO 147
<211> LENGTH: 300
<212> TYPE: DNA
<213> ORGANISM: Bacillus thuringiensis

<400> SEQUENCE: 147
catttcaaat aatgaacgct tcgattgaat cggagctatt ttcaaatcaa tttcagtata 60
ttgatccagc atttgaatag aagtatcaac agcaacttta agttgatgca atgcagattg 120
tacaaacatt gtaattctcc tcttctccgt atataatagt ttcttgaggg tattatatca 180
tgctcaaaat tccgaaaatt ctagtagttt gactagcata ttgaaaagta ttatattgta 240
aaaggtcata tgaaacgtga aatagaatgg aatgcaatta ttgagttagg agttagacca 300

<210> SEQ ID NO 148
<211> LENGTH: 70
<212> TYPE: DNA
<213> ORGANISM: Bacillus thuringiensis

<400> SEQUENCE: 148
ttatattgta aaaggtcata tgaaacgtga aatagaatgg aatgcaatta ttgagttagg 60
agttagacca 70

<210> SEQ ID NO 149
<211> LENGTH: 300
<212> TYPE: DNA
<213> ORGANISM: Bacillus cereus

<400> SEQUENCE: 149
atcgatggaa cctgtatcaa ccactataat ttcatccaca attttttcaa ctgagtctaa 60
acaacgggct attgtcttct cctcatctcg aacaatcata cataaactaa ttgtaattcc 120
ttgcttgttc aacataatca ccctcttcca aatcaatcat atgttataca tatactaaac 180
tttccatttt tttaaattgt tcaagtagtt taagatttct tttcaataat tcaaatgtcc 240
gtgtcatttt ctttcggttt tgcatctact atataatgaa cgctttatgg aggtgaattt 300

<210> SEQ ID NO 150
<211> LENGTH: 150
<212> TYPE: DNA
<213> ORGANISM: Bacillus cereus

<400> SEQUENCE: 150
aatcaatcat atgttataca tatactaaac tttccatttt tttaaattgt tcaagtagtt 60
taagatttct tttcaataat tcaaatgtcc gtgtcatttt ctttcggttt tgcatctact 120
atataatgaa cgctttatgg aggtgaattt 150

<210> SEQ ID NO 151
<211> LENGTH: 300
<212> TYPE: DNA
<213> ORGANISM: Bacillus thuringiensis

<400> SEQUENCE: 151
gacctgtaag tctgtaggga agaataattt caagagccag tgataataga tttttttgtt 60
ttttcattct tatcttgaat ataaatcacc tcatctttta attagaacgt aaccaattta 120
gtattttgaa atagagctat cattttataa tatgaatact actagttata gaaacggcaa 180
aaagtttaat atatgtaaaa atcatttgga tatgaaaaaa gtagccatag attttttcga 240
aatgataaat gttttatttt gttaattagg aaacaaaaat gtggaatgag gggatttaa 300

<210> SEQ ID NO 152
<211> LENGTH: 91
<212> TYPE: DNA
<213> ORGANISM: Bacillus thuringiensis

<400> SEQUENCE: 152
atatgaaaaa agtagccata gattttttcg aaatgataaa tgttttattt tgttaattag 60
gaaacaaaaa tgtggaatga gggggattta a 91

<210> SEQ ID NO 153
<211> LENGTH: 300
<212> TYPE: DNA
<213> ORGANISM: Bacillus anthracis

<400> SEQUENCE: 153
ttttcatctg ctacatcgtg aagtaatgct gccatttcaa ttataaaacg atttcctcct 60
tcttgctcgg ataaagaaat cgccagttta tgtacacgct caatatgata ccaatcatgc 120
ccactggcat ctttttctaa aatatgtttt acaaaagtaa ttgttttttc tatctttttct 180 tgttttgtca ttttatcttc acccagttac ttattgtaac acgcccgcat tttttcatca 240
catattttct tgtccgccca tacactaggt ggtaggcatc atcatgaagg aggaatagat 300

<210> SEQ ID NO 154
<211> LENGTH: 61
<212> TYPE: DNA
<213> ORGANISM: Bacillus anthracis

<400> SEQUENCE: 154
acatattttc ttgtccgccc atacactagg tggtaggcat catcatgaag gaggaataga 60
t 61

<210> SEQ ID NO 155
<211> LENGTH: 300
<212> TYPE: DNA
<213> ORGANISM: Bacillus anthracis

<400> SEQUENCE: 155
ggtgacgaca acatatacaa gaggcactcc tgctggtact gtaacaggaa caaatatggg 60
gcaaagtgta aatacatcgg gtatagcaca agctgtcccg aatacagata atatggattc 120
aacggcggga ctcccttaag aaattagggg agtctttatt tggaaaaaga gcttatgtta 180
cataaaaaca ggagtaattg ttttaaaagt agtattggtg acgttgttag aaaatacaat 240
ttaagtagaa ggtgcgtttt tatatgaaat atattttata gctgtacttt acctttcaag 300

<210> SEQ ID NO 156
<211> LENGTH: 213
<212> TYPE: DNA
<213> ORGANISM: Bacillus anthracis

<400> SEQUENCE: 156
acaagctgtc ccgaatacag ataatatgga ttcaacggcg ggactccctt aagaaattag 60
gggagtcttt atttggaaaa agagcttatg ttacataaaa acaggagtaa ttgttttaaa 120
agtagtattg gtgacgttgt tagaaaatac aatttaagta gaaggtgcgt tttatatga 180 aatatatttt atagctgtac tttacctttc aag 213

<210> SEQ ID NO 157
<211> LENGTH: 300

<212> TYPE: DNA
<213> ORGANISM: Bacillus anthracis

<400> SEQUENCE: 157
atttatttca ttcaattttt cctatttagt acctaccgca ctcacaaaaa gcacctctca 60
ttaatttata ttatagtcat tgaaatctaa tttaatgaaa tcatcatact atatgtttta 120
taagaagtaa aggtaccata cttaattaat acatatctat acacttcaat atcacagcat 180
gcagttgaat tatatccaac tttcatttca aattaaataa gtgcctccgc tattgtgaat 240
gtcatttact ctccctacta catttaataa ttatgacaag caatcatagg aggttactac 300

<210> SEQ ID NO 158
<211> LENGTH: 180
<212> TYPE: DNA
<213> ORGANISM: Bacillus anthracis

<400> SEQUENCE: 158
taagaagtaa aggtaccata cttaattaat acatatctat acacttcaat atcacagcat 60
gcagttgaat tatatccaac tttcatttca aattaaataa gtgcctccgc tattgtgaat 120
gtcatttact ctccctacta catttaataa ttatgacaag caatcatagg aggttactac 180

<210> SEQ ID NO 159
<211> LENGTH: 300
<212> TYPE: DNA
<213> ORGANISM: Bacillus cereus

<400> SEQUENCE: 159
agttgtacaa gaatttaaat cttcacaaac atatgtaaat gacttactac agctagttgc 60
aagtacgatt tctaacaacg taacagatga aatattaatt tcaactaatg gcgatgtatt 120
gaagggtgaa acgggcgcag cggtagaaag taaaaaagga aattgtggtt gttaaagaga 180
tgtcgaaatg acatctcttt ttttagtgga ttaaacgtaa gttcttctca aaaaaagaat 240
gacacattcc gctattgtca cgcatatgat taagtgaata gtgattgagg agggttacga 300

<210> SEQ ID NO 160
<211> LENGTH: 57
<212> TYPE: DNA
<213> ORGANISM: Bacillus cereus

<400> SEQUENCE: 160
acattccgct attgtcacgc atatgattaa gtgaatagtg attgaggagg gttacga 57

<210> SEQ ID NO 161
<211> LENGTH: 300
<212> TYPE: DNA
<213> ORGANISM: Bacillus cereus

<400> SEQUENCE: 161
aacgttatta gcgtagacaa acaagtaacg gcagaagcag ttcttgcatt aaatcgtatg 60
ttagagcgtg tgtaaagcaa cggtattccc gttgcttttt ttcatacata taatcataac 120
gagaacgaaa tgggcataca ttgttttgaa gaaatcattg tggttcttta tgcttattcc 180
acttcgaatg atattgaaaa tcgaagaagt gataaaagta aaaagaagtt aatgttattt 240
agaaagagtt acttcatgag atttgttact tatagataag ttatacagga gggggaaaat 300

<210> SEQ ID NO 162
<211> LENGTH: 47
<212> TYPE: DNA

<213> ORGANISM: Bacillus cereus

<400> SEQUENCE: 162
tcatgagatt tgttacttat agataagtta tacaggaggg ggaaaat 47

<210> SEQ ID NO 163
<211> LENGTH: 300
<212> TYPE: DNA
<213> ORGANISM: Bacillus thuringiensis

<400> SEQUENCE: 163
aagccgcggt caatgctgta tatgcaaata agattgcagc tttacctgaa gaagagcgtg 60
atagcttcat tgctgaaaaa cgagaagagt ataagaaaga tattgatatt taccatttag 120
catcagagat ggtcattgat ggtattgttc atccaaacaa tttaagagaa gagttaaaag 180
gacgattcga aatgtatatg agtaaatatc aagtatttac ggatcgtaaa catcctgttt 240
atccagttta aaagccctat ttagggcttt cttgctcaaa aagttaagga ggggaaaaca 300

<210> SEQ ID NO 164
<211> LENGTH: 92
<212> TYPE: DNA
<213> ORGANISM: Bacillus thuringiensis

<400> SEQUENCE: 164
tcaagtattt acggatcgta aacatcctgt ttatccagtt taaaagccct atttagggct 60
ttcttgctca aaaagttaag gaggggaaaa ca 92

<210> SEQ ID NO 165
<211> LENGTH: 300
<212> TYPE: DNA
<213> ORGANISM: Bacillus cereus

<400> SEQUENCE: 165
aggatttcag tgggacgcct cctctcttct tacattaaat taatcatact ataaaatgaa 60
agaaatgaaa tgaaaaatag cggaaaaatc agaaattttt tctggtagta tacaatatgt 120
tacaataagc tttgtcaatg aaagaaggaa ttccgtgcaa tgcacgggag aggttcgcga 180
actccctcta taaaaaacta tggaaacaac aatatcttta ggtattgttt tgttttttta 240
ttgtgacagt tcaagaacgt tctttcttct tattcgtagt agagaaggag aatgagtgaa 300

<210> SEQ ID NO 166
<211> LENGTH: 104
<212> TYPE: DNA
<213> ORGANISM: Bacillus cereus

<400> SEQUENCE: 166
actatggaaa caacaatatc tttaggtatt gttttgtttt tttattgtga cagttcaaga 60
acgttctttc ttcttattcg tagtagagaa ggagaatgag tgaa 104

<210> SEQ ID NO 167
<211> LENGTH: 300
<212> TYPE: DNA
<213> ORGANISM: Bacillus cereus

<400> SEQUENCE: 167
ttttgcacaa cgccgtaaaa ctttaatgaa taatttatca aataatttaa atggtttccc 60
gaaagataaa gagctgttgg atcgaatttt aacagaagta ggaattgatc caaaacgaag 120
aggcgaaacg ctatctatcg aagagtttgc gacattaagt aatgcattag ttcttcataa 180
gttatcataa gaatacaaaa gggacagttc aatttgaact gtcccttttg tcacctttct 240
cctcctaaat tcatacttta aaaacaggta agatggccta acgagtttgg aggtaggaga 300

<210> SEQ ID NO 168
<211> LENGTH: 63
<212> TYPE: DNA
<213> ORGANISM: Bacillus cereus

<400> SEQUENCE: 168
tctcctccta aattcatact ttaaaaacag gtaagatggc ctaacgagtt tggaggtagg 60
aga 63

<210> SEQ ID NO 169
<211> LENGTH: 300
<212> TYPE: DNA
<213> ORGANISM: Bacillus thuringiensis

<400> SEQUENCE: 169
ggaaacagaa gtcatcccat ttgaaaatgc agcaggtcgt attatagctg atttcgttat 60
ggtttatccg ccagggattc caatctttac tccgggggaa attattacac aagacaactt 120
agagtatatt cgtaaaaact tagaagcagg tttacctgta caaggtcctg aagatatgac 180
attacaaaca ttacgcgtga tcaaagagta caagcctatc agttgatagg cttttttca 240 cccttttcc cttttctcat acgatattat gtaatgtaac gtataggtgg ggatactact 300

<210> SEQ ID NO 170
<211> LENGTH: 61
<212> TYPE: DNA
<213> ORGANISM: Bacillus thuringiensis

<400> SEQUENCE: 170 acccttttc ccttttctca tacgatatta tgtaatgtaa cgtataggtg gggatactac 60
t 61

<210> SEQ ID NO 171
<211> LENGTH: 300
<212> TYPE: DNA
<213> ORGANISM: Bacillus cereus

<400> SEQUENCE: 171
attgtggacc cttagctcag ctggttagag cagacggctc ataaccgtcc ggtcgtaggt 60
tcgagtccta cagggtccat atccatttca catgtttatt atgtcggcag gaagcttcct 120
tgtagaaggg agcttttttt atgaaatata tgagcatttt aattgaaatg aagtgggaat 180
tttgctactt taatgatagc aagacaatgt gatttatttg tttgcaccct atggcaatta 240
gggtagaatg aagttgtatg tcacttaagt ggcaatacat aaactgggag gaatataaca 300

<210> SEQ ID NO 172
<211> LENGTH: 38
<212> TYPE: DNA
<213> ORGANISM: Bacillus cereus

<400> SEQUENCE: 172
acttaagtgg caatacataa actgggagga atataaca 38

<210> SEQ ID NO 173
<211> LENGTH: 300
<212> TYPE: DNA

<213> ORGANISM: Bacillus cereus

<400> SEQUENCE: 173
aatataacag aaaattctga tgttttttca aatcctataa taaggagtgt tccgtatgat 60
gcctttatat tttccggaag ataaaacaga atatattatt ccagggattg tttgtgttct 120
atttatcatc ggtgcgattg ctacgtggcg tatgttcatt cgtgtatcaa aacgagaagc 180
agagcgatta cagaaagttg aagaaaagct gttagctgaa aagaaacagt aactcatttt 240
tgtatgtttc cctctatgct cggacaatct aagggcagaa tgtattttgg agggaatgaa 300

<210> SEQ ID NO 174
<211> LENGTH: 228
<212> TYPE: DNA
<213> ORGANISM: Bacillus cereus

<400> SEQUENCE: 174
tccggaagat aaaacagaat atattattcc agggattgtt tgtgttctat ttatcatcgg 60
tgcgattgct acgtggcgta tgttcattcg tgtatcaaaa cgagaagcag agcgattaca 120
gaaagttgaa gaaaagctgt tagctgaaaa gaaacagtaa ctcatttttg tatgtttccc 180
tctatgctcg gacaatctaa gggcagaatg tattttggag ggaatgaa 228

<210> SEQ ID NO 175
<211> LENGTH: 166
<212> TYPE: DNA
<213> ORGANISM: Bacillus anthracis

<400> SEQUENCE: 175
taatcaccct cttccaaatc aatcatatgt tatacatata ctaaactttc catttttta 60 aattgttcaa gtagtttaag atttcttttc aataattcaa atgtccgtgt cattttcttt 120
cggttttgca tctactatat aatgaacgct ttatggaggt gaattt 166

<210> SEQ ID NO 176
<211> LENGTH: 173
<212> TYPE: DNA
<213> ORGANISM: Bacillus anthracis

<400> SEQUENCE: 176
aattacataa caagaactac attagggagc aagcagtcta gcgaaagcta actgcttttt 60
tattaaataa ctattttatt aaatttcata tatacaatcg cttgtccatt tcatttggct 120
ctacccacgc atttactatt agtaatatga atttttcaga ggtggatttt att 173

<210> SEQ ID NO 177
<211> LENGTH: 121
<212> TYPE: DNA
<213> ORGANISM: Bacillus weihenstephanensis

<400> SEQUENCE: 177
ctatgattta agatacacaa tagcaaaaga gaaacatatt atataacgat aaatgaaact 60
tatgtatatg tatggtaact gtatatatta ctacaataca gtatactcat aggaggtagg 120
t 121

<210> SEQ ID NO 178
<211> LENGTH: 373
<212> TYPE: DNA
<213> ORGANISM: Bacillus weihenstephanensis

<400> SEQUENCE: 178

```
ggtaggtaga tttgaaatat gatgaagaaa aggaataact aaaaggagtc gatatccgac      60

tccttttagt tataaataat gtggaattag agtataattt tatataggta tattgtatta     120

gatgaacgct ttatccttta attgtgatta atgatggatt gtaagagaag gggcttacag     180

tccttttttt atggtgttct ataagccttt ttaaaagggg taccacccca cacccaaaaa     240

caggggggt tataactaca tattggatgt tttgtaacgt acaagaatcg gtattaatta      300

ccctgtaaat aagttatgtg tatataaggt aactttatat attctcctac aataaaataa     360

aggaggtaat aaa                                                        373
```

<210> SEQ ID NO 179
<211> LENGTH: 225
<212> TYPE: DNA
<213> ORGANISM: Bacillus thuringiensis

<400> SEQUENCE: 179

```
aacccttaat gcattggtta aacattgtaa agtctaaagc atggataatg ggcgagaagt      60

aagtagattg ttaacaccct gggtcaaaaa ttgatattta gtaaaattag ttgcactttg     120

tgcatttttt cataagatga gtcatatgtt ttaaattgta gtaatgaaaa acagtattat     180

atcataatga attggtatct taataaaaga gatggaggta actta                     225
```

<210> SEQ ID NO 180
<211> LENGTH: 115
<212> TYPE: DNA
<213> ORGANISM: Bacillus thuringiensis

<400> SEQUENCE: 180

```
taattccacc ttcccttatc ctctttcgcc tatttaaaaa aaggtcttga gattgtgacc      60

aaatctcctc aactccaata tcttattaat gtaaatacaa acaagaagat aagga          115
```

<210> SEQ ID NO 181
<211> LENGTH: 144
<212> TYPE: DNA
<213> ORGANISM: Bacillus thuringiensis

<400> SEQUENCE: 181

```
aggatgtctt tttttatatt gtattatgta catccctact atataaattc cctgctttta      60

tcgtaagaat taacgtaata tcaaccatat cccgttcata ttgtagtagt gtatgtcaga     120

actcacgaga aggagtgaac ataa                                            144
```

<210> SEQ ID NO 182
<211> LENGTH: 125
<212> TYPE: DNA
<213> ORGANISM: Bacillus thuringiensis

<400> SEQUENCE: 182

```
ttaatgtcac tccttatctt cttgtttgta tttacattaa taagatattg gagttgagga      60

gatttggtca caatctcaag accttttttt taaataggcg aaagaggata agggaaggtg     120

gaatt                                                                 125
```

<210> SEQ ID NO 183
<211> LENGTH: 87
<212> TYPE: DNA
<213> ORGANISM: Bacillus thuringiensis

<400> SEQUENCE: 183

```
atatattttc ataatacgag aaaaagcgga gtttaaaaga atgagggaac ggaaataaag     60

agttgttcat atagtaaata gacagaa                                          87


<210> SEQ ID NO 184
<211> LENGTH: 168
<212> TYPE: DNA
<213> ORGANISM: Bacillus thuringiensis

<400> SEQUENCE: 184

aaactaaata atgagctaag catggattgg gtggcagaat tatctgccac ccaatccatg     60

cttaacgagt attattatgt aaatttctta aaattgggaa cttgtctaga acatagaacc    120

tgtccttttc attaactgaa agtagaaaca gataaaggag tgaaaaac                 168


<210> SEQ ID NO 185
<211> LENGTH: 111
<212> TYPE: DNA
<213> ORGANISM: Bacillus thuringiensis

<400> SEQUENCE: 185

attcactaca acggggatga gtttgatgcg gatacatatg agaagtaccg gaaagtgttt     60

gtagaacatt acaaagatat attatctcca tcataaagga gagatgcaaa g             111


<210> SEQ ID NO 186
<211> LENGTH: 273
<212> TYPE: DNA
<213> ORGANISM: Bacillus anthracis

<400> SEQUENCE: 186

cgcgcaccac ttcgtcgtac aacaacgcaa gaagaagttg gggatacagc agtattctta     60

ttcagtgatt tagcacgcgg cgtaacagga gaaaacattc acgttgattc agggtatcat    120

atcttaggat aaatataata ttaattttaa aggacaatct ctacatgttg agattgtcct    180

ttttatttgt tcttagaaag aacgattttt aacgaaagtt cttaccacgt tatgaatata    240

agtataatag tacacgattt attcagctac gta                                 273


<210> SEQ ID NO 187
<211> LENGTH: 240
<212> TYPE: DNA
<213> ORGANISM: Bacillus anthracis

<400> SEQUENCE: 187

tatatcatat gtaaaattag ttcttattcc cacatatcat atagaatcgc catattatac     60

atgcagaaaa ctaagtatgg tattattctt aaattgttta gcaccttcta atattacaga    120

tagaatccgt cattttcaac agtgaacatg gatttcttct gaacacaact ctttttcttt    180

ccttatttcc aaaaagaaaa gcagcccatt ttaaaatacg gctgcttgta atgtacatta    240


<210> SEQ ID NO 188
<211> LENGTH: 267
<212> TYPE: DNA
<213> ORGANISM: Bacillus thuringiensis

<400> SEQUENCE: 188

tatcacataa ctctttattt ttaatatttc gacataaagt gaaactttaa tcagtggggg     60

ctttgttcat ccccccactg attattaatt gaaccaaggg ataaaaagat agagggtctg    120

accagaaaac tggagggcat gattctataa caaaaagctt aatgtttata gaattatgtc    180

tttttatata gggagggtag taaacagaga tttggacaaa aatgcaccga tttatctgaa    240
```

ttttaagttt tataaagggg agaaatg 267

<210> SEQ ID NO 189
<211> LENGTH: 124
<212> TYPE: DNA
<213> ORGANISM: Bacillus thuringiensis

<400> SEQUENCE: 189 atttttact tagcagtaaa actgatatca gttttactgc tttttcattt ttaaattcaa 60
tcattaaatc ttccttttct acatagtcat aatgttgtat gacattccgt aggaggcact 120
tata 124

<210> SEQ ID NO 190
<211> LENGTH: 170
<212> TYPE: DNA
<213> ORGANISM: Bacillus thuringiensis

<400> SEQUENCE: 190
acataaattc acctccataa agcgttcatt atatagtaga tgcaaaaccg aaagaaaatg 60
acacggacat ttgaattatt gaaaagaaat cttaaactac ttgaacaatt taaaaaaatg 120
gaaagtttag tatatgtata acatatgatt gatttggaag agggtgatta 170

<210> SEQ ID NO 191
<211> LENGTH: 212
<212> TYPE: DNA
<213> ORGANISM: Bacillus thuringiensis

<400> SEQUENCE: 191
ttctattttc caacataaca tgctacgatt aaatggtttt ttgcaaatgc cttcttggga 60
agaaggatta gagcgttttt ttatagaaac caaaagtcat taacaatttt aagttaatga 120 ctttttgtt tgcctttaag aggttttatg ttactataat tatagtatca ggtactaata 180
acaagtataa gtatttctgg gaggatatat ca 212

<210> SEQ ID NO 192
<211> LENGTH: 180
<212> TYPE: PRT
<213> ORGANISM: Bacillus cereus

<400> SEQUENCE: 192

Met Ser Glu Phe Arg Glu Ile Ile Thr Lys Ala Val Val Gly Lys Gly
1 5 10 15

Arg Lys Tyr Thr Lys Ser Thr His Thr Cys Glu Ser Asn Asn Glu Pro
20 25 30

Thr Ser Ile Leu Gly Cys Trp Val Ile Asn His Ser Tyr Glu Ala Arg
35 40 45

Lys Asn Gly Lys His Val Glu Ile Glu Gly Phe Tyr Asp Val Asn Thr
50 55 60

Trp Tyr Ser Phe Asp Gly Asn Thr Lys Thr Glu Val Val Thr Glu Arg
65 70 75 80

Val Asn Tyr Thr Asp Glu Val Ser Ile Gly Tyr Arg Asp Lys Asn Phe
85 90 95

Ser Gly Asp Asp Leu Glu Ile Ile Ala Arg Val Ile Gln Pro Pro Asn
100 105 110

Cys Leu Glu Ala Leu Val Ser Pro Asn Gly Asn Lys Ile Val Val Thr
115 120 125

```
Val Glu Arg Glu Phe Val Thr Glu Val Val Gly Glu Thr Lys Ile Cys
    130                 135                 140

Val Ser Val Asn Pro Glu Gly Cys Val Glu Ser Asp Glu Asp Phe Gln
145                 150                 155                 160

Ile Asp Asp Asp Glu Phe Glu Glu Leu Asp Pro Asn Phe Ile Val Asp
                165                 170                 175

Ala Glu Glu Glu
            180


<210> SEQ ID NO 193
<211> LENGTH: 155
<212> TYPE: PRT
<213> ORGANISM: Bacillus thuringiensis

<400> SEQUENCE: 193

Met Thr Leu Met Ser Cys Asn Glu Asn Lys His His Gly Ser Ser His
1               5                   10                  15

Cys Val Val Asp Val Val Lys Phe Ile Asn Glu Leu Gln Asp Cys Ser
            20                  25                  30

Thr Thr Thr Cys Gly Ser Gly Cys Glu Ile Pro Phe Leu Gly Ala His
        35                  40                  45

Asn Thr Ala Ser Val Ala Asn Thr Arg Pro Phe Ile Leu Tyr Thr Lys
    50                  55                  60

Ala Gly Ala Pro Phe Glu Ala Phe Ala Pro Ser Ala Asn Leu Thr Ser
65                  70                  75                  80

Cys Arg Ser Pro Ile Phe Arg Val Glu Ser Val Asp Asp Asp Ser Cys
                85                  90                  95

Ala Val Leu Arg Val Leu Ser Val Val Leu Gly Asp Ser Ser Pro Val
            100                 105                 110

Pro Pro Thr Asp Asp Pro Ile Cys Thr Phe Leu Ala Val Pro Asn Ala
        115                 120                 125

Arg Leu Val Ser Thr Ser Thr Cys Ile Thr Val Asp Leu Ser Cys Phe
    130                 135                 140

Cys Ala Ile Gln Cys Leu Arg Asp Val Thr Ile
145                 150                 155


<210> SEQ ID NO 194
<211> LENGTH: 366
<212> TYPE: PRT
<213> ORGANISM: Bacillus anthracis

<400> SEQUENCE: 194

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
        35                  40                  45

Gly Pro Thr Gly Thr Thr Gly Ala Thr Gly Ala Thr Gly Ile Thr Gly
    50                  55                  60

Val Thr Gly Ala Thr Gly Ile Thr Gly Val Thr Gly Ala Thr Gly Ile
65                  70                  75                  80

Thr Gly Val Thr Gly Ala Thr Gly Ile Thr Gly Val Thr Gly Pro Thr
                85                  90                  95

Gly Ile Thr Gly Ala Thr Gly Pro Thr Gly Ile Thr Gly Ala Thr Gly
            100                 105                 110
```

```
Pro Ala Gly Ile Thr Gly Val Thr Gly Pro Thr Gly Ile Thr Gly Ala
        115                 120                 125

Thr Gly Pro Thr Gly Thr Thr Gly Val Thr Gly Pro Thr Gly Asp Thr
    130                 135                 140

Gly Leu Ala Gly Ala Thr Gly Pro Thr Gly Ala Thr Gly Leu Ala Gly
145                 150                 155                 160

Ala Thr Gly Pro Thr Gly Asp Thr Gly Ala Thr Gly Pro Thr Gly Ala
                165                 170                 175

Thr Gly Leu Ala Gly Ala Thr Gly Pro Thr Gly Ala Thr Gly Leu Thr
            180                 185                 190

Gly Ala Thr Gly Ala Thr Gly Ala Thr Gly Gly Gly Ala Ile Ile Pro
        195                 200                 205

Phe Ala Ser Gly Thr Thr Pro Ala Leu Leu Val Asn Ala Val Leu Ala
    210                 215                 220

Asn Thr Gly Thr Leu Leu Gly Phe Gly Phe Ser Gln Pro Gly Ile Ala
225                 230                 235                 240

Pro Gly Val Gly Gly Thr Leu Thr Ile Leu Pro Gly Val Val Gly Asp
                245                 250                 255

Tyr Ala Phe Val Ala Pro Arg Asp Gly Ile Ile Thr Ser Leu Ala Gly
            260                 265                 270

Phe Phe Ser Ala Thr Ala Ala Leu Ala Pro Leu Thr Pro Val Gln Ile
        275                 280                 285

Gln Met Gln Ile Phe Ile Ala Pro Ala Ala Ser Asn Thr Phe Thr Pro
    290                 295                 300

Val Ala Pro Pro Leu Leu Leu Thr Pro Ala Leu Pro Ala Ile Ala Ile
305                 310                 315                 320

Gly Thr Thr Ala Thr Gly Ile Gln Ala Tyr Asn Val Pro Val Val Ala
                325                 330                 335

Gly Asp Lys Ile Leu Val Tyr Val Ser Leu Thr Gly Ala Ser Pro Ile
            340                 345                 350

Ala Ala Val Ala Gly Phe Val Ser Ala Gly Leu Asn Ile Val
        355                 360                 365


<210> SEQ ID NO 195
<211> LENGTH: 347
<212> TYPE: PRT
<213> ORGANISM: Bacillus anthracis

<400> SEQUENCE: 195

Met Gln Asn Asp Lys Leu Trp Leu Asp Lys Gly Ile Ile Gly Pro Glu
1               5                   10                  15

Asn Ile Gly Pro Thr Phe Pro Val Leu Pro Pro Ile His Ile Pro Thr
            20                  25                  30

Gly Ile Thr Gly Ala Thr Gly Ala Thr Gly Ile Thr Gly Ala Thr Gly
        35                  40                  45

Pro Thr Gly Thr Thr Gly Ala Thr Gly Ala Thr Gly Ile Thr Gly Val
    50                  55                  60

Thr Gly Ala Thr Gly Ile Thr Gly Val Thr Gly Ala Thr Gly Ile Thr
65                  70                  75                  80

Gly Val Thr Gly Ala Thr Gly Ile Thr Gly Val Thr Gly Ala Thr Gly
                85                  90                  95

Ile Thr Gly Val Thr Gly Pro Thr Gly Ile Thr Gly Ala Thr Gly Pro
            100                 105                 110

Thr Gly Thr Thr Gly Val Thr Gly Pro Thr Gly Asp Thr Gly Leu Ala
        115                 120                 125
```

```
Gly Ala Thr Gly Pro Thr Gly Ala Thr Gly Leu Ala Gly Ala Thr Gly
    130                 135                 140

Pro Thr Gly Asp Thr Gly Ala Thr Gly Pro Thr Gly Ala Thr Gly Leu
145                 150                 155                 160

Ala Gly Ala Thr Gly Pro Thr Gly Ala Thr Gly Leu Thr Gly Ala Thr
                165                 170                 175

Gly Ala Thr Gly Ala Thr Gly Gly Gly Ala Ile Ile Pro Phe Ala Ser
            180                 185                 190

Gly Thr Thr Pro Ala Leu Leu Val Asn Ala Val Leu Ala Asn Thr Gly
        195                 200                 205

Thr Leu Leu Gly Phe Gly Phe Ser Gln Pro Gly Ile Ala Pro Gly Val
    210                 215                 220

Gly Gly Thr Leu Thr Ile Leu Pro Gly Val Val Gly Asp Tyr Ala Phe
225                 230                 235                 240

Val Ala Pro Arg Asp Gly Ile Ile Thr Ser Leu Ala Gly Phe Phe Ser
                245                 250                 255

Ala Thr Ala Ala Leu Ala Pro Leu Thr Pro Val Gln Ile Gln Met Gln
            260                 265                 270

Ile Phe Ile Ala Pro Ala Ala Ser Asn Thr Phe Thr Pro Val Ala Pro
        275                 280                 285

Pro Leu Leu Leu Thr Pro Ala Leu Pro Ala Ile Ala Ile Gly Thr Thr
    290                 295                 300

Ala Thr Gly Ile Gln Ala Tyr Asn Val Pro Val Val Ala Gly Asp Lys
305                 310                 315                 320

Ile Leu Val Tyr Val Ser Leu Thr Gly Ala Ser Pro Ile Ala Ala Val
                325                 330                 335

Ala Gly Phe Val Ser Ala Gly Leu Asn Ile Val
            340                 345
```

<210> SEQ ID NO 196
<211> LENGTH: 61
<212> TYPE: PRT
<213> ORGANISM: Bacillus cereus

<400> SEQUENCE: 196

```
Met Phe Ala Val Ser Asn Asn Pro Arg Gln Asn Ser Tyr Asp Leu Gln
1               5                   10                  15

Gln Trp Tyr His Met Gln Gln Gln His Gln Ala Gln Gln Gln Ala Tyr
            20                  25                  30

Gln Glu Gln Leu Gln Gln Gln Gly Phe Val Lys Lys Lys Gly Cys Asn
        35                  40                  45

Cys Gly Lys Lys Lys Ser Thr Ile Lys His Tyr Glu Glu
    50                  55                  60
```

<210> SEQ ID NO 197
<211> LENGTH: 66
<212> TYPE: PRT
<213> ORGANISM: Bacillus cereus

<400> SEQUENCE: 197

```
Leu Thr Val Glu Glu Met Phe Ala Val Ser Asn Asn Pro Arg Gln Asn
1               5                   10                  15

Ser Tyr Asp Leu Gln Gln Trp Tyr His Met Gln Gln Gln His Gln Ala
            20                  25                  30

Gln Gln Gln Ala Tyr Gln Glu Gln Leu Gln Gln Gln Gly Phe Val Lys
        35                  40                  45
```

```
Lys Lys Gly Cys Asn Cys Gly Lys Lys Lys Ser Thr Ile Lys His Tyr
    50                  55                  60

Glu Glu
65


<210> SEQ ID NO 198
<211> LENGTH: 156
<212> TYPE: PRT
<213> ORGANISM: Bacillus cereus

<400> SEQUENCE: 198

Met Ser Cys Asn Cys Asn Glu Asp His His His His Asp Cys Asp Phe
1               5                   10                  15

Asn Cys Val Ser Asn Val Val Arg Phe Ile His Glu Leu Gln Glu Cys
            20                  25                  30

Ala Thr Thr Thr Cys Gly Ser Gly Cys Glu Val Pro Phe Leu Gly Ala
        35                  40                  45

His Asn Ser Ala Ser Val Ala Asn Thr Arg Pro Phe Ile Leu Tyr Thr
    50                  55                  60

Lys Ala Gly Ala Pro Phe Glu Ala Phe Ala Pro Ser Ala Asn Leu Thr
65                  70                  75                  80

Ser Cys Arg Ser Pro Ile Phe Arg Val Glu Ser Ile Asp Asp Asp Asp
                85                  90                  95

Cys Ala Val Leu Arg Val Leu Ser Val Val Leu Gly Asp Thr Ser Pro
            100                 105                 110

Val Pro Pro Thr Asp Asp Pro Ile Cys Thr Phe Leu Ala Val Pro Asn
        115                 120                 125

Ala Arg Leu Ile Ser Thr Asn Thr Cys Leu Thr Val Asp Leu Ser Cys
    130                 135                 140

Phe Cys Ala Ile Gln Cys Leu Arg Asp Val Thr Ile
145                 150                 155


<210> SEQ ID NO 199
<211> LENGTH: 182
<212> TYPE: PRT
<213> ORGANISM: Bacillus anthracis

<400> SEQUENCE: 199

Met Glu Val Gly Gly Thr Ser Val Lys Asn Lys Asn Lys Ser Ser Thr
1               5                   10                  15

Val Gly Lys Pro Leu Leu Tyr Ile Ala Gln Val Ser Leu Glu Leu Ala
            20                  25                  30

Ala Pro Lys Thr Lys Arg Ile Ile Leu Thr Asn Phe Glu Asn Glu Asp
        35                  40                  45

Arg Lys Glu Glu Ser Asn Arg Asn Glu Asn Val Val Ser Ser Ala Val
    50                  55                  60

Glu Glu Val Ile Glu Gln Glu Glu Gln Gln Gln Glu Gln Glu Gln Glu
65                  70                  75                  80

Gln Glu Glu Gln Val Glu Glu Lys Thr Glu Glu Glu Glu Gln Val Gln
                85                  90                  95

Glu Gln Gln Glu Pro Val Arg Thr Val Pro Tyr Asn Lys Ser Phe Lys
            100                 105                 110

Asp Met Asn Asn Glu Glu Lys Ile His Phe Leu Leu Asn Arg Pro His
        115                 120                 125

Tyr Ile Pro Lys Val Arg Cys Arg Ile Lys Thr Ala Thr Ile Ser Tyr
    130                 135                 140
```

Val Gly Ser Ile Ile Ser Tyr Arg Asn Gly Ile Val Ala Ile Met Pro
145 150 155 160

Pro Asn Ser Met Arg Asp Ile Arg Leu Ser Ile Glu Glu Ile Lys Ser
165 170 175

Ile Asp Met Ala Gly Phe
180

<210> SEQ ID NO 200
<211> LENGTH: 9
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: (5)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 200 catannntn 9

<210> SEQ ID NO 201
<211> LENGTH: 17
<212> TYPE: PRT
<213> ORGANISM: Bacillus anthracis

<400> SEQUENCE: 201

Met Lys Ile Leu Ser Asp Leu Val Gly Pro Thr Phe Pro Pro Val Pro
1 5 10 15

Thr

<210> SEQ ID NO 202
<211> LENGTH: 17
<212> TYPE: PRT
<213> ORGANISM: Bacillus anthracis

<400> SEQUENCE: 202

Met Ile Ile Gly Pro Glu Asn Ile Gly Pro Thr Phe Pro Val Leu Pro
1 5 10 15

Pro

<210> SEQ ID NO 203
<211> LENGTH: 156
<212> TYPE: PRT
<213> ORGANISM: Bacillus anthracis

<400> SEQUENCE: 203

Met Ser Cys Asn Cys Asn Glu Asp His His Glu His Asp Cys Asp Phe
1 5 10 15

Asn Cys Val Ser Asn Val Val Arg Phe Ile His Glu Leu Gln Asp Cys
20 25 30

Ala Thr Thr Thr Cys Gly Ser Gly Cys Glu Val Pro Phe Leu Gly Ala
35 40 45

His Asn Thr Ala Ser Val Ala Asn Thr Arg Pro Phe Ile Leu Tyr Thr
50 55 60

Lys Ala Gly Ala Pro Phe Glu Ala Phe Ala Pro Ser Ala Ser Leu Thr
65 70 75 80

```
Ser Cys Arg Ser Pro Ile Phe Arg Val Glu Ser Ile Asp Asp Asp Asp
                85                  90                  95

Cys Ala Val Leu Arg Val Leu Thr Val Val Leu Gly Asp Asn Ser Pro
            100                 105                 110

Val Pro Pro Thr Asp Asp Pro Ile Cys Thr Phe Leu Ala Val Pro Asn
        115                 120                 125

Ala Arg Leu Val Ser Thr Ser Thr Cys Ile Thr Val Asp Leu Ser Cys
    130                 135                 140

Phe Cys Ala Ile Gln Cys Leu Arg Asp Val Thr Ile
145                 150                 155


<210> SEQ ID NO 204
<211> LENGTH: 296
<212> TYPE: PRT
<213> ORGANISM: Bacillus thuringiensis

<400> SEQUENCE: 204

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Thr Gly Pro
        35                  40                  45

Thr Gly Pro Thr Gly Pro Thr Gly Gly Gly Thr Gly Ile Thr Gly Pro
    50                  55                  60

Thr Gly Pro Thr Gly Asp Thr Gly Ala Thr Gly Pro Thr Gly Pro Thr
65                  70                  75                  80

Gly Asp Thr Gly Ala Thr Gly Leu Thr Gly Pro Thr Gly Asp Thr Gly
                85                  90                  95

Ala Thr Gly Pro Thr Gly Pro Thr Gly Asp Thr Gly Ala Thr Gly Pro
            100                 105                 110

Thr Gly Pro Thr Gly Asp Thr Gly Ala Thr Gly Leu Thr Gly Pro Thr
        115                 120                 125

Gly Asp Thr Gly Ala Thr Gly Pro Thr Gly Pro Thr Gly Ala Thr Gly
    130                 135                 140

Pro Thr Gly Ala Thr Gly Pro Thr Gly Ala Thr Gly Pro Thr Gly Pro
145                 150                 155                 160

Ser Gly Leu Gly Leu Pro Ala Gly Leu Tyr Ala Phe Asn Ser Gly Gly
                165                 170                 175

Ile Ser Leu Asp Leu Gly Ile Asn Asp Pro Val Pro Phe Asn Thr Val
            180                 185                 190

Gly Ser Gln Phe Gly Thr Ala Ile Ser Gln Leu Asp Ala Asp Thr Phe
        195                 200                 205

Val Ile Ser Glu Thr Gly Phe Tyr Lys Ile Thr Val Ile Ala Tyr Thr
    210                 215                 220

Ala Thr Val Ser Leu Leu Gly Gly Leu Thr Ile Gln Val Asn Gly Val
225                 230                 235                 240

Pro Val Pro Gly Thr Gly Ser Ser Leu Ile Ser Leu Gly Ala Pro Ile
                245                 250                 255

Val Ile Gln Ala Ile Thr Gln Ile Thr Thr Thr Pro Ser Leu Val Glu
            260                 265                 270

Val Ile Val Thr Gly Leu Gly Leu Ser Leu Ala Leu Gly Thr Ser Ala
        275                 280                 285

Ser Ile Ile Ile Glu Lys Val Ala
    290                 295
```

<210> SEQ ID NO 205
<211> LENGTH: 166
<212> TYPE: PRT
<213> ORGANISM: Bacillus thuringiensis

<400> SEQUENCE: 205

```
Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Thr Gly Pro
        35                  40                  45

Thr Gly Pro Thr Gly Pro Thr Gly Gly Gly Thr Gly Ile Thr Gly Pro
    50                  55                  60

Thr Gly Pro Thr Gly Asp Thr Gly Ala Thr Gly Pro Thr Gly Pro Thr
65                  70                  75                  80

Gly Asp Thr Gly Ala Thr Gly Leu Thr Gly Pro Thr Gly Asp Thr Gly
                85                  90                  95

Ala Thr Gly Pro Thr Gly Pro Thr Gly Asp Thr Gly Ala Thr Gly Pro
            100                 105                 110

Thr Gly Pro Thr Gly Asp Thr Gly Ala Thr Gly Leu Thr Gly Pro Thr
        115                 120                 125

Gly Asp Thr Gly Ala Thr Gly Pro Thr Gly Pro Thr Gly Ala Thr Gly
    130                 135                 140

Pro Thr Gly Ala Thr Gly Pro Thr Gly Ala Thr Gly Pro Thr Gly Pro
145                 150                 155                 160

Ser Gly Leu Gly Leu Pro
                165
```

<210> SEQ ID NO 206
<211> LENGTH: 322
<212> TYPE: PRT
<213> ORGANISM: Bacillus anthracis

<400> SEQUENCE: 206

```
Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Thr Gly Pro
        35                  40                  45

Thr Gly Pro Thr Gly Pro Thr Gly Pro Thr Gly Pro Thr Gly Pro Thr
    50                  55                  60

Gly Pro Thr Gly Pro Thr Gly Asp Thr Gly Thr Thr Gly Pro Thr Gly
65                  70                  75                  80

Pro Thr Gly Pro Thr Gly Pro Thr Gly Pro Thr Gly Pro Thr Gly Pro
                85                  90                  95

Thr Gly Pro Thr Gly Pro Thr Gly Pro Thr Gly Pro Thr Gly Pro Thr
            100                 105                 110

Gly Pro Thr Gly Asp Thr Gly Thr Thr Gly Pro Thr Gly Pro Thr Gly
        115                 120                 125

Pro Thr Gly Pro Thr Gly Pro Thr Gly Asp Thr Gly Thr Thr Gly Pro
    130                 135                 140

Thr Gly Pro Thr Gly Pro Thr Gly Pro Thr Gly Pro Thr Gly Pro Thr
145                 150                 155                 160
```

```
Gly Pro Thr Gly Pro Thr Gly Pro Thr Gly Pro Thr Gly Ala Thr Gly
                165                 170                 175

Leu Thr Gly Pro Thr Gly Pro Thr Gly Pro Ser Gly Leu Gly Leu Pro
            180                 185                 190

Ala Gly Leu Tyr Ala Phe Asn Ser Gly Gly Ile Ser Leu Asp Leu Gly
        195                 200                 205

Ile Asn Asp Pro Val Pro Phe Asn Thr Val Gly Ser Gln Phe Gly Thr
    210                 215                 220

Ala Ile Ser Gln Leu Asp Ala Asp Thr Phe Val Ile Ser Glu Thr Gly
225                 230                 235                 240

Phe Tyr Lys Ile Thr Val Ile Ala Asn Thr Ala Thr Ala Ser Val Leu
                245                 250                 255

Gly Gly Leu Thr Ile Gln Val Asn Gly Val Pro Val Pro Gly Thr Gly
            260                 265                 270

Ser Ser Leu Ile Ser Leu Gly Ala Pro Ile Val Ile Gln Ala Ile Thr
        275                 280                 285

Gln Ile Thr Thr Thr Pro Ser Leu Val Glu Val Ile Val Thr Gly Leu
    290                 295                 300

Gly Leu Ser Leu Ala Leu Gly Thr Ser Ala Ser Ile Ile Ile Glu Lys
305                 310                 315                 320

Val Ala


<210> SEQ ID NO 207
<211> LENGTH: 196
<212> TYPE: PRT
<213> ORGANISM: Bacillus anthracis

<400> SEQUENCE: 207

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Thr Gly Pro
        35                  40                  45

Thr Gly Pro Thr Gly Pro Thr Gly Pro Thr Gly Pro Thr Gly Pro Thr
    50                  55                  60

Gly Pro Thr Gly Pro Thr Gly Asp Thr Gly Thr Thr Gly Pro Thr Gly
65                  70                  75                  80

Pro Thr Gly Pro Thr Gly Pro Thr Gly Pro Thr Gly Pro Thr Gly Pro
                85                  90                  95

Thr Gly Pro Thr Gly Pro Thr Gly Pro Thr Gly Pro Thr Gly Pro Thr
            100                 105                 110

Gly Pro Thr Gly Asp Thr Gly Thr Thr Gly Pro Thr Gly Pro Thr Gly
        115                 120                 125

Pro Thr Gly Pro Thr Gly Pro Thr Gly Asp Thr Gly Thr Thr Gly Pro
    130                 135                 140

Thr Gly Pro Thr Gly Pro Thr Gly Pro Thr Gly Pro Thr Gly Pro Thr
145                 150                 155                 160

Gly Pro Thr Gly Pro Thr Gly Pro Thr Gly Pro Thr Gly Ala Thr Gly
                165                 170                 175

Leu Thr Gly Pro Thr Gly Pro Thr Gly Pro Ser Gly Leu Gly Leu Pro
            180                 185                 190

Ala Gly Leu Tyr
        195
```

<210> SEQ ID NO 208
<211> LENGTH: 8
<212> TYPE: PRT
<213> ORGANISM: Artificial Sequence
<220> FEATURE:
<223> OTHER INFORMATION: Synthetic construct

<400> SEQUENCE: 208

```
Ala Ala Ala Ala Ala Asp Leu Glu
1               5
```

<210> SEQ ID NO 209
<211> LENGTH: 8
<212> TYPE: PRT
<213> ORGANISM: Artificial Sequence
<220> FEATURE:
<223> OTHER INFORMATION: Synthetic construct

<400> SEQUENCE: 209

```
Ala Ala Ala Ala Ala Ala Leu Glu
1               5
```

<210> SEQ ID NO 210
<211> LENGTH: 321
<212> TYPE: PRT
<213> ORGANISM: Bacillus firmus

<400> SEQUENCE: 210

```
Met Glu Gln Tyr Val Arg Val Ile Pro Tyr Lys Val Ile Gln Gln Glu
1               5                   10                  15

Glu Asn Val Lys Glu Val Pro Lys Gly Val Glu Leu Ile Gln Ala Pro
            20                  25                  30

Lys Val Trp Ser Glu Thr Lys Gly Lys Gly Ile Lys Ile Ala Val Leu
        35                  40                  45

Asp Thr Gly Cys Asp Ile Ser His Pro Asp Leu Lys Asp Arg Val Thr
    50                  55                  60

Gly Gly Arg Asn Phe Thr Asp Asp Asp Asn Ser Asp Pro Asn Ser Phe
65                  70                  75                  80

Lys Asp Tyr Asn Gly His Gly Thr His Val Ala Gly Thr Ile Ala Ala
                85                  90                  95

Tyr Glu Asn Asn Ala Gly Val Ile Gly Val Ala Pro Glu Ala Glu Leu
            100                 105                 110

Leu Ile Val Lys Val Leu Asn Lys Asp Gly Ser Gly Gln Tyr Glu Trp
        115                 120                 125

Ile Ile Lys Gly Ile His Tyr Ala Ile Glu Gln Asn Ala Asp Ile Ile
    130                 135                 140

Ser Met Ser Leu Gly Gly Pro Ala Asp Val Pro Glu Leu His Asp Ala
145                 150                 155                 160

Ile Lys Ala Ala Val Asn Lys Asn Ile Leu Val Val Cys Ala Ala Gly
                165                 170                 175

Asn Glu Gly Asp Gly Asp Asp Ser Thr Asp Glu Phe Ala Tyr Pro Gly
            180                 185                 190

Cys Tyr Asn Glu Val Ile Ser Val Gly Ala Ile Asn Leu Glu Arg Asp
        195                 200                 205

Ser Ser Asp Phe Thr Asn Ser His Asn Glu Ile Asp Leu Val Ala Pro
    210                 215                 220

Gly Glu Gly Ile Leu Ser Thr Phe Leu Asn Gly Lys Tyr Ala Thr Leu
225                 230                 235                 240
```

```
Ser Gly Thr Ser Met Ala Ala Pro His Val Ser Gly Ala Leu Ala Leu
                245                 250                 255

Ile Lys Asp Phe Ala Asn Arg Gln Phe Glu Arg Lys Leu Ser Glu Pro
            260                 265                 270

Glu Leu Tyr Ala Gln Leu Ile Arg Arg Thr Val Pro Leu Gly Asn Ser
        275                 280                 285

Pro Lys Leu Glu Gly Asn Gly Leu Val Tyr Leu Thr Val Pro Asp His
    290                 295                 300

Leu Ala Gly Ile Phe Asp Gln Glu Leu Lys Ser Thr Val Leu Asn Ala
305                 310                 315                 320

Ile


<210> SEQ ID NO 211
<211> LENGTH: 321
<212> TYPE: PRT
<213> ORGANISM: Bacillus firmus

<400> SEQUENCE: 211

Met Glu Gln Tyr Val Arg Val Ile Pro Tyr Lys Val Ile Gln Gln Glu
1               5                   10                  15

Glu Asn Val Lys Glu Val Pro Lys Gly Val Glu Leu Ile Gln Ala Pro
            20                  25                  30

Lys Val Trp Ser Glu Thr Lys Gly Lys Gly Ile Lys Ile Ala Val Leu
        35                  40                  45

Asp Thr Gly Cys Asp Ile Ser His Pro Asp Leu Lys Asp Arg Val Thr
    50                  55                  60

Gly Gly Arg Asn Phe Thr Asp Asp Asp Asn Ser Asp Pro Asn Ser Phe
65                  70                  75                  80

Lys Asp Tyr Asn Gly His Gly Thr His Val Ala Gly Thr Ile Ala Ala
                85                  90                  95

Tyr Glu Asn Asp Ala Gly Val Ile Gly Val Ala Pro Glu Ala Asp Leu
            100                 105                 110

Leu Ile Val Lys Val Leu Asn Lys Asp Gly Ser Gly Gln Tyr Glu Trp
        115                 120                 125

Ile Ile Lys Gly Ile His Tyr Ala Ile Glu Gln Asn Ala Asp Ile Ile
    130                 135                 140

Ser Met Ser Leu Gly Gly Pro Ala Asp Val Pro Glu Leu His Asp Ala
145                 150                 155                 160

Ile Lys Ala Ala Val Asn Lys Asn Ile Leu Val Val Cys Ala Ala Gly
                165                 170                 175

Asn Glu Gly Asp Gly Asp Asp Ser Thr Asp Glu Phe Ala Tyr Pro Gly
            180                 185                 190

Cys Tyr Asn Glu Val Ile Ser Val Gly Ala Ile Asn Leu Glu Arg Asp
        195                 200                 205

Ser Ser Glu Phe Thr Asn Ser His Asn Glu Ile Asp Leu Val Ala Pro
    210                 215                 220

Gly Glu Gly Ile Leu Ser Thr Phe Leu Asn Gly Lys Tyr Ala Thr Leu
225                 230                 235                 240

Ser Gly Thr Ser Met Ala Ala Pro His Val Ser Gly Ala Leu Ala Leu
                245                 250                 255

Ile Lys Glu Phe Ala Asn Arg Gln Phe Glu Arg Lys Leu Ser Glu Pro
            260                 265                 270

Glu Leu Tyr Ala Gln Leu Ile Arg Arg Thr Val Pro Leu Gly Asn Ser
        275                 280                 285
```

```
Pro Lys Leu Glu Gly Asn Gly Leu Val Tyr Leu Thr Val Pro Asp His
    290                 295                 300

Leu Ala Gly Ile Phe Asp Gln Glu Phe Lys Ser Thr Val Leu Asn Ala
305                 310                 315                 320

Ile


<210> SEQ ID NO 212
<211> LENGTH: 261
<212> TYPE: PRT
<213> ORGANISM: Bacillus firmus

<400> SEQUENCE: 212

Met Glu Gln Tyr Val Arg Val Ile Pro Tyr Lys Val Ile Gln Gln Glu
1               5                   10                  15

Glu Asn Val Lys Glu Val Pro Lys Gly Val Glu Leu Ile Gln Ala Pro
            20                  25                  30

Lys Val Trp Ser Glu Thr Lys Gly Lys Gly Ile Lys Ile Ala Val Leu
        35                  40                  45

Asp Thr Gly Cys Asp Ile Ser His Pro Asp Leu Lys Asp Arg Val Thr
    50                  55                  60

Gly Gly Arg Asn Phe Thr Asp Asp Asp Asn Ser Asp Pro Asn Ser Phe
65                  70                  75                  80

Lys Asp Tyr Asn Gly His Gly Thr His Val Ala Gly Thr Ile Ala Ala
                85                  90                  95

Tyr Glu Asn Asn Ala Gly Val Ile Gly Val Ala Pro Glu Ala Glu Leu
            100                 105                 110

Leu Ile Val Lys Val Leu Asn Lys Asp Gly Ser Gly Gln Tyr Glu Trp
        115                 120                 125

Ile Ile Lys Gly Ile His Tyr Ala Ile Glu Gln Asn Ala Asp Ile Ile
    130                 135                 140

Ser Met Ser Leu Gly Gly Pro Ala Asp Val Pro Glu Leu His Asp Ala
145                 150                 155                 160

Ile Lys Ala Ala Val Asn Lys Asn Ile Leu Val Val Cys Ala Ala Gly
                165                 170                 175

Asn Glu Gly Asp Ser Gly Thr Ser Met Ala Ala Pro His Val Ser Gly
            180                 185                 190

Ala Leu Ala Leu Ile Lys Asp Phe Ala Asn Arg Gln Phe Glu Arg Lys
        195                 200                 205

Leu Ser Glu Pro Glu Leu Tyr Ala Gln Leu Ile Arg Arg Thr Val Pro
    210                 215                 220

Leu Gly Asn Ser Pro Lys Leu Glu Gly Asn Gly Leu Val Tyr Leu Thr
225                 230                 235                 240

Val Pro Asp His Leu Ala Gly Ile Phe Asp Gln Glu Leu Lys Ser Thr
                245                 250                 255

Val Leu Asn Ala Ile
            260


<210> SEQ ID NO 213
<211> LENGTH: 783
<212> TYPE: DNA
<213> ORGANISM: Bacillus firmus

<400> SEQUENCE: 213

atggaacagt atgtgcgcgt gatcccgtat aaagtgatcc agcaagaaga aaacgtgaaa      60

gaagtcccga aaggagttga actgattcaa gcgccgaaag tgtggtcaga aacaaaaggc     120
```

```
aaaggcatta aaattgccgt tttggatacg ggctgcgaca tcagccatcc ggatctgaaa    180

gatcgtgtca caggcggccg caactttacg gacgatgaca actcagaccc gaatagcttt    240

aaagactata atggccatgg cacacatgtc gcgggcacaa tcgcggcgta tgaaaataat    300

gcgggcgtca tcggcgtcgc gcctgaggcc gaactgctga ttgtgaaagt cctgaataaa    360

gacggaagcg gccagtatga atggatcatc aaaggcattc attatgcgat tgaacagaat    420

gccgacatca tctcgatgtc actgggagga cctgcggatg tgccggaact tcatgatgcg    480

attaaagcgg cggtgaacaa aaacatcctg gtcgtgtgcg ccgcgggaaa cgagggcgat    540

agcggcacga gcatggcggc gccgcatgtg tctggcgcgc tggcactgat taaagatttt    600

gccaatcggc agtttgaacg gaaactgagc gaaccggaac tgtatgcgca gcttatccgc    660

cgcacggtcc ctctgggcaa ttctccgaaa ctggagggca atggcctggt ttatctgaca    720

gttccggatc atctggcggg cattttcgat caggaactga aaagcacagt cctgaatgcg    780

att                                                                  783
```

FUSION PROTEINS, RECOMBINANT BACTERIA, AND EXOSPORIUM FRAGMENTS FOR PEST CONTROL AND PLANT HEALTH

CROSS-REFERENCE TO RELATED APPLICATIONS

This application claims priority to U.S. Provisional Patent Application No. 62/820,773, which was filed on Mar. 19, 2019, the entire contents of which are incorporated herein by reference in its entirety.

FIELD OF THE INVENTION

The present invention relates to fusion proteins containing a targeting sequence, exosporium protein, or exosporium protein fragment that targets the fusion protein to the exosporium of a recombinant *Bacillus cereus* family member. The fusion proteins further comprise a serine protease. The invention further relates to recombinant *Bacillus cereus* family members that express the fusion proteins, exosporium fragments derived from the recombinant *Bacillus cereus* family members, and formulations containing the recombinant *Bacillus cereus* family members or exosporium fragments. Plant seeds treated with the recombinant *Bacillus cereus* family members, exosporium fragments, or formulations are also provided. The invention further relates to methods for stimulating plant growth and/or promoting plant health using the recombinant *Bacillus cereus* family members, exosporium fragments, or formulations.

REFERENCE TO SEQUENCE LISTING SUBMITTED ELECTRONICALLY

The official copy of the sequence listing is submitted electronically via EFS-Web as an ASCII-formatted sequence listing with a file named "BCS199002WO_ST25.txt" created on Mar. 16, 2020, and having a size of 272 kilobytes, and is filed concurrently with the specification. The sequence listing contained in this ASCII-formatted document is part of the specification and is herein incorporated by reference in its entirety.

BACKGROUND OF THE INVENTION

Within the zone surrounding a plant's roots is a region called the rhizosphere. In the rhizosphere, bacteria, fungi, and other organisms compete for nutrients and for binding to the root structures of the plant. Both detrimental and beneficial bacteria and fungi can occupy the rhizosphere. The bacteria, fungi, and the root system of the plant can all be influenced by the actions of peptides, enzymes, and other proteins in the rhizosphere. Augmentation of soil or treatment of plants with certain of these peptides, enzymes, or other proteins would have beneficial effects on the overall populations of beneficial soil bacteria and fungi, create a healthier overall soil environment for plant growth, improve plant growth, and provide for the protection of plants against certain bacterial and fungal pathogens. However, previous attempts to introduce peptides, enzymes, and other proteins into soil to induce such beneficial effects on plants have been hampered by the low survival of enzymes, proteins, and peptides in soil. Additionally, the prevalence of proteases naturally present in the soil can lead to degradation of the proteins in the soil. The environment around the roots of a plant (the rhizosphere) is a unique mixture of bacteria, fungi, nutrients, and roots that has different qualities than that of native soil. The symbiotic relationship between these organisms is unique, and could be altered for the better with inclusion of exogenous proteins. The high concentration of fungi and bacteria in the rhizosphere causes even greater degradation of proteins due to abnormally high levels of proteases and other elements detrimental to proteins in the soil. In addition, enzymes and other proteins introduced into soil can dissipate away from plant roots quickly.

Thus, there exists a need in the art for a method for effectively delivering peptides, enzymes, and other proteins to plants (e.g., to plant root systems) and for extending the period of time during which such molecules remain active. Furthermore, there exists a need in the art for a method of selectively targeting such peptides, enzymes, and proteins to the rhizosphere and to plant leaves and plant roots in particular.

BRIEF SUMMARY OF THE INVENTION

A fusion protein is provided. The fusion protein comprises a targeting sequence, exosporium protein, or exosporium protein fragment that targets the fusion protein to the exosporium of a recombinant *Bacillus cereus* family member. The fusion protein also comprises an enzyme having serine protease activity. The enzyme having such activity comprises:

- an amino acid sequence comprising at least one amino acid deletion relative to the sequence of a wild-type serine protease enzyme from a *Bacillus firmus* bacterium, wherein the amino acid deletion retains the catalytic residues of the wild-type enzyme and results in the same or increased serine protease activity as compared to the serine protease activity of the wild-type serine protease enzyme under the same conditions;
- a *Bacillus firmus* enzyme;
- an amino acid sequence having at least 70%, at least 75%, at least 80%, at least 85%, at least 90%, at least 95%, at least 98%, or at least 99% identity to any one of SEQ ID NOs: 210-212.

A recombinant *Bacillus cereus* family member is provided. The recombinant *Bacillus cereus* family member expresses a fusion protein. The fusion protein can be any of the fusion proteins described herein.

A whole broth culture of the recombinant *Bacillus cereus* family member is provided. A fermentation product of the recombinant *Bacillus cereus* family member is provided.

Exosporium fragments are provided. The exosporium fragments are derived from a recombinant *Bacillus cereus* family member, including a whole broth or fermentation product of a recombinant *Bacillus cereus* family member. The recombinant *Bacillus cereus* family member can be any of the recombinant *Bacillus cereus* family members described herein. The exosporium fragments can comprise any of the fusion proteins described herein.

A formulation is provided. The formulation comprises any of the recombinant *Bacillus cereus* family members described herein, including a fermentation product of any of the recombinant *Bacillus cereus* family members described herein. The formulation further comprises an agriculturally acceptable carrier.

Another formulation is provided. The formulation comprises exosporium fragments derived from any of the recombinant *Bacillus cereus* family members described herein, including a whole broth of a recombinant *Bacillus cereus* family member described herein. The formulation further comprises an agriculturally acceptable carrier.

Yet another formulation is provided. The formulation comprises a recombinant *Bacillus cereus* family member that expresses a fusion protein. Alternatively, or in addition, the formulation comprises exosporium fragments derived from a *Bacillus cereus* family member that expresses a fusion protein. The fusion protein comprises a targeting sequence, exosporium protein, or exosporium protein fragment that targets the fusion protein to the exosporium of a recombinant *Bacillus cereus* family member. The fusion protein also comprises a serine protease or a serine protease variant described herein. The formulation further comprises a second enzyme.

A treated plant seed is provided. The plant seed can be treated with any of the recombinant *Bacillus cereus* family members described herein. The recombinant *Bacillus cereus* family member can express any of the fusion proteins described herein.

Another treated plant seed is provided. The plant seed can be treated with any of the exosporium fragments described herein. The exosporium fragments can be derived from any of the *Bacillus cereus* family members described herein. The exosporium fragments can comprise any of the fusion proteins described herein.

Yet another treated plant seed is provided. The plant seed can be treated with any of the formulations described herein.

A method for stimulating plant growth and/or promoting plant health is provided. The method comprises applying a recombinant *Bacillus cereus* family member to a plant growth medium, a plant, a plant seed, or an area surrounding a plant or a plant seed. The recombinant *Bacillus cereus* family member can comprise any of the recombinant *Bacillus cereus* family members described herein. The recombinant *Bacillus cereus* family member can express any of the fusion proteins described herein.

Another method for stimulating plant growth and/or promoting plant health is provided. The method comprises applying exosporium fragments to a plant growth medium, a plant, a plant seed, or an area surrounding a plant or a plant seed. The exosporium fragments can comprise exosporium fragments derived from any of the recombinant *Bacillus cereus* family members described herein. The exosporium fragments can comprise any of the fusion proteins described herein.

Yet another method for stimulating plant growth and/or promoting plant health is provided. The method comprises applying a formulation to a plant growth medium, a plant, a plant seed, or an area surrounding a plant or a plant seed. The formulation can comprise any of the formulations described herein.

Another method for stimulating plant growth and/or promoting plant health is provided. The method comprises applying a recombinant *Bacillus cereus* family member expressing a fusion protein to a plant growth medium, a plant, a plant seed, or an area surrounding a plant or a plant seed. The fusion protein comprises a targeting sequence, exosporium protein, or exosporium protein fragment that targets the fusion protein to the exosporium of a recombinant *Bacillus cereus* family member. The fusion protein further comprises an enzyme having serine protease activity.

Yet another method for stimulating plant growth and/or promoting plant health is provided. The method comprises applying exosporium fragments derived from spores of a recombinant *Bacillus cereus* family member expressing a fusion protein to a plant growth medium, a plant, a plant seed, or an area surrounding a plant or a plant seed. The fusion protein comprises a targeting sequence, exosporium protein, or exosporium protein fragment that targets the fusion protein to the exosporium of a recombinant *Bacillus cereus* family member. The fusion protein further comprises an enzyme having serine protease activity.

A further method for stimulating plant growth and/or promoting plant health is provided. The method comprises applying a recombinant *Bacillus cereus* family member expressing a fusion protein to a plant growth medium, a plant, a plant seed, or an area surrounding a plant or a plant seed. The fusion protein comprises a targeting sequence, exosporium protein, or exosporium protein fragment that targets the fusion protein to the exosporium of a recombinant *Bacillus cereus* family member. The fusion protein further comprises an enzyme having serine protease activity. The method further comprises applying a second enzyme to the plant growth medium, the plant, the plant seed, or the area surrounding the plant or the plant seed.

Another method for stimulating plant growth and/or promoting plant health is provided. The method comprises applying exosporium fragments derived from spores of a recombinant *Bacillus cereus* expressing a fusion protein to a plant growth medium, a plant, a plant seed, or an area surrounding a plant or a plant seed. The fusion protein comprises a targeting sequence, exosporium protein, or exosporium protein fragment that targets the fusion protein to the exosporium of a recombinant *Bacillus cereus* family member. The fusion protein further comprises an enzyme having serine protease activity. The method further comprises applying a second enzyme to the plant growth medium, the plant, the plant seed, or the area surrounding the plant or the plant seed.

A nucleic acid molecule comprising a nucleotide sequence encoding an amino acid sequence for a serine protease variant having nematode control activity is provided. In one embodiment, the nucleotide sequence is (i) the nucleotide sequence of SEQ ID NO: 213; (ii) a nucleotide sequence that encodes a peptide comprising the amino acid sequence of SEQ ID NO: 212; or (iii) a nucleotide sequence that encodes a peptide comprising an amino acid sequence having at least 90% sequence identity to the amino acid sequence of SEQ ID NO: 212. In one embodiment, such nucleotide sequence is operably linked to a promoter capable of directing expression of the nucleotide sequence in a host cell. In one aspect of that embodiment the promoter is heterologous or foreign to the nucleotide sequence of the invention and is not the native or naturally occurring promoter for the nucleotide sequence of the invention.

The expression "operably linked" means that elements of the nucleic acid molecule are linked to one another in such a way that their function is coordinated and allows expression of the coding sequence, i.e., they are functionally linked. By way of example, a promoter is functionally linked to another nucleotide sequence when it is capable of ensuring transcription and ultimately expression of such other nucleotide sequence. Two proteins encoding nucleotide sequences, e.g., a signal peptide-encoding nucleic acid sequence and a nucleic acid sequence encoding a protein having serine protease activity are functionally or operably linked to each other if they are connected in such a way that a fusion protein of first and second protein or peptide can be formed.

A vector containing the above-described nucleic acid molecule is provided. "Vector" refers to a nucleic acid construct, such as a plasmid, designed for transfer of foreign nucleic acid sequence into a host cell. An expression vector is a type of vector that is constructed to allow for expression of the foreign nucleic acid sequence in the host cell.

A host cell that contains the above-described vector is provided. In one embodiment, the host cell is a bacterial host cell. In one aspect of this embodiment, the host cell is a *Bacillus* cell. In a particular aspect of this embodiment, the host cell is a *Bacillus cereus* family member. In another aspect of this embodiment, the host cell is an *E. coli* cell.

A peptide comprising a serine protease variant having nematode control activity is provided. Such peptide comprises (i) a peptide comprising the amino acid sequence of SEQ ID NO: 212; (ii) a peptide comprising an amino acid sequence having at least 90% sequence identity to the amino acid sequence of SEQ ID NO: 212; or (iii) a peptide that is encoded by SEQ ID NO: 213. In one embodiment, the peptide further comprises heterologous amino acid sequences.

Further provided is a composition comprising the peptide described in the preceding paragraph. In one embodiment, the composition comprises from 1% to 99% by weight of such peptide.

Other objects and features will be in part apparent and in part pointed out hereinafter.

Definitions

When the articles "a", "an", "one", "the", and "said" are used herein, they mean "at least one" or "one or more" unless otherwise indicated.

The term "*Bacillus cereus* family member" as used herein refers to any *Bacillus* species that is capable of producing an exosporium. Thus, the *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis, Bacillus weihenstephensis*, and *Bacillus toyoiensis*. *Bacillus cereus* family members are also referred to in the art as "*Bacillus cereus* senso lato."

The terms "comprising," "including" and "having" are intended to be inclusive and mean that there may be additional elements other than the listed elements.

The term "free enzyme" as used herein refers to an enzyme preparation that is substantially free of intact cells. The term "free enzyme" includes, but is not limited to, crude cell extracts containing an enzyme, partially purified, substantially purified, or purified enzyme. Free enzymes can optionally be immobilized on a chemical matrix or support to allow for controlled release of the enzyme. The term "immobilizing" as used herein in reference to immobilizing an enzyme on a matrix or support refers to the binding of the enzyme to the matrix or support such that the enzyme is maintained on the matrix or support or released from the support over a controlled period of time, instead of dissipating into the environment in an uncontrolled manner. Illustrative matrices and supports include, but are not limited to, charcoal, biochar, nanocarbon, agarose, an alginate, cellulose, a cellulose derivative, silica, plastic, stainless steel, glass, polystyrene, a ceramic, dolomite, a clay, diatomaceous earth, talc, a polymer, a gum, a water-dispersable material, and combinations of any thereof.

The term "foliar" used herein with respect to the application of enzymes or recombinant microorganisms to plants means that the enzyme or recombinant microorganism is applied to one or more aerial portions of the plant, including stems, leaves, fruits, flowers, or other exposed aerial portions of the plant.

The term "fusion protein" as used herein refers to a protein having a polypeptide sequence that comprises sequences derived from two or more separate proteins. A fusion protein can be generated by joining together a nucleic acid molecule that encodes all or part of a first polypeptide with a nucleic acid molecule that encodes all or part of a second polypeptide to create a nucleic acid sequence which, when expressed, yields a single polypeptide having functional properties derived from each of the original proteins.

The term "germination rate" as used herein refers to the number of seeds that germinate during a particular time period. For example, a germination rate of 85% indicates that 85 out of 100 seeds germinate during a given time period.

The term "inactivate" or "inactivation" as used herein in reference to the inactivation of spores of a recombinant *Bacillus cereus* family member means that the spores are unable to germinate, or that the spores can germinate, but are damaged such that germination does not result in a living bacterium. The terms "partially inactivate" or "partial inactivation" mean that a percentage of the spores are inactivated, but that some spores retain the ability to germinate and return to a live, replicating state. The term "genetic inactivation" refers to inactivation of spores a recombinant *Bacillus cereus* family member by a mutation of the spore's DNA that results in complete or partial inactivation of the spore. The terms "physical inactivation" and "chemical inactivation" refer to inactivation of spores using any physical or chemical means, e.g., by heat treatment, gamma irradiation, x-ray irradiation, UV-A irradiation, UV-B irradiation, or treatment with a solvent such as glutaraldehyde, formaldehyde, hydrogen peroxide, acetic acid, bleach, chloroform, phenol, or any combination thereof.

The terms "native sequence", "native amino acid sequence", "wild-type sequence", and "wild-type amino acid sequence" are used interchangeably herein to refer to an amino acid sequence as it exists in a naturally occurring protein.

A "plant growth medium" includes any material that is capable of supporting the growth of a plant.

The terms "promoting plant growth" and "stimulating plant growth" are used interchangeably herein, and refer to the ability to enhance or increase at least one of the plant's height, weight, leaf size, root size, fruit size, shoot size or stem size, and/or the ability to increase protein yield from the plant, and/or to increase crop yield, and/or to improve plant vigor. For example, this may relate to increased length and/or fresh and/or dry weights of roots and/or shoots of treated plants or crops compared to untreated plants or crops.

Increased yield of a plant, in particular of an agricultural, silvicultural and/or ornamental plant, means that the yield of a product of the respective plant is increased by a measurable amount over the yield of the same product of the plant produced under the same conditions, but without the application of the compositions disclosed herein.

Improved plant vigor includes the following: (a) improved vitality of the plant, (b) improved quality of the plant and/or of the plant products, e.g., enhanced protein content, (c) improved visual appearance, (d) delay of senescence, (e) enhanced root growth and/or more developed root system (e.g., determined by the dry mass of the root), (f) enhanced nodulation, in particular rhizobial nodulation, (g) longer panicles, (h) bigger leaf blade, (i) less dead basal leaves, (j) increased chlorophyll content, (k) prolonged photosynthetically active period, (l) increased or improved plant stand density, (m) less plant verse (lodging), (n) increased plant weight, (o) increased plant height, (p) tillering increase, (q) stronger and/or more productive tillers, (r) less non-productive tillers, (s) enhanced photosynthetic activity and/or enhanced pigment content and thus greener leaf color, (t) earlier and/or improved germination, (u) improved and/or more uniform and/or earlier emergence, (v) increased shoot growth, (w) earlier flowering, (x) earlier fruiting, (y) earlier grain maturity, (z) less fertilizers needed, (aa) less seeds needed.

The term "recombinant" as used in reference to the bacteria described herein encompasses bacteria having any genetic modification as compared to wild-type bacteria of the same type, including bacteria that have been modified to delete of a gene or a portion of a gene (e.g., bacteria that have a "knock-out" of a gene), as well as bacteria that have been modified to express an exogenous peptide or protein.

The term "rhizosphere" is used interchangeably with "root zone" to denote that segment of the soil that surrounds the roots of a plant and is influenced by them.

The term "synergistically effective amount" as used herein refers an amount of a first substance (e.g., a first enzyme) that when used in combination with a second substance (e.g., a second enzyme) produces a biological effect that is greater than the sum of the biological effects of each of the respective first and second substances when used alone.

The term "targeting sequence" as used herein refers to a polypeptide sequence that, when present as part of a longer polypeptide or a protein, results in the localization of the longer polypeptide or the protein to a specific subcellular location. The targeting sequences described herein result in localization of proteins to the exosporium of a *Bacillus cereus* family member.

BRIEF DESCRIPTION OF THE DRAWINGS

FIGS. 1A and 1B depict alignments of the amino acid sequence of an amino-terminal portion of *Bacillus anthracis* Sterne strain BclA and with the corresponding region from various exosporium proteins from *Bacillus cereus* family members.

DETAILED DESCRIPTION OF THE INVENTION

Figure 2:
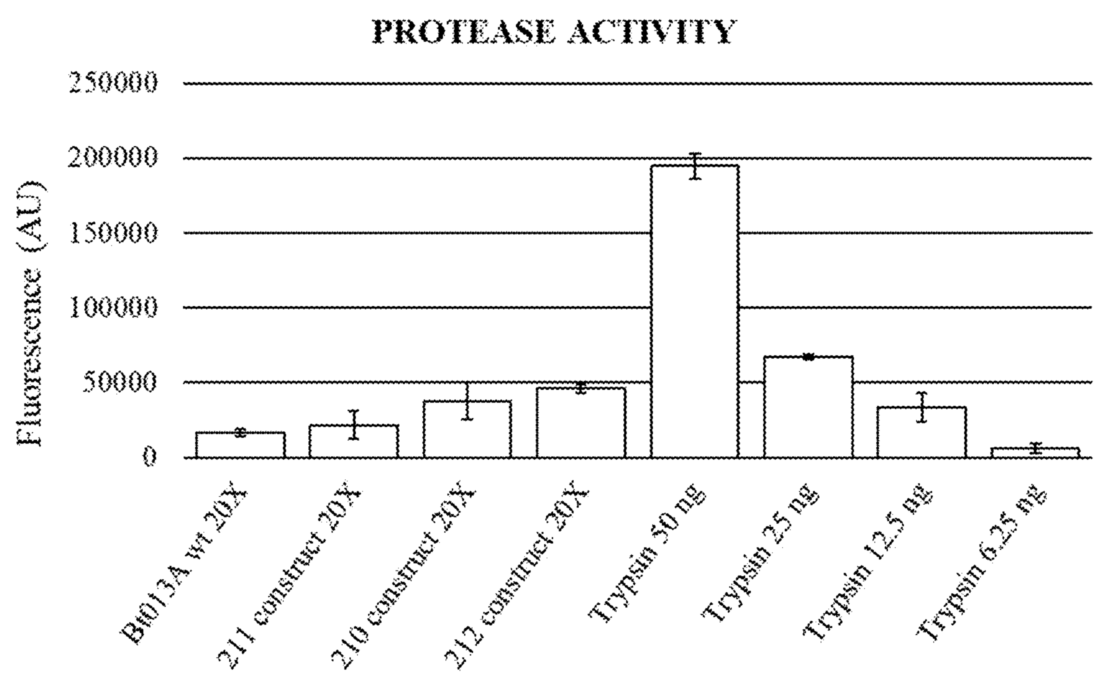
FIG. 2 depicts results of an enzyme assay comparing protease activity of whole broth cultures of *Bacillus thuringiensis* BT013A, BT013A-pBC210, BT013A-pBC211 and BT013A-pSuper212.

I. Fusion Proteins for Expression in *Bacillus Cereus* Family Members

The present invention relates to fusion proteins comprising a targeting sequence, exosporium protein, or exosporium protein fragment that targets the fusion protein to the exosporium of a recombinant *Bacillus cereus* family member. The fusion proteins further comprise an enzyme having serine protease activity. When expressed in *Bacillus cereus* family member bacteria, these fusion proteins are targeted to the exosporium layer of the spore and are physically oriented such that the serine protease is displayed on the outside of the spore.

This *Bacillus* exosporium display (BEMD) system can be used to deliver the serine protease to plants (e.g., to plant foliage, fruits, flowers, stems, or roots) or to a plant growth medium such as soil. Enzymes and proteins delivered to the soil or another plant growth medium in this manner persist and exhibit activity in the soil for extended periods of time. Introduction of recombinant *Bacillus cereus* family member bacteria expressing the fusion proteins described herein into soil or the rhizosphere of a plant leads to a beneficial enhancement of plant growth and/or to control pests, such as nematodes, in many different soil conditions. The use of the BEMD to create these enzymes allows them to continue to exert their beneficial results to the plant and the rhizosphere over the first months of a plant's life.

In addition, as is described further hereinbelow, the BEMD system can be modified such that the exosporium of the recombinant *Bacillus cereus* family member can be removed from the spore, generating exosporium fragments containing the fusion proteins. The exosporium fragments can also be used to deliver the serine proteases to plants in a cell-free preparation.

A. Targeting Sequences, Exosporium Proteins, and Exosporium Protein Fragments for Targeting Enzymes Having Serine Protease Activity to the Exosporium of a *Bacillus cereus* Family Member For ease of reference, descriptions of the amino acid sequences for the targeting sequences, exosporium proteins, and exosporium protein fragments that can be used for targeting of enzymes or proteins (e.g., enzymes having serine protease activity) to the exosporium of a *Bacillus cereus* family members, are provided in Table 1 together with their SEQ ID NOs.

TABLE 1

Peptide and Protein Sequences Used for Targeting of Proteins or Peptides of Interest to the Exosporium of *Bacillus cereus* Family Members

| Protein, Protein Fragment, or Targeting Sequence | SEQ ID NO: |
|---|---|
| AA 1-41 of BclA (*B. anthracis* Sterne) | 1 |
| Full length BclA (*B. anthracis* Sterne) | 2 |
| AA 1-33 of BetA/BAS3290 (*B. anthracis* Sterne) | 3 |
| Full length BetA/BAS3290 (*B. anthracis* Sterne) | 4 |
| Met + AA 2-43 of BAS4623 (*B. anthracis* Sterne) | 5 |
| Full length BAS4623 (*B. anthracis* Sterne) | 6 |
| AA 1-34 of BclB (*B. anthracis* Sterne) | 7 |
| Full length BclB (*B. anthracis* Sterne) | 8 |
| AA 1-30 of BAS1882 (*B. anthracis* Sterne) | 9 |
| Full length BAS1882 (*B. anthracis* Sterne) | 10 |
| AA 1-39 of gene 2280 (*B. weihenstephensis* KBAB4) | 11 |
| Full length KBAB4 gene 2280 (*B. weihenstephensis* KBAB4) | 12 |
| AA 1-39 of gene 3572 (*B. weihenstephensis* KBAB4) | 13 |
| Full Length KBAB4 gene 3572 (*B. weihenstephensis* KBAB4) | 14 |
| AA 1-49 of Exosporium Leader Peptide (*B. cereus* VD200) | 15 |
| Full Length Exosporium Leader Peptide(*B. cereus* VD200) | 16 |
| AA 1-33 of Exosporium Leader Peptide (*B. cereus* VD166) | 17 |
| Full Length Exosporium Leader Peptide (*B. cereus* VD166) | 18 |
| AA 1-39 of hypothetical protein IKG_04663 (*B. cereus* VD200) | 19 |
| Hypothetical protein IKG_04663, partial (*B. cereus* VD200) | 20 |
| AA 1-39 of YVTN β-propeller protein (*B. weihenstephensis* KBAB4) | 21 |
| Full length YVTN β-propeller protein KBAB4 (*B. weihenstephensis* KBAB4) | 22 |
| AA 1-30 of hypothetical protein bcerkbab4_2363 (*B. weihenstephensis* KBAB4) | 23 |
| Full length hypothetical protein bcerkbab4_2363 KBAB4 (*B. weihenstephensis* KBAB4) | 24 |

TABLE 1-continued

Peptide and Protein Sequences Used for Targeting of Proteins or Peptides of Interest to the Exosporium of *Bacillus cereus* Family Members

| Protein, Protein Fragment, or Targeting Sequence | SEQ ID NO: |
|---|---|
| AA 1-30 of hypothetical protein bcerkbab4_2131 (*B. weihenstephensis* KBAB4) | 25 |
| Full length hypothetical protein bcerkbab4_2131 (*B. weihenstephensis* KBAB4) | 26 |
| AA 1-36 of triple helix repeat containing collagen (*B. weihenstephensis* KBAB4) | 27 |
| Full length triple helix repeat-containing collagen KBAB4 | 28 |
| AA 1-39 of hypothetical protein bmyco0001_21660 (*B. mycoides* 2048) | 29 |
| Full length hypothetical protein bmyco0001_21660 (*B. mycoides* 2048) | 30 |
| AA 1-30 of hypothetical protein bmyc0001_22540 (*B. mycoides* 2048) | 31 |
| Full length hypothetical protein bmyc0001_22540 (*B. mycoides* 2048) | 32 |
| AA 1-21 of hypothetical protein bmyc0001_21510 (*B. mycoides* 2048) | 33 |
| Full length hypothetical protein bmyc0001_21510 (*B. mycoides* 2048) | 34 |
| AA 1-22 of collagen triple helix repeat protein (*B. thuringiensis* 35646) | 35 |
| Full length collagen triple helix repeat protein (*B. thuringiensis* 35646) | 36 |
| AA 1-35 of hypothetical protein WP_69652 (*B. cereus*) | 43 |
| Full length hypothetical protein WP_69652 (*B. cereus*) | 44 |
| AA 1-41 of exosporium leader WP016117717 (*B. cereus*) | 45 |
| Full length exosporium leader WP016117717(*B. cereus*) | 46 |
| AA 1-49 of exosporium peptide WP002105192 (*B. cereus*) | 47 |
| Full length exosporium peptide WP002105192 (*B. cereus*) | 48 |
| AA 1-38 of hypothetical protein WP87353 (*B. cereus*) | 49 |
| Full length hypothetical protein WP87353 (*B. cereus*) | 50 |
| AA 1-39 of exosporium peptide 02112369 (*B. cereus*) | 51 |
| Full length exosporium peptide 02112369 (*B. cereus*) | 52 |
| AA 1-39 of exosporium protein WP016099770 (*B. cereus*) | 53 |
| Full length exosporium protein WP016099770 (SEQ ID NO: 54) | 54 |
| AA 1-36 of hypothetical protein YP006612525 (*B. thuringiensis*) | 55 |
| Full length hypothetical protein YP006612525 (*B. thuringiensis*) | 56 |
| AA 1-136 of hypothetical protein TIGR03720 (*B. mycoides*) | 57* |
| Full length hypothetical protein TIGR03720 (*B. mycoides*) | 58* |
| AA 1-36 of collagen triple helix repeat domain protein (*B. cereus* ATCC 10987) | 59 |
| Full length collagen triple helix repeat domain protein (*B. cereus* ATCC 10987) | 60 |
| AA 1-39 of collagen-like protein (*B. cereus* E33L) | 61 |
| Full length collagen-like protein (*B. cereus* E33L) | 62 |
| AA 1-41 of triple helix repeat-containing collagen (*B. weihenstephanensis* KBAB4) | 63 |
| Full length triple helix repeat-containing collagen (*B. weihenstephanensis* KBAB4) | 64 |
| AA 1-30 of hypothetical protein BALH_2230 (*B. thuringiensis* str. Al Hakam) | 65 |
| Full length hypothetical protein BALH_2230 (*B. thuringiensis* str. Al Hakam) | 66 |
| AA 1-33 of triple helix repeat-containing collagen (*B. cereus* ATCC 14579) | 67 |
| Full length triple helix repeat-containing collagen (*B. cereus* ATCC 14579) | 68 |
| AA 1-44 of collagen triple helix repeat (*B. cereus*) | 69 |
| Full length collagen triple helix repeat (*B. cereus*) | 70 |
| AA 1-38 of triple helix repeat-containing collagen (*B. cereus* ATCC 14579) | 71 |
| Full length triple helix repeat-containing collagen (*B. cereus* ATCC 14579) | 72 |
| AA 1-30 of hypothetical protein BCZK1835 (*B. cereus* E33L) | 73 |
| Full length hypothetical protein BCZK1835 (*B. cereus* E33L) | 74 |
| AA 1-48 of triple helix repeat-containing collagen (*B. weihenstephanensis* KBAB4) | 75 |
| Full length triple helix repeat-containing collagen (*B. weihenstephanensis* KBAB4) | 76 |
| AA 1-30 of triple helix repeat-containing collagen (*B. cereus* ATCC 14579) | 77 |

TABLE 1-continued

Peptide and Protein Sequences Used for Targeting of Proteins or Peptides of Interest to the Exosporium of *Bacillus cereus* Family Members

| Protein, Protein Fragment, or Targeting Sequence | SEQ ID NO: |
|---|---|
| Full length triple helix repeat-containing collagen (*B. cereus* ATCC 14579) | 78 |
| AA 1-39 of hypothetical protein BC4725 (*B. cereus* ATCC 14579) | 79 |
| Full length hypothetical protein BC4725 (*B. cereus* ATCC 14579) | 80 |
| AA 1-44 of hypothetical protein BCZK4476 (*B. cereus* E33L) | 81 |
| Full length hypothetical protein BCZK4476 (*B. cereus* E33L) | 82 |
| AA 1-40 of triple helix repeat-containing collagen (*B. anthracis* str. 'Ames Ancestor') | 83 |
| Full length triple helix repeat-containing collagen (*B. anthracis* str. 'Ames Ancestor') | 84 |
| AA 1-34 of BclA protein (*B. thuringiensis* serovar konkukian str. 97-27) | 85 |
| Full length BclA protein (*B. thuringiensis* serovar konkukian str. 97-27) | 86 |
| AA 1-34 of conserved hypothetical protein (*B. cereus* ATCC 10987) | 87 |
| Full length conserved hypothetical protein (*B. cereus* ATCC 10987) | 88 |
| AA 1-34 of triple helix repeat-containing collagen (*B. cereus* ATCC 14579) | 89 |
| Full length triple helix repeat-containing collagen (*B. cereus* ATCC 14579) | 90 |
| AA 1-99 of exosporium leader peptide partial sequence (*B. cereus*) | 91 |
| Exosporium leader peptide partial sequence (*B. cereus*) | 92 |
| AA 1-136 of hypothetical protein ER45_27600, partial sequence (*B. weihenstephanensis*) | 93 |
| Hypothetical protein ER45_27600, partial sequence (*B. weihenstephanensis*) | 94 |
| AA 1-196 of BclA (*B. anthracis* Sterne) | 95 |
| Met + AA 20-35 of BclA (*B. anthracis* Sterne) | 96 |
| Met + AA 12-27 of BetA/BAS3290 (*B. anthracis* Sterne) | 97 |
| Met + AA 18-33 of gene 2280 (*B. weihenstephensis* KBAB4) | 98 |
| Met + AA 18-33 of gene 3572 (*B. weihenstephensis* KBAB4) | 99 |
| Met + AA 12-27 of Exosporium Leader Peptide (*B. cereus* VD166) | 100 |
| Met + AA 18-33 of YVTN β-propeller protein (*B. weihenstephensis* KBAB4) | 101 |
| Met + AA 9-24 of hypothetical protein bcerkbab4_2363 (*B. weihenstephensis* KBAB4) | 102 |
| Met + AA 9-24 of hypothetical protein bcerkbab4_2131 (*B. weihenstephensis* KBAB4) | 103 |
| Met + AA 9-24 of hypothetical protein bmyc0001_22540 (*B. mycoides* 2048) | 104 |
| Met + AA 9-24 of BAS 18 82 (*B. anthracis* Sterne) | 105 |
| Met + AA 20-35 of exosporium leader WP016117717 (*B. cereus*) | 106 |
| Met + AA 9-24 of hypothetical protein BALH_2230 (*B. thuringiensis* str. Al Hakam) | 107 |
| Full length InhA (*B. mycoides*) | 108 |
| Full length BAS 1141 (ExsY) (*B. anthracis* Sterne) | 109 |
| Full length BAS 1144 (BxpB/ExsFA) (*B. anthracis* Sterne) | 110 |
| Full length BAS 1145 (CotY)(*B. anthracis* Sterne) | 111 |
| Full length BAS1140(*B. anthracis* Sterne) | 112 |
| Full length ExsFB (*B. anthracis* H9401) | 113 |
| Full length InhA1(*B. thuringiensis* HD74) | 114 |
| Full length ExsJ (*B. cereus* ATCC 10876) | 115 |
| Full length ExsH (*B. cereus*) | 116 |
| Full length YjcA (*B. anthracis* Ames) | 117 |
| Full length YjcB (*B. anthracis*) | 118 |
| Full length BclC (*B. anthracis* Sterne) | 119 |
| Full length acid phosphatase (*Bacillus thuringiensis* serovar konkukian str. 97-27) | 120 |
| Full length InhA2 (*B. thuringiensis* HD74) | 121 |
| Full length InhA3 (*B. mycoides*) | 122 |
| Met + AA 23-38 of BAS4623 (*B. anthracis* Sterne) | 201 |
| Met + AA 13-28 of BclB (*B. anthracis* Sterne) | 202 |
| Cot Y variant (*Bacillus anthracis*) | 203 |
| BclA (*Bacillus thuringiensis*) | 204 |

TABLE 1-continued

Peptide and Protein Sequences Used for Targeting of Proteins or Peptides of Interest to the Exosporium of *Bacillus cereus* Family Members

| Protein, Protein Fragment, or Targeting Sequence | SEQ ID NO: |
|---|---|
| AA 1-166 of BclA (*Bacillus thuringiensis*) | 205 |
| BclA (*Bacillus anthracis*) | 206 |
| AA 1-196 of BclA (*Bacillus anthracis*) | 207 |

AA = amino acids

*B. mycoides hypothetical protein TIGR03720 has 100% sequence identity with B. mycoides hypothetical protein WP003189234. Thus, SEQ ID NOs: 57 and 58 also represent amino acids 1-136 of B. mycoides hypothetical protein WP003189234 and full length B. mycoides hypothetical protein WP003189234, respectively.

*Bacillus* is a genus of rod-shaped bacteria. The *Bacillus cereus* family of bacteria includes any *Bacillus* species that is capable of producing an exosporium. Thus, the *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis, Bacillus weihenstephensis*, and *Bacillus toyoiensis*. Under stressful environmental conditions, *Bacillus cereus* family bacteria undergo sporulation and form oval endospores that can stay dormant for extended periods of time. The outermost layer of the endospores is known as the exosporium and comprises a basal layer surrounded by an external nap of hair-like projections. Filaments on the hair-like nap are predominantly formed by the collagen-like glycoprotein BclA, while the basal layer is comprised of a number of different proteins. Another collagen-related protein, BclB, is also present in the exosporium and exposed on endospores of *Bacillus cereus* family members. BclA, the major constituent of the surface nap, has been shown to be attached to the exosporium with its amino-terminus (N-terminus) positioned at the basal layer and its carboxy-terminus (C-terminus) extending outward from the spore.

The scientific literature describes the *Bacillus cereus* "family" or "group" as a subgroup within the genus *Bacillus*. See Priest et al., "Population Structure and Evolution of the *Bacillus cereus* Group," J. Bacteriology, 2004, vol. 186. no. 23, pp. 7959-7970; Peng et al., "The Regulation of Exosporium-Related Genes in *Bacillus thuringiensis*," Nature Scientific Reports, 2016, vol. 6, no. 19005, pp. 1-12. Peng et al. states:

> Spores of the *B. cereus* group are complex, multilayered structures. The nucleoid containing core is enclosed within a peptidoglycan cortex, which is surrounded by the spore coat. Spores of all the *B. cereus* group species are encircled by an additional loose-fitting layer called the exosporium, which is not present on other species such as *Bacillus subtilis*, for which the coat constitutes the outermost layer of the mature spore. The exosporium is a balloon-like layer that acts as the outer permeability barrier of the spore and contributes to spore survival and virulence.

It was previously discovered that certain sequences from the N-terminal regions of BclA and BclB could be used to target a peptide or protein to the exosporium of a *Bacillus cereus* family member endospore (see U.S. Patent Application Publication Nos. 2010/0233124 and 2011/0281316, and Thompson et al., "Targeting of the BclA and BclB Proteins to the *Bacillus anthracis* Spore Surface", Molecular Microbiology 70(2):421-34 (2008)). It was also found that the BetA/BAS3290 protein of *Bacillus anthracis* localized to the exosporium. Further targeting sequences, as well as exosporium proteins and fragments of exosporium proteins, that can be incorporated into a fusion protein and used to target a peptide or protein of interest to the exosporium of a recombinant *Bacillus cereus* family member are described in U.S. Patent Application Publication Nos. 2016/0031948 and 2016/0108096, which are incorporated by reference herein in their entirety.

In particular, amino acids 20-35 of BclA from *Bacillus anthracis* Sterne strain have been found to be sufficient for targeting to the exosporium. A sequence alignment of amino acids 1-41 of BclA (SEQ ID NO: 1) with the corresponding N-terminal regions of several other *Bacillus cereus* family exosporium proteins and *Bacillus cereus* family proteins having related sequences is shown in FIGS. 1A and 1B. As can be seen from FIGS. 1A and 1B, there is a region of high homology among all of the proteins in the region corresponding to amino acids 20-41 of BclA. However, in these sequences, the amino acids corresponding to amino acids 36-41 of BclA contain secondary structure and are not necessary for fusion protein localization to the exosporium. The conserved targeting sequence region of BclA (amino acids 20-35 of SEQ ID NO: 1) is shown in bold in FIGS. 1A and 1B. A more highly conserved region spanning amino acids 25-35 of BclA within the targeting sequence is underlined in the sequences in FIGS. 1A and 1B, and is the recognition sequence for ExsFA/BxpB/ExsFB and homologs, which direct and assemble the described proteins on the surface of the exosporium. The amino acid sequences of SEQ ID NOs. 3, 5, and 7 in FIG. 1A are amino acids 1-33 of *Bacillus anthracis* Sterne strain BetA/BAS3290, a methionine followed by amino acids 2-43 of *Bacillus anthracis* Sterne strain BAS4623, and amino acids 1-34 of *Bacillus anthracis* Sterne strain BclB, respectively. (For BAS4623, it was found that replacing the valine present at position 1 in the native protein with a methionine resulted in better expression.) As can be seen from FIG. 1A, each of these sequences contains a conserved region corresponding to amino acids 20-35 of BclA (SEQ ID NO: 1; shown in bold), and a more highly conserved region corresponding to amino acids 25-35 of BclA (underlined).

Additional proteins from *Bacillus cereus* family members also contain the conserved targeting region. In particular, in FIGS. 1A and 1B, SEQ ID NO: 9 is amino acids 1-30 of *Bacillus anthracis* Sterne strain BAS1882, SEQ ID NO: 11 is amino acids 1-39 of the *Bacillus weihenstephensis* KBAB4 2280 gene product, SEQ ID NO: 13 is amino acids 1-39 of the *Bacillus weihenstephensis* KBAB4 3572 gene product, SEQ ID NO: 15 is amino acids 1-49 of *Bacillus cereus* VD200 exosporium leader peptide, SEQ ID NO: 17 is amino acids 1-33 of *Bacillus cereus* VD166 exosporium leader peptide, SEQ ID NO: 19 is amino acids 1-39 of *Bacillus cereus* VD200 hypothetical protein IKG_04663, SEQ ID NO: 21 is amino acids 1-39 of *Bacillus weihenstephensis* KBAB4 YVTN β-propeller protein, SEQ ID NO: 23 is amino acids 1-30 of *Bacillus weihenstephensis* KBAB4 hypothetical protein bcerkbab4_2363, SEQ ID NO: 25 is amino acids 1-30 of *Bacillus weihenstephensis* KBAB4 hypothetical protein bcerkbab4_2131, SEQ ID NO: 27 is amino acids 1-36 of *Bacillus weihenstephensis* KBAB4 triple helix repeat containing collagen, SEQ ID NO: 29 is amino acids 1-39 of *Bacillus mycoides* 2048 hypothetical protein bmyco0001_21660, SEQ ID NO: 31 is amino acids 1-30 of *Bacillus mycoides* 2048 hypothetical protein bmyc0001_22540, SEQ ID NO: 33 is amino acids 1-21 of *Bacillus mycoides* 2048 hypothetical protein bmyc0001_21510, SEQ ID NO: 35 is amino acids 1-22 of *Bacillus thuringiensis* 35646 collagen triple helix repeat protein, SEQ ID NO: 43 is amino acids 1-35 of *Bacillus cereus* hypothetical protein WP_69652, SEQ ID NO: 45 is amino acids 1-41 of *Bacillus cereus* exosporium leader WP016117717, SEQ ID NO: 47 is amino acids 1-49 of *Bacillus cereus* exosporium peptide WP002105192, SEQ ID NO: 49 is amino acids 1-38 of *Bacillus cereus* hypothetical protein WP87353, SEQ ID NO: 51 is amino acids 1-39 of *Bacillus cereus* exosporium peptide 02112369, SEQ ID NO: 53 is amino acids 1-39 of *Bacillus cereus* exosporium protein WP016099770, SEQ ID NO: 55 is amino acids 1-36 of *Bacillus thuringiensis* hypothetical protein YP006612525, SEQ ID NO: 57 is amino acids 1-136 of *Bacillus mycoides* hypothetical protein TIGR03720, SEQ ID NO: 59 is amino acids 1-36 of *B. cereus* ATCC 10987 collagen triple helix repeat domain protein, SEQ ID NO: 61 is amino acids 1-39 of *B. cereus* E33L collagen-like protein, SEQ ID NO: 63 is amino acids 1-41 of *B. weihenstephanensis* KBAB4 triple helix repeat-containing collagen, SEQ ID NO: 65 is amino acids 1-30 of *B. thuringiensis* str. Al Hakam hypothetical protein BALH_2230, SEQ ID NO: 67 is amino acids 1-33 of *B. cereus* ATCC 14579 triple helix repeat-containing collagen, SEQ ID NO: 69 is amino acids 1-44 of *B. cereus* collagen triple helix repeat, SEQ ID NO: 71 is amino acids 1-38 of *B. cereus* ATCC 14579 triple helix repeat-containing collagen, SEQ ID NO: 73 is amino acids 1-30 of *B. cereus* E33L hypothetical protein BCZK1835, SEQ ID NO: 75 is amino acids 1-48 of *B. weihenstephanensis* KBAB4 triple helix repeat-containing collagen, SEQ ID NO: 77 is amino acids 1-30 of *B. cereus* ATCC 14579 triple helix repeat-containing collagen, SEQ ID NO: 79 is amino acids 1-39 of *B. cereus* ATCC 14579 hypothetical protein BC4725, SEQ ID NO: 81 is amino acids 1-44 of *B. cereus* E33L hypothetical protein BCZK4476, SEQ ID NO: 83 is amino acids 1-40 of *B. anthracis* str. 'Ames Ancestor' triple helix repeat-containing collagen, SEQ ID NO: 85 is amino acids 1-34 of *B. thuringiensis* serovar konkukian str. 97-27 BclA protein, SEQ ID NO: 87 is amino acids 1-34 of *B. cereus* ATCC 10987 conserved hypothetical protein, SEQ ID NO: 89 is amino acids 1-34 of *B. cereus* ATCC 14579 triple helix repeat-containing collagen, SEQ ID NO: 91 is amino acids 1-99 of *B. cereus* exosporium leader peptide partial sequence, and SEQ ID NO: 93 is amino acids 1-136 of *B. weihenstephanensis* hypothetical protein ER45_27600. As shown in FIGS. 1A and 1B, each of the N-terminal regions of these proteins contains a region that is conserved with amino acids 20-35 of BclA (SEQ ID NO: 1), and a more highly conserved region corresponding to amino acids 25-35 of BclA.

Amino acids 1-41 of BclA from *B. thuringiensis* (SEQ ID NO: 204) and amino acids 1-41 of BclA from *B. anthracis* (SEQ ID NO: 206) are identical to SEQ ID NO: 2 and are thus not depicted in FIG. 1.

Any portion of BclA which includes amino acids 20-35 can be used as to target a fusion protein to the exosporium. In addition, full-length exosporium proteins or exosporium protein fragments can be used for targeting the fusion proteins to the exosporium. Thus, full-length BclA or a fragment of BclA that includes amino acids 20-35 can be used for targeting to the exosporium. For example, full length BclA (SEQ ID NO: 2, 204, or 206) or a midsized fragment of BclA that lacks the carboxy-terminus such as SEQ ID NO: 95 or 207 (amino acids 1-196 of BclA) or 205 (amino acids 1-166 of BclA) can be used to target the fusion proteins to the exosporium. Midsized fragments such as the fragments of SEQ ID NO: 95, 205, and 207 have less secondary structure than full length BclA and have been found to be suitable for use as a targeting sequence. The targeting sequence can also comprise much shorter portions of BclA which include amino acids 20-35, such as SEQ ID NO: 1 (amino acids 1-41 of BclA), amino acids 1-35 of SEQ ID NO: 1, amino acids 20-35 of SEQ ID NO: 1, or SEQ ID NO: 96 (a methionine residue linked to amino acids 20-35 of BclA). Even shorter fragments of BclA which include only some of amino acids 20-35 also exhibit the ability to target fusion proteins to the exosporium. For example, the targeting sequence can comprise amino acids 22-31 of SEQ ID NO: 1, amino acids 22-33 of SEQ ID NO: 1, or amino acids 20-31 of SEQ ID NO: 1.

Alternatively, any portion of BetA/BAS3290, BAS4623, BclB, BAS1882, the KBAB4 2280 gene product, the KBAB4 3572 gene product, *B. cereus* VD200 exosporium leader peptide, *B. cereus* VD166 exosporium leader peptide, *B. cereus* VD200 hypothetical protein IKG_04663, *B. weihenstephensis* KBAB4 YVTN β-propeller protein, *B. weihenstephensis* KBAB4 hypothetical protein bcerkbab4_2363, *B. weihenstephensis* KBAB4 hypothetical protein bcerkbab4_2131, *B. weihenstephensis* KBAB4 triple helix repeat containing collagen, *B. mycoides* 2048 hypothetical protein bmyco0001_21660, *B. mycoides* 2048 hypothetical protein bmyc0001_22540, *B. mycoides* 2048 hypothetical protein bmyc0001_21510, *B. thuringiensis* 35646 collagen triple helix repeat protein, *B. cereus* hypothetical protein WP_69652, *B. cereus* exosporium leader WP016117717, *B. cereus* exosporium peptide WP002105192, *B. cereus* hypothetical protein WP87353, *B. cereus* exosporium peptide 02112369, *B. cereus* exosporium protein WP016099770, *B. thuringiensis* hypothetical protein YP006612525, *B. mycoides* hypothetical protein TIGR03720, *B. cereus* ATCC 10987 collagen triple helix repeat domain protein, *B. cereus* E33L collagen-like protein, *B. weihenstephanensis* KBAB4 triple helix repeat-containing collagen, *B. thuringiensis* str. A1 Hakam hypothetical protein BALH_2230, *B. cereus* ATCC 14579 triple helix repeat-containing collagen, *B. cereus* collagen triple helix repeat, *B. cereus* ATCC 14579 triple helix repeat-containing collagen, *B. cereus* E33L hypothetical protein BCZK1835, *B. weihenstephanensis* KBAB4 triple helix repeat-containing collagen, *B. cereus* ATCC 14579 triple helix repeat-containing collagen, *B. cereus* ATCC 14579 hypothetical protein BC4725, *B. cereus* E33L hypothetical protein BCZK4476, *B. anthracis* str. 'Ames Ancestor' triple helix repeat-containing collagen, *B. thuringiensis* serovar konkukian str. 97-27 BclA protein, *B. cereus* ATCC 10987 conserved hypothetical protein, *B. cereus* ATCC 14579 triple helix repeat-containing collagen, *B. cereus* exosporium leader peptide partial sequence, or *B. weihenstephanensis* hypothetical protein ER45_27600 which includes the amino acids corresponding to amino acids 20-35 of BclA can serve as the targeting sequence.

As can be seen from FIG. 1A, amino acids 12-27 of BetA/BAS3290, amino acids 23-38 of BAS4623, amino acids 13-28 of BclB, amino acids 9-24 of BAS1882, amino acids 18-33 of KBAB4 2280 gene product, amino acids 18-33 of KBAB4 3572 gene product, amino acids 28-43 of *B. cereus* VD200 exosporium leader peptide, amino acids 12-27 of *B. cereus* VD166 exosporium leader peptide, amino acids 18-33 of *B. cereus* VD200 hypothetical protein IKG_04663, amino acids 18-33 *B. weihenstephensis* KBAB4 YVTN β-propeller protein, amino acids 9-24 of *B. weihenstephensis* KBAB4 hypothetical protein bcerkbab4_2363, amino acids 9-24 of *B. weihenstephensis* KBAB4 hypothetical protein bcerkbab4_2131, amino acids 15-30 of *B. weihenstephensis* KBAB4 triple helix repeat containing collagen, amino acids 18-33 of *B. mycoides* 2048 hypothetical protein bmyco0001_21660, amino acids 9-24 of *B. mycoides* 2048 hypothetical protein bmyc0001_22540, amino acids 1-15 of *B. mycoides* 2048 hypothetical protein bmyc0001_21510, amino acids 1-16 of *B. thuringiensis* 35646 collagen triple helix repeat protein, amino acids 14-29 of *B. cereus* hypothetical protein WP_69652, amino acids 20-35 of *B. cereus* exosporium leader WP016117717, amino acids 28-43 of *B. cereus* exosporium peptide WP002105192, amino acids 17-32 of *B. cereus* hypothetical protein WP87353, amino acids 18-33 of *B. cereus* exosporium peptide 02112369, amino acids 18-33 of *B. cereus* exosporium protein WP016099770, amino acids 15-30 of *B. thuringiensis* hypothetical protein YP006612525, and amino acids 115-130 of *B. mycoides* hypothetical protein TIGR03720 correspond to amino acids 20-35 of BclA. As can be seen from FIG. 1B of the '661 Publication, amino acids 15-30 of *B. cereus* ATCC 10987 collagen triple helix repeat domain protein, amino acids 18-33 of *B. cereus* E33L collagen-like protein, amino acids 20-35 of *B. weihenstephanensis* KBAB4 triple helix repeat-containing collagen, amino acids 9-24 of *B. thuringiensis* str. Al Hakam hypothetical protein BALH_2230, amino acids 12-27 of *B. cereus* ATCC 14579 triple helix repeat-containing collagen, amino acids 23-38 of *B. cereus* collagen triple helix repeat, amino acids 17-32 of *B. cereus* ATCC 14579 triple helix repeat-containing collagen, amino acids 9-24 of *B. cereus* E33L hypothetical protein BCZK1835, amino acids 27-42 of *B. weihenstephanensis* KBAB4 triple helix repeat-containing collagen, amino acids 9-24 of *B. cereus* ATCC 14579 triple helix repeat-containing collagen, amino acids 18-33 of *B. cereus* ATCC 14579 hypothetical protein BC4725, amino acids 23-38 of *B. cereus* E33L hypothetical protein BCZK4476, amino acids 19-34 *B. anthracis* str. 'Ames Ancestor' triple helix repeat-containing collagen, amino acids 13-28 of *B. thuringiensis* serovar konkukian str. 97-27 BclA protein, amino acids 13-28 of *B. cereus* ATCC 10987 conserved hypothetical protein, amino acids 13-28 of *B. cereus* ATCC 14579 triple helix repeat-containing collagen, amino acids 78-93 of *B. cereus* exosporium leader peptide partial sequence, and amino acids 115-130 of *B. weihenstephanensis* hypothetical protein ER45_27600 correspond to amino acids 20-35 of BclA. Thus, any portion of these proteins that includes the above-listed corresponding amino acids can serve as the targeting sequence.

Furthermore, any amino acid sequence comprising amino acids 20-35 of BclA, or any of the above-listed corresponding amino acids, can serve as the targeting sequence.

The targeting sequence can comprise amino acids 1-35 of SEQ ID NO: 1, amino acids 20-35 of SEQ ID NO: 1, SEQ ID NO: 1, SEQ ID NO: 96, amino acids 22-31 of SEQ ID NO: 1, amino acids 22-33 of SEQ ID NO: 1, or amino acids 20-31 of SEQ ID NO: 1. Alternatively, the targeting sequence can consist of amino acids 1-35 of SEQ ID NO: 1, amino acids 20-35 of SEQ ID NO: 1, SEQ ID NO: 1, or SEQ ID NO: 96. Alternatively, the targeting sequence can consist of amino acids 22-31 of SEQ ID NO: 1, amino acids 22-33 of SEQ ID NO: 1, or amino acids 20-31 of SEQ ID NO: 1. Alternatively, the exosporium protein can comprise full length BclA (SEQ ID NO: 2), or the exosporium protein fragment can comprise a midsized fragment of BclA that lacks the carboxy-terminus, such as SEQ ID NO: 95 (amino acids 1-196 of BclA). Alternatively, the exosporium protein fragment can consist of SEQ ID NO: 95.

The targeting sequence can comprise amino acids 2-35 of SEQ ID NO: 1; amino acids 5-35 of SEQ ID NO: 1; amino acids 8-35 of SEQ ID NO: 1; amino acids 10-35 of SEQ ID NO: 1; or amino acids 15-35 of SEQ ID NO: 1.

The targeting sequence can comprise amino acids 1-27 of SEQ ID NO: 3, amino acids 12-27 of SEQ ID NO: 3, or SEQ ID NO: 3, or the exosporium protein can comprise full length BetA/BAS3290 (SEQ ID NO: 4). It has also been found that a methionine residue linked to amino acids 12-27 of BetA/BAS3290 can be used as a targeting sequence. Thus, the targeting sequence can comprise SEQ ID NO: 97. Alternatively, the targeting sequence can comprise amino acids 14-23 of SEQ ID NO: 3, amino acids 14-25 of SEQ ID NO: 3, or amino acids 12-23 of SEQ ID NO: 3.

The targeting sequence can comprise amino acids 2-27 of SEQ ID NO: 3; amino acids 5-27 of SEQ ID NO: 3; amino acids 8-27 of SEQ ID NO: 3; or amino acids 10-27 of SEQ ID NO: 3.

The targeting sequence can comprise amino acids 1-38 of SEQ ID NO: 5, amino acids 23-38 of SEQ ID NO: 5, SEQ ID NO: 5, or SEQ ID NO: 201 (a methionine residue linked to amino acids 23-38 of BAS4623) or the exosporium protein can comprise full length BAS4623 (SEQ ID NO: 6).

The targeting sequence can comprise amino acids 2-38 of SEQ ID NO: 5; amino acids 5-38 of SEQ ID NO: 5; amino acids 8-38 of SEQ ID NO: 5; amino acids 10-38 of SEQ ID NO: 5; amino acids 15-38 of SEQ ID NO: 5; or amino acids 20-38 of SEQ ID NO: 5.

Alternatively, the targeting sequence can comprise amino acids 1-28 of SEQ ID NO: 7, amino acids 13-28 of SEQ ID NO: 7, SEQ ID NO: 7, or SEQ ID NO: 202 (a methionine residue linked to amino acids 13-28 of BclB) or the exosporium protein can comprise full length BclB (SEQ ID NO: 8).

The targeting sequence can comprise amino acids 2-28 of SEQ ID NO: 7; amino acids 5-28 of SEQ ID NO: 7; amino acids 8-28 of SEQ ID NO: 7; or amino acids 10-28 of SEQ ID NO: 7.

The targeting sequence can comprise amino acids 1-24 of SEQ ID NO: 9, amino acids 9-24 of SEQ ID NO: 9, or SEQ ID NO: 9, or the exosporium protein can comprise full length BAS1882 (SEQ ID NO: 10). A methionine residue linked to amino acids 9-24 of BAS1882 can be used as a targeting sequence. Thus, the targeting sequence can comprise SEQ ID NO: 105.

The targeting sequence can comprise amino acids 2-24 of SEQ ID NO: 9; amino acids 5-24 of SEQ ID NO: 9; or amino acids 8-24 of SEQ ID NO: 9.

The targeting sequence can comprise amino acids 1-33 of SEQ ID NO: 11, amino acids 18-33 of SEQ ID NO: 11, or SEQ ID NO: 11, or the exosporium protein can comprise the full length *B. weihenstephensis* KBAB4 2280 gene product (SEQ ID NO: 12). A methionine residue linked to amino acids 18-33 of the *B. weihenstephensis* KBAB4 2280 gene product can be used as a targeting sequence. Thus, the targeting sequence can comprise SEQ ID NO: 98.

The targeting sequence can comprise amino acids 2-33 of SEQ ID NO: 11; amino acids 5-33 of SEQ ID NO: 11; amino acids 8-33 of SEQ ID NO: 11; amino acids 10-33 of SEQ ID NO: 11; or amino acids 15-33 of SEQ ID NO: 11.

The targeting sequence can also comprise amino acids 1-33 of SEQ ID NO: 13, amino acids 18-33 of SEQ ID NO: 13, or SEQ ID NO: 13, or the exosporium protein can comprise the full length *B. weihenstephensis* KBAB4 3572 gene product (SEQ ID NO: 14). A methionine residue linked to amino acids 18-33 of the *B. weihenstephensis* KBAB4 3572 gene product can be used as a targeting sequence. Thus, the targeting sequence can comprise SEQ ID NO: 99.

The targeting sequence can comprise amino acids 2-33 of SEQ ID NO: 13; amino acids 5-33 of SEQ ID NO: 13; amino acids 8-33 of SEQ ID NO: 13; amino acids 10-33 of SEQ ID NO: 13; or amino acids 15-33 of SEQ ID NO: 13.

Alternatively, the targeting sequence can comprise amino acids 1-43 of SEQ ID NO: 15, amino acids 28-43 of SEQ ID NO: 15, or SEQ ID NO: 15, or the exosporium protein can comprise full length *B. cereus* VD200 exosporium leader peptide (SEQ ID NO: 16).

The targeting sequence can comprise amino acids 2-43 of SEQ ID NO: 15; amino acids 5-43 of SEQ ID NO: 15; amino acids 8-43 of SEQ ID NO: 15; amino acids 10-43 of SEQ ID NO: 15; amino acids 15-43 of SEQ ID NO: 15; amino acids 20-43 of SEQ ID NO: 15; or amino acids 25-43 of SEQ ID NO: 15.

The targeting sequence can also comprise amino acids 1-27 of SEQ ID NO: 17, amino acids 12-27 of SEQ ID NO: 17, or SEQ ID NO: 17, or the exosporium protein can comprise full-length *B. cereus* VD166 exosporium leader peptide (SEQ ID NO: 18). A methionine residue linked to amino acids 12-27 of the *B. cereus* VD166 exosporium leader peptide can be used as a targeting sequence. Thus, the targeting sequence can comprise SEQ ID NO: 100.

The targeting sequence can comprise amino acids 2-27 of SEQ ID NO: 17; amino acids 5-27 of SEQ ID NO: 17; amino acids 8-27 of SEQ ID NO: 17; or amino acids 10-27 of SEQ ID NO: 17.

The targeting sequence can also comprise amino acids 1-33 of SEQ ID NO: 19, amino acids 18-33 of SEQ ID NO: 19, or SEQ ID NO: 19, or the exosporium protein can comprise full length *B. cereus* VD200 hypothetical protein IKG_04663 (SEQ ID NO: 20).

The targeting sequence can comprise amino acids 2-33 of SEQ ID NO: 19; amino acids 5-33 of SEQ ID NO: 19; amino acids 8-33 of SEQ ID NO: 19; amino acids 10-33 of SEQ ID NO: 19; or amino acids 15-33 of SEQ ID NO: 19.

Alternatively, the targeting sequence comprises amino acids 1-33 of SEQ ID NO: 21, amino acids 18-33 of SEQ ID NO: 21, or SEQ ID NO: 21, or the exosporium protein can comprise full length *B. weihenstephensis* KBAB4 YVTN β-propeller protein (SEQ ID NO: 22). A methionine residue linked to amino acids 18-33 of the *B. weihenstephensis* KBAB4 YVTN β-propeller protein can be used as a targeting sequence. Thus, the targeting sequence can comprise SEQ ID NO: 101.

The targeting sequence can comprise amino acids 2-33 of SEQ ID NO: 21; amino acids 5-33 of SEQ ID NO: 21; amino acids 8-33 of SEQ ID NO: 21; amino acids 10-33 of SEQ ID NO: 21; or amino acids 15-33 of SEQ ID NO: 21.

The targeting sequence can also comprise amino acids 1-24 of SEQ ID NO: 23, amino acids 9-24 of SEQ ID NO: 23, or SEQ ID NO: 23, or the exosporium protein can comprise full length *B. weihenstephensis* KBAB4 hypothetical protein bcerkbab4_2363 (SEQ ID NO: 24). A methionine residue linked to amino acids 9-24 of *B. weihenstephensis* KBAB4 hypothetical protein bcerkbab4_2363 can be used as a targeting sequence. Thus, the targeting sequence can comprise SEQ ID NO: 102.

The targeting sequence can comprise amino acids 2-24 of SEQ ID NO: 23; amino acids 5-24 of SEQ ID NO: 23; or amino acids 8-24 of SEQ ID NO: 23.

The targeting sequence comprise amino acids 1-24 of SEQ ID NO: 25, amino acids 9-24 of SEQ ID NO: 25, or SEQ ID NO: 25, or the exosporium protein can comprise full length *B. weihenstephensis* KBAB4 hypothetical protein bcerkbab4_2131 (SEQ ID NO: 26). A methionine residue linked to amino acids 9-24 of *B. weihenstephensis* KBAB4 hypothetical protein bcerkbab4_2131 can be used as a targeting sequence. Thus, the targeting sequence can comprise SEQ ID NO: 103.

The targeting sequence can comprise amino acids 2-24 of SEQ ID NO: 25; amino acids 5-24 of SEQ ID NO: 25; or amino acids 8-24 of SEQ ID NO: 25.

Alternatively, the targeting sequence comprises amino acids 1-30 of SEQ ID NO: 27, amino acids 15-30 of SEQ ID NO: 27, or SEQ ID NO: 27, or the exosporium protein can comprise full length *B. weihenstephensis* KBAB4 triple helix repeat containing collagen (SEQ ID NO: 28).

The targeting sequence can comprise amino acids 2-30 of SEQ ID NO: 27; amino acids 5-30 of SEQ ID NO: 27; amino acids 8-30 of SEQ ID NO: 27; or amino acids 10-30 of SEQ ID NO: 27.

The targeting sequence can also comprise amino acids 1-33 of SEQ ID NO: 29, amino acids 18-33 of SEQ ID NO: 29, or SEQ ID NO: 29, or the exosporium protein can comprise full length *B. mycoides* 2048 hypothetical protein bmyco0001_21660 (SEQ ID NO: 30).

The targeting sequence can comprise amino acids 2-33 of SEQ ID NO: 29; amino acids 5-33 of SEQ ID NO: 29; amino acids 8-33 of SEQ ID NO: 29; amino acids 10-33 of SEQ ID NO: 29; or amino acids 15-33 of SEQ ID NO: 29.

The targeting sequence can also comprise amino acids 1-24 of SEQ ID NO: 31, amino acids 9-24 of SEQ ID NO: 31, or SEQ ID NO: 31, or the exosporium protein can comprise full length *B. mycoides* 2048 hypothetical protein bmyc0001_22540 (SEQ ID NO: 32). A methionine residue linked to amino acids 9-24 of *B. mycoides* 2048 hypothetical protein bmyc0001_22540 can be used as a targeting sequence. Thus, the targeting sequence can comprise SEQ ID NO: 104.

The targeting sequence can comprise amino acids 2-24 of SEQ ID NO: 31; amino acids 5-24 of SEQ ID NO: 31; or amino acids 8-24 of SEQ ID NO: 31.

Alternatively, the targeting sequence comprises amino acids 1-15 of SEQ ID NO: 33, SEQ ID NO: 33, or the exosporium protein comprises full length *B. mycoides* 2048 hypothetical protein bmyc0001_21510 (SEQ ID NO: 34).

The targeting sequence can also comprise amino acids 1-16 of SEQ ID NO: 35, SEQ ID NO: 35, or the exosporium protein can comprise full length *B. thuringiensis* 35646 collagen triple helix repeat protein (SEQ ID NO: 36).

The targeting sequence can comprise amino acids 1-29 of SEQ ID NO: 43, amino acids 14-29 of SEQ ID NO: 43, or SEQ ID NO: 43, or the exosporium protein can comprise full length *B. cereus* hypothetical protein WP_69652 (SEQ ID NO: 44).

The targeting sequence can comprise amino acids 2-29 of SEQ ID NO: 43; amino acids 5-29 of SEQ ID NO: 43; amino acids 8-29 of SEQ ID NO: 43; or amino acids 10-29 of SEQ ID NO: 43.

Alternatively, the targeting sequence can comprise amino acids 1-35 of SEQ ID NO: 45, amino acids 20-35 of SEQ ID NO: 45, or SEQ ID NO: 45, or the exosporium protein can comprise full length *B. cereus* exosporium leader WP016117717 (SEQ ID NO: 46). A methionine residue linked to amino acids 20-35 of *B. cereus* exosporium leader WP016117717 can be used as a targeting sequence. Thus, the targeting sequence can comprise SEQ ID NO: 106.

The targeting sequence can comprise amino acids 2-35 of SEQ ID NO: 45; amino acids 5-35 of SEQ ID NO: 45; amino acids 8-35 of SEQ ID NO: 45; amino acids 10-35 of SEQ ID NO: 45; or amino acids 15-35 of SEQ ID NO: 45.

The targeting sequence can comprise amino acids 1-43 of SEQ ID NO: 47, amino acids 28-43 of SEQ ID NO: 47, or SEQ ID NO: 47, or the exosporium protein can comprise full length *B. cereus* exosporium peptide WP002105192 (SEQ ID NO: 48).

The targeting sequence can comprise amino acids 2-43 of SEQ ID NO: 47; amino acids 5-43 of SEQ ID NO: 47; amino acids 8-43 of SEQ ID NO: 47; amino acids 10-43 of SEQ ID NO: 47; amino acids 15-43 of SEQ ID NO: 47; amino acids 20-43 of SEQ ID NO: 47; or amino acids 25-43 of SEQ ID NO: 47.

The targeting sequence can comprise amino acids 1-32 of SEQ ID NO: 49, amino acids 17-32 of SEQ ID NO: 49, or SEQ ID NO: 49, or the exosporium protein can comprise full length *B. cereus* hypothetical protein WP87353 (SEQ ID NO: 50).

The targeting sequence can comprise amino acids 2-32 of SEQ ID NO: 49; amino acids 5-32 of SEQ ID NO: 49; amino acids 8-32 of SEQ ID NO: 49; amino acids 10-32 of SEQ ID NO: 49; or amino acids 15-32 of SEQ ID NO: 49.

Alternatively, the targeting sequence can comprise amino acids 1-33 of SEQ ID NO: 51, amino acids 18-33 of SEQ ID NO: 51, or SEQ ID NO: 51, or the exosporium protein can comprise full length *B. cereus* exosporium peptide 02112369 (SEQ ID NO: 52).

The targeting sequence can comprise amino acids 2-33 of SEQ ID NO: 51; amino acids 5-33 of SEQ ID NO: 51; amino acids 8-33 of SEQ ID NO: 51; amino acids 10-33 of SEQ ID NO: 51; or amino acids 15-33 of SEQ ID NO: 51.

The targeting sequence can comprise amino acids 1-33 of SEQ ID NO: 53, amino acids 18-33 of SEQ ID NO: 53, or SEQ ID NO: 53, or the exosporium protein can comprise full length *B. cereus* exosporium protein WP016099770 (SEQ ID NO: 54).

The targeting sequence can comprise amino acids 2-33 of SEQ ID NO: 53; amino acids 5-33 of SEQ ID NO: 53; amino acids 8-33 of SEQ ID NO: 53; amino acids 10-33 of SEQ ID NO: 53; or amino acids 15-33 of SEQ ID NO: 53.

Alternatively, the targeting sequence can comprise acids 1-30 of SEQ ID NO: 55, amino acids 15-30 of SEQ ID NO: 55, or SEQ ID NO: 55, or the exosporium protein can comprise full length *B. thuringiensis* hypothetical protein YP006612525 (SEQ ID NO: 56).

The targeting sequence can comprise amino acids 2-30 of SEQ ID NO: 55; amino acids 5-30 of SEQ ID NO: 55; amino acids 8-30 of SEQ ID NO: 55; or amino acids 10-30 of SEQ ID NO: 55.

The targeting sequence can comprise amino acids 1-130 of SEQ ID NO: 57, amino acids 115-130 of SEQ ID NO: 57, or SEQ ID NO: 57, or the exosporium protein can comprise full length *B. mycoides* hypothetical protein TIGR03720 (SEQ ID NO: 58).

The targeting sequence can comprise amino acids 2-130 of SEQ ID NO: 57; amino acids 5-130 of SEQ ID NO: 57; amino acids 10-130 of SEQ ID NO: 57; amino acids 20-130 of SEQ ID NO: 57; amino acids 30-130 of SEQ ID NO: 57; amino acids 40-130 of SEQ ID NO: 57; amino acids 50-130 of SEQ ID NO: 57; amino acids 60-130 of SEQ ID NO: 57; amino acids 70-130 of SEQ ID NO: 57; amino acids 80-130 of SEQ ID NO: 57; amino acids 90-130 of SEQ ID NO: 57; amino acids 100-130 of SEQ ID NO: 57; or amino acids 110-130 of SEQ ID NO: 57.

The targeting sequence can comprise amino acids 1-30 of SEQ ID NO: 59; or SEQ ID NO: 59; or the exosporium protein can comprise full length *B. cereus* ATCC 10987 collagen triple helix repeat domain protein (SEQ ID NO: 60).

The targeting sequence can comprise amino acids 2-30 of SEQ ID NO: 59; amino acids 4-30 of SEQ ID NO: 59; or amino acids 6-30 of SEQ ID NO: 59.

The targeting sequence can comprise amino acids 1-33 of SEQ ID NO: 61; amino acids 18-33 of SEQ ID NO: 61; or SEQ ID NO: 61; or the exosporium protein can comprise full length *B. cereus* E33L collagen-like protein (SEQ ID NO: 62).

The targeting sequence can comprise amino acids 2-33 of SEQ ID NO: 61; amino acids 5-33 of SEQ ID NO: 61; amino acids 10-33 of SEQ ID NO: 61; or amino acids 15-33 of SEQ ID NO: 61.

The targeting sequence can comprise amino acids 1-35 of SEQ ID NO: 63; or SEQ ID NO: 63; or the exosporium protein can comprise full length *B. weihenstephanensis* KBAB4 triple helix repeat-containing collagen (SEQ ID NO: 64).

The targeting sequence can comprise amino acids 2-35 of SEQ ID NO: 63; amino acids 5-35 of SEQ ID NO: 63; amino acids 8-35 of SEQ ID NO: 63; amino acids 10-35 of SEQ ID NO: 63; or amino acids 15-35 of SEQ ID NO: 63.

The targeting sequence can comprise amino acids 1-24 of SEQ ID NO: 65; acids 9-24 of SEQ ID NO: 65; SEQ ID NO: 65; or SEQ ID NO: 107; or the exosporium protein can comprise full length *B. thuringiensis* str. Al Hakam hypothetical protein BALH_2230 (SEQ ID NO: 66).

The targeting sequence can comprise amino acids 2-24 of SEQ ID NO: 65; or amino acids 5-24 of SEQ ID NO: 65.

The targeting sequence can comprise acids 1-27 of SEQ ID NO: 67; amino acids 12-27 of SEQ ID NO: 67; or SEQ ID NO: 67; or the exosporium protein can comprise full length *B. cereus* ATCC 14579 triple helix repeat-containing collagen (SEQ ID NO: 68).

The targeting sequence can comprise amino acids 2-27 of SEQ ID NO: 67; amino acids 5-27 of SEQ ID NO: 67; or amino acids 10-27 of SEQ ID NO: 67.

The targeting sequence can comprise amino acids 1-38 of SEQ ID NO: 69; amino acids 23-38 of SEQ ID NO: 69; or SEQ ID NO: 69; or the exosporium protein can comprise full length *B. cereus* collagen triple helix repeat (SEQ ID NO: 70).

The targeting sequence can comprise amino acids 2-38 of SEQ ID NO: 69; amino acids 5-38 of SEQ ID NO: 69; amino acids 10-38 of SEQ ID NO: 69; or amino acids 15-38 of SEQ ID NO: 69.

The exosporium protein can comprise full length *B. cereus* ATCC 14579 triple helix repeat-containing collagen (SEQ ID NO: 72).

The targeting sequence can comprise SEQ ID NO: 73, or the exosporium protein can comprise full length *B. cereus* E33L hypothetical protein BCZK1835 (SEQ ID NO: 74).

The targeting sequence can comprise amino acids 1-42 of SEQ ID NO: 75; amino acids 27-42 of SEQ ID NO: 75; or SEQ ID NO: 75; or the exosporium protein can comprise full length *B. weihenstephanensis* KBAB4 triple helix repeat-containing collagen (SEQ ID NO: 76).

The targeting sequence can comprise amino acids 2-42 of SEQ ID NO: 75; amino acids 5-42 of SEQ ID NO: 75; amino acids 10-42 of SEQ ID NO: 75; amino acids 15-42 of SEQ ID NO: 75; amino acids 20-42 of SEQ ID NO: 75; or amino acids 25-42 of SEQ ID NO: 75.

The targeting sequence can comprise amino acids 1-24 of SEQ ID NO: 77; amino acids 9-24 of SEQ ID NO: 77; or SEQ ID NO: 77; or the exosporium protein can comprise full length *B. cereus* ATCC 14579 triple helix repeat-containing collagen (SEQ ID NO: 78).

The targeting sequence can comprise amino acids 2-24 of SEQ ID NO: 77; or amino acids 5-24 of SEQ ID NO: 77.

The exosporium protein can comprise full length *B. cereus* ATCC 14579 hypothetical protein BC4725 (SEQ ID NO: 80).

The targeting sequence can comprise amino acids 1-38 of SEQ ID NO: 81; amino acids 23-38 of SEQ ID NO: 81; or SEQ ID NO: 81; or the exosporium protein can comprise full length *B. cereus* E33L hypothetical protein BCZK4476 (SEQ ID NO: 82).

The targeting sequence can comprise amino acids 2-38 of SEQ ID NO: 81; acids 5-38 of SEQ ID NO: 81; amino acids 10-38 of SEQ ID NO: 81; amino acids 15-38 of SEQ ID NO: 81; or amino acids 20-38 of SEQ ID NO: 81.

The targeting sequence can comprise amino acids 1-34 of SEQ ID NO: 83; or SEQ ID NO: 83; or the exosporium protein can comprise full length *B. anthracis* str. 'Ames Ancestor' triple helix repeat-containing collagen (SEQ ID NO: 84).

The exosporium protein can comprise full length *B. thuringiensis* serovar konkukian str. 97-27 BclA protein (SEQ ID NO: 86).

The targeting sequence can comprise amino acids 1-28 of SEQ ID NO: 87; amino acids 13-28 of SEQ ID NO: 87; or SEQ ID NO: 87; or the exosporium protein can comprise full length *B. cereus* ATCC 10987 conserved hypothetical protein (SEQ ID NO: 88).

The targeting sequence can comprise amino acids 2-28 of SEQ ID NO: 87; amino acids 5-28 of SEQ ID NO: 87; or amino acids 10-28 of SEQ ID NO: 87.

The targeting sequence can comprise amino acids 1-28 of SEQ ID NO: 89; or SEQ ID NO: 89; or the exosporium protein can comprise full length *B. cereus* ATCC 14579 triple helix repeat-containing collagen (SEQ ID NO: 90).

The targeting sequence can comprise amino acids 2-28 of SEQ ID NO: 89; amino acids 5-28 of SEQ ID NO: 89; or amino acids 10-28 of SEQ ID NO: 89.

The targeting sequence can comprise amino acids 1-93 of SEQ ID NO: 91; or SEQ ID NO: 91; or the exosporium protein can comprise *B. cereus* exosporium leader peptide partial sequence (SEQ ID NO: 92).

The targeting sequence can comprise amino acids 2-93 of SEQ ID NO: 91; amino acids 10-93 of SEQ ID NO: 91; amino acids 20-93 of SEQ ID NO: 91; amino acids 30-93 of SEQ ID NO: 91; amino acids 40-93 of SEQ ID NO: 91; amino acids 50-93 of SEQ ID NO: 91; or amino acids 60-93 of SEQ ID NO: 91.

The targeting sequence can comprise amino acids 1-130 of SEQ ID NO: 93; or SEQ ID NO: 93; or the exosporium protein can comprise *B. weihenstephanensis*) hypothetical protein ER45_27600, partial sequence (SEQ ID NO: 94).

The targeting sequence can comprise amino acids 2-130 of SEQ ID NO: 93; amino acids 10-130 of SEQ ID NO: 93; amino acids 20-130 of SEQ ID NO: 93; or amino acids 30-130 of SEQ ID NO: 93.

The targeting sequence can comprise amino acids 1-35 of SEQ ID NO: 204, amino acids 20-35 of SEQ ID NO: 204, SEQ ID NO: 204, or SEQ ID NO: 205.

The targeting sequence can comprise amino acids 1-35 of SEQ ID NO: 206, amino acids 20-35 of SEQ ID NO: 206, SEQ ID NO: 206, or SEQ ID NO: 207.

Furthermore, it has been found that sequences shorter than amino acids 20-35 of BclA can be used to target a fusion protein to the exosporium of a recombinant *Bacillus cereus* family member. In particular, amino acids 20-33 of BclA, amino acids 20-31 of BclA, amino acids 21-33 of BclA, or amino acids 23-31 of BclA can be used to target a fusion protein to the exosporium of a recombinant *Bacillus cereus* family member. Thus, the targeting sequence can consist of amino acids 20-33 of SEQ ID NO: 1, amino acids 20-31 of SEQ ID NO: 1, amino acids 21-33 of SEQ ID NO: 1, or amino acids 23-31 of SEQ ID NO: 1. The corresponding regions of any of the SEQ ID NOs. shown in FIGS. 1A and 1B can also be used to target a fusion protein to the exosporium of a recombinant *Bacillus cereus* family member. By "corresponding regions," it is meant that when the sequences are aligned with SEQ ID NO: 1, as shown in FIGS. 1A and 1B, the regions of the other amino acid sequences that align with the amino acids of SEQ ID NO: are the "corresponding regions" of those sequences. Thus, for example, amino acids 12-25 of SEQ ID NO: 3, amino acids 23-36 of SEQ ID NO: 5, amino acids 13-26 of SEQ ID NO: 7, etc., can be used to target a fusion protein to the exosporium of a recombinant *Bacillus cereus* family member, since these regions align with amino acids 20-33 of SEQ ID NO: 1 as shown in FIG. 1A.

Even shorter regions within amino acids 20-35 of BclA can also be used for targeting a fusion protein to the exosporium of a recombinant *Bacillus cereus* family member. In particular, any amino acid sequence that includes amino acids 25-30 of SEQ ID NO: 1 or the corresponding amino acids from any of the sequences shown in FIGS. 1A and 1B can be used. A skilled person will recognize that starting with amino acids 25-30 of SEQ ID NO: 1 or the corresponding region of any of the sequences shown in FIGS. 1A and 1B, additional amino acids can be added to the amino-terminus, the carboxy terminus, or both the amino- and carboxy termini to create a targeting sequence that will be effective for targeting a fusion protein to the exosporium of a recombinant *Bacillus cereus* family member.

In addition, it can readily be seen from the sequence alignment in FIGS. 1A and 1B of the '661 Publication that while amino acids 20-35 of BclA are conserved, and amino acids 25-35 are more conserved, some degree of variation can occur in this region without affecting the ability of the targeting sequence to target a protein to the exosporium. FIGS. 1A and 1B of the '661 Publication list the percent identity of each of the corresponding amino acids of each sequence to amino acids 20-35 of BclA ("20-35% Identity") and to amino acids 25-35 of BclA ("25-35% Identity"). Thus, for example, as compared to amino acids 20-35 of BclA, the corresponding amino acids of BetA/BAS3290 are about 81.3% identical, the corresponding amino acids of BAS4623 are about 50.0% identical, the corresponding amino acids of BclB are about 43.8% identical, the corresponding amino acids of BAS1882 are about 62.5% identical, the corresponding amino acids of the KBAB4 2280 gene product are about 81.3% identical, and the corresponding amino acids of the KBAB4 3572 gene product are about 81.3% identical. The sequence identities over this region for the remaining sequences are listed in FIGS. 1A and 1B.

With respect to amino acids 25-35 of BclA, the corresponding amino acids of BetA/BAS3290 are about 90.9% identical, the corresponding amino acids of BAS4623 are about 72.7% identical, the corresponding amino acids of BclB are about 54.5% identical, the corresponding amino acids of BAS1882 are about 72.7% identical, the corresponding amino acids of the KBAB4 2280 gene product are about 90.9% identical, and the corresponding amino acids of the KBAB4 3572 gene product are about 81.8% identical. The sequence identities over this region for the remaining sequences are listed in FIGS. 1A and 1B.

Thus, the targeting sequence can comprise an amino acid sequence having at least about 43% identity with amino acids 20-35 of SEQ ID NO: 1, wherein the identity with amino acids 25-35 is at least about 54%. Alternatively, the targeting sequence consists of an amino acid sequence consisting of 16 amino acids and having at least about 43% identity with amino acids 20-35 of SEQ ID NO: 1, wherein the identity with amino acids 25-35 is at least about 54%.

The targeting sequence can also comprise an amino acid sequence having at least about 50% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 63%.

The targeting sequence can also comprise an amino acid sequence having at least about 50% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 72%.

The targeting sequence can also comprise an amino acid sequence having at least about 56% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 56% identity with amino acids 20-35 of SEQ ID NO: 1, wherein the identity with amino acids 25-35 is at least about 63%.

The targeting sequence can comprise an amino acid sequence having at least about 62% identity with amino acids 20-35 of SEQ ID NO: 1, wherein the identity with amino acids 25-35 is at least about 72%. Alternatively, the targeting sequence can consist of an amino acid sequence consisting of 16 amino acids and having at least about 62% identity with amino acids 20-35 of SEQ ID NO: 1, wherein the identity with amino acids 25-35 of SEQ ID NO: 1 is at least about 72%.

The targeting sequence can comprise an amino acid sequence having at least 68% identity with amino acids 20-35 of SEQ ID NO: 1, wherein the identity with amino acids 25-35 is at least about 81%. Alternatively, the targeting sequence consists of an amino acid sequence consisting of 16 amino acids and having at least 68% identity with amino acids 20-35 of SEQ ID NO: 1, wherein the identity with amino acids 25-35 is at least about 81%.

The targeting sequence can also comprises an amino sequence having at least about 75% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO: 1 is at least about 72%.

The targeting sequence can also comprise an amino sequence having at least about 75% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO: 1 is at least about 81%.

The targeting sequence can also comprise an amino acid sequence having at least about 81% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 90%.

The skilled person will recognize that variants of the above sequences can also be used as targeting sequences, so long as the targeting sequence comprises amino acids 20-35 of BclA, the corresponding amino acids of BetA/BAS3290, BAS4263, BclB, BAS1882, the KBAB4 2280 gene product, or the KBAB 3572 gene product, or a sequence comprising any of the above noted sequence identities to amino acids 20-35 and 25-35 of BclA is present.

Certain *Bacillus cereus* family exosporium proteins which lack regions having homology to amino acids 25-35 of BclA can also be used to target a peptide or protein to the exosporium of a *Bacillus cereus* family member. In particular, the fusion proteins can comprise an exosporium protein comprising SEQ ID NO: 108 (*B. mycoides* InhA), an exosporium protein comprising SEQ ID NO: 109 (*B. anthracis* Sterne BAS1141 (ExsY)), an exosporium protein comprising SEQ ID NO: 110 (*B. anthracis* Sterne BAS1144 (BxpB/ExsFA)), an exosporium protein comprising SEQ ID NO: 111 (*B. anthracis* Sterne BAS1145 (CotY)), an exosporium protein comprising SEQ ID NO: 112 (*B. anthracis* Sterne BAS1140), an exosporium protein comprising SEQ ID NO: 113 (*B. anthracis* H9401 ExsFB), an exosporium protein comprising SEQ ID NO: 114 (*B. thuringiensis* HD74 InhA1), an exosporium protein comprising SEQ ID NO: 115 (*B. cereus* ATCC 10876 ExsJ), an exosporium protein comprising SEQ ID NO: 116 (*B. cereus* ExsH), an exosporium protein comprising SEQ ID NO: 117 (*B. anthracis* Ames YjcA), an exosporium protein comprising SEQ ID NO: 118 (*B. anthracis* YjcB), an exosporium protein comprising SEQ ID NO: 119 (*B. anthracis* Sterne BclC), an exosporium protein comprising SEQ ID NO: 120 (*Bacillus thuringiensis* serovar konkukian str. 97-27 acid phosphatase), an exosporium protein comprising SEQ ID NO: 121 (*B. thuringiensis* HD74 InhA2), an exosporium protein comprising SEQ ID NO: 122 (*B. mycoides* InhA3), or an exosporium protein comprising SEQ ID NO: 203 (*B. anthracis* CotY variant). Inclusion of an exosporium protein comprising any of SEQ ID NOs: 108-122 or 203 in the fusion proteins described herein will result in targeting to the exosporium of a *B. cereus* family member.

Moreover, exosporium proteins having a high degree of sequence identity with any of the full-length exosporium proteins or the exosporium protein fragments described above can also be used to target a peptide or protein to the exosporium of a *Bacillus cereus* family member. Thus, the fusion protein can comprise an exosporium protein or exosporium protein fragment comprising an amino acid sequence having at least 85% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, 122, and 203.

Alternatively, the fusion protein can comprise an exosporium protein having at least 90% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, 122, and 203.

The fusion protein can comprise an exosporium protein having at least 95% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, 122, and 203.

The fusion protein can comprise an exosporium protein having at least 98% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, 122, and 203.

The fusion protein can comprise an exosporium protein having at least 99% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, 122, and 203.

The fusion protein can comprise an exosporium protein having 100% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, 122, and 203.

The targeting sequence, exosporium protein or exosporium protein fragment of the present invention may also be described in terms of a motif that provides the targeting function. FIGS. 1A and 1B show a sequence alignment of the amino-terminal region of BclA (SEQ ID NO: 1) with the corresponding amino-terminal regions of a number of other *Bacillus cereus* family member exosporium proteins. As can be seen from FIG. 1, there is a conserved motif at amino acids 20-35 of BclA (shown in bold in FIG. 1), with a more highly conserved motif at amino acids 25-35 of BclA (shown in bold and underlined in FIG. 1). This more highly conserved region is the recognition sequence for ExsFA/BxpB/ExsFB and homologs, which direct and assemble the described exosporium proteins on the surface of the exosporium.

Furthermore, while amino acids 20-35 of BclA are conserved, and amino acids 25-35 are more conserved, some degree of variation can occur in this region without affecting the ability of the targeting sequence to target a protein to the exosporium. FIG. 1 lists the percent identity of the corresponding amino acids of each sequence to amino acids 20-35 of BclA ("20-35% Identity") and to amino acids 25-35 of BclA ("25-35% Identity"). Sequences having a targeting sequence identity as low as 43.8% with amino acids 20-35 of BclA (SEQ ID NO: 1), wherein the identity with amino acids 25-35 of BclA is 54.5%, retain the ability to target fusion proteins to the exosporium. Data are provided in Table 58 in Example 59 of PCT Publication No. WO 2016/044661, which is incorporated herein by reference in its entirety. Table 58 shows the enzyme levels of phosphatidylcholine-specific phospholipase C gene (PC-PLC) and lipase on *Bacillus cereus* family member spores expressing fusion proteins containing these enzymes and various targeting sequences. The relevant portion of Table 58 of PCT Publication No. WO 2016/044661 is reproduced below, with two additional columns added to show the percent identity of each of the targeting sequences with amino acids 20-35 and 25-35 of BclA (SEQ ID NO: 1):

| Targeting Sequence | Sequence Identity to AA 20-35 of BclA | Sequence Identity to AA 25-35 of BclA | PC-PLC Enzyme Levels | Lipase Enzyme Levels |
|---|---|---|---|---|
| Control ($H_2O$) | N/A | N/A | 0.0 | 0.0 |
| AA 20-35 of SEQ ID NO: 1 | 100% | 100% | .787 | .436 |
| AA 23-38 of SEQ ID NO: 5 | 50.0% | 72.7% | .688 | .602 |
| AA 28-43 of SEQ ID NO: 15 | 68.8% | 81.8% | .372 | .228 |
| AA 9-24 of SEQ ID NO: 25 | 56.3% | 63.6% | .247 | .359 |

These data show that targeting of a protein of interest (e.g., an enzyme) to the exosporium proteins can be achieved using targeting sequences having 50-68.8% identity to amino acids 20-35 of BclA (SEQ ID NO: 1), wherein the identity to amino acids 25-35 of BclA is 63.6% to 81.8%. Such motif is present in a targeting sequence, exosporium protein, or exosporium protein fragment that targets the fusion protein to the exosporium of the recombinant *Bacillus* bacterium and comprises the sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$, wherein:

$X_1$ is any amino acid or absent;

$X_2$ is phenylalanine (F), leucine (L), isoleucine (I), or methionine (M);

$X_3$ is any amino acid;

$X_4$ is proline (P) or serine (S);

$X_5$ is any amino acid;

$X_6$ is leucine (L), asparagine (N), serine (S), or isoleucine (I);

$X_7$ is valine (V) or isoleucine (I);

$X_8$ is glycine (G);

$X_9$ is proline (P);

$X_{10}$ is threonine (T) or proline (P);

$X_{11}$ is leucine (L) or phenylalanine (F);

$X_{12}$ is proline (P);

$X_{13}$ is any amino acid;

$X_{14}$ is any amino acid;

$X_{15}$ is proline (P), glutamine (Q), or threonine (T); and $X_{16}$ is proline (P), threonine (T), or serine (S).

Any of the targeting sequences, exosporuim proteins, or exosporium protein fragments can be used to target any protein or peptide of interest, including the proteins having serine protease activity described herein, to the exosporium of a recombinant *Bacillus cereus* family member.

For example, any of the targeting sequences, exosporium proteins, or exosporium protein fragments (e.g., any of SEQ ID NOs: 203-207) can be used to target a protein or peptide of interest (e.g., an enzyme having the serine protease activity of SEQ ID NO: 210, 211, or 212) to the exosporium of a recombinant *Bacillus cereus* family member.

During sporulation of a recombinant *Bacillus cereus* family member expressing any of the fusion proteins described herein, the targeting motif, exosporium protein, or exosporium protein fragment is recognized by the spore exosporium assembly machinery and directed to the exosporium, resulting in display of the protein or peptide of interest portion of the fusion protein (e.g., the enzyme having serine protease activity) on the outside of the spore.

The use of different targeting sequences allows for control of the expression level of the fusion protein on the surface of the *Bacillus cereus* family member spore. Use of certain of the targeting sequences described herein will result in a higher level of expression of the fusion protein, whereas use of others of the targeting sequences will result in lower levels of expression of the fusion protein on the surface of the spore.

In any of the fusion proteins described herein, the targeting sequence, exosporium protein, or exosporium protein fragment can comprise the amino acid sequence GXT at its carboxy terminus, wherein X is any amino acid.

In any of the fusion proteins described herein, the targeting sequence, exosporium protein, or exosporium protein fragment, can comprise an alanine residue at the position of the targeting sequence that corresponds to amino acid 20 of SEQ ID NO: 1.

In any of the fusion proteins described herein, the targeting sequence, exosporium protein, or exosporium protein fragment can further comprise a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

B. Serine Protease Proteins

The fusion proteins can comprise an enzyme having serine protease activity.

Serine proteases are one of the largest and mostly widely distributed class of proteases. Serine proteases cleave peptide bonds at serine residues within a specific recognition site in a protein. These proteases are frequently used by bacteria for nutrient scavenging in the environment. Serine proteases have also been show to exhibit nematicidal activity through digestion of intestinal tissue in nematodes. Studies of *Bacillus firmus* strain DS-1, which shows nematicidal activity against *Meloidogyne incognita* and soybean cyst nematode, revealed that the serine protease produced by that strain has serine protease activity and degraded the intestinal tissues of nematodes. Geng, C., et al., "A Novel Serine Protease, Sep1, from *Bacillus firmus* DS-1 Has Nematicidal Activity and Degrades Multiple Intestinal-Associated Nematode Proteins", Scientific Reports, 2016, vol. 6, no. 25012.

Other studies have shown that serine proteases have activity against pathogens such as fungal plant pathogens and oomycetes, such as *Pythium*. See Dunne et al., "Overproduction of an Inducible Extracellular Serine Protease Improves Biological Control of *Pythium ultimum* by *Stenotrophomonas maltophilia* strain W81," Microbiology, 2000, vol. 146, pp. 2069-2078, and Yen, Y., et al., "An Antifungal Protease Produced by *Pseudomonas aeruginosa* M-1001 with Shrimp and Crab Shell Powder as a Carbon Source," Enzyme and Microbial Technology, 2006, vol. 39, pp. 311-317.

In Table 2, SEQ ID NOs: 210-212 are amino acid sequences for wild-type enzymes and a variant enzyme that exhibit or are predicted to exhibit serine protease activity. Thus, for example, SEQ ID NOs: 210 and 211 provide the amino acid sequence for wild-type serine protease enzymes from two different *Bacillus firmus* strains and have 98% sequence similarity. SEQ ID NO: 212 provides the amino acid sequence for the same enzyme as in SEQ ID NO: 210, except for a deletion of amino acids 181-240 of SEQ ID NO: 210, such that SEQ ID NOs: 210 and 212 have 81% sequence similarity. The catalytic residues referenced in Geng, et al., 2016, above, are maintained in the variant serine protease amino acid sequence of SEQ ID NO: 212.

TABLE 2

| Amino Acid Sequences for Serine Protease and Variant | |
|---|---|
| Enzyme | SEQ ID NO: |
| Serine Protease from *Bacillus firmus* DS-1 (Sep1) | 210 |
| Serine Protease from *Bacillus firmus* Strain 1 (Sep1) | 211 |
| Serine Protease Variant with Deletion | 212 |

Signal Peptides

When a fusion protein comprises an enzyme whose native sequence includes a signal peptide, the enzyme can be used without the signal peptide. Alternatively, the native signal peptide (or another signal peptide) can optionally be included at the amino terminus of the enzyme, immediately preceding the first amino acid of the enzyme sequence.

In addition, a signal peptide can optionally be included at the amino terminus of the enzymes whose native sequences do not include a signal peptide.

C. Fusion Proteins for Expression in Recombinant *Bacillus cereus* Family Members Fusion proteins comprising a targeting sequence, exosporium protein, or exosporium protein fragment that targets the fusion protein to the exosporium of a recombinant *Bacillus cereus* family member are provided. The fusion proteins further comprise an enzyme having serine protease activity.

In any of the fusion proteins described herein, the fusion protein can comprise: (1) a targeting sequence comprising an amino acid sequence having at least about 43% identity with amino acids 20-35 of SEQ ID NO: 1, wherein the identity with amino acids 25-35 is at least about 54%; (2) a targeting sequence comprising amino acids 1-35 of SEQ ID NO: 1; (3) a targeting sequence comprising amino acids 20-35 of SEQ ID NO: 1; (4) a targeting sequence comprising SEQ ID NO: 1; (5) an exosporium protein comprising an amino acid sequence having at least 85% identity with SEQ ID NO: 2; (6) a targeting sequence comprising amino acids 2-35 of SEQ ID NO: 1; (7) a targeting sequence comprising amino acids 5-35 of SEQ ID NO: 1; (8) a targeting sequence comprising amino acids 8-35 of SEQ ID NO: 1; (9) a targeting sequence comprising amino acids 10-35 of SEQ ID NO: 1; (10) a targeting sequence comprising amino acids 15-35 of SEQ ID NO: 1; (11) a targeting sequence comprising amino acids 1-27 of SEQ ID NO: 3; (12) a targeting sequence comprising amino acids 12-27 of SEQ ID NO: 3; (13) a targeting sequence comprising SEQ ID NO: 3; (14) an exosporium protein comprising an amino acid sequence having at least 85% identity with SEQ ID NO: 4; (15) a targeting sequence comprising amino acids 2-27 of SEQ ID NO: 3; (16) a targeting sequence comprising amino acids 5-27 of SEQ ID NO: 3; (17) a targeting sequence comprising amino acids 8-27 of SEQ ID NO: 3; (18) a targeting sequence comprising amino acids 10-27 of SEQ ID NO: 3; (19) a targeting sequence comprising amino acids 1-38 of SEQ ID NO: 5; (20) a targeting sequence comprising amino acids 23-38 of SEQ ID NO: 5; (21) a targeting sequence comprising SEQ ID NO: 5; (22) an exosporium protein comprising an amino acid sequence having at least 85% identity with SEQ ID NO: 6; (23) a targeting sequence comprising amino acids 2-38 of SEQ ID NO: 5; (24) a targeting sequence comprising amino acids 5-38 of SEQ ID NO: 5; (25) a targeting sequence comprising amino acids 8-38 of SEQ ID NO: 5; (26) a targeting sequence comprising amino acids 10-38 of SEQ ID NO: 5; (27) a targeting sequence comprising amino acids 15-38 of SEQ ID NO: 5; (28) a targeting sequence comprising amino acids 20-38 of SEQ ID NO: 5; (29) a targeting sequence comprising amino acids 1-28 of SEQ ID NO: 7; (30) a targeting sequence comprising amino acids 13-28 of SEQ ID NO: 7; (31) a targeting sequence comprising SEQ ID NO: 7; (32) an exosporium protein comprising an amino acid sequence having at least 85% identity with SEQ ID NO: 8; (33) a targeting sequence comprising amino acids 2-28 of SEQ ID NO: 7; (34) a targeting sequence comprising amino acids 5-28 of SEQ ID NO: 7; (35) a targeting sequence comprising amino acids 8-28 of SEQ ID NO: 7; (36) a targeting sequence comprising amino acids 10-28 of SEQ ID NO: 7; (37) a targeting sequence comprising amino acids 1-24 of SEQ ID NO: 9; (38) a targeting sequence comprising amino acids 9-24 of SEQ ID NO: 9; (39) a targeting sequence comprising SEQ ID NO: 9; (40) an exosporium protein comprising an amino acid sequence having at least 85% identity with SEQ ID NO: 10; (41) a targeting sequence comprising amino acids 2-24 of SEQ ID NO: 9; (42) a targeting sequence comprising amino acids 5-24 of SEQ ID NO: 9; (43) a targeting sequence comprising amino acids 8-24 of SEQ ID NO: 9; (44) a targeting sequence comprising amino acids 1-33 of SEQ ID NO: 11; (45) a targeting sequence comprising amino acids 18-33 of SEQ ID NO: 11; (46) a targeting sequence comprising SEQ ID NO: 11; (47) an exosporium protein comprising an amino acid sequence having at least 85% identity with SEQ ID NO: 12; (48) a targeting sequence comprising amino acids 2-33 of SEQ ID NO: 11; (49) a targeting sequence comprising amino acids 5-33 of SEQ ID NO: 11; (50) a targeting sequence comprising amino acids 8-33 of SEQ ID NO: 11; (51) a targeting sequence comprising amino acids 10-33 of SEQ ID NO: 11; (52) a targeting sequence comprising amino acids 15-33 of SEQ ID NO: 11; (53) a targeting sequence comprising amino acids 1-33 of SEQ ID NO: 13; (54) a targeting sequence comprising amino acids 18-33 of SEQ ID NO: 13; (55) a targeting sequence comprising SEQ ID NO: 13; (56) an exosporium protein comprising an amino acid sequence having at least 85% identity with SEQ ID NO: 14; (57) a targeting sequence comprising amino acids 2-33 of SEQ ID NO: 13; (58) a targeting sequence comprising amino acids 5-33 of SEQ ID NO: 13; (59) a targeting sequence comprising amino acids 8-33 of SEQ ID NO: 13; (60) a targeting sequence comprising amino acids 10-33 of SEQ ID NO: 13; (61) a targeting sequence comprising amino acids 15-33 of SEQ ID NO: 13; (62) a targeting sequence comprising amino acids 1-43 of SEQ ID NO: 15; (63) a targeting sequence comprising amino acids 28-43 of SEQ ID NO: 15; (64) a targeting sequence comprising SEQ ID NO: 15; (65) an exosporium protein comprising an amino acid sequence having at least 85% identity with SEQ ID NO: 16; (66) a targeting sequence comprising amino acids 2-43 of SEQ ID NO: 15; (67) a targeting sequence comprising amino acids 5-43 of SEQ ID NO: 15; (68) a targeting sequence comprising amino acids 8-43 of SEQ ID NO: 15; (69) a targeting sequence comprising amino acids 10-43 of SEQ ID NO: 15; (70) a targeting sequence comprising amino acids 15-43 of SEQ ID NO: 15; (71) a targeting sequence comprising amino acids 20-43 of SEQ ID NO: 15; (72) a targeting sequence comprising amino acids 25-43 of SEQ ID NO: 15; (73) a targeting sequence comprising amino acids 1-27 of SEQ ID NO: 17; (74) a targeting sequence comprising amino acids 12-27 of SEQ ID NO: 17; (75) a targeting sequence comprising SEQ ID NO: 17; (76) an exosporium protein comprising an amino acid sequence having at least 85% identity with SEQ ID NO: 18; (77) a targeting sequence comprising amino acids 2-27 of SEQ ID NO: 17; (78) a targeting sequence comprising amino acids 5-27 of SEQ ID NO: 17; (79) a targeting sequence comprising amino acids 8-27 of SEQ ID NO: 17; (80) a targeting sequence comprising amino acids 10-27 of SEQ ID NO: 17; (81) a targeting sequence comprising amino acids 1-33 of SEQ ID NO: 19; (82) a targeting sequence comprising amino acids 18-33 of SEQ ID NO: 19; (83) a targeting sequence comprising SEQ ID NO: 19; (84) an exosporium protein comprising an amino acid sequence having at least 85% identity with SEQ ID NO: 20; (85) a targeting sequence comprising amino acids 2-33 of SEQ ID NO: 19; (86) a targeting sequence comprising amino acids 5-33 of SEQ ID NO: 19; (87) a targeting sequence comprising amino acids 8-33 of SEQ ID NO: 19; (88) a targeting sequence comprising amino acids 10-33 of SEQ ID NO: 19; (89) a targeting sequence comprising amino acids 15-33 of SEQ ID NO: 19; (90) a targeting sequence comprising amino acids 1-33 of SEQ ID NO: 21; (91) a targeting sequence comprising amino acids 18-33 of SEQ ID NO: 21; (92) a targeting sequence comprising SEQ ID NO: 21; (93) an exosporium protein comprising an amino acid sequence having at least 85% identity with SEQ ID NO: 22; (94) a targeting sequence comprising amino acids 2-33 of SEQ ID NO: 21; (95) a targeting sequence comprising amino acids 5-33 of SEQ ID NO: 21; (96) a targeting sequence comprising amino acids 8-33 of SEQ ID NO: 21; (97) a targeting sequence comprising amino acids 10-33 of SEQ ID NO: 21; (98) a targeting sequence comprising amino acids 15-33 of SEQ ID NO: 21; (99) a targeting sequence comprising amino acids 1-24 of SEQ ID NO: 23; (100) a targeting sequence comprising amino acids 9-24 of SEQ ID NO: 23; (101) a targeting sequence comprising SEQ ID NO: 23; (102) an exosporium protein comprising an amino acid sequence having at least 85% identity with SEQ ID NO: 24; (103) a targeting sequence comprising amino acids 2-24 of SEQ ID NO: 23; (104) a targeting sequence comprising amino acids 5-24 of SEQ ID NO: 23; (105) a targeting sequence comprising amino acids 8-24 of SEQ ID NO: 23; (106) a targeting sequence comprising amino acids 1-24 of SEQ ID NO: 25; (107) a targeting sequence comprising amino acids 9-24 of SEQ ID NO: 25; (108) a targeting sequence comprising SEQ ID NO: 25; (109) an exosporium protein comprising an amino acid sequence having at least 85% identity with SEQ ID NO: 26; (110) a targeting sequence comprising amino acids 2-24 of SEQ ID NO: 25; (111) a targeting sequence comprising amino acids 5-24 of SEQ ID NO: 25; (112) a targeting sequence comprising amino acids 8-24 of SEQ ID NO: 25; (113) a targeting sequence comprising amino acids 1-30 of SEQ ID NO: 27; (114) a targeting sequence comprising amino acids 15-30 of SEQ ID NO: 27; (115) a targeting sequence comprising SEQ ID NO: 27; (116) an exosporium protein comprising an amino acid sequence having at least 85% identity with SEQ ID NO: 28; (117) a targeting sequence comprising amino acids 2-30 of SEQ ID NO: 27; (118) a targeting sequence comprising amino acids 5-30 of SEQ ID NO: 27; (119) a targeting sequence comprising amino acids 8-30 of SEQ ID NO: 27; (120) a targeting sequence comprising amino acids 10-30 of SEQ ID NO: 27; (121) a targeting sequence comprising amino acids 1-33 of SEQ ID NO: 29; (122) a targeting sequence comprising amino acids 18-33 of SEQ ID NO: 29; (123) a targeting sequence comprising SEQ ID NO: 29; (124) an exosporium protein comprising an amino acid sequence having at least 85% identity with SEQ ID NO: 30; (125) a targeting sequence comprising amino acids 2-33 of SEQ ID NO: 29; (126) a targeting sequence comprising amino acids 5-33 of SEQ ID NO: 29; (127) a targeting sequence comprising amino acids 8-33 of SEQ ID NO: 29; (128) a targeting sequence comprising amino acids 10-33 of SEQ ID NO: 29; (129) a targeting sequence comprising amino acids 15-33 of SEQ ID NO: 29; (130) a targeting sequence comprising amino acids 1-24 of SEQ ID NO: 31; (131) a targeting sequence comprising amino acids 9-24 of SEQ ID NO: 31; (132) a targeting sequence comprising SEQ ID NO: 31; (133) an exosporium protein comprising an amino acid sequence having at least 85% identity with SEQ ID NO: 32; (134) a targeting sequence comprising amino acids 2-24 of SEQ ID NO: 31; (135) a targeting sequence comprising amino acids 5-24 of SEQ ID NO: 31; (136) a targeting sequence comprising amino acids 8-24 of SEQ ID NO: 31; (137) a targeting sequence comprising amino acids 1-15 of SEQ ID NO: 33; (138) a targeting sequence comprising SEQ ID NO: 33; (139) an exosporium protein comprising an amino acid sequence having at least 85% identity with SEQ ID NO: 34; (140) a targeting sequence comprising amino acids 1-16 of SEQ ID NO: 35; (141) a targeting sequence comprising SEQ ID NO: 35; (142) an exosporium protein comprising an amino acid sequence having at least 85% identity with SEQ ID NO: 36; (143) a targeting sequence comprising amino acids 1-29 of SEQ ID NO: 43; (144) a targeting sequence comprising amino acids 14-29 of SEQ ID NO: 43; (145) a targeting sequence comprising SEQ ID NO: 43; (146) an exosporium protein comprising an amino acid sequence having at least 85% identity with SEQ ID NO: 44; (147) a targeting sequence comprising amino acids 2-29 of SEQ ID NO: 43; (148) a targeting sequence comprising amino acids 5-29 of SEQ ID NO: 43; (149) a targeting sequence comprising amino acids 8-29 of SEQ ID NO: 43; (150) a targeting sequence comprising amino acids 10-29 of SEQ ID NO: 43; (151) a targeting sequence comprising amino acids 1-35 of SEQ ID NO: 45; (152) a targeting sequence comprising amino acids 20-35 of SEQ ID NO: 45; (153) a targeting sequence comprising SEQ ID NO: 45; (154) an exosporium protein comprising an amino acid sequence having at least 85% identity with SEQ ID NO: 46; (155) a targeting sequence comprising amino acids 2-35 of SEQ ID NO: 45; (156) a targeting sequence comprising amino acids 5-35 of SEQ ID NO: 45; (157) a targeting sequence comprising amino acids 8-35 of SEQ ID NO: 45; (158) a targeting sequence comprising amino acids 10-35 of SEQ ID NO: 45; (159) a targeting sequence comprising amino acids 15-35 of SEQ ID NO: 45; (160) a targeting sequence comprising amino acids 1-43 of SEQ ID NO: 47; (161) a targeting sequence comprising amino acids 28-43 of SEQ ID NO: 47; (162) a targeting sequence comprising SEQ ID NO: 47; (163) an exosporium protein comprising an amino acid sequence having at least 85% identity with SEQ ID NO: 48; (164) a targeting sequence comprising amino acids 2-43 of SEQ ID NO: 47; (165) a targeting sequence comprising amino acids 5-43 of SEQ ID NO: 47; (166) a targeting sequence comprising amino acids 8-43 of SEQ ID NO: 47; (167) a targeting sequence comprising amino acids 10-43 of SEQ ID NO: 47; (168) a targeting sequence comprising amino acids 15-43 of SEQ ID NO: 47; (169) a targeting sequence comprising amino acids 20-43 of SEQ ID NO: 47; (170) a targeting sequence comprising amino acids 25-43 of SEQ ID NO: 47; (171) a targeting sequence comprising amino acids 1-32 of SEQ ID NO: 49; (172) a targeting sequence comprising amino acids 17-32 of SEQ ID NO: 49; (173) a targeting sequence comprising SEQ ID NO: 49; (174) an exosporium protein comprising an amino acid sequence having at least 85% identity with SEQ ID NO: 50; (175) a targeting sequence comprising amino acids 2-32 of SEQ ID NO: 49; (176) a targeting sequence comprising amino acids 5-32 of SEQ ID NO: 49; (177) a targeting sequence comprising amino acids 8-32 of SEQ ID NO: 49; (178) a targeting sequence comprising amino acids 10-32 of SEQ ID NO: 49; (179) a targeting sequence comprising amino acids 15-32 of SEQ ID NO: 49; (180) a targeting sequence comprising amino acids 1-33 of SEQ ID NO: 51; (181) a targeting sequence comprising amino acids 18-33 of SEQ ID NO: 51; (182) a targeting sequence comprising SEQ ID NO: 51; (183) an exosporium protein comprising an amino acid sequence having at least 85% identity with SEQ ID NO: 52; (184) a targeting sequence comprising amino acids 2-33 of SEQ ID NO: 51; (185) a targeting sequence comprising amino acids 5-33 of SEQ ID NO: 51; (186) a targeting sequence comprising amino acids 8-33 of SEQ ID NO: 51; (187) a targeting sequence comprising amino acids 10-33 of SEQ ID NO: 51; (188) a targeting sequence comprising amino acids 15-33 of SEQ ID NO: 51; (189) a targeting sequence comprising amino acids 1-33 of SEQ ID NO: 53; (190) a targeting sequence comprising amino acids 18-33 of SEQ ID NO: 53; (191) a targeting sequence comprising SEQ ID NO: 53; (192) an exosporium protein comprising an amino acid sequence having at least 85% identity with SEQ ID NO: 54; (193) a targeting sequence comprising amino acids 2-33 of SEQ ID NO: 53; (194) a targeting sequence comprising amino acids 5-33 of SEQ ID NO: 53; (195) a targeting sequence comprising amino acids 8-33 of SEQ ID NO: 53; (196) a targeting sequence comprising amino acids 10-33 of SEQ ID NO: 53; (197) a targeting sequence comprising amino acids 15-33 of SEQ ID NO: 53; (198) a targeting sequence comprising amino acids 1-30 of SEQ ID NO: 55; (199) a targeting sequence comprising amino acids 15-30 of SEQ ID NO: 55; (200) a targeting sequence comprising SEQ ID NO: 55; (201) an exosporium protein comprising an amino acid sequence having at least 85% identity with SEQ ID NO: 56; (202) a targeting sequence comprising amino acids 2-30 of SEQ ID NO: 55; (203) a targeting sequence comprising amino acids 5-30 of SEQ ID NO: 55; (204) a targeting sequence comprising amino acids 8-30 of SEQ ID NO: 55; (205) a targeting sequence comprising amino acids 10-30 of SEQ ID NO: 55; (206) a targeting sequence comprising amino acids 1-130 of SEQ ID NO: 57; (207) a targeting sequence comprising amino acids 115-130 of SEQ ID NO: 57; (208) a targeting sequence comprising SEQ ID NO: 57; (209) an exosporium protein comprising an amino acid sequence having at least 85% identity with SEQ ID NO: 58; (210) a targeting sequence comprising amino acids 2-130 of SEQ ID NO: 57; (211) a targeting sequence comprising amino acids 5-130 of SEQ ID NO: 57; (212) a targeting sequence comprising amino acids 10-130 of SEQ ID NO: 57; (213) a targeting sequence comprising amino acids 20-130 of SEQ ID NO: 57; (214) a targeting sequence comprising amino acids 30-130 of SEQ ID NO: 57; (215) a targeting sequence comprising amino acids 40-130 of SEQ ID NO: 57; (216) a targeting sequence comprising amino acids 50-130 of SEQ ID NO: 57; (217) a targeting sequence comprising amino acids 60-130 of SEQ ID NO: 57; (218) a targeting sequence comprising amino acids 70-130 of SEQ ID NO: 57; (219) a targeting sequence comprising amino acids 80-130 of SEQ ID NO: 57; (220) a targeting sequence comprising amino acids 90-130 of SEQ ID NO: 57; (221) a targeting sequence comprising amino acids 100-130 of SEQ ID NO: 57; (222) a targeting sequence comprising amino acids 110-130 of SEQ ID NO: 57; (223) an exosporium protein fragment comprising an amino acid sequence having at least 85% identity with SEQ ID NO: 95; (224) a targeting sequence comprising SEQ ID NO: 96; (225) a targeting sequence comprising SEQ ID NO: 97; (226) a targeting sequence comprising SEQ ID NO: 98;

(227) a targeting sequence comprising SEQ ID NO: 99; (228) a targeting sequence comprising SEQ ID NO: 100; (229) a targeting sequence comprising SEQ ID NO: 101; (230) a targeting sequence comprising SEQ ID NO: 102; (231) a targeting sequence comprising SEQ ID NO: 103; (232) a targeting sequence comprising SEQ ID NO: 104; (233) a targeting sequence comprising SEQ ID NO: 105; (234) a targeting sequence comprising SEQ ID NO: 106; (235) an exosporium protein comprising an amino acid sequence having at least 85% identity with SEQ ID NO: 108; (236) an exosporium protein comprising an amino acid sequence having at least 85% identity with SEQ ID NO: 109; (237) an exosporium protein comprising an amino acid sequence having at least 85% identity with SEQ ID NO: 110; (238) an exosporium protein comprising an amino acid sequence having at least 85% identity with SEQ ID NO: 111; (239) an exosporium protein comprising an amino acid sequence having at least 85% identity with SEQ ID NO: 112; (240) an exosporium protein comprising an amino acid sequence having at least 85% identity with SEQ ID NO: 113; (241) an exosporium protein comprising an amino acid sequence having at least 85% identity with SEQ ID NO: 114; (242) an exosporium protein comprising an amino acid sequence having at least 85% identity with SEQ ID NO: 115; (243) an exosporium protein comprising an amino acid sequence having at least 85% identity with SEQ ID NO: 116; (244) an exosporium protein comprising an amino acid sequence having at least 85% identity with SEQ ID NO: 117; (245) an exosporium protein comprising an amino acid sequence having at least 85% identity with SEQ ID NO: 118; (246) an exosporium protein comprising an amino acid sequence having at least 85% identity with SEQ ID NO: 119; (247) an exosporium protein comprising an amino acid sequence having at least 85% identity with SEQ ID NO: 120; (248) an exosporium protein comprising an amino acid sequence having at least 85% identity with SEQ ID NO: 121; (249) a targeting sequence comprising amino acids 22-31 of SEQ ID NO: 1; (250) a targeting sequence comprising amino acids 22-33 of SEQ ID NO: 1; (251) a targeting sequence comprising amino acids 20-31 of SEQ ID NO: 1; (252) a targeting sequence comprising amino acids 14-23 of SEQ ID NO: 3; (253) a targeting sequence comprising amino acids 14-25 of SEQ ID NO: 3; (254) a targeting sequence comprising amino acids 12-23 of SEQ ID NO: 3; (255) a targeting sequence comprising amino acids 1-30 of SEQ ID NO: 59; (256) a targeting sequence comprising SEQ ID NO: 59; (257) an exosporium protein comprising an amino acid sequence having at least 85% identity with SEQ ID NO: 60; (258) a targeting sequence comprising amino acids 2-30 of SEQ ID NO: 59; (259) a targeting sequence comprising amino acids 4-30 of SEQ ID NO: 59; (260) a targeting sequence comprising amino acids 6-30 of SEQ ID NO: 59; (261) a targeting sequence comprising amino acids 1-33 of SEQ ID NO: 61; (262) a targeting sequence comprising amino acids 18-33 of SEQ ID NO: 61; (263) a targeting sequence comprising SEQ ID NO: 61; (264) an exosporium protein comprising an amino acid sequence having at least 85% sequence identity with SEQ ID NO: 62; (265) a targeting sequence comprising amino acids 2-33 of SEQ ID NO: 61; (266) a targeting sequence comprising amino acids 5-33 of SEQ ID NO: 61; (267) a targeting sequence comprising amino acids 10-33 of SEQ ID NO: 61; (268) a targeting sequence comprising amino acids 15-33 of SEQ ID NO: 61; (269) a targeting sequence comprising amino acids 1-35 of SEQ ID NO: 63; (270) a targeting sequence comprising SEQ ID NO: 63; (271) an exosporium protein comprising an amino acid sequence having at least 85% identity with SEQ ID NO: 64; (272) a targeting sequence comprising amino acids 2-35 of SEQ ID NO: 63; (273) a targeting sequence comprising amino acids 5-35 of SEQ ID NO: 63; (274) a targeting sequence comprising amino acids 8-35 of SEQ ID NO: 63; (275) a targeting sequence comprising amino acids 10-35 of SEQ ID NO: 63; (276) a targeting sequence comprising amino acids 15-35 of SEQ ID NO: 63; (277) a targeting sequence comprising amino acids 1-24 of SEQ ID NO: 65; (278) a targeting sequence comprising amino acids 9-24 of SEQ ID NO: 65; (279) a targeting sequence comprising SEQ ID NO: 65; (280) an exosporium protein comprising an amino acid sequence having at least 85% identity with SEQ ID NO: 66; (281) a targeting sequence comprising SEQ ID NO: 107; (282) a targeting sequence comprising amino acids 2-24 of SEQ ID NO: 65; (283) a targeting sequence comprising amino acids 5-24 of SEQ ID NO: 65; (284) a targeting sequence comprising amino acids 1-27 of SEQ ID NO: 67; (285) a targeting sequence comprising amino acids 12-27 of SEQ ID NO: 67; (286) a targeting sequence comprising SEQ ID NO: 67; (287) an exosporium protein comprising an amino acid sequence having at least 85% identity with SEQ ID NO: 68; (288) an targeting sequence comprising amino acids 2-27 of SEQ ID NO: 67; (289) a targeting sequence comprising amino acids 5-27 of SEQ ID NO: 67; (290) a targeting sequence comprising amino acids 10-27 of SEQ ID NO: 67; (291) a targeting sequence comprising amino acids 1-38 of SEQ ID NO: 69; (292) a targeting sequence comprising amino acids 23-38 of SEQ ID NO: 69; (293) a targeting sequence comprising SEQ ID NO: 69; (294) an exosporium protein comprising an amino acid sequence having at least 85% identity with SEQ ID NO: 70; (295) a targeting sequence comprising amino acids 2-38 of SEQ ID NO: 69; (296) a targeting sequence comprising amino acids 5-38 of SEQ ID NO: 69; (297) a targeting sequence comprising amino acids 10-38 of SEQ ID NO: 69; (298) a targeting sequence comprising amino acids 15-38 of SEQ ID NO: 69; (299) an exosporium protein comprising SEQ ID NO: 72; (300) a targeting sequence comprising SEQ ID NO: 73; (301) an exosporium protein comprising an amino acid sequence having at least 95% identity with SEQ ID NO: 74; (302) a targeting sequence comprising amino acids 1-42 of SEQ ID NO: 75; (303) a targeting sequence comprising amino acids 27-42 of SEQ ID NO: 75; (304) a targeting sequence comprising SEQ ID NO: 75; (305) an exosporium protein comprising an amino acid sequence having at least 85% identity with SEQ ID NO: 76; (306) a targeting sequence comprising amino acids 2-42 of SEQ ID NO: 75; (307) a targeting sequence comprising amino acids 5-42 of SEQ ID NO: 75; (308) a targeting sequence comprising amino acids 10-42 of SEQ ID NO: 75; (309) a targeting sequence comprising amino acids 15-42 of SEQ ID NO: 75; (310) a targeting sequence comprising amino acids 20-42 of SEQ ID NO: 75; (311) a targeting sequence comprising amino acids 25-42 of SEQ ID NO: 75; (312) a targeting sequence comprising amino acids 1-24 of SEQ ID NO: 77; (313) a targeting sequence comprising amino acids 9-24 of SEQ ID NO: 77; (314) a targeting sequence comprising SEQ ID NO: 77; (315) an exosporium protein comprising an amino acid sequence having at least 85% identity with SEQ ID NO: 78; (316) a targeting sequence comprising amino acids 2-24 of SEQ ID NO: 77; (317) a targeting sequence comprising amino acids 5-24 of SEQ ID NO: 77; (318) an exosporium protein comprising an amino acid sequence having at least 85% identity with SEQ ID NO: 80; (319) a targeting sequence comprising amino acids 1-38 of SEQ ID NO: 81; (320) a targeting sequence comprising amino acids 23-38 of SEQ ID NO: 81; (321) a targeting sequence comprising SEQ ID NO: 81; (322) an exosporium protein comprising an amino acid sequence having at least 85% identity with SEQ ID NO: 82; (323) a targeting sequence comprising amino acids 2-38 of SEQ ID NO: 81; (324) a targeting sequence comprising amino acids 5-38 of SEQ ID NO: 81; (325) a targeting sequence comprising amino acids 10-38 of SEQ ID NO: 81; (326) a targeting sequence comprising amino acids 15-38 of SEQ ID NO: 81; (327) a targeting sequence comprising amino acids 20-38 of SEQ ID NO: 81; (328) a targeting sequence comprising amino acids 1-34 of SEQ ID NO: 83; (329) a targeting sequence comprising SEQ ID NO: 83; (330) an exosporium protein comprising an amino acid sequence having at least 85% identity with SEQ ID NO: 84; (331) an exosporium protein comprising an amino acid sequence having at least 85% identity with SEQ ID NO: 86; (332) a targeting sequence comprising amino acids 1-28 of SEQ ID NO: 87; (333) a targeting sequence comprising amino acids 13-28 of SEQ ID NO: 87; (334) a targeting sequence comprising SEQ ID NO: 87; (335) an exosporium protein comprising an amino acid sequence having at least 85% identity with SEQ ID NO: 88; (336) a targeting sequence comprising amino acids 2-28 of SEQ ID NO: 87; (337) a targeting sequence comprising amino acids 5-28 of SEQ ID NO: 87; (338) a targeting sequence comprising amino acids 10-28 of SEQ ID NO: 87; (339) a targeting sequence comprising amino acids 1-28 of SEQ ID NO: 89; (340) a targeting sequence comprising SEQ ID NO: 89; (341) an exosporium protein comprising an amino acid sequence having at least 85% identity with SEQ ID NO: 90; (342) a targeting sequence comprising amino acids 2-28 of SEQ ID NO: 89; (343) a targeting sequence comprising amino acids 5-28 of SEQ ID NO: 89; (344) a targeting sequence comprising amino acids 10-28 of SEQ ID NO: 89; (345) a targeting sequence comprising amino acids 1-93 of SEQ ID NO: 91; (346) a targeting sequence comprising SEQ ID NO: 91; (347) an exosporium protein comprising an amino acid sequence having at least 85% identity with SEQ ID NO: 92; (348) a targeting sequence comprising amino acids 2-93 of SEQ ID NO: 91; (349) a targeting sequence comprising amino acids 10-93 of SEQ ID NO: 91; (350) a targeting sequence comprising amino acids 20-93 of SEQ ID NO: 91; (351) a targeting sequence comprising amino acids 30-93 of SEQ ID NO: 91; (352) a targeting sequence comprising amino acids 40-93 of SEQ ID NO: 91; (353) a targeting sequence comprising amino acids 50-93 of SEQ ID NO: 91; (354) a targeting sequence comprising amino acids 60-93 of SEQ ID NO: 91; (355) a targeting sequence comprising amino acids 1-130 of SEQ ID NO: 93; (356) a targeting sequence comprising SEQ ID NO: 93; (357) an exosporium protein comprising an amino acid sequence having at least 85% identity with SEQ ID NO: 94; (358) a targeting sequence comprising amino acids 2-130 of SEQ ID NO: 93; (359) a targeting sequence comprising amino acids 10-130 of SEQ ID NO: 93; (360) a targeting sequence comprising amino acids 20-130 of SEQ ID NO: 93; (361) a targeting sequence comprising amino acids 30-130 of SEQ ID NO: 93; (362) an exosporium protein comprising an amino acid sequence having at least 85% identity with SEQ ID NO: 122; (363) a targeting sequence consisting of amino acids 20-33 of SEQ ID NO: 1; (364) a targeting sequence consisting of amino acids 21-33 of SEQ ID NO: 1; (365) a targeting sequence consisting of amino acids 23-31 of SEQ ID NO: 1; (366) a targeting sequence consisting of amino acids 1-15 of SEQ ID NO: 96; (367) a targeting sequence consisting of amino acids 1-13 of SEQ ID NO: 96; (368) a targeting sequence consisting of amino acids 12-25 of SEQ ID NO: 3; (369) a targeting sequence consisting of amino acids 13-25 of SEQ ID NO: 3; (370) a targeting sequence consisting of amino acids 15-23 of SEQ ID NO: 3; (371) a targeting sequence consisting of amino acids 1-15 of SEQ ID NO: 97; (372) a targeting sequence consisting of amino acids 1-13 of SEQ ID NO: 98; (373) a targeting sequence consisting of amino acids 23-36 of SEQ ID NO: 5; (374) a targeting sequence consisting of amino acids 23-34 of SEQ ID NO: 5; (375) a targeting sequence consisting of amino acids 24-36 of SEQ ID NO: 5; (376) a targeting sequence consisting of amino acids 26-34 of SEQ ID NO: 5; (377) a targeting sequence consisting of amino acids 13-26 of SEQ ID NO: 7; (378) a targeting sequence consisting of amino acids 13-24 of SEQ ID NO: 7; (379) a targeting sequence consisting of amino acids 14-26 of SEQ ID NO: 7; (380) a targeting sequence consisting of amino acids 16-24 of SEQ ID NO: 7; (381) a targeting sequence consisting of amino acids 9-22 of SEQ ID NO: 9; (382) a targeting sequence consisting of amino acids 9-20 of SEQ ID NO: 9; (383) a targeting sequence consisting of amino acids 10-22 of SEQ ID NO: 9; (384) a targeting sequence consisting of amino acids 12-20 of SEQ ID NO: 9; (385) a targeting sequence consisting of amino acids 1-15 of SEQ ID NO: 105; (386) a targeting sequence consisting of amino acids 1-13 of SEQ ID NO: 105; (387) a targeting sequence consisting of amino acids 18-31 of SEQ ID NO: 11; (388) a targeting sequence consisting of amino acids 18-29 of SEQ ID NO: 11; (389) a targeting sequence consisting of amino acids 19-31 of SEQ ID NO: 11; (390) a targeting sequence consisting of amino acids 1-15 of SEQ ID NO: 98; (391) a targeting sequence consisting of amino acids 1-13 of SEQ ID NO: 98; (392) a targeting sequence consisting of amino acids 18-31 of SEQ ID NO: 13; (393) a targeting sequence consisting of amino acids 18-29 of SEQ ID NO: 13; (394) a targeting sequence consisting of amino acids 19-31 of SEQ ID NO: 13; (395) a targeting sequence consisting of amino acids 21-29 of SEQ ID NO: 13; (396) a targeting sequence consisting of amino acids 1-15 of SEQ ID NO: 99; (397) a targeting sequence consisting of amino acids 1-13 of SEQ ID NO: 99; (398) a targeting sequence consisting of amino acids 28-41 of SEQ ID NO: 15; (399) a targeting sequence consisting of amino acids 28-39 of SEQ ID NO: 15; (400) a targeting sequence consisting of amino acids 29-41 of SEQ ID NO: 15; (401) a targeting sequence consisting of amino acids 31-39 of SEQ ID NO: 15; (402) a targeting sequence consisting of amino acids 12-25 of SEQ ID NO: 17; (403) a targeting sequence consisting of amino acids 13-25 of SEQ ID NO: 17; (404) a targeting sequence consisting of amino acids 1-15 of SEQ ID NO: 100; (405) a targeting sequence consisting of amino acids 18-31 of SEQ ID NO: 19; (406) a targeting sequence consisting of amino acids 18-29 of SEQ ID NO: 19; (407) a targeting sequence consisting of amino acids 19-31 of SEQ ID NO: 19; (408) a targeting sequence consisting of amino acids 21-29 of SEQ ID NO: 19; (409) a targeting sequence consisting of amino acids 18-31 of SEQ ID NO: 21; (410) a targeting sequence consisting of amino acids 18-29 of SEQ ID NO: 21; (411) a targeting sequence consisting of amino acids 19-31 of SEQ ID NO: 21; (412) a targeting sequence consisting of amino acids 21-29 of SEQ ID NO: 21; (413) a targeting sequence consisting of amino acids 1-15 of SEQ ID NO: 101; (414) a targeting sequence consisting of amino acids 1-13 of SEQ ID NO: 101; (415) a targeting sequence consisting of amino acids 9-22 of SEQ ID NO: 23; (416) a targeting sequence consisting of amino acids 9-20 of SEQ ID NO: 23; (417) a targeting sequence consisting of amino acids 10-22 of SEQ ID NO: 23; (418) a targeting sequence consisting of amino acids 12-20 of SEQ ID NO: 23; (419) a targeting sequence consisting of amino acids 1-15 of SEQ ID NO: 102; (420) a targeting sequence consisting of amino acids 1-13 of SEQ ID NO: 102; (421) a targeting sequence consisting of amino acids 9-22 of SEQ ID NO: 25; (422) a targeting sequence consisting of amino acids 9-20 of SEQ ID NO: 25; (423) a targeting sequence consisting of amino acids 10-22 of SEQ ID NO: 25; (424) a targeting sequence consisting of amino acids 12-20 of SEQ ID NO: 25; (425) a targeting sequence consisting of amino acids 1-15 of SEQ ID NO: 103; (426) a targeting sequence consisting of amino acids 1-13 of SEQ ID NO: 103; (427) a targeting sequence consisting of amino acids 15-28 of SEQ ID NO: 27; (428) a targeting sequence consisting of amino acids 15-26 of SEQ ID NO: 27; (429) a targeting sequence consisting of amino acids 16-28 of SEQ ID NO: 27; (430) a targeting sequence consisting of amino acids 18-26 of SEQ ID NO: 27; (431) a targeting sequence consisting of amino acids 1-15 of SEQ ID NO: 104; (432) a targeting sequence consisting of amino acids 1-13 of SEQ ID NO: 104; (433) a targeting sequence consisting of amino acids 1-13 of SEQ ID NO: 33; (434) a targeting sequence consisting of amino acids 1-11 of SEQ ID NO: 33; (435) a targeting sequence consisting of amino acids 3-11 of SEQ ID NO: 33; (436) a targeting sequence consisting of amino acids 1-14 of SEQ ID NO: 35; (437) a targeting sequence consisting of amino acids 1-12 of SEQ ID NO: 35; (438) a targeting sequence consisting of amino acids 2-14 of SEQ ID NO: 35; (439) a targeting sequence consisting of amino acids 14-27 of SEQ ID NO: 43; (440) a targeting sequence consisting of amino acids 14-25 of SEQ ID NO: 43; (441) a targeting sequence consisting of amino acids 15-27 of SEQ ID NO: 43; (442) a targeting sequence consisting of amino acids 20-33 of SEQ ID NO: 45; (443) a targeting sequence consisting of amino acids 20-31 of SEQ ID NO: 45; (444) a targeting sequence consisting of amino acids 21-33 of SEQ ID NO: 45; (445) a targeting sequence consisting of amino acids 1-15 of SEQ ID NO: 106; (446) a targeting sequence consisting of amino acids 1-13 of SEQ ID NO: 106; (447) a targeting sequence consisting of amino acids 28-41 of SEQ ID NO: 47; (448) a targeting sequence consisting of amino acids 28-39 of SEQ ID NO: 47; (449) a targeting sequence consisting of amino acids 18-31 of SEQ ID NO: 53; (450) a targeting sequence consisting of amino acids 18-29 of SEQ ID NO: 53; (451) a targeting sequence consisting of amino acids 19-31 of SEQ ID NO: 53; (452) a targeting sequence comprising amino acids 18-31 of SEQ ID NO: 61; (453) a targeting sequence comprising amino acids 18-29 of SEQ ID NO: 61; (454) a targeting sequence comprising amino acids 19-31 of SEQ ID NO: 61; (455) a targeting sequence comprising amino acids 9-22 of SEQ ID NO: 65; (456) a targeting sequence comprising amino acids 9-20 of SEQ ID NO: 65; (457) a targeting sequence comprising amino acids 10-22 of SEQ ID NO: 65; (458) a targeting sequence comprising amino acids 1-15 of SEQ ID NO: 107; (459) a targeting sequence comprising amino acids 1-13 of SEQ ID NO: 107; (460) a targeting sequence comprising amino acids 12-25 of SEQ ID NO: 67; (461) a targeting sequence comprising amino acids 12-23 of SEQ ID NO: 67; (462) a targeting sequence comprising amino acids 13-25 of SEQ ID NO: 67; (463) a targeting sequence comprising amino acids 15-23 of SEQ ID NO: 67; (464) a targeting sequence comprising amino acids 23-36 of SEQ ID NO: 69; (465) a targeting sequence comprising amino acids 23-34 of SEQ ID NO: 69; (466) a targeting sequence comprising amino acids 24-36 of SEQ ID NO: 69; (467) a targeting sequence comprising amino acids 26-34 of SEQ ID NO: 69; (468) a targeting sequence comprising amino acids 27-40 of SEQ ID NO: 75; (469) a targeting sequence comprising amino acids 27-38 of SEQ ID NO: 75; (470) a targeting sequence comprising amino acids 9-22 of SEQ ID NO: 77; (471) a targeting sequence comprising amino acids 9-20 of SEQ ID NO: 77; (472) a targeting sequence comprising amino acids 10-22 of SEQ ID NO: 77; (473) a targeting sequence comprising amino acids 12-20 of SEQ ID NO: 77; (474) a targeting sequence comprising amino acids 23-36 of SEQ ID NO: 81; (475) a targeting sequence comprising amino acids 23-34 of SEQ ID NO: 81; (476) a targeting sequence comprising amino acids 24-36 of SEQ ID NO: 81; (477) a targeting sequence comprising amino acids 26-34 of SEQ ID NO: 81; (478) a targeting sequence comprising amino acids 13-26 of SEQ ID NO: 87; (479) a targeting sequence comprising amino acids 13-24 of SEQ ID NO: 87; or (480) a targeting sequence comprising amino acids 14-26 of SEQ ID NO: 87; (481) a targeting sequence comprising SEQ ID NO: 201; (482) a targeting sequence comprising SEQ ID NO: 202; (483) an exosporium protein comprising an amino acid sequence having at least 85% identity with SEQ ID NO: 203; (484) an exosporium protein comprising an amino acid sequence having at least 85% identity with SEQ ID NO: 204; (485) an exosporium protein fragment comprising an amino acid sequence having at least 85% identity with SEQ ID NO: 205; (486) an exosporium protein comprising an amino acid sequence having at least 85% identity with SEQ ID NO: 206; or (487) an exosporium protein fragment comprising an amino acid sequence having at least 85% identity with SEQ ID NO: 207.

For example, the targeting sequence can comprise an amino acid sequence having at least about 50% identity with amino acids 20-35 of SEQ ID NO: 1, wherein the identity with amino acids 25-35 is at least about 63%.

Alternatively, the targeting sequence can consist of an amino acid sequence having at least about 50% identity with amino acids 20-35 of SEQ ID NO: 1, wherein the identity with amino acids 25-35 is at least about 63%.

The targeting sequence can comprise an amino acid sequence having at least about 50% identity with amino acids 20-35 of SEQ ID NO: 1, wherein the identity with amino acids 25-35 is at least about 72%.

Alternatively, the targeting sequence can consist of an amino acid sequence having at least about 50% identity with amino acids 20-35 of SEQ ID NO: 1, wherein the identity with amino acids 25-35 is at least about 72%.

The targeting sequence can comprise an amino acid sequence having at least about 56% identity with amino acids 20-35 of SEQ ID NO: 1, wherein the identity with amino acids 25-35 is at least about 63%.

Alternatively, the targeting sequence can consist of an amino acid sequence having at least about 56% identity with amino acids 20-35 of SEQ ID NO: 1, wherein the identity with amino acids 25-35 is at least about 63%.

The targeting sequence can comprise an amino sequence having at least about 62% identity with amino acids 20-35 of SEQ ID NO: 1, wherein the identity with amino acids 25-35 is at least about 72%.

Alternatively, the targeting sequence can consist of an amino sequence having at least about 62% identity with amino acids 20-35 of SEQ ID NO: 1, wherein the identity with amino acids 25-35 is at least about 72%.

The targeting sequence can comprise an amino acid sequence having at least about 68% identity with amino acids 20-35 of SEQ ID NO: 1, wherein the identity with amino acids 25-35 is at least about 81%.

Alternatively, the targeting sequence can consist of an amino acid sequence having at least about 68% identity with amino acids 20-35 of SEQ ID NO: 1, wherein the identity with amino acids 25-35 is at least about 81%.

The targeting sequence can comprise an amino sequence having at least about 75% identity with amino acids 20-35 of SEQ ID NO: 1, wherein the identity with amino acids 25-35 is at least about 72%.

Alternatively, the targeting sequence can consist of an amino sequence having at least about 75% identity with amino acids 20-35 of SEQ ID NO: 1, wherein the identity with amino acids 25-35 is at least about 72%.

The targeting sequence can comprise an amino sequence having at least about 75% identity with amino acids 20-35 of SEQ ID NO: 1, wherein the identity with amino acids 25-35 is at least about 81%.

Alternatively, the targeting sequence can consist of an amino sequence having at least about 75% identity with amino acids 20-35 of SEQ ID NO: 1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 81%.

Alternatively, the targeting sequence can consist of an amino acid sequence having at least about 81% identity with amino acids 20-35 of SEQ ID NO: 1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%.

Alternatively, the targeting sequence can consist of an amino acid sequence having at least about 81% identity with amino acids 20-35 of SEQ ID NO: 1, wherein the identity with amino acids 25-35 is at least about 90%.

For example, the targeting sequence can consist of: (a) an amino acid sequence consisting of 16 amino acids and having at least about 43% identity with amino acids 20-35 of SEQ ID NO: 1, wherein the identity with amino acids 25-35 is at least about 54%; (b) amino acids 1-35 of SEQ ID NO: 1; (c) amino acids 20-35 of SEQ ID NO: 1; (d) SEQ ID NO: 1; (e) SEQ ID NO: 96; or (f) SEQ ID NO: 120.

In any of the fusion proteins described herein, the fusion protein can comprise an exosporium protein or an exosporium protein fragment comprising an amino acid sequence having at least 90% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 95, 108, 109, 110, 111, 112, 113, 114, 115, 116, 117, 118, 119, 120, and 121.

The fusion protein can comprise an exosporium protein or an exosporium protein fragment comprising an amino acid sequence having at least 95% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 95, 108, 109, 110, 111, 112, 113, 114, 115, 116, 117, 118, 119, 120, and 121.

The fusion protein can comprise an exosporium protein or an exosporium protein fragment comprising an amino acid sequence having at least 98% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 95, 108, 109, 110, 111, 112, 113, 114, 115, 116, 117, 118, 119, 120, and 121.

The fusion protein can comprise an exosporium protein or an exosporium protein fragment comprising an amino acid sequence having at least 99% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 95, 108, 109, 110, 111, 112, 113, 114, 115, 116, 117, 118, 119, 120, and 121.

The fusion protein can comprise an exosporium protein or an exosporium protein fragment comprising an amino acid sequence having 100% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 95, 108, 109, 110, 111, 112, 113, 114, 115, 116, 117, 118, 119, 120, and 121.

In any of the fusion proteins described herein, the fusion protein can comprise an exosporium protein comprising an amino acid sequence having at least 90% identity with SEQ ID NO: 60, 62, 64, 66, 68, 70, 76, 78, 80, 82, 84, 86, 88, 90, 92, 94, or 122.

The fusion protein can comprise an exosporium protein comprising an amino acid sequence having at least 95% identity with SEQ ID NO: 60, 62, 64, 66, 68, 70, 76, 78, 80, 82, 84, 86, 88, 90, 92, 94, or 122.

The fusion protein can comprise an exosporium protein comprising an amino acid sequence having at least 98% identity with SEQ ID NO: 60, 62, 64, 66, 68, 70, 76, 78, 80, 82, 84, 86, 88, 90, 92, 94, or 122.

The fusion protein can comprise an exosporium protein comprising an amino acid sequence having at least 99% identity with SEQ ID NO: 60, 62, 64, 66, 68, 70, 76, 78, 80, 82, 84, 86, 88, 90, 92, 94, or 122.

The fusion protein can comprise an exosporium protein comprising an amino acid sequence having 100% identity with SEQ ID NO: 60, 62, 64, 66, 68, 70, 76, 78, 80, 82, 84, 86, 88, 90, 92, 94, or 122.

In any of the fusion proteins described herein, the fusion protein can comprise an exosporium protein or an exosporium protein fragment comprising an amino acid sequence having at least 90% identity with any one of SEQ ID NOs: 203-207.

The fusion protein can comprise an exosporium protein or an exosporium protein fragment comprising an amino acid sequence having at least 95% identity with any one of SEQ ID NOs: 203-207.

The fusion protein can comprise an exosporium protein or an exosporium protein fragment comprising an amino acid sequence having at least 98% identity with any one of SEQ ID NOs: 203-207.

The fusion protein can comprise an exosporium protein or an exosporium protein fragment comprising an amino acid sequence having at least 99% identity with any one of SEQ ID NOs: 203-207.

The fusion protein can comprise an exosporium protein or an exosporium protein fragment comprising an amino acid sequence having 100% identity with any one of SEQ ID NOs: 203-207.

The fusion protein can comprise a targeting sequence, exosporium protein, or exosporium protein fragment that targets the fusion protein to the exosporium of the recombinant *Bacillus* bacterium, wherein the targeting sequence, exosporium protein, or exosporium protein fragment comprises the sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$, wherein:

$X_1$ is any amino acid or absent;

$X_2$ is phenylalanine (F), leucine (L), isoleucine (I), or methionine (M);

$X_3$ is any amino acid;

$X_4$ is proline (P) or serine (S);

$X_8$ is any amino acid;

$X_6$ is leucine (L), asparagine (N), serine (S), or isoleucine (I);

$X_7$ is valine (V) or isoleucine (I);

$X_8$ is glycine (G);

$X_9$ is proline (P);

$X_{10}$ is threonine (T) or proline (P);

$X_{11}$ is leucine (L) or phenylalanine (F);
$X_{12}$ is proline (P);
$X_{13}$ is any amino acid;
$X_{14}$ is any amino acid;
$X_{15}$ is proline (P), glutamine (Q), or threonine (T); and
$X_{16}$ is proline (P), threonine (T), or serine (S)

In any of the fusion proteins described herein, the targeting sequence, exosporium protein, or exosporium protein fragment can comprise the amino acid sequence GXT at its carboxy terminus, wherein X is any amino acid.

In any of the fusion proteins described herein, the targeting sequence, exosporium protein, or exosporium protein fragment can comprise an alanine residue at the position of the targeting sequence that corresponds to amino acid 20 of SEQ ID NO: 1.

In any of the fusion proteins described herein, the targeting sequence, exosporium protein, or exosporium protein fragment can further comprise a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

Fusion Proteins Comprising an Enzyme Having Serine Protease Activity

Fusion proteins comprising a targeting sequence, exosporium protein, or exosporium protein fragment that targets the fusion protein to the exosporium of a recombinant *Bacillus cereus* family member and an enzyme having serine protease activity are provided.

The enzyme having serine protease activity can comprise a serine protease from *Bacillus firmus*, also referred to as a *Bacillus firmus* serine protease enzyme. In yet another embodiment, the serine protease from *Bacillus firmus* can be Sep1 from a *Bacillus firmus* strain. In yet another embodiment, the serine protease can be Sep1 from *Bacillus firmus* DS-1, which is SEQ ID NO: 210. See Geng, et al., 2016, above. In yet another embodiment, the serine protease can be Sep1 from another *Bacillus firmus* strain, such as SEQ ID NO: 211.

For serine protease enzymes described herein, sequence identity is determined by aligning the entire length of the sequences in such a way as to obtain optimal matching so that the minimal number of edit operations (e.g., inserts, deletions and substitutions) are needed in order to transform the one sequence into an exact copy of the other sequence being aligned. The Needleman-Wünsch Global Alignmment of Protein Sequences, which is an algorithm that is available through the U.S. National Library of Medicine's National Center for Biotechnology Information ("NCBI") website, is one example of such analysis.

Alternatively or in addition, the enzyme having serine protease activity can comprise an amino acid sequence having at least 70% identity to any one of SEQ ID NOs: 210-211.

For example, the enzyme having serine protease activity can comprise an amino acid sequence having at least 75% identity to any one of SEQ ID NOs: 210-211.

The enzyme having serine protease activity can comprise an amino acid sequence having at least 80% identity to any one of SEQ ID NOs: 210-211.

The enzyme having serine protease activity can comprise an amino acid sequence having at least 85% identity to any one of SEQ ID NOs: 210-211.

The enzyme having serine protease activity can comprise an amino acid sequence having at least 90% identity to any one of SEQ ID NOs: 210-211.

The enzyme having serine protease activity can comprise an amino acid sequence having at least 95% identity to any one of SEQ ID NOs: 210-211.

The enzyme having serine protease activity can comprise an amino acid sequence having at least 98% identity to any one of SEQ ID NOs: 210-211.

The enzyme having serine protease activity can comprise an amino acid sequence having at least 99% identity to any one of SEQ ID NOs: 210-211.

The enzyme having serine protease activity can comprise an amino acid sequence having 100% identity to any one of SEQ ID NOs: 210-211.

For example, the enzyme can comprise SEQ ID NOs: 210-211.

Alternatively, the enzyme can consist of SEQ ID NOs: 210-211.

Additionally, or alternatively, the enzyme having serine protease activity can comprise an amino acid sequence having at least one amino acid deletion relative to the sequence of a wild-type serine protease enzyme from a *Bacillus firmus* bacterium, wherein the amino acid deletion retains the catalytic residues of the wild-type enzyme and results in the same or increased serine protease activity as compared to the serine protease activity of the wild-type serine protease enzyme under the same conditions. In one embodiment the wild-type serine protease enzyme is Sep1 from *Bacillus firmus* DS-1. See Geng, et al., 2016, above.

In one embodiment, the enzyme has increased serine protease activity as compared to the serine protease activity of the wild-type serine protease enzyme under the same conditions.

For example, the amino acid sequence of the enzyme can comprise SEQ ID NO: 212.

Alternatively or in addition, the enzyme having serine protease activity can comprise an amino acid sequence having at least 70% identity to SEQ ID NO: 212.

For example, the enzyme having serine protease activity can comprise an amino acid sequence having at least 75% identity to SEQ ID NO: 212.

The enzyme having serine protease activity can comprise an amino acid sequence having at least 80% identity to SEQ ID NO: 212.

The enzyme having serine protease activity can comprise an amino acid sequence having at least 85% identity to SEQ ID NO: 212.

The enzyme having serine protease activity can comprise an amino acid sequence having at least 90% identity to SEQ ID NO: 212.

The enzyme having serine protease activity can comprise an amino acid sequence having at least 95% identity to SEQ ID NO: 212.

The enzyme having serine protease activity can comprise an amino acid sequence having at least 98% identity to SEQ ID NO: 212.

The enzyme having serine protease activity can comprise an amino acid sequence having at least 99% identity to SEQ ID NO: 212.

The enzyme having serine protease activity can comprise an amino acid sequence having 100% identity to SEQ ID NO: 212.

Alternatively, the enzyme can consist of SEQ ID NO: 212.

In addition, the enzyme having serine protease activity and having 70%, 75%, 80%, 85%, 90%, 95%, 98%, or 99% sequence identity to SEQ ID NO: 212 maintains the deletion in SEQ ID NO: 212 (of amino acid 181-240 of SEQ ID NO: 211).

Optional Inclusion of Signal Peptides in the Fusion Proteins

In any of the fusion proteins described herein, the enzyme having serine protease activity can further comprise a signal peptide.

Where the signal peptide is present, it is preferably present at the amino terminus of the enzyme having serine protease activity.

The signal peptide preferably immediately precedes the first amino acid of the enzyme having serine protease activity.

Where the fusion protein comprises a signal peptide, the signal peptide can be present at the amino terminus of the enzyme having serine protease activity.

D. Methods for Making the Fusion Proteins

Any of the fusion proteins described herein can be made using standard cloning and molecular biology methods known in the art. For example, a gene encoding a protein or peptide of interest (e.g., an enzyme having serine protease activity) can be amplified by polymerase chain reaction (PCR) and ligated to DNA coding for any of the targeting sequences, exosporium proteins, or exosporium protein fragments described herein, to form a DNA molecule that encodes the fusion protein. The DNA molecule encoding the fusion protein can be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. Alternatively, DNA coding for the fusion protein can be integrated into the chromosomal DNA of the *B. cereus* family member or spore-forming bacterium host.

E. Tags, Markers, and Linkers that can be Included in the Fusion Proteins

Any of the fusion proteins described herein can also comprise additional polypeptide sequences that are not part of the targeting sequence, exosporium protein, exosporium protein fragment, or the enzyme having serine protease activity. For example, the fusion protein can include tags or markers to facilitate purification or visualization of the fusion protein (e.g., a polyhistidine tag or a fluorescent protein such as GFP or YFP) or visualization of recombinant *Bacillus cereus* family member spores expressing the fusion protein.

Expression of fusion proteins on the exosporium of a *Bacillus cereus* family member using the targeting sequences, exosporium proteins, and exosporium protein fragments described herein is enhanced due to a lack of secondary structure in the amino-termini of these sequences, which allows for native folding of the fused proteins and retention of activity. Proper folding can be further enhanced by the inclusion of a short amino acid linker between the targeting sequence, exosporium protein, exosporium protein fragment, spore coat protein, and the enzyme having serine protease activity.

Thus, any of the fusion proteins described herein can comprise an amino acid linker between the targeting sequence, the exosporium protein, or the exosporium protein fragment and the enzyme having serine protease activity.

The linker can comprise a polyalanine linker or a polyglycine linker. A linker comprising a mixture of both alanine and glycine residues can also be used. Examples of polyalanine linkers are provided as SEQ ID NOs: 208 and 209.

For example, in a fusion protein where the targeting sequence comprises SEQ ID NO: 1, a fusion protein can have one of the following structures:

No linker: SEQ ID NO: 1-POI

Alanine Linker: SEQ ID NO: 1-$A_n$-POI

Glycine Linker: SEQ ID NO: 1-$G_n$-POI

Mixed Alanine and Glycine Linker: SEQ ID NO: 1-$(A/G)_n$-POI where $A_n$, $G_n$, and $(A/G)_n$ are any number of alanines, any number of glycines, or any number of a mixture of alanines and glycines, respectively. For example, n can be 1 to 25, and is preferably 6 to 10. Where the linker comprises a mixture of alanine and glycine residues, any combination of glycine and alanine residues can be used. In the above structures, "POI" stands for "protein of interest" and represents the enzyme having serine protease activity.

Alternatively or in addition, the linker can comprise a protease recognition site. Inclusion of a protease recognition site allows for targeted removal, upon exposure to a protease that recognizes the protease recognition site, of the enzyme having serine protease activity.

Where the fusion protein comprises both a linker and signal peptide, the linker would typically be amino-terminal to the signal peptide. For example, where the fusion protein comprises SEQ ID NO: 96, a polyalanine linker, a signal sequence, and the serine protease of SEQ ID NO: 210, these elements would typically be arranged in the following order within the fusion protein, going from the amino-terminus of the fusion protein to the carboxy-terminus: SEQ ID NO: 96-$A_n$-signal sequence-SEQ ID NO: 210.

II. Recombinant *Bacillus cereus* Family Members Hosts for Expression of the Fusion Proteins The invention further relates to recombinant *Bacillus cereus* family members that express a fusion protein. The fusion protein can be any of the fusion proteins described in Section I above.

The recombinant *Bacillus cereus* family member can comprise any *Bacillus* species that is capable of producing an exosporium. For example, the recombinant *Bacillus cereus* family member can comprise *Bacillus anthracis, Bacillus cereus, Bacillus thuringiensis, Bacillus mycoides, Bacillus pseudomycoides, Bacillus samanii, Bacillus gaemokensis, Bacillus weihenstephensis, Bacillus toyoiensis*, or a combination of any thereof. The recombinant *Bacillus cereus* family member suitably comprises *Bacillus thuringiensis* or *Bacillus mycoides*.

To generate a recombinant *Bacillus cereus* family member expressing a fusion protein, any *Bacillus cereus* family member can be conjugated, transduced, or transformed with a vector encoding the fusion protein using standard methods known in the art (e.g., by electroporation). The bacteria can then be screened to identify transformants by any method known in the art. For example, where the vector includes an antibiotic resistance gene, the bacteria can be screened for antibiotic resistance. Alternatively, DNA encoding the fusion protein can be integrated into the chromosomal DNA of a *B. cereus* family member host. The recombinant *Bacillus cereus* family member can then exposed to conditions which will induce sporulation. Suitable conditions for inducing sporulation are known in the art. For example, the recombinant *Bacillus cereus* family member can be plated onto agar plates, and incubated at a temperature of about 30° C. for several days (e.g., 3 days).

Thus, the recombinant *Bacillus cereus* family member can be in the form of a spore.

Inactivated strains, non-toxic strains, or genetically manipulated strains of any of the above species can also suitably be used. For example, a *Bacillus thuringiensis* that lacks the Cry toxin can be used. Alternatively or in addition, once the recombinant *B. cereus* family member spores expressing the fusion protein have been generated, they can be inactivated to prevent further germination once in use. Any method for inactivating bacterial spores that is known in the art can be used. Suitable methods include, without limitation, heat treatment, gamma irradiation, x-ray irradiation, UV-A irradiation, UV-B irradiation, chemical treatment (e.g., treatment with glutaraldehyde, formaldehyde, hydrogen peroxide, acetic acid, bleach, or any combination thereof), or a combination thereof. Alternatively, spores derived from nontoxigenic strains, or genetically or physically inactivated strains, can be used.

Thus, the recombinant *Bacillus cereus* family member can be in the form of a spore, wherein the spore is inactivated.

The recombinant *Bacillus cereus* family member can coexpress two or more of any of the fusion proteins described herein. For example, the recombinant *Bacillus cereus* family member can coexpress at least one fusion protein that comprises SEQ ID NO: 210 together with a fusion protein that comprises SEQ ID NO: 212.

Many *Bacillus cereus* family member strains have inherent beneficial attributes. For example, some strains have plant-growth promoting effects. Other strains are endophytic. Some strains are both endophytic and have plant-growth promoting effects.

Thus, any of the recombinant *Bacillus cereus* family members described herein can comprise a plant-growth promoting strain of bacteria, an endophytic strain of bacteria, or a strain of bacteria that is both plant-growth promoting and endophytic.

The plant-growth promoting strain of bacteria can comprise a strain of bacteria that produces an insecticidal toxin (e.g., a Cry toxin), produces a fungicidal compound (e.g., a β-1,3-glucanase, a chitosanase, a lyticase, or a combination of any thereof), produces a nematocidal compound (e.g., a Cry toxin), produces a bacteriocidal compound, is resistant to one or more antibiotics, comprises one or more freely replicating plasmids, binds to plant roots, colonizes plant roots, forms biofilms, solubilizes nutrients, secretes organic acids, or any combination thereof.

The recombinant *Bacillus cereus* family member can comprises an endophytic strain of bacteria.

The recombinant *Bacillus cereus* family member can comprise an inactivating mutation in its BclA gene, its CotE gene, or its CotO gene (e.g., a knock-out of the BclA gene, CotE gene, or CotO gene). For example, the recombinant *Bacillus cereus* family member can comprise an inactivating mutation in its BclA gene (e.g., a knock-out of the BclA gene). It has been found that expression of fusion proteins in a recombinant *Bacillus cereus* family member having such a mutation results in increased expression levels of the fusion protein.

Compositions of the present invention include cultures, such as whole broth cultures, of the strains described herein. The term culture refers to a population of cells growing in the absence of other species in a predetermined culture media under controlled laboratory or manufacturing conditions. Biologically pure cultures of the recombinant *Bacillus cereus* family members of the present invention may be obtained according to methods well known in the art.

Conventional large-scale microbial culture processes include submerged fermentation, solid state fermentation, or liquid surface culture. During the fermentation, as nutrients are depleted, cells begin the transition from growth phase to sporulation phase, such that the final product of fermentation is largely spores, metabolites and residual fermentation medium. Sporulation is part of the natural life cycle of *Bacillus cereus* family members and is generally initiated by the cell in response to stressful environmental conditions, such as nutrient limitation. Fermentation is configured to obtain high levels of colony forming units and to promote sporulation. The bacterial cells, spores and metabolites in culture media resulting from fermentation may be used directly or concentrated by conventional industrial methods, such as centrifugation or filtration such as tangential-flow filtration or depth filtration, and evaporation.

Compositions of the present invention include the products of the microbial culture processes described herein. In embodiments in which submerged fermentation is used as the culture process, the product is referred to as a "fermentation broth" or a "whole broth culture." Such broth may be concentrated, as described above. The concentrated fermentation broth may be washed, for example, via a diafiltration process, to remove residual fermentation broth and metabolites. The term "broth concentrate," as used herein, refers to fermentation broth that has been concentrated by conventional industrial methods, as described above, but remains in liquid form. The term "fermentation product," as used herein, refers to fermentation broth or whole broth culture, broth concentrate and/or dried fermentation broth or broth concentrate.

The fermentation broth or broth concentrate can be dried with or without the addition of carriers using conventional drying processes or methods such as spray drying, freeze drying, tray drying, fluidized-bed drying, drum drying, or evaporation. The term "fermentation product," as used herein, refers to fermentation broth or whole broth culture, broth concentrate and/or dried fermentation broth or broth concentrate.

The resulting dry products may be further processed, such as by milling or granulation, to achieve a specific particle size or physical format. Carriers, described below, may also be added post-drying.

Cell-free preparations of fermentation broth of the strains of the present invention can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its application to plants or to plant growth media. Concentration methods and drying techniques described above for fermentation broth are also applicable to cell-free preparations.

As described further below in Section IV, the recombinant *Bacillus cereus* family member can comprise a mutation or other modification that allows for collection of exosporium fragments comprising the fusion proteins from spores of the recombinant *Bacillus cereus* family member.

III. Promoters for Expression of Fusion Proteins in Recombinant *Bacillus cereus* Family Members The DNA encoding the fusion proteins used in the recombinant *Bacillus cereus* family members, exosporium fragments, formulations, plant seeds, and methods, described herein is suitably under the control of a sporulation promoter which will cause expression of the fusion protein on the exosporium of a *B. cereus* family member endospore (e.g., a native bclA promoter from a *B. cereus* family member).

Thus, any of the fusion proteins described above in Section I can be expressed in the recombinant *Bacillus*

*cereus* family member under the control of a sporulation promoter that is native to the targeting sequence, exosporium protein, or exosporium protein fragment of the fusion protein, or a portion of such a promoter.

Any of the fusion proteins can be expressed under the control of a high-expression sporulation promoter.

The high-expression sporulation promoter can comprise a sigma-K sporulation-specific polymerase promoter sequence.

For ease of reference, illustrative nucleotide sequences for promoters that can be used to express any of the fusion proteins in a recombinant *Bacillus cereus* family member are provided in Table 3 below, together with their SEQ ID NOs. Table 3 also provides illustrative minimal promoter sequences for many of the promoters. In Table 3, sigma-K sporulation-specific polymerase promoter sequences in the promoters are indicated by bold and underlined text. Several of the sequences have multiple sigma K sequences that overlap with one another. The overlaps are indicated by double underlining in the table. The promoter sequences are immediately upstream of the start codon for each of the indicated genes. In other words, in the sequences shown in Table 3 below, the last nucleotide of the promoter sequence immediately precedes the first nucleotide of the start codon for the coding region of the gene encoding the indicated protein.

TABLE 3

Promoter Sequences for Expression of Fusion Proteins in Recombinant *Bacillus cereus* Family Members

| Promoter (SEQ ID NO:) | Promoter Sequence |
|---|---|
| ExsY promoter<br>(*B. cereus* F837/76)<br>(SEQ ID NO: 37) | TTTCTTAATCCTTTACCCTTTACTTTTGTAAAAGTTGATACACTTCCATCCGGCTCTGTAATTTCTAA<br>TTCATCAATAAATGGTCTTCGCAAAAAGCCTGTAATTTTATCATAAACAATTAAACGAGTGAGCCT<br>AAAAGCAGCTAACGCGAAAATAAAAAATAAAAGCCAGCTTGTAAACAGCATAATTCCACCTTCCC<br>TTATCCTCTTTCGCCTATTTAAAAAAAGGTCTTGAGATTGTGACCAAATCTCCTCAACTCC**AATATC**<br>**TTA**TTAATGTAAATACAAACAAGAAGATAAGGA |
| ExsY minimal promoter<br>(*B. cereus* F837/76)<br>(SEQ ID NO: 38) | ACCAAATCTCCTCAACTCC**AATATCTTA**TTAATGTAAATACAAACAAGAAGATAAGGA |
| ExsFA/BxpB promoter<br>(*B. anthracis* Sterne)<br>(SEQ ID NO: 39) | ACCACCTACCGACGATCCAATCTGTACATTCCTAGCTGTACCAAATGCAAGATTAATATCGACTAA<br>CACTTGTCTTACTGTTGATTTAAGTTGCTTCTGTGCGATTCAATGCTTGCGTGATGTTACGATTTAA<br>AACTAAATAATGAGCTAAG**CATGGATTG**GGTGGCAGAATTATCTGCCACCCAATCCATGCTTAAC<br>GAGTATTATTATGTAAATTTCTTAAAATTGGGAACTTGTCTAGAACATAGAACCTGTCCTTTT**CATT**<br>**AACTG**AAAGTAGAAACAGATAAAGGAGTGAAAAAC |
| ExsFA/BxpB minimal promoter<br>(*B. anthracis* Sterne)<br>(SEQ ID NO: 40) | ACATAGAACCTGTCCTTTT**CATTAACTG**AAAGTAGAAACAGATAAAGGAGTGAAAAAC |
| CotY/CotZ promoter<br>(*B. anthracis* Sterne)<br>(SEQ ID NO: 41) | TAGAAGAAGAACGCCGACTACTTTATGTCGCAATTACACGGGCGAAAGAAGAACTTTACATTTCCT<br>CTCCGCAATTTTTTAGAGGAAAAAAATTAGATATATCTCGTTTTTTATACACTGTGCGAAAAGATTT<br>ACCTGAAAAGACATCCACTAAATAAGGATGTCTTTTTTTATATTGTATTATGTACATCCCTACTATA<br>TAAATTCCCTGCTTTTATCGTAAGAATTAACGTAATATCAACCATATCCCGTT**CATATTGTA**GTAGT<br>GTATGTCAGAACTCACGAGAAGGAGTGAACATA |
| CotY/CotZ minimal promoter<br>(*B. anthracis* Sterne)<br>(SEQ ID NO: 42) | TCAACCATATCCCGTT**CATATTGTA**GTAGTGTATGTCAGAACTCACGAGAAGGAGTGAACATA |
| CotO promoter<br>(*B. cereus*)<br>(SEQ ID NO: 123) | TAACTCAATCTTAAGAGAAATTGAGGAGCGCGCACCACTTCGTCGTACAACAACGCAAGAAGAAG<br>TTGGGGATACAGCAGTATTCTTATTCAGTGATTTAGCACGCGGCGTAACAGGAGAAAACATTCACG<br>TTGATTCAGGGTAT**CATATCTTA**GGATA**AATATAATA**TTAATTTTAAAGGACAATCTCTACATGTT<br>GAGATTGTCCTTTTTATTTGTTCTTAGAAAGAACGATTTTTAACGAAAGTTCTTACCACGTTATGAA<br>TATAAGTATAATAGTACACGATTTATTCAGCTACGT |
| CotO minimal promoter<br>(*B. cereus*)<br>(SEQ ID NO: 124) | ACGTTGATTCAGGGTAT**CATATCTTA**GGATA**AATATAATA**TTAATTTTAAAGGACAATCTCTACAT<br>GTTGAGATTGTCCTTTTTATTTGTTCTTAGAAAGAACGATTTTTAACGAAAGTTCTTACCACGTTAT<br>GAATATAAGTATAATAGTACACGATTTATTCAGCTACGT |
| ExsFB promoter<br>(*B. cereus* F837/76)<br>(SEQ ID NO: 125) | CATAAAAATCTACTTTTCTTGTCAAAGAGTATGCTTATATGCGTGCTCTTTTTATTTGGTTTTCTTTC<br>ATTTCTAAATAACATTTTCAACTCTATTCATACTATTCTTTCAACTTTAGGTTACAAACTATTTCTGT<br>AAGCGTAGTGTTTCTTTTGTACTATAGGCAGTTAGTTTTATCCATAACAGTACACCTCTGCACTATT<br>CACTATAAATTTT**CATATATTA**TATTGTGCTTGTCCAAAACATGTGGTTATTACTCACGCGATCTAA<br>ATGAAAGAAAGGAGTGAAAAT |
| ExsFB minimal promoter<br>(*B. cereus* F837/76)<br>(SEQ ID NO: 126) | ACTATTCACTATAAATTTT**CATATATTA**TATTGTGCTTGTCCAAAACATGTGGTTATTACTCACGCG<br>ATCTAAATGAAAGAAAGGAGTGAAAAT |
| InhA1 promoter<br>(*B. thuringiensis* serovar *kurstaki* str. HD-1)<br>(SEQ ID NO: 127) | AATACATGATAATGAAATCCGATTTTGTGTTTTATATAGTGAATTATCAAATATTGTGTAGATGAA<br>ACAAAGATAAAATCCCCATTAAACTCCCTCTATGGAAATTATAAATTGTTCGATAAAAACTTTCAA<br>TATTTTCAGAAAACATTGTTGAATTGTGATATATTCGTATGCTAACTATGAAATTTTTACAAATATA<br>TTAAAAACATTA**CATAATATG**ACTAAATATTGAAAAAATATTGAATTTTTAATAAAATTTAATTTG<br>TAATA**CATATTATT**TATTAGGGGAGGAAATAAGGG |

TABLE 3-continued

Promoter Sequences for Expression of Fusion Proteins in Recombinant *Bacillus cereus* Family Members

| Promoter (SEQ ID NO:) | Promoter Sequence |
|---|---|
| InhA1 minimal promoter (*B. thuringiensis* serovar *kurstaki* str. HD-1) (SEQ ID NO: 128) | AAAATTTAATTTGTAATA**CATATTATT**TATTAGGGGAGGAAATAAGGG |
| InhA2 promoter (*B. mycoides* strain 219298) (SEQ ID NO: 129) | AATTGTGCATATTGTCTTTTAAATTTTCTATCTAAGTTATTTAATATATAATAAATAACTCTTTTTTG<br>TGAGTTTTTTTGATACGAGGTAAATAATCAGTACAGGGTCTGACCAGAGGACTGGAGGGCATGATT<br>CTATAAGGGAATATTTACTATTCCATGATTATAGAACTATGTCTTTTTATTGTATATAGAAGGGGG<br>GATAGGTC**TATATTATA**GAACTTATATATATTGTGCATTC**CATATTATC**AATTATCTAAATTTTAA<br>GTCTTGTTACAATTAATAAGGGAGGAAATAGTA |
| InhA2 minimal promoter (*B. mycoides* strain 219298) (SEQ ID NO: 130) | ACTTATATATATTGTGCATTC**CATATTATC**AATTATCTAAATTTTAAGTCTTGTTACAATTAATAAG<br>GGAGGAAATAGTA |
| ExsJ promoter (*B. thuringiensis* serovar *kurstaki*) (SEQ ID NO: 131) | AATGACGTTTTCAAGTTTGATTATCATTCATGTTTCCTATTTTAAGAGAAACATATAACTCAACTAC<br>TTTTTTCAATGG**CATCTTTTA**TAGTACTTAGAATAGGAAAACACTCAACTATAAGAAAAGTAAGG<br>AGGAAATAA |
| ExsJ minimal promoter (*B. thuringiensis* serovar *kurstaki*) (SEQ ID NO: 132) | ACTACTTTTTTCAATGG**CATCTTTTA**TAGTACTTAGAATAGGAAAACACTCAACTATAAGAAAAGT<br>AAGGAGGAAATAA |
| ExsH promoter (*B. cereus* F837/76) (SEQ ID NO: 133) | ATATGCTAATGCTTAGTTTTTATACTCAAGTTAAAATGTGCTTTTGGACCTAAGAGATAAACGTGG<br>AAA**AATAAAATA**AACTCTTAAGTTTAGGTGTTTAATCTAAGCAGTCAATTATTAAAAA**CATATAAT**<br>**T**AATATGTGAGTCATGAA**CATAATTAA**ATAATGTTTTCAAGTTTAATTATCGTTCATGTTTCCTATT<br>TTAAGCAGAACAAATAACTCAATTACTTTTTTCGATTGGATCTTTTTTAACTCTTATAATAGGAAAA<br>CACTCAACTATAAAAATAAGTAAGGAGGAAATAA |
| ExsH minimal promoter (*B. cereus* F837/76) (SEQ ID NO: 134) | AATATGTGAGTCATGAA**CATAATTA**AATAATGTTTTCAAGTTTAATTATCGTTCATGTTTCCTATTT<br>TAAGCAGAACAAATAACTCAATTACTTTTTTCGATTGGATCTTTTTTAACTCTTATAATAGGAAAAC<br>ACTCAACTATAAAAATAAGTAAGGAGGAAATAA |
| YjcA promoter (*B. thuringiensis* serovar *kurstaki* str. HD73) (SEQ ID NO: 135) | TATAAAATAAAAGGGCGTGTATTTGCTACTGATGCAGTATTGTGTGCGCCTAAAAATGGAATTTCA<br>CAACCAGATCCACATGTTGTTGTAGAACAATCTTGTAATTCATTGATGAATTTTACAACGTCAACTA<br>CACAATGAGAAGAGCCATGGTGTTTATTTTCGTTACAACTCATTAATGTCACTCCTTATCTTCTTGT<br>TTGTATTTACATT**AATAAGATA**TTGGAGTTGAGGAGATTTGGTCACAATCTCAAGACCTTTTTTTA<br>AATAGGCGAAAGAGGATAAGGGAAGGTGGAATT |
| YjcA minimal promoter (*B. thuringiensis* serovar *kurstaki* str. HD73) (SEQ ID NO: 136) | TCTTGTTTGTATTTACATT**AATAAGATA**TTGGAGTTGAGGAGATTTGGTCACAATCTCAAGACCTTT<br>TTTTTAAATAGGCGAAAGAGGATAAGGGAAGGTGGAATT |
| YjcB promoter (*B. thuringiensis* serovar *kurstaki* str. HD73) (SEQ ID NO: 137) | ATCAACTTTTACAAAAGTAAAGGGTAAAGGATTAAGAAAGTGGATTGGCGAATTATTAAGCTGTT<br>ATTGGTGTACAGGTGTATGGGTTAGTGCTTTTTTATTAGTTTTATATAATTGGATTCCGATCGTTGC<br>AGAGCCGTTACTTGCATTATTAGCTATTGCAGGAGCAGCAGCAATCATTGAAACGATTACAG**GATA**<br>**TTTTA**TGGGAG**AATAATATA**TTTTCATAATACGAGAAAAAGCGGAGTTTAAAAGAATGAGGGAAC<br>GGAAATAAAGAGTTGTT**CATATAGTA**AATAGACAGAA |
| YjcB minimal promoter (*B. thuringiensis* serovar *kurstaki* str. HD73) (SEQ ID NO: 138) | ACGGAAATAAAGAGTTGTT**CATATAGTA**AATAGACAGAA |
| Bc1C promoter (*B. anthracis* Sterne) (SEQ ID NO: 139) | TGAAGTATCTAGAGCTAATTTACGCAAAGGAATCTCAGGACAACACTTTCGCAACACC**TATATTTT**<br>**A**AATTTAATAAAAAAAGAGACTCCGGAGTCAGAAATTATAAAGCTAGCTGGGTTCAAATCAAAAA<br>TTTCACTAAAACGATATTATCAATACGCAGAAAATGGAAAAAACGCCTTATCATAAGGCGTTTTTT<br>CCATTTTTTCTTCAAACAAACGATTTTACTATGACCATTTAACTAATTTTTG**CATCTACTA**TGATGA<br>GTTTCATTCACATTCTCATTAGAAAGGAGAGATTTA |
| Bc1C minimal promoter (*B. anthracis* Sterne) (SEQ ID NO: 140) | ACCATTTAACTAATTTTTG**CATCTACTA**TGATGAGTTTCATTCACATTCTCATTAGAAAGGAGAGA<br>TTTA |
| AcpC promoter (*B. cereus* F837/76) (SEQ ID NO: 141) | GACTATGTTTATTCAG**GATAAAATA**TAGCACTACACTCTCTCCTCTTATTATGTAGCATCTCTCTAA<br>TCCATCATTTGTTTCATTTAGTTAAAATTGTAAATAAAATCACATGATTTGTCAATTATAATTGTCA<br>TTTCGACAATTAAACTTGTCAAAATAATTCTCATCATTTTTTCTCATCTTTCTAATATAGGACATACT<br>ACTATATATACAAAAGACAATATGCAAATGTT**CATACAAAA**AATATTATTTTTCGA**TATATAATA**T<br>TAACTGATTTTCTAACATCAAGGAGGGTACAT |

TABLE 3-continued

Promoter Sequences for Expression of Fusion Proteins in Recombinant *Bacillus cereus* Family Members

| Promoter (SEQ ID NO:) | Promoter Sequence |
| --- | --- |
| AcpC minimal promoter<br>(*B. cereus* F837/76)<br>(SEQ ID NO: 142) | AGACAATATGCAAATGTT**CATACAAAA**AATATTATTTTTCGA**TATATAATA**TTAACTGATTTTCTAACATCAAGGAGGGTACAT |
| InhA3 promoter<br>(*B. thuringiensis* serovar<br>*kurstalu* str. HD73)<br>(SEQ ID NO: 143) | ATAGTGAGTAATATGGTAATC**CATAGATTAAATAGTATA**GAAAATATTTAATTCTTATTTTTATTAAAAAAGCATGAATCCCAGATTTACTGGGTTTTGATTGTAACTAAGAA**CATATAAAA**GTTCACTGTTATTTATAGGAGAGTCTGTTTGTTTT**TATATCTTA**TGTATTTCACCCTG**CATAAAAAA**ATATTTCTCAACATTTTATTTGTTGAAAAATATTGAATATTCGTATTATAACGAATATTATGTTGTTATCGGCAAAAAACGATAATTTGCAGACACTGGGGAGGAAATACA |
| InhA3 minimal promoter<br>(*B. thuringiensis* serovar<br>*kurstaki* str. HD73)<br>(SEQ ID NO: 144) | TCTTATGTATTTCACCCTG**CATAAAAAA**ATATTTCTCAACATTTTATTTGTTGAAAAATATTGAATATTCGTATTATAACGAATATTATGTTGTTATCGGCAAAAAACGATAATTTGCAGACACTGGGGAGGAAATACA |
| Alanine racemase 1 promoter<br>(*B. cereus* F837/76)<br>(SEQ ID NO: 145) | CTTCGTCAGCAATAAGTGTGAGCGGAGAATTGGTTGATCTTGGCTTTACAATTGGAGCATTGACGAAAGACTCTTTAACGTGGTCG**CATAACGGA**GTAGAATATATGCTCGTGTCTAAAGGTTTAGAGCCGAAGGAGCTATTAATGGTTGCTCGTTCAGTTACAGAGAAGCAAGTGAAGTAAACTTCTTAGACGTGGTGATATATGTGCACCACGTCTTTTCTTAGTTTGAAGGGTGGATTT**CATAAAAGA**AG**CATATAAAA**GAATAAGCTTCG**CATATCGTG**TATAAGGAAGTGTATTT |
| Alanine racemase 1 minimal promoter<br>(*B. cereus* F837/76)<br>(SEQ ID NO: 146) | ATAAAAGAATAAGCTTCG**CATATCGTG**TATAAGGAAGTGTATTT |
| Alanine racemase 2 promoter<br>(*B. thuringiensis* serovar<br>*kurstaki* str. HD73)<br>(SEQ ID NO: 147) | CATTTCAAATAATGAACGCTTCGATTGAATCGGAGCTATTTTCAAATCAATTTCAGTATATTGATCCAGCATTTGAATAGAAGTATCAACAGCAACTTTAAGTTGATGCAATGCAGATTGTACAAACATTGTAATTCTCCTCTTCTCCG**TATATAATA**GTTTCTTGAGGGTATTATATCATGCTCAAAATTCCGAAAATTCTAGTAGTTTGACTAG**CATATTGAA**AAGTAT**TATATTGTA**AAAGGT**CATATGAAA**CGTGAAATAGAATGGAATGCAATTATTGAGTTAGGAGTTAGACCA |
| Alanine racemase 2 minimal promoter<br>(*B. thuringiensis* serovar<br>*kurstaki* str. HD73)<br>(SEQ ID NO: 148) | T**TATATTGTA**AAAGGT**CATATGAAA**CGTGAAATAGAATGGAATGCAATTATTGAGTTAGGAGTTAGACCA |
| Bc1A promoter<br>(*B. cereus* F837/76)<br>(SEQ ID NO: 149) | ATCGATGGAACCTGTATCAACCACTATAATTTCATCCACAATTTTTTCAACTGAGTCTAAACAACGGGCTATTGTCTTCTCCTCATCTCGAACAAT**CATACATAAACTA**ATTGTAATTCCTTGCTTGTTCAACATAATCACCCTCTTCCAAATCAAT**CATATGTTA**TA**CATATACTA**AACTTTCCATTTTTTTAAATTGTTCAAGTAGTTTAAGATTTCTTTTCAATAATTCAAATGTCCGTGTCATTTTCTTTCGGTTTTG**CATCTACTA**TATAATGAACGCTTTATGGAGGTGAATTT |
| Bc1A minimal promoter<br>(*B. cereus* F837/76)<br>(SEQ ID NO: 150) | AATCAAT**CATATGTTA**TA**CATATACTA**AACTTTCCATTTTTTTAAATTGTTCAAGTAGTTTAAGATTTCTTTTCAATAATTCAAATGTCCGTGTCATTTTCTTTCGGTTTTG**CATCTACTA**TATAATGAACGCTTTATGGAGGTGAATTT |
| Bc1B promoter<br>(*B. thuringiensis* serovar<br>*konkukian* str. 97-27)<br>(SEQ ID NO: 151) | GACCTGTAAGTCTGTAGGGAAGAATAATTTCAAGAGCCAGTGATAATAGATTTTTTTGTTTTTTCATTCTTATCTTGAATATAAATCACCT**CATCTTTTA**ATTAGAACGTAACCAATTTAGTATTTTGAAATAGAGCTAT**CATTTTATA**ATATGAATACTACTAGTTATAGAAACGGCAAAAAGTTTAATATATGTAAAAATCATTTGGATATGAAAAAAGTAGC**CATAGATTT**TTTCGAAATGATAAATGTTTTATTTTGTTAATTAGGAAACAAAAAATGTGGAATGAGGGGGATTTAA |
| Bc1B minimal promoter<br>(*B. thuringiensis* serovar<br>*konkukian* str. 97-27)<br>(SEQ ID NO: 152) | ATATGAAAAAAGTAGC**CATAGATTT**TTTCGAAATGATAAATGTTTTATTTTGTTAATTAGGAAACAAAAATGTGGAATGAGGGGGATTTAA |
| BxpA promoter<br>(*B. anthracis* str. Sterne)<br>(SEQ ID NO: 153) | TTTT**CATCTGCTA**CATCGTGAAGTAATGCTGCCATTTCAATTATAAAACGATTTCCTCCTTCTTGCTCGGATAAAGAAATCGCCAGTTTATGTACACGCTC**AATATGATA**CCAATCATGCCCACTGGCATCTTTTTCTAAAATATGTTTTACAAAAGTAATTGTTTTTTCTATCTTTTCTTGTTTTGTCATTTTATCTTCACCCAGTTACTTATTGTAACACGCCCGCATTTTTT**CATCA**CATA**TTTTC**TTGTCCGCC**CATACACTA**GGTGGTAGGCATCATCATGAAGGAGGAATAGAT |
| BxpA minimal promoter<br>(*B. anthracis* str. Sterne)<br>(SEQ ID NO: 154) | **ACATATTTTC**TTGTCCGCC**CATACACTA**GGTGGTAGGCATCATCATGAAGGAGGAATAGAT |
| Bc1E promoter<br>(*B. anthracis* Δ Sterne)<br>(SEQ ID NO: 155) | GGTGACGACAA**CATATACAA**GAGGCACTCCTGCTGGTACTGTAACAGGAACAAATATGGGGCAAAGTGTAAATA**CATCGGGTA**TAGCACAAGCTGTCCCGAATACA**GATAATATG**GATTCAACGGCGGGACTCCCTTAAGAAATTAGGGGAGTCTTTATTTGGAAAAAGAGCTTATGTTACATAAAAACAGGAGTAATTGTTTTAAAAGTAGTATTGGTGACGTTGTTAGAAAATACAATTTAAGTAGAAGGTGCGTTTTTATATGA**AATATATTT**TATAGCTGTACTTTACCTTTCAAG |

TABLE 3-continued

Promoter Sequences for Expression of Fusion Proteins in Recombinant *Bacillus cereus* Family Members

| Promoter (SEQ ID NO:) | Promoter Sequence |
|---|---|
| Bc1E minimal promoter<br>(*B. anthracis* Δ Sterne)<br>(SEQ ID NO: 156) | ACAAGCTGTCCCGAATACA**GATAATATG**GATTCAACGGCGGGACTCCCTTAAGAAATTAGGGGAG<br>TCTTTATTTGGAAAAAGAGCTTATGTTACATAAAAACAGGAGTAATTGTTTTAAAAGTAGTATTGG<br>TGACGTTGTTAGAAAATACAATTTAAGTAGAAGGTGCGTTTTTATATGA**AATATATTT**TATAGCTG<br>TACTTTACCTTTCAAG |
| BetA promoter<br>(*B. anthracis* Sterne)<br>(SEQ ID NO: 157) | ATTTATTTCATTCAATTTTTCCTATTTAGTACCTACCGCACTCACAAAAAGCACCTCTCATTAATTTA<br>TATTATAGTCATTGAAATCTAATTTAATGAAATCAT**CATACTATA**TGTTTTATAAGAAGTAAAGGT<br>AC**CATACTTAA**TTAATACATATCTATACACTTCAATATCACAGCATGCAGTTGAATTATATCCAAC<br>TTTCATTTCAAATTAAATAAGTGCCTCCGCTATTGTGAATGTCATTTACTCTCCCTACTA**CATTTAA**<br>**TA**ATTATGACAAGCAATCATAGGAGGTTACTAC |
| BetA minimal promoter<br>(*B. anthracis* Sterne)<br>(SEQ ID NO: 158) | TAAGAAGTAAAGGTAC**CATACTTAA**TTAATACATATCTATACACTTCAATATCACAGCATGCAGTT<br>GAATTATATCCAACTTTCATTTCAAATTAAATAAGTGCCTCCGCTATTGTGAATGTCATTTACTCTC<br>CCTACTA**CATTTAATA**ATTATGACAAGCAATCATAGGAGGTTACTAC |
| CotE promoter<br>(*B. cereus* AH820)<br>(SEQ ID NO: 159) | AGTTGTACAAGAATTTAAATCTTCACAAA**CATATGTAA**ATGACTTACTACAGCTAGTTGCAAGTAC<br>GATTTCTAACAACGTAACAGATGAAATATTAATTTCAACTAATGGCGATGTATTGAAGGGTGAAAC<br>GGGCGCAGCGGTAGAAAGTAAAAAAGGAAATTGTGGTTGTTAAAGAGATGTCGAAATGACATCTC<br>TTTTTTTAGTGGATTAAACGTAAGTTCTTCTCAAAAAAAGAATGACACATTCCGCTATTGTCACG**CA**<br>**TATGATT**AAGTGAATAGTGATTGAGGAGGGTTACGA |
| CotE minimal promoter<br>(*B. cereus* AH820)<br>(SEQ ID NO: 160) | ACATTCCGCTATTGTCACG**CATATGATT**AAGTGAATAGTGATTGAGGAGGGTTACGA |
| ExsA promoter<br>(*B. cereus* strain<br>ATCC 10876)<br>(SEQ ID NO: 161) | AACGTTATTAGCGTAGACAAACAAGTAACGGCAGAAGCAGTTCTTG**CATTAAATC**GTATGTTAGA<br>GCGTGTGTAAAGCAACGGTATTCCCGTTGCTTTTTTTCATA**CATATAATC**ATAACGAGAACGAAAT<br>GGG**CATACATTG**TTTTGAAGAAATCATTGTGGTTCTTTATGCTTATTCCACTTCGAATGATATTGAA<br>AATCGAAGAAGTGATAAAAGTAAAAAGAAGTTAATGTTATTTAGAAAGAGTTACTTCATGAGATT<br>TGTTACTTATA**GATAAGTTA**TACAGGAGGGGGAAAAT |
| ExsA minimal promoter<br>(*B. cereus* strain<br>ATCC 10876)<br>(SEQ ID NO: 162) | TCATGAGATTTGTTACTTATA**GATAAGTTA**TACAGGAGGGGGAAAAT |
| ExsK promoter<br>(*B. thuringiensis* serovar<br>*konkukian* str. 97-27)<br>(SEQ ID NO: 163) | AAGCCGCGGTCAATGCTGTATATGCA**AATAAGATT**GCAGCTTTACCTGAAGAAGAGCGT**GATAGC**<br>**TTC**ATTGCTGAAAAACGAGAAGAGTATAAGAAAGATATTGATATTTACCATTTAGCATCAGAGAT<br>GGTCATTGATGGTATTGTTCATCCAAACAATTTAAGAGAAGAGTTAAAAGGACGATTCGAAATGTA<br>TATGAGTAAATATCAAGTATTTACGGATCGTAAA**CATCCTGTT**TATCCAGTTTAAAAGCCCTATTT<br>AGGGCTTTCTTGCTCAAAAAGTTAAGGAGGGGAAAACA |
| ExsK minimal promoter<br>(*B. thuringiensis* serovar<br>*konkukian* str. 97-27)<br>(SEQ ID NO: 164) | TCAAGTATTTACGGATCGTAAA**CATCCTGTT**TATCCAGTTTAAAAGCCCTATTTAGGGCTTTCTTG<br>CTCAAAAAGTTAAGGAGGGGAAAACA |
| ExsB promoter<br>(*B. cereus* F837/76)<br>(SEQ ID NO: 165) | AGGATTTCAGTGGGACGCCTCCTCTCTTCTTACATTAAATTAAT**CATACTATA**AAATGAAAGAAAT<br>GAAATGAAAAATAGCGGAAAAATCAGAAATTTTTTCTGGTAG**TATACAATATGTTA**CAATAAGCT<br>TTGTCAATGAAAGAAGGAATTCCGTGCAATGCACGGGAGAGGTTCGCGAACTCCCTCTATAAAAA<br>ACTATGGAAACAAC**AATATCTTT**AGGTATTGTTTTGTTTTTTTATTGTGACAGTTCAAGAACGTTCT<br>TTCTTCTTATTCGTAGTAGAGAAGGAGAATGAGTGAA |
| ExsB minimal promoter<br>(*B. cereus* F837/76)<br>(SEQ ID NO: 166) | ACTATGGAAACAAC**AATATCTTT**AGGTATTGTTTTGTTTTTTTATTGTGACAGTTCAAGAACGTTCT<br>TTCTTCTTATTCGTAGTAGAGAAGGAGAATGAGTGAA |
| YabG promoter<br>(*B. cereus* AH820)<br>(SEQ ID NO: 167) | TTTTGCACAACGCCGTAAAACTTTAATG**AATAATTTA**TCA**AATAATTTA**AATGGTTTCCCGAAAGA<br>TAAAGAGCTGTTGGATCGAATTTTAACAGAAGTAGGAATTGATCCAAAACGAAGAGGCGAAACGC<br>TATCTATCGAAGAGTTTGCGACATTAAGTAATGCATTAGTTCTT**CATAAGTTA**TCATAAGAATACA<br>AAAGGGACAGTTCAATTTGAACTGTCCCTTTTGTCACCTTTCTCCTCCTAAATT**CATACTTTA**AAAA<br>CAGGTAAGATGGCCTAACGAGTTTGGAGGTAGGAGA |
| YabG minimal promoter<br>(*B. cereus* AH820)<br>(SEQ ID NO: 168) | TCTCCTCCTAAATT**CATACTTTA**AAAACAGGTAAGATGGCCTAACGAGTTTGGAGGTAGGAGA |
| Tg1 promoter<br>(*B. thuringiensis* serovar<br>*konkukian* str. 97-27)<br>(SEQ ID NO: 169) | GGAAACAGAAGTCATCCCATTTGAAAATGCAGCAGGTCGTATTATAGCTGATTTCGTTATGGTTTA<br>TCCGCCAGGGATTCCAATCTTTACTCCGGGGGAAATTATTACACAAGACAACTTAGAGTATATTCG<br>TAAAAACTTAGAAGCAGGTTTACCTGTACAAGGTCCTGAAGATATGACATTACAAACATTACGCGT<br>GATCAAAGAGTACAAGCCTATCAGTTGATAGGCTTTTTTTCACCCTTTTTCCCTTTTCT**CATACGAT**<br>**A**TTATGTAATGTAACGTATAGGTGGGGATACTACT |

TABLE 3-continued

| Promoter Sequences for Expression of Fusion Proteins in Recombinant *Bacillus cereus* Family Members | |
|---|---|
| Promoter (SEQ ID NO:) | Promoter Sequence |
| Tgl minimal promoter (*B. thuringiensis* serovar *konkukian* str. 97-27) (SEQ ID NO: 170) | ACCCTTTTTCCCTTTTCT**CATACGATA**TTATGTAATGTAACGTATAGGTGGGGATACTACT |
| Superoxide dismutase (SODA1) promoter (*B. cereus* F837/76) (SEQ ID NO: 171) | ATTGTGGACCCTTAGCTCAGCTGGTTAGAGCAGACGGCTCATAACCGTCCGGTCGTAGGTTCGAGTCCTACAGGGTCCATATCCATTTCACATGTTTATTATGTCGGCAGGAAGCTTCCTTGTAGAAGGGAGCTTTTTTTATGAAATATATGAGCATTTTAATTGAAATGAAGTGGGAATTTTGCTACTTTAATGATAGCAAGACAATGTGATTTATTTGTTTGCACCCTATGGCAATTAGGGTAGAATGAAGTTGTATGTCACTTAAGTGGCAATA**CATAAACTG**GGAGGAATATAACA |
| Superoxide dismutase (SODA1) minimal promoter (*B. cereus* F837/76) (SEQ ID NO: 172) | ACTTAAGTGGCAATA**CATAAACTG**GGAGGAATATAACA |
| Superoxide dismutase (SODA2)promoter (*B. cereus* AH820) (SEQ ID NO: 173) | AATATAACAGAAAATTCTGATGTTTTTTCAAATCCTATAATAAGGAGTGTTCCGTATGATGCCTT**TATATTTTC**CGGAAGATAAAACAG**AATATATTA**TTCCAGGGATTGTTTGTGTTCTATTTATCATCGGTGCGATTGCTACGTGGCGTATGTTCATTCGTGTATCAAAACGAGAAGCAGAGCGATTACAGAAAGTTGAAGAAAAGCTGTTAGCTGAAAAGAAACAGTAACTCATTTTTGTATGTTTCCCTCTATGCTCGGACAATCTAAGGGCAGAATGTATTTTGGAGGGAATGAA |
| Superoxide dismutase (SODA2) minimal promoter (*B. cereus* AH820) (SEQ ID NO: 174) | TCCGGAAGATAAAACAG**AATATATTA**TTCCAGGGATTGTTTGTGTTCTATTTATCATCGGTGCGATTGCTACGTGGCGTATGTTCATTCGTGTATCAAAACGAGAAGCAGAGCGATTACAGAAAGTTGAAGAAAAGCTGTTAGCTGAAAAGAAACAGTAACTCATTTTTGTATGTTTCCCTCTATGCTCGGACAATCTAAGGGCAGAATGTATTTTGGAGGGAATGAA |
| Bc1A promoter (*B. anthracis* Sterne) (SEQ ID NO: 175) | TAATCACCCTCTTCCAAATCAAT**CATATGTTA**TA**CATATACTA**AACTTTCCATTTTTTTAAATTGTTCAAGTAGTTTAAGATTTCTTTTCAATAATTCAAATGTCCGTGTCATTTTCTTTCGGTTTTG**CATCTACTA**TATAATGAACGCTTTATGGAGGTGAATTT |
| BAS1882 promoter (*B. anthracis* Sterne) (SEQ ID NO: 176) | AATTACATAACAAGAACTACATTAGGGAGCAAGCAGTCTAGCGAAAGCTAACTGCTTTTTTATTAAATAACTATTTTATTAAATTTCATATATACAATCGCTTGTCCATTTCATTTGGCTCTACCCACG**CATTTACTA**TTAGTAATATGAATTTTTCAGAGGTGGATTTTATT |
| Gene 3572 promoter (*B. weihenstephensis* KBAB 4) (SEQ ID NO: 177) | CTATGATTTAAGATACACAATAGCAAAAGAGAAA**CATATTATA**TAACGATAAATGAAACTTATGTATATGTATGGTAACTGTATATATTACTACAATACAGTATACTCATAGGAGGTAGGT |
| YVTN β-propeller protein promoter (*B. weihenstephensis* KBAB 4) (SEQ ID NO: 178) | GGTAGGTAGATTTGAAATATGATGAAGAAAAGGAATAACTAAAAGGAGTCGATATCCGACTCCTTTTAGTTATAAATAATGTGGAATTAGAGTATAATTTTATATAGGTATATTGTATTAGATGAACGCTTTATCCTTTAATTGTGATTAATGATGGATTGTAAGAGAAGGGGCTTACAGTCCTTTTTTTATGGTGTTCTATAAGCCTTTTTAAAAGGGGTACCACCCCACACCCAAAAACAGGGGGGGTTATAACTACATATTGGATGTTTTGTAACGTACAAGAATCGGTATTAATTACCCTGTAAATAAGTTATGTGTATATAAGGTAACTT**TATATATTC**TCCTACAATAAAATAAAGGAGGTAATAAA |
| Cry1A promoter (*B. thuringiensis* HD-73) (SEQ ID NO: 179) | AACCCTTAATGCATTGGTTAAACATTGTAAAGTCTAAAGCATGGATAATGGGCGAGAAGTAAGTAGATTGTTAACACCCTGGGTCAAAAATTGATATTTAGTAAAATTAGTTGCACTTTGTGCATTTTTT**CATAAGATG**AGT**CATATGTTT**TAAATTGTAGTAATGAAAAACAGTAT**TATATCATAATGAA**TTGGTATCTTAATAAAAGAGATGGAGGTAACTTA |
| ExsY promoter (*B. thuringiensis* serovar *konkukian* str. 97-27) (SEQ ID NO: 180) | TAATTCCACCTTCCCTTATCCTCTTTCGCCTATTTAAAAAAAGGTCTTGAGATTGTGACCAAATCTCCTCAACTCC**AATATCTTA**TTAATGTAAATACAAACAAGAAGATAAGGA |
| CotY promoter (*B. thuringiensis* Al Hakam) (SEQ ID NO: 181) | AGGATGTCTTTTTTTATATTGTATTATGTACATCCCTACTATATAAATTCCCTGCTTTTATCGTAAGAATTAACGTAATATCAACCATATCCCGTT**CATATTGTA**GTAGTGTATGTCAGAACTCACGAGAAGGAGTGAACATAA |
| YjcA promoter (*B. thuringiensis* serovar *kurstaki* str. HD73) (SEQ ID NO: 182) | TTAATGTCACTCCTTATCTTCTTGTTTGTATTTACATT**AATAAGATA**TTGGAGTTGAGGAGATTTGGTCACAATCTCAAGACCTTTTTTTTAAATAGGCGAAAGAGGATAAGGGAAGGTGGAATT |
| YjcB promoter (*B. thuringiensis* serovar *kurstaki* str. HD73) (SEQ ID NO: 183) | ATATATTTTCATAATACGAGAAAAAGCGGAGTTTAAAAGAATGAGGGAACGGAAATAAAGAGTTGTT**CATATAGTA**AATAGACAGAA |
| ExsFA/BxpB promoter (*B. thuringiensis* Al Hakam) (SEQ ID NO: 184) | AAACTAAATAATGAGCTAAGCATGGATTGGGTGGCAGAATTATCTGCCACCCAATC**CATGCTTAA**CGAGTATTATTATGTAAATTTCTTAAAATTGGGAACTTGTCTAGAACATAGAACCTGTCCTTTT**CATTAACTG**AAAGTAGAAACAGATAAAGGAGTGAAAAAC |

TABLE 3-continued

Promoter Sequences for Expression of Fusion Proteins in Recombinant *Bacillus cereus* Family Members

| Promoter (SEQ ID NO:) | Promoter Sequence |
|---|---|
| Rhamnose promoter (*B. thuringiensis* Al Hakam) (SEQ ID NO: 185) | ATTCACTACAACGGGGATGAGTTTGATGCGGATA**CATATGAGA**AGTACCGGAAAGTGTTTGTAGA<br>A**CATTACAA**AGATATATTATCTCCATCATAAAGGAGAGATGCAAAG |
| CotO promoter (*B. anthracis* Sterne) (SEQ ID NO: 186) | CGCGCACCACTTCGTCGTACAACAACGCAAGAAGAAGTTGGGGATACAGCAGTATTCTTATTCAGT<br>GATTTAGCACGCGGCGTAACAGGAGAAAACATTCACGTTGATTCAGGGTAT**CATATCTTA**GGATA<br>AATATAATATTAATTTTAAAGGACAATCTCTACATGTTGAGATTGTCCTTTTTATTTGTTCTTAGAA<br>AGAACGATTTTTAACGAAAGTTCTTACCACGTTATGAATATAAGTATAATAGTACACGATTTATTC<br>AGCTACGTA |
| Sigma K promoter (*B. anthracis* Sterne) (SEQ ID NO: 187) | TATATCATATGTAAAATTAGTTCTTATTCCCA**CATATCATA**TAGAATCGC**CATATTATA**CATGCAG<br>AAAACTAAGTATGGTATTATTCTTAAATTGTTTAGCACCTTCTAATATTACAGATAGAATCCGTCAT<br>TTTCAACAGTGAACATGGATTTCTTCTGAACACAACTCTTTTTCTTTCCTTATTTCCAAAAAGAAAA<br>GCAGCCCATTTTAAAATACGGCTGCTTGTAATGTACATTA |
| InhA1 promoter (*B. thuringiensis* Al Hakam) (SEQ ID NO: 188) | TATCACATAACTCTTTATTTTTAATATTTCGA**CATAAAGTG**AAACTTTAATCAGTGGGGGCTTTGTT<br>CATCCCCCCACTGATTATTAATTGAACCAAGGGATAAAAAGATAGAGGGTCTGACCAGAAAACTG<br>GAGGGCATGATTCTATAACAAAAAGCTTAATGTTTATAGAATTATGTCTTTTTATATAGGGAGGGT<br>AGTAAACAGAGATTTGGACAAAAATGCACCGATTTATCTGAATTTTAAGTTTTATAAAGGGGAGAA<br>ATG |
| BclA cluster glycosyl transferase operon 1 (*B. thuringiensis* serovar *konkukian* str. 97-27) (SEQ ID NO: 189) | ATTTTTTACTTAGCAGTAAAACTGATATCAGTTTTACTGCTTTTTCATTTTTAAATTCAATCATTAAA<br>TCTTCCTTTTCTACATAGT**CATAATGTT**GTATGACATTCCGTAGGAGGCACTTATA |
| BclA cluster glycosyl transferase operon 2 (*B. thuringiensis* serovar *kurstaki* str. HD73) (SEQ ID NO: 190) | ACATAAATTCACCTCCATAAAGCGTTCATTATATAGTAGATGCAAAACCGAAAGAAAATGACACG<br>GACATTTGAATTATTGAAAAGAAATCTTAAACTACTTGAACAATTTAAAAAAATGGAAAGTTTAGT<br>ATATGTATAA**CATATGATT**GATTTGGAAGAGGGTGATTA |
| Glycosyl transferase promoter (*B. thuringiensis* Al Hakam) (SEQ ID NO: 191) | TTCTATTTTCCAA**CATAACATG**CTACGATTAAATGGTTTTTTGCAAATGCCTTCTTGGGAAGAAGG<br>ATTAGAGCGTTTTTTTATAGAAACCAAAAGTCATTAACAATTTTAAGTTAATGACTTTTTTGTTTGC<br>CTTTAAGAGGTTTTATGTTACTATAATTATAGTATCAGGTACTAATAACAAGTATAAGTATTTCTGG<br>GAGGATATATCA |

The sigma-K sporulation-specific polymerase promoter sequences in the promoter sequences shown in Table 3 result in high expression levels of the fusion protein during late sporulation. The consensus sequence for the sigma-K sporulation-specific polymerase promoter sequence is CATANNNTN (SEQ ID NO: 200); however, this sequence can comprise up to two mutations and still be functional. The sigma-K sporulation-specific polymerase promoter sequence is generally found upstream of the ribosome binding site (RBS).

Promoters having a high degree of sequence identity to any of the sequences shown above in Table 3 can also be used to express the fusion proteins.

For example, the fusion protein can be expressed under the control of a promoter comprising a nucleic acid sequence having at least 80% identity with a nucleic acid sequence of any one of SEQ ID NOs: 37-42 and 123-191.

The fusion protein can be expressed under the control of a promoter comprising a nucleic acid sequence having at least 85% identity with a nucleic acid sequence of any one of SEQ ID NOs: 37-42 and 123-191.

The fusion protein can be expressed under the control of a promoter comprising a nucleic acid sequence having at least 90% identity with a nucleic acid sequence of any one of SEQ ID NOs: 37-42 and 123-191.

The fusion protein can be expressed under the control of a promoter comprising a nucleic acid sequence having at least 95% identity with a nucleic acid sequence of any one of SEQ ID NOs: 37-42 and 123-191.

The fusion protein can be expressed under the control of a promoter comprising a nucleic acid sequence having at least 98% identity with a nucleic acid sequence of any one of SEQ ID NOs: 37-42 and 123-191.

The fusion protein can be expressed under the control of a promoter comprising a nucleic acid sequence having at least 99% identity with a nucleic acid sequence of any one of SEQ ID NOs: 37-42 and 123-191.

The fusion protein can be expressed under the control of a promoter comprising a nucleic acid sequence having 100% identity with a nucleic acid sequence of any one of SEQ ID NOs: 37-42 and 123-191.

For example, fusion protein can be expressed under the control of a BclA promoter (e.g., SEQ ID NO: 149, 150, 175, 189, or 190), a CotY promoter (e.g., SEQ ID NO: 41, 42, or 181), an ExsY promoter (e.g., SEQ ID NO: 37, 38, or 180), or a rhamnose promoter (e.g., SEQ ID NO: 185), or a promoter having a high degree of sequence identity to any of these promoters.

Thus, for example, the fusion protein can be expressed under the control of a promoter comprising a nucleic acid sequence having at least 80% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 85% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 90% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 95% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 98% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 99% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having 100% identity with a nucleic acid sequence of any one of SEQ ID NOs: 37, 38, 41, 42, 149, 150, 175, 180, 181, 185, 189, or 190.

The fusion protein can be expressed under the control of a promoter comprising a sigma-K sporulation specific polymerase promoter sequence, wherein the sigma-K sporulation-specific polymerase promoter sequence or sequences have 100% identity with the corresponding nucleotides of any of SEQ ID NOs: 37-42 and 123-191.

The fusion proteins can be expressed under the control of a promoter that is native to the targeting sequence, exosporium protein, or exosporium protein fragment of the fusion protein. Thus, for example, where the targeting sequence is derived from BclA, the fusion protein can be expressed under the control of a native BclA promoter (e.g., SEQ ID NO: 149, 150, 175, 189 or 190).

Table 3 also provides illustrative minimal promoter sequences. The fusion proteins can be expressed under any of these minimal promoter sequences.

Furthermore, the fusion protein can be expressed under a portion of any of the promoters listed above in Table 3, so long as the portion of the promoter includes a sigma-K sporulation-specific polymerase promoter sequence. For example, the fusion protein can be expressed under a promoter region that comprises the first 25, 50, 100, 150, 200, 250, or 300 nucleotides upstream of the start codon, so long as that region comprises a sigma-K sporulation-specific polymerase promoter sequence.

IV. Mutations and Other Genetic Alterations to Recombinant *Bacillus cereus* Family Members that Allow for Collection of Free Exosporium and Exosporium Fragments Derived from Such Recombinant *Bacillus cereus* Family Members As is described further hereinbelow, the recombinant *Bacillus cereus* family members that express fusion proteins comprising a protein or peptide of interest (e.g., an enzyme having serine protease activity) and a targeting sequence, an exosporium protein, or an exosporium protein fragment that targets the fusion protein to the exosporium of the recombinant *Bacillus cereus* family member can be used for various purposes, including delivering the proteins or peptides of interest plants, seeds, a plant growth medium, or an area surrounding a seed or a plant (e.g., via soil drench, foliar application, or as a seed treatment). However, in some cases, the presence of the living microorganisms may not be desirable, and instead, it would be desirable to separate the living spore from the fusion proteins in the exosporium on the outside surface of the spore. For example, in some applications it will be desirable to increase enzyme activity without concern for spore integrity. In such situations, use of exosporium fragments that have been separated from the spores may be preferred over the use of living microorganisms having the enzyme on their exosporium.

In addition, for some uses, it may be desirable to reduce the density of the product. In such instances, it would be desirable to separate the dense spore from the exosporium (containing the fusion proteins). Furthermore, under some circumstances the presence of live spores would lead to potential for bacterial growth in a product, which would be undesirable for some applications.

Mutations or other genetic alterations (e.g., overexpression of a protein) can be introduced into the recombinant *Bacillus cereus* family members that allow free exosporium to be separated from spores of the recombinant *Bacillus cereus* family member. This separation process yields exosporium fragments that contain the fusion proteins but that are substantially free of the spores themselves. By "substantially free of spores" it is meant that once the free exosporium is separated from the spores, a preparation is obtained that contains less than 5% by volume of spores, preferably less than 3% by volume of spores, even more preferably less than 1% by volume of spores, and most preferably contains no spores or if spores are present, they are undetectable. These exosporium fragments can be used in place of the recombinant *Bacillus cereus* family members themselves in any of the formulations, plant seeds, and methods described herein.

Exosporium fragments derived from spores of a recombinant *Bacillus cereus* family member can be used in any of the formulations, plant seeds, and methods described herein. The recombinant *Bacillus cereus* family member expresses any of the fusion proteins described herein. The recombinant *Bacillus cereus* family member also comprises a mutation or expresses a protein, wherein the expression of the protein is increased as compared to the expression of the protein in a wild-type *Bacillus cereus* family member under the same conditions. The mutation or the increased expression of the protein results in *Bacillus cereus* family member spores having an exosporium that is easier to remove from the spore as compared to the exosporium of a wild-type spore.

The recombinant *Bacillus cereus* family member: (i) can comprise a mutation in a CotE gene; (ii) can express an ExsY protein, wherein the expression of the ExsY protein is increased as compared to the expression of the ExsY protein in a wild-type *Bacillus cereus* family member under the same conditions, and wherein the ExsY protein comprises a carboxy-terminal tag comprising a globular protein; (iii) can express a BclB protein, wherein the expression of the BclB protein is increased as compared to the expression of the BclB protein in a wild-type *Bacillus cereus* family member under the same conditions; (iv) can express a YjcB protein, wherein the expression of the YjcB protein is increased as compared to the expression of the YjcB protein in a wild-type *Bacillus cereus* family member under the same conditions; (v) can comprise a mutation in an ExsY gene; (vi) can comprise a mutation in a CotY gene; (vii) can comprise a mutation in an ExsA gene; or (viii) can comprise a mutation in a CotO gene.

The recombinant *Bacillus cereus* family member can comprise a mutation in the CotE gene, such as a knock-out of the CotE gene or a dominant negative form of the CotE gene. The mutation in the CotE gene can partially or completely inhibit the ability of CotE to attach the exosporium to the spore.

The recombinant *Bacillus cereus* family member can express an ExsY protein. The ExsY protein comprises a carboxy-terminal tag comprising a globular protein (e.g., a green fluorescent protein (GFP) or a variant thereof), and the expression of the ExsY protein is increased as compared to the expression of the ExsY protein in a wild-type *Bacillus cereus* family member under the same conditions. The globular protein can have a molecular weight of between 25 kDa and 100 kDa. Expression of the ExsY protein comprising the carboxy-terminal tag comprising a globular protein can inhibit binding of the ExsY protein to its targets in the exosporium.

The recombinant *Bacillus cereus* family member can express a BclB protein. Expression of the BclB protein can result in the formation of a fragile exosporium. The expression of the BclB protein can be increased as compared to the expression of the BclB protein in a wild-type *Bacillus cereus* family member under the same conditions.

The recombinant *Bacillus cereus* family member can express a YjcB protein. Expression of the YjcB protein can cause the exosporium to form in pieces rather than in a complete structure. The expression of the YjcB protein can be increased as compared to the expression of the YjcB protein in a wild-type *Bacillus cereus* family member under the same conditions.

The recombinant *Bacillus cereus* family member can comprise a mutation an ExsY gene, such as a knock-out of the ExsY gene. The mutation in the ExsY gene can partially or completely inhibit the ability of ExsY to complete the formation of the exosporium or attach the exosporium to the spore.

The recombinant *Bacillus cereus* family member can comprise a mutation a CotY gene, such as a knock-out of the CotY gene. The mutation in the CotY gene can result in the formation of a fragile exosporium.

The recombinant *Bacillus cereus* family member can comprise a mutation an ExsA gene, such as a knock-out of the ExsA gene. The mutation in the ExsA gene can result in the formation of a fragile exosporium.

The recombinant *Bacillus cereus* family member can comprise a mutation a CotO gene, such as a knock-out of the CotO gene or a dominant negative form of the CotO gene. The mutation in the CotO gene can cause the exosporium to form in strips.

For ease of reference, descriptions of illustrative sequences for CotE, ExsY, BclB, YjcB, CotY, ExsA, and CotO are provided in Table 4 below.

TABLE 4

Sequences of Proteins that Can be Mutated or Otherwise Genetically Altered to Allow for Collection of Free Exosporium

| Protein | SEQ ID NO: |
|---|---|
| CotE, *Bacillus cereus* group | 192 |
| ExsY, *Bacillus thuringiensis* | 193 |
| BclB, variant 1, *Bacillus anthracis* Sterne | 194 |
| BclB, variant 2, *Bacillus anthracis* Sterne | 195 |
| YjcB, Variant 1, *Bacillus cereus* | 196 |
| YjcB, Variant 2, *Bacillus cereus* | 197 |
| CotY, *Bacillus cereus* | 198 |
| CotO, *Bacillus anthracis* | 199 |

Exosporium fragments can be prepared from any of these recombinant *Bacillus cereus* family members and used for various purposes as described further herein below. Where the recombinant *Bacillus cereus* family member expresses a fusion protein, the exosporium fragments will comprise the fusion proteins. Upon purification of the exosporium fragments that contain the fusion proteins from the spores, a cell-free protein preparation is obtained in which the fusion proteins are stabilized and supported through covalent bonds to the exosporium fragments.

To remove the exosporium from spores of the recombinant *Bacillus cereus* family members that have mutations or other genetic alterations that allow for collection of free exosporium, a suspension or fermentation broth of the spores can be subjected to centrifugation or filtration to produce fragments of exosporium that are separated from the spores. Where the recombinant *Bacillus cereus* family member expresses a fusion protein, the exosporium fragments will comprise the fusion protein.

A suspension or fermentation broth comprising the spores can be subjected to centrifugation, followed by collection of the supernatant. The supernatant comprises the fragments of the exosporium and is substantially free of spores.

Alternatively, a suspension or fermentation broth comprising the spores can be subjected to filtration, followed by collection of the filtrate. The filtrate comprises the fragments of the exosporium and is substantially free of spores.

The suspension or fermentation broth of spores can be agitated or mechanically disrupted prior to centrifugation or filtration.

The exosporium fragments can also be separated from the spores by gradient centrifugation, affinity purification, or by allowing the spores to settle out of the suspension.

Due to the strong covalent bonds between the fusion proteins and the exosporium fragments, the fusion proteins become resistant to heat. The heat resistance of the fusion proteins bound to the exosporium fragments allows them to be used for applications that require heat-resistant proteins or enzymes.

Exosporium fragments derived from a recombinant *Bacillus cereus* family member are provided.

The exosporium fragments can be derived from any of the recombinant *Bacillus cereus* family members that comprise any of the mutations or other genetic alterations described herein that allow for collection of free exosporium.

The exosporium fragments can comprise any of the fusion proteins described above in Section I.

V. Formulations

A formulation is provided. The formulation comprises any of the recombinant *Bacillus cereus* family members described herein. The formulation further comprises an agriculturally acceptable carrier.

Another formulation is provided. The formulation comprises exosporium fragments derived from any of the recombinant *Bacillus cereus* family members described herein. The formulation further comprises an agriculturally acceptable carrier.

VI. Treated Seeds

A treated plant seed is provided. The plant seed can be treated with any of the recombinant *Bacillus cereus* family members described herein. The recombinant *Bacillus cereus* family member can express any of the fusion proteins described herein.

Another treated plant seed is provided. The plant seed can be treated with any of the exosporium fragments described herein. The exosporium fragments can be derived from any of the *Bacillus cereus* family members described herein. The exosporium fragments can comprise any of the fusion proteins described herein.

Yet another treated plant seed is provided. The plant seed can be treated with any of the formulations described herein.

In any of the treated plant seeds, the plant seed can be coated with the recombinant *Bacillus cereus* family member, the exosporium fragments, or the formulation.

The recombinant *Bacillus cereus* family members, exosporium fragments, or formulations can used as seed treatments, e.g., seed coatings or dressings. Seed coating or dressing formulations may be in the form of a liquid carrier formulation, a slurry formulation, or a powder formulation.

Seed coating or dressing formulations can be applied with conventional additives that are provided to make the seed treatment have sticky qualities to stick to and coat the seeds. Suitable additives comprise: talcs, graphites, gums, stabilizing polymers, coating polymers, finishing polymers, slip agents for seed flow and plantability, cosmetic agents, and cellulosic materials such as carboxymethyl cellulose and the like.

The seed treatments formulations can further comprise colorant agents and/or other additives.

The seed treatment formulations(s) may be applied to seeds in a suitable carrier such as water or a powder. The seeds can then be allowed to dry and planted in conventional fashion. The recombinant *Bacillus cereus* family members or exosporium fragments can be applied directly to the seed as a solution or in combination with other commercially available additives. For example, the recombinant *Bacillus cereus* family members or exosporium fragments can be applied in combination with seedling-acceptable carrier(s) (e.g., a liquid carrier or a solid carrier).

Solutions containing the recombinant *Bacillus cereus* family members or exosporium fragments can be sprayed or otherwise applied to the seed (e.g., in a seed slurry or a seed soak).

Solid or dry materials containing recombinant *Bacillus cereus* family members or exosporium fragments are also useful to promote effective seedling germination, growth, and protection during early seedling establishment.

The recombinant *Bacillus cereus* family members or exosporium fragments can be used with a solubilizing carrier such as water, a buffer (e.g., citrate or phosphate buffer), other treating agents (e.g., alcohol or another solvent), and/or any soluble agent.

In addition, small amounts of drying agent enhancers, such as lower alcohols, etc. can be used in seed coating formulations.

Surfactants, emulsifiers and preservatives can also be added at relatively low (e.g., about 0.5% w/v or less) levels in order to enhance the stability of the seed coating product.

Seeds can be treated using a variety of methods including, but not limited to, pouring, pumping, drizzling, or spraying an aqueous solution containing the recombinant *Bacillus cereus* family members or exosporium fragments on or over a seed; or spraying or applying the recombinant *Bacillus cereus* family members or exosporium fragments onto a layer of seeds either with or without the use of a conveyor system.

Mixing devices useful for seed treatment include but are not limited to tumblers, mixing basins, mixing drums, and fluid application devices that include basins or drums used to contain the seed while coating.

After seed treatment, the seed may be air-dried or a stream of dry air may be optionally used to aid in the drying of the seed coatings.

Seed treatments containing the recombinant *Bacillus cereus* family members or exosporium fragments can be applied using any commercially available seed treatment machinery or can also be applied using any acceptable non-commercial method(s) such as the use of syringes or any other seed treatment device.

VII. Methods for Stimulating Plant Growth and/or Promoting Plant Health and/or Controlling Plant Pathogens A method for stimulating plant growth and/or promoting plant health and/or controlling plant pests, such as nematodes, and/or controlling plant pathogens is provided. The method comprises applying a recombinant *Bacillus cereus* family member to a plant growth medium, a plant, a plant seed, or an area surrounding a plant or a plant seed contacting the plant pest with a recombinant *Bacillus cereus* family member. The recombinant *Bacillus cereus* family member can comprise any of the recombinant *Bacillus cereus* family members described herein. The recombinant *Bacillus cereus* family member can express any of the fusion proteins described herein.

Another method for stimulating plant growth and/or promoting plant health and/or controlling plant pests, such as nematodes, and/or controlling plant pathogens is provided. The method comprises applying exosporium fragments to a plant growth medium, a plant, a plant seed, or an area surrounding a plant or a plant seed or contacting the plant pest with exosporium fragments. The exosporium fragments can comprise exosporium fragments derived from any of the recombinant *Bacillus cereus* family members described herein. The exosporium fragments can comprise any of the fusion proteins described herein.

Yet another method for stimulating plant growth and/or promoting plant health and/or controlling plant pests, such as nematodes, and/or controlling plant pathogens is provided. The method comprises applying a formulation to a plant growth medium, a plant, a plant seed, or an area surrounding a plant or a plant seed. The formulation can comprise any of the formulations described herein.

In any of the methods described herein, the method can further comprise inactivating the recombinant *Bacillus cereus* family member prior to applying the recombinant *Bacillus cereus* family member to the plant growth medium, the plant, the plant seed, or the area surrounding the plant or the plant seed.

In any of the methods described herein, the method can comprise applying the recombinant *Bacillus cereus* family member, the exosporium fragments, or the formulation to the plant growth medium.

In any of the methods described herein involving the use of a plant growth medium, the plant growth medium can comprise soil, water, an aqueous solution, sand, gravel, a polysaccharide, mulch, compost, peat moss, straw, logs, clay, soybean meal, yeast extract, or a combination thereof.

The plant growth medium can comprise a fertilizer.

Any of the methods described herein can further comprise supplementing the plant growth medium with a substrate for an enzyme. Suitable substrates include, but are not limited to protein meal, casein, gelatin, albumin, or a combination of any thereof.

In any of the methods described herein, the method can comprise applying the recombinant *Bacillus cereus* family member, the exosporium fragments, or the formulation to the plant.

For example, the method can comprise applying the recombinant *Bacillus cereus* family member, the exosporium fragments, or the formulation to roots of the plant.

Alternatively or in addition, the method can comprise applying the recombinant *Bacillus cereus* family member, the exosporium fragments, or the formulation foliarly.

In any of the methods described herein, the method can comprise applying the recombinant *Bacillus cereus* family member, the exosporium fragments, or the formulation to the plant seed.

Where the method comprises applying the recombinant *Bacillus cereus* family member, the exosporium fragments, or the formulation to the plant seed, applying the recombinant *Bacillus cereus* family member, the exosporium fragments, or the formulation to the plant seed can comprise: (a) applying recombinant *Bacillus cereus* family member, the exosporium fragments, or the formulation to the plant seed at the time of planting; or (b) coating the plant seed with the recombinant *Bacillus cereus* family member, the exosporium fragments, or the formulation.

In any of the methods described herein, the plant pest that are controlled can be phytoparasitic pests from the phylum Nematoda, for example, *Aglenchus* spp., *Anguina* spp., *Aphelenchoides* spp., *Belonolaimus* spp., *Bursaphelenchus* spp., *Cacopaurus* spp., *Criconemella* spp., *Criconemoides* spp., *Ditylenchus* spp., *Dolichodorus* spp., *Globodera* spp., *Helicotylenchus* spp., *Hemicriconemoides* spp., *Hemicycliophora* spp., *Heterodera* spp., *Hoplolaimus* spp., *Longidorus* spp., *Lygus* spp., *Meloidogyne* spp., *Meloinema* spp., *Nacobbus* spp., *Neotylenchus* spp., *Paralongidorus* spp., *Paraphelenchus* spp., *Paratrichodorus* spp., *Pratylenchus* spp., *Pseudohalenchus* spp., *Psilenchus* spp., *Punctodera* spp., *Quinisulcius* spp., *Radopholus* spp., *Rotylenchulus* spp., *Rotylenchus* spp., *Scutellonema* spp., *Subanguina* spp., *Trichodorus* spp., *Tylenchulus* spp., *Tylenchorhynchus* spp., *Xiphinema* spp.

In any of the methods described herein, plants grown in the presence of the recombinant *Bacillus cereus* family member, the exosporium fragments, or the formulation can exhibit increased growth as compared to plants grown in the absence of the enzyme or the microorganism under the same conditions.

In any of the methods described herein, seeds to which the recombinant *Bacillus cereus* family member, the exosporium fragments, or the formulation has been applied can exhibit increased germination rates as compared to seeds to which the enzyme or microorganism has not been applied, under the same conditions.

In any of the methods described herein, plants grown in the presence of the recombinant *Bacillus cereus* family member, the exosporium fragments, or the formulation can exhibit increased nutrient uptake as compared to plants grown in the absence of the enzyme or the microorganism, under the same conditions.

In any of the methods described herein, plants grown in the presence of the recombinant *Bacillus cereus* family member, the exosporium fragments, or the formulation can exhibit decreased susceptibility to a pest, such as nematodes, as compared to plants grown in the absence of the enzyme or the microorganism, under the same conditions.

In any of the methods described herein, plants grown in the presence of the recombinant *Bacillus cereus* family member, the exosporium fragments, or the formulation can exhibit decreased nematode damage, including reduced galling, reduced cysts, and/or reduced nematodes per weight of root, as compared to plants grown in the absence of the enzyme or the microorganism, under the same conditions.

In any of the methods described herein, plants or the locus in which the plant is grown, such as soil, to which the recombinant *Bacillus cereus* family member, the exosporium fragments, or the formulation has been applied can exhibit reduced nematode eggs and/or reduced nematodes per volume of soil, as compared to plants grown in the absence of the enzyme or the microorganism, under the same conditions.

In one embodiment, the recombinant *Bacillus cereus* family member of the present invention decreases nematodes and/or nematode damage by at least about 0.5%, or by at least about 1%, or by at least about 2%, or by at least about 3%, or by at least about 5%, or by at least about 6%, or by at least about 7%, or by at least about 8%, or by at least about 9%, or by at least about 10%, or by at least about 11%, or by at least about 12% when compared to plants produced under the same conditions but without treatment by a recombinant *Bacillus cereus* family member.

In any of the methods described herein, plants grown in the presence of the recombinant *Bacillus cereus* family member, the exosporium fragments, or the formulation can exhibit decreased susceptibility to a pathogen as compared to plants grown in the absence of the enzyme or the microorganism, under the same conditions.

In any of the methods described herein, plants grown in the presence of the recombinant *Bacillus cereus* family member, the exosporium fragments, or the formulation can exhibit decreased susceptibility to an environmental stress (e.g., drought, flood, heat, freezing, salt, heavy metals, low pH, high pH, or a combination of any thereof) as compared to plants grown in the absence of the enzyme or the microorganism, under the same conditions.

In any of the methods described herein, plants grown in the presence of the recombinant *Bacillus cereus* family member, the exosporium fragments, or the formulation exhibit can increased root nodulation as compared to plants grown in the absence of the enzyme or the microorganism, under the same conditions.

In any of the methods described herein, plants grown in the presence of the recombinant *Bacillus cereus* family member, the exosporium fragments, or the formulation can exhibit greater crop yield as compared to plants grown in the absence of the enzyme, or the microorganism, under the same conditions. In one embodiment, the recombinant *Bacillus cereus* family member of the present invention increases yield or total plant weight by at least about 0.5%, or by at least about 1%, or by at least about 2%, or by at least about 3%, or by at least about 5%, or by at least about 6%, or by at least about 7%, or by at least about 8%, or by at least about 9%, or by at least about 10%, or by at least about 11%, or by at least about 12% when compared to plants produced under the same conditions but without treatment by a recombinant *Bacillus cereus* family member. In another embodiment, the recombinant *Bacillus cereus* family member of the present invention improves some aspect of plant vigor, such as germination, by at least about 0.5%, or by at least about 1%, or by at least about 2%, or by at least about 3%, or by at least about 5%, or by at least about 6%, or by at least about 7%, or by at least about 8%, or by at least about 9%, or by at least about 10%, or by at least about 11%, or by at least about 12% when compared to plants produced under the same conditions but without treatment by a recombinant *Bacillus cereus* family member.

In any of the methods described herein, plants grown in the presence of the recombinant *Bacillus cereus* family member, the exosporium fragments, or the formulation can exhibit altered leaf senescence as compared to plants grown in the absence of the enzyme or the microorganism, under the same conditions.

XIII. Carriers

As described above, the formulations described herein comprise an agriculturally acceptable carrier.

The agriculturally acceptable carrier can comprise a dispersant, a surfactant (e.g., a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination of any thereof), an additive (e.g., an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutane dioate, a benzene acetonitrile derivative, a proteinaceous material, or a combination of any thereof), water, a thickener (a long chain alkylsulfonate of polyethylene glycol, a polyoxyethylene oleate, or a combination of any thereof), an anti-caking agent (e.g., sodium salt, a calcium carbonate, diatomaceous earth, or a combination of any thereof), a residue breakdown product, a composting formulation, a granular application, diatomaceous earth, an oil, a coloring agent, a stabilizer, a preservative, a polymer, a coating, or a combination of any thereof.

Where the agriculturally acceptable carrier comprises a surfactant, the surfactant can comprise a non-ionic surfactant.

Where the agriculturally acceptable carrier comprises an additive and the additive comprises a proteinaceous material, the proteinaceous material can comprise a milk product, wheat flour, soybean meal, blood, albumin, gelatin, alfalfa meal, yeast extract, or a combination of any thereof.

Where the agriculturally acceptable carrier comprises an anti-caking agent and the anti-caking agent comprises a sodium salt, the sodium salt can comprise a sodium salt of monomethyl naphthalene sulfonate, a sodium salt of dimethyl naphthalene sulfonate, a sodium sulfite, a sodium sulfate, or a combination of any thereof.

The agriculturally acceptable carrier can comprise vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination of any thereof.

Any of the formulations described herein can comprise a seed coating formulation (e.g., an aqueous or oil-based solution for application to seeds or a powder or granular formulation for application to seeds), a liquid formulation for application to plants or to a plant growth medium (e.g., a concentrated formulation or a ready-to-use formulation), or a solid formulation for application to plants or to a plant growth medium (e.g., a granular formulation or a powder agent).

The agriculturally acceptable carrier may comprise a formulation ingredient. The formulation ingredient may be a wetting agent, extender, solvent, spontaneity promoter, emulsifier, dispersant, frost protectant, thickener, and/or an adjuvant. In one embodiment, the formulation ingredient is a wetting agent.

Compositions of the present invention may include formulation ingredients added to compositions of the present invention to improve recovery, efficacy, or physical properties and/or to aid in processing, packaging and administration. Such formulation ingredients may be added individually or in combination.

The formulation ingredients may be added to compositions comprising cells, cell-free preparations and/or exosporium fragments to improve efficacy, stability, and physical properties, usability and/or to facilitate processing, packaging and end-use application. Such formulation ingredients may include inerts, stabilization agents, preservatives, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the formulation ingredient is a binder, adjuvant, or adhesive that facilitates adherence of the composition to a plant part, such as leaves, seeds, or roots. See, for example, Taylor, A. G., et al., "Concepts and Technologies of Selected Seed Treatments," Annu. Rev. Phytopathol., 28: 321-339 (1990). The stabilization agents may include anti-caking agents, anti-oxidation agents, anti-settling agents, antifoaming agents, desiccants, protectants or preservatives. The nutrients may include carbon, nitrogen, and phosphorus sources such as sugars, polysaccharides, oil, proteins, amino acids, fatty acids and phosphates. The physical property modifiers may include bulking agents, wetting agents, thickeners, pH modifiers, rheology modifiers, dispersants, adjuvants, surfactants, film-formers, hydrotropes, builders, antifreeze agents or colorants. In some embodiments, the composition comprising cells, cell-free preparation and/or exosporium fragments produced by fermentation of the recombinant *Bacillus cereus* family member may be used directly with or without water as the diluent without any other formulation preparation. In a particular embodiment, a wetting agent, or a dispersant, is added to a dried concentrate of the whole bruth resulting from the fermentation, such as a freeze-dried or spray-dried powder. A wetting agent increases the spreading and penetrating properties, or a dispersant increases the dispersibility and solubility of the active ingredient (once diluted) when it is applied to surfaces. Exemplary wetting agents are known to those of skill in the art and include sulfosuccinates and derivatives, such as MULTIWET™ MO-70R (Croda Inc., Edison, N.J.); siloxanes such as BREAK-THRU® (Evonik, Germany); nonionic compounds, such as ATLOX™ 4894 (Croda Inc., Edison, N.J.); alkyl polyglucosides, such as TERWET® 3001 (Huntsman International LLC, The Woodlands, Tex.); C12-C14 alcohol ethoxylate, such as TERGITOL® 15-S-15 (The Dow Chemical Company, Midland, Mich.); phosphate esters, such as RHODAFAC® BG-510 (Rhodia, Inc.); and alkyl ether carboxylates, such as EMULSOGEN™ LS (Clariant Corporation, North Carolina).

As described above, any of the formulations described herein can comprise an agrochemical.

IX. Free Enzymes

Any of the enzymes described herein can also be used as free enzymes or as enzymes expressed in recombinant microorganisms.

X. Plants

In any of the above methods relating to plants, the plant can be a dicotyledon, a monocotyledon, a gymnosperm, or an angiosperm.

Likewise, for any of the seeds described herein the seed can be a seed of a dicotyledon, a monocotyledon, a gymnosperm, or an angiosperm.

For example, where the plant is a dicotyledon or the seed is a seed of a dicotyledon, the dicotyledon can be selected from the group consisting of bean, pea, tomato, pepper, squash, alfalfa, almond, aniseseed, apple, apricot, arracha, artichoke, avocado, bambara groundnut, beet, bergamot, black pepper, black wattle, blackberry, blueberry, bitter orange, bok-choi, Brazil nut, breadfruit, broccoli, broad bean, Brussels sprouts, buckwheat, cabbage, camelina, Chinese cabbage, cacao, cantaloupe, caraway seeds, cardoon, carob, carrot, cashew nuts, cassava, castor bean, cauliflower, celeriac, celery, cherry, chestnut, chickpea, chicory, chili pepper, chrysanthemum, cinnamon, citron, citrus, clementine, clove, clover, coffee, cola nut, colza, corn, cotton, cottonseed, cowpea, crambe, cranberry, cress, cucumber, currant, custard apple, drumstick tree, earth pea, eggplant, endive, fennel, fenugreek, fig, filbert, flax, geranium, gooseberry, gourd, grape, grapefruit, guava, hemp, hempseed, henna, hop, horse bean, horseradish, indigo, jasmine, Jerusalem artichoke, jute, kale, kapok, kenaf, kiwi, kohlrabi, kumquat, lavender, lemon, lentil, lespedeza, lettuce, lime, liquorice, litchi, loquat, lupine, macadamia nut, mace, mandarin, mangel, mango, medlar, melon, mint, mulberry, mustard, nectarine, niger seed, nutmeg, okra, olive, opium, orange, papaya, parsnip, pea, peach, peanut, pear, pecan nut, persimmon, pigeon pea, pistachio nut, plantain, plum, pomegranate, pomelo, poppy seed, potato, sweet potato, prune, pumpkin, quebracho, quince, trees of the genus Cinchona, quinoa, radish, ramie, rapeseed, raspberry, rhea, rhubarb, rose, rubber, rutabaga, safflower, sainfoin, salsify, sapodilla, Satsuma, scorzonera, sesame, shea tree, soybean, spinach, squash, strawberry, sugar beet, sugarcane, sunflower, swede, sweet pepper, tangerine, tea, teff, tobacco, tomato, trefoil, tung tree, turnip, urena, vetch, walnut, watermelon, yerba mate, wintercress, shepherd's purse, garden cress, peppercress, watercress, pennycress, star anise, laurel, bay laurel, cassia, jamun, dill, tamarind, peppermint, oregano, rosemary, sage, soursop, pennywort, calophyllum, balsam pear, kukui nut, Tahitian chestnut, basil, huckleberry, hibiscus, passionfruit, star apple, sassafras, cactus, St. John's wort, loosestrife, hawthorn, cilantro, curry plant, kiwi, thyme, zucchini, ulluco, jicama, waterleaf, spiny monkey orange, yellow mombin, starfruit, amaranth, wasabi, Japanese pepper, yellow plum, mashua, Chinese toon, New Zealand spinach, bower spinach, ugu, tansy, chickweed, jocote, Malay apple, paracress, sowthistle, Chinese potato, horse parsley, hedge mustard, campion, agate, cassod tree, thistle, burnet, star gooseberry, saltwort, glasswort, sorrel, silver lace fern, collard greens, primrose, cowslip, purslane, knotgrass, terebinth, tree lettuce, wild betel, West African pepper, yerba santa, tarragon, parsley, chervil, land cress, burnet saxifrage, honeyherb, butterbur, shiso, water pepper, perilla, bitter bean, oca, kampong, Chinese celery, lemon basil, Thai basil, water mimosa, cicely, cabbage-tree, moringa, mauka, ostrich fern, rice paddy herb, yellow sawah lettuce, lovage, pepper grass, maca, bottle gourd, hyacinth bean, water spinach, catsear, fishwort, Okinawan spinach, lotus sweetjuice, gallant soldier, culantro, arugula, cardoon, caigua, mitsuba, chipilin, samphire, mampat, ebolo, ivy gourd, cabbage thistle, sea kale, chaya, huauzontle, Ethiopian mustard, magenta spreen, good king henry, epazole, lamb's quarters, centella plumed cockscomb, caper, rapini, napa cabbage, mizuna, Chinese savoy, kai-lan, mustard greens, Malabar spinach, chard, marshmallow, climbing wattle, China jute, paprika, annatto seed, spearmint, savory, marjoram, cumin, chamomile, lemon balm, allspice, bilberry, cherimoya, cloudberry, damson, pitaya, durian, elderberry, feijoa, jackfruit, jambul, jujube, physalis, purple mangosteen, rambutan, redcurrant, blackcurrant, salal berry, satsuma, ugli fruit, azuki bean, black bean, black-eyed pea, borlotti bean, common bean, green bean, kidney bean, lima bean, mung bean, navy bean, pinto bean, runner bean, mangetout, snap pea, sweet pea, broccoflower, calabrese, nettle, bell pepper, raddichio, daikon, white radish, skirret, tat soi, broccolini, black radish, burdock root, fava bean, broccoli raab, lablab, lupin, sterculia, velvet beans, winged beans, yam beans, mulga, ironweed, umbrella bush, tjuntjula, wakalpulka, witchetty bush, wiry wattle, chia, beech nut, candlenut, colocynth, mamoncillo, Maya nut, mongongo, ogbono nut, paradise nut, and cempedak.

Where the plant is a monocotyledon or the seed is a seed of a monocotyledon, the monocotyledon can be selected from the group consisting of corn, wheat, oat, rice, barley, millet, banana, onion, garlic, asparagus, ryegrass, millet, fonio, raishan, nipa grass, turmeric, saffron, galangal, chive, cardamom, date palm, pineapple, shallot, leek, scallion, water chestnut, ramp, Job's tears, bamboo, ragi, spotless watermeal, arrowleaf elephant ear, Tahitian spinach, abaca, areca, bajra, betel nut, broom millet, broom sorghum, citronella, coconut, cocoyam, maize, dasheen, durra, durum wheat, edo, fique, formio, ginger, orchard grass, esparto grass, Sudan grass, guinea corn, Manila hemp, henequen, hybrid maize, jowar, lemon grass, maguey, bulrush millet, finger millet, foxtail millet, Japanese millet, proso millet, New Zealand flax, oats, oil palm, palm palmyra, sago palm, redtop, sisal, sorghum, spelt wheat, sweet corn, sweet sorghum, sugarcane, taro, teff, timothy grass, triticale, vanilla, wheat, and yam.

Where the plant is a gymnosperm or the seed is a seed of a gymnosperm, the gymnosperm can be from a family selected from the group consisting of Araucariaceae, Boweniaceae, Brassicaceae, Cephalotaxaceae, Cupressaceae, Cycadaceae, Ephedraceae, Ginkgoaceae, Gnetaceae, Pinaceae, Podocarpaceae, Taxaceae, Taxodiaceae, Welwitschiaceae, and Zamiaceae.

When the plant is from the family Brassicaceae, the plant can comprise a plant of the genus *Brassica*. For example, the plant of the family Brassicaceae can comprise *Brassica napus, Brassica rapa, Brassica juncea, Brassica hirta, Brassica oleracea, Raphanus sativus, Sinapus alba*, or *Lepidium sativum.*

The plants and plant seeds described herein may include transgenic plants or plant seeds, such as transgenic cereals (wheat, rice), maize, soybean, potato, cotton, tobacco, oilseed rape and fruit plants (fruit of apples, pears, citrus fruits and grapes, including wine grapes). Preferred transgenic plants include corn, soybeans, potatoes, cotton, tobacco, sugar beet, sugarcane, and oilseed rape.

Suitable transgenic plants and seeds can be characterized by the plant's formation of toxins, especially from the *Bacillus thuringiensis* genetic material (e.g., by gene CryIA (a), CryIA (b), CryIA (c), CryIIA, CryIIIA, CryIIIB2, Cry9c, Cry2Ab, Cry3Bb, CryIF or a combination thereof). The formation of toxins in plants increases the plant's resistance to insects, arachnids, nematodes and slugs and snails (hereinafter referred to as "Bt plants"). Bt plants, for example, are commercially available under the tradename YIELD GARD® (for example maize, cotton, soybeans), KNOCKOUT® (for example maize), STARLINK® (for example maize), BOLLGARD® (cotton), NUCOTN® (cotton) and NEWLEAF® (potato) maize varieties, cotton varieties, soybean varieties and potato varieties. Herbicide tolerance plants include plants under the trade names ROUNDUP READY® (a glyphosate tolerance, such as corn, cotton, soybeans), CLEARFIELD® (for example maize), LIBERTY LINK® (tolerance with glufosinate, for example oilseed rape), IMV® (with imnidazolinone tolerance) and STS® (tolerance to a sulfonylurea, such as maize).

Plant seeds as described herein can be genetically modified (e.g., any seed that results in a genetically modified plant or plant part that expresses herbicide tolerance, tolerance to environmental factors such as water stress, drought, viruses, and nitrogen production, or resistance to bacterial, fungi or insect toxins). Suitable genetically modified seeds include those of cole crops, vegetables, fruits, trees, fiber crops, oil crops, tuber crops, coffee, flowers, legume, cereals, as well as other plants of the monocotyledonous and dicotyledonous species. Preferably, the genetically modified seeds include peanut, tobacco, grasses, wheat, barley, rye, sorghum, rice, rapeseed, sugarbeet, sunflower, tomato, pepper, bean, lettuce, potato, and carrot. Most preferably, the genetically modified seeds include cotton, soybean, and corn (sweet, field, seed, or popcorn).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php).

Having described the invention in detail, it will be apparent that modifications and variations are possible without departing from the scope of the invention defined in the appended claims.

EXAMPLES

The following non-limiting examples are provided to further illustrate the present invention.

Example 1. Construction of a *Bacillus cereus* Family Member Displaying a Serine Protease or Serine Protease Variant To construct a *Bacillus cereus* family member displaying the serine protease of SEQ ID NO: 210 or SEQ ID NO: 211 or the serine protease variant of SEQ ID NO: 212, the pSUPER plasmid was generated through fusion of the pUC57 plasmid (containing an ampicillin resistance cassette and a ColE1 origin of replication) with the pBC16-1 plasmid from *Bacillus cereus* (containing a tetracycline resistance gene, repU replication gene and oriU origin of replication). This 5.8 kb plasmid can replicate in both *E. coli* and *Bacillus* spp. and can be selected by conferring resistance to β-lactam antibiotics in *E. coli* and resistance to tetracycline in *Bacillus* spp. The basal pSUPER plasmid was modified by insertion of a PCR-generated fragment that fused the BclA promoter (SEQ ID NO: 149), a start codon, amino acids 20-35 of BclA (amino acids 20-35 of SEQ ID NO: 1) and an alanine linker sequence in frame with SEQ ID NO: 210, SEQ ID NO: 211, or SEQ ID NO: 212, resulting in a plasmid termed pSUPER-BclA 20-35-SEQ ID NO: 210, pSUPER-BclA 20-35-SEQ ID NO: 211, or pSUPER-BclA 20-35-SEQ ID NO: 212, respectively. This construct was transformed into *E. coli* and plated on Lysogeny broth plates plus ampicillin (100 μg/mL) to obtain single colonies. Individual colonies were used to inoculate Lysogeny broth plus ampicillin and incubated overnight at 37° C., 300 rpm. Plasmids from resulting cultures were extracted using a commercial plasmid purification kit. DNA concentrations of these plasmid extracts were determined via spectrophotometry, and obtained plasmids subjected to analytical digests with appropriate combinations of restriction enzymes. The resulting digestion patterns were visualized by agarose gel electrophoresis to investigate plasmid size and presence of distinct plasmid features. Relevant sections, such as the SEQ ID NO: 210, SEQ ID NO: 211 or SEQ ID NO: 212 expression cassette, of the purified pSUPER derivatives were further investigated by Sanger sequencing.

Additionally and alternatively, a derivative plasmid of the pSUPER plasmids described above was created as follows. The pBC fragment (pBC16-1-derived section of pSUPER including BclA/serine protease variant expression cassette and tetracycline resistance) of the pSUPER plasmids described above was amplified by PCR and subsequently circularized by blunt-end ligation.

pSUPER, verified as described above, and pBC plasmid ligations were introduced by electroporation into *Bacillus thuringiensis* BT013A. Single transformed colonies were isolated by plating on nutrient broth plates containing tetracycline (10 μg/mL). Individual positive colonies were used to inoculate brain heart infusion broth containing tetracycline (10 μg/mL) and incubated overnight at 30° C., 300 rpm. Genomic DNA of resulting cultures was purified and relevant sections of the pSUPER plasmid or the pBC plasmid were re-sequenced to confirm genetic purity of the cloned sequences and, for pBC, the correct ligation site. Verified colonies were grown overnight in brain heart infusion broth with 10 μg/mL tetracycline and induced to sporulate through incubation in a yeast extract-based media at 30° C. for 48 hours. Short names for BT013A carrying the above-described plasmids are described in Table 5, below.

*Bacillus thuringiensis* BT013A was deposited with the United States Department of Agriculture (USDA) Agricultural Research Service (ARS), having the address 1815 North University Street, Peoria, Ill. 61604, U.S.A., on Mar. 10, 2014, and assigned accession number NRRL B-50924. *Bacillus thuringiensis* BT013A is also known as *Bacillus thuringiensis* 4Q7.

Example 2. Construction and Purification of Exosporium Fragments from a *Bacillus cereus* Family Member Expressing Serine Protease Variant Knock Out (KO) Mutants:

To make exsY knockout (KO) mutant strains of *Bacillus thuringiensis* BT013A, the plasmid pKOKI shuttle and integration vector was constructed that contained the pUC57 backbone, which is able to replicate in *E. coli*, as well as the origin of replication and the erythromycin resistance cassette from pE194. This construct is able to replicate in both *E. coli* and *Bacillus* spp. A construct was made that contained the 1 kb DNA region that corresponded to the upstream region of the exsY gene and a 1 kb region that corresponded to the downstream region of the gene exsY, both of which were PCR amplified from *Bacillus thuringiensis* BT013A. For each construct, the two 1 kb regions were then spliced together using homologous recombination with overlapping regions to each other and with the pKOKI plasmid, respectively. This plasmid construct was verified by digestion and DNA sequencing. Clones were screened for erythromycin resistance.

Clones were passaged under high temperature (40° C.) in brain heart infusion broth. Individual colonies were toothpicked onto LB agar plates containing erythromycin 5 μg/mL, grown at 30° C., and screened for the presence of the pKOKI plasmid integrated into the chromosome by colony PCR. Colonies that had an integration event were continued through passaging to screen for single colonies that lost erythromycin resistance (signifying loss of the plasmid by recombination and removal of the exsY gene). Verified deletions were confirmed by PCR amplification and sequencing of the target region of the chromosome. Finally, the PCR-amplified, circularized pBC section of the pSUPER-BclA 20-35 SEQ ID NO: 210 plasmid, pSUPER-BclA 20-35 SEQ ID NO: 211 plasmid or pSUPER-BclA 20-35 SEQ ID NO: 212 plasmid (described above in Example 1) was transformed into this exsY mutant strain of BT013A.

For each esxYKO mutant expressing the serine protease of SEQ ID NO: 210 or 211 or the serine protease variant of SEQ ID NO: 212, an overnight culture was grown in BHI media at 30° C., 300 rpm, in baffled flasks with antibiotic selection. One milliliter of this overnight culture was inoculated into a yeast extract-based media (50 mL) in a baffled flask and grown at 30° C. for 2 days. An aliquot of spores was removed and the spores were agitated by vortexing. The spores were collected via centrifugation at 8,000×g for 10 minutes, and supernatant containing the exosporium fragments was filtered through a 0.22 μm filter to remove any residual spores. No spores were found in the filtrate.

Short names for BT013AexsYKO carrying the above-described plasmids are described in Table 5, below.

Example 3. Use of an Expression Cassette Comprising a Non-Antibiotic Selectable Marker to Express the Serine Protease Variant on the Surface of *Bacillus cerus* Family Member Spores SEQ ID NO: 212 was cloned into a derivative of the pSUPER plasmid described in Example 1. In this derivative, the tetracycline resistance marker had previously been exchanged with a non-antibiotic selectable marker. The pBC fragment of this derivative pSUPER plasmid was created as described in Example 1. The resulting pBC ligation, referred to as pBCnam212, was introduced using electroporation into a *Bacillus thuringiensis* BT013A derivative strain that had been modified to support the use of the non-antibiotic selectable marker. Single colonies of transformations were obtained by plating on suitable selection media on petri plates. Individual colonies were used to inoculate a suitable selection media and incubated overnight at 30° C., 300 rpm. Genomic DNA of resulting cultures was purified and the pBC plasmid re-sequenced to verify genetic purity. Verified colonies were grown overnight in suitable selection media and induced to sporulate through incubation in a yeast extract-based media at 30° C. for 48 hours.

TABLE 5

Short Names for Bacteria Carrying Various Plasmids

| Shortened Name of Recombinant *Bacillus cereus* Family Member | Plasmid | Example Describing Construction of Bacteria and Whole Broth or Exosporium Fragment Preparation |
|---|---|---|
| BT013A-pSuper212 | pSUPER-BclA 20-35-SEQ ID NO: 212 | 1 |
| BT013A-pBC210 | pBCtet-BclA 20-35-SEQ ID NO: 210 | 1 |
| BT013A-pBC211 | pBCtet-BclA 20-35-SEQ ID NO: 211 | 1 |
| BT013A-pBC212 | pBCtet-BclA 20-35-SEQ ID NO: 212 | 1 |
| BT013AexsYKO-pBC210 | pBCtet-BclA 20-35-SEQ ID NO: 210 | 2 |
| BT013AexsYKO-pBC211 | pBCtet-BclA 20-35-SEQ ID NO: 211 | 2 |
| BT013AexsYKO-pBC212 | pBCtet-BclA 20-35-SEQ ID NO: 212 | 2 |
| BT013A-pBCnam212 | pBCnam-BclA 20-35-SEQ ID NO: 212 | 3 |

Example 4. Soybean Growth Room Studies

To measure plant growth and development, a growth room assay was conducted. Seeds of two soybean varieties were treated with the whole broth from BT013A-pBCnam212 or the exosporium fragment preparation from BT013AexsYKO-pBC212 along with a chemical base treatment having fungicidal and other pesticidal activities. Control seeds were treated with the chemical base only. Whole broth and the exosporium fragment preparation, respectively, were applied at a rate of 3.6 fluid ounces per cwt, which, for the whole broth was equivalent to $3.8\times10^4$ colony forming units ("CFU")/seed. (The same volume of the exosporium fragment preparation as whole broth was applied to seeds to achieve a comparable application rate to that of the whole broth, as very little liquid is lost during the centrifugation and filtration processes that are used to separate exosporium fragments from cells.) To set up the growth room assay, top soil was mixed with sand at a volume ratio of 2:1 inside a cement mixer until homogenous. The soil mixture was then added to small pots (3.5" L×3.5" W×4" D), which were placed into plastic trays, with nine pots per tray. Trays were moved to the growth room trial location. After 48 hours, 50 mL of water was evenly added to each pot. Subsequently, two seed were planted per pot to a depth of 1" and covered with dry soil mixture. In total, 16 seeds were planted per replicate. Each seed treatment was tested in three replicates per variety. The resulting trays were placed on shelves under high-intensity lights set to a 13-hour light/11-hour dark schedule. Watering was done as needed. No fertilizer was used. The trays were rotated every two days to minimize position effects. Data was gathered from each germinated plant.

Height measurements were taken to the corresponding leaf node at the two plant growth milestones cotyledon elongation and unifoliate emergence. These measurements were taken when approximately 50% of the control plants exhibited the corresponding milestone growth stage. Leaf surface area percentage was taken at the unifoliate emergence milestone utilizing the mobile application Canopeo developed at Oklahoma State University (Stillwater, Okla.; (https://appcenter.okstate.edu/content/canopeo). This application utilizes a digital photograph to determine the percentage of the recorded area occupied by plant material. Once the plants were at the second trifoliate growth stage, they were removed from their inserts and dirt adhered to the root structure was removed using water. Post removal of surplus water by padding with paper towels the fresh root biomass was recorded. In each case, results from plants treated with the serine protease construct in addition to the chemical base were normalized to plants in each trial that had received only the chemical base treatment. Table 6 shows the percent increase as compared to the seeds treated with the chemical base only. Results indicate that both treatments enhance plant growth in some manner.

TABLE 6

| | Whole Broth from BT013A-pBCnam212 Variety 1/Variety 2 | Exosporium Fragment Preparation from BT013AexsYKO-pBC212 Variety 1/Variety 2 |
|---|---|---|
| Cotyledon Height | 4.5%/18.0% | 11.2%/18.2% |
| Unifoliate Height | 7.3%/20.1% | 7.4%/15.6% |
| Unifoliate Canopeo | 13.9%/32.3% | 13.2%/17.4% |
| Biomass Root | No difference from control | 10.4%/3.8% |

Example 5. Use of a Recombinant *Bacillus cereus* Family Member Displaying a Serine Protease Variant to Control Soybean Cyst Nematodes Seed were treated with either an insecticide/fungicide (chemical) base or the same chemical base plus 234.8 mL/100 kg of the whole broth culture of BT013A-pBC-nam212, which is equivalent to $1\times10^{10}$ colony forming units (of the recombinant cell expressing the serine protease variant) ("CFU")/100 kg seed. Both treatments were planted into a sandy loam soil. Ten days post emergence, soybean plants were inoculated with 2,000 second stage juvenile soybean cyst nematodes (*Heterodera glycine*). Plants were harvested four weeks later and cysts were removed and collected using a system of sieves, centrifugation, and a sucrose solution. Cysts were then crushed to release the eggs which were enumerated by taking three sub-samples from the total solution collected from each of ten plants from each treatment. The Sep1-treated seed showed a reduction in both the total number of nematode eggs and the number of eggs per gram of root, which was calculated by a dry weight of each plants root system post cyst extraction, as shown in Table 7, below. The average eggs/gram root was decreased by over 50% in the Sep1-treated seed.

TABLE 7

| | Fungicide/Insecticide Chemical Base | Fungicide/Insecticide Base + Whole Broth of Serine Protease Construct from Example 3 |
|---|---|---|
| Average Total Eggs | 13,907 | 10,867 |
| Average Eggs/ Gram Root | 32,895 | 15,643 |
| Average Dry Root Weight (g) | 0.49 | 0.72 |

Additional experiments were conducted, as above, to test the activity of a whole broth culture of BT013A-pBC-nam212 and exosporium fragments of BT013AexsYKO-pBC212, preparation of which is described in Examples 3 and 2, above. All seeds were treated with (i) an insecticide/fungicide (chemical) base as shown in Table 8; (ii) the chemical base of Table 8 with a commercial nematicide (applied at 0.25 mg ai/seed); or (iii) the chemical base of Table 8 and 234.8 mL/100 kg of either the whole broth culture or the exosporium fragment preparation, both expressing the serine protease variant. The concentration of each whole broth culture was $5\times10^6$ CFU/mL. As noted above, the same volume of the exosporium fragment preparation as whole broth was applied to seeds to achieve a comparable application rate to that of the whole broth, as very little liquid is lost during the centrifugation and filtration processes that are used to separate exosporium fragments from cells. The eggs/gram of root was calculated utilizing the dry weight of the root systems from each sampled plant (as represented in Table 9). Both serine protease constructs performed similarly to the commercial nematicide with regards to reducing the number of SCN eggs recovered per gram of root (~40%) and increasing root volume (most likely related to reduced nematode pressure).

TABLE 8

| Active Ingredient | Application Rate | |
|---|---|---|
| Imidacloprid | 0.127 | mg ai/seed |
| Fluoxastrobin | 0.012 | mg ai/seed |
| Prothioconazole | 0.012 | mg ai/seed |
| Metalaxyl | 0.025 | mg ai/seed |
| Color Coat Red | 0.8 | fl oz/cwt |

TABLE 9

| | Chemical Base | Serine Protease Construct (whole broth) | Serine Protease Construct (exosporium fragment) | Commercial Nematicide |
|---|---|---|---|---|
| Average Total Eggs | 34,899 | 47,389 | 32,111 | 33,611 |
| Average Eggs/ Gram of Root | 53,244 | 33,139 | 30,010 | 30,723 |
| Average Dry Root Weight (g) | 0.66 | 1.43 | 1.07 | 1.09 |

Example 6. Use of a Recombinant *Bacillus cereus* Family Member Displaying a Serine Protease Variant or Purified Exosporium to Stimulate Plant Growth in Soybeans Field trials were conducted in soy to test the plant growth promotion capabilities of the whole broth culture of BT013A-pBCnam212 and exosporium fragments of BT013AexsYKO-pBC212, preparation of which is described in Examples 3 and 2, above. The whole broth culture or exosporium fragment preparation, each displaying the serine protease variant of SEQ ID NO: 212, was applied to soybean seed along with a chemical base treatment having fungicidal and pesticidal activities. The whole broth was applied at a rate of $1\times10^{10}$ colony forming units ("CFU")/100 kg seed, which is 234 mL per 100 kg seeds. The same volume of the exosporium fragment preparation as the whole broth was applied to seeds to achieve a comparable application rate to that of the whole broth, as very little liquid is lost during the centrifugation and filtration processes that are used to separate exosporium fragments from cells. Such treated soybean seeds were planted and grown during the normal season until harvest. Table 10, below, shows how the above constructs performed in ten trials, each consisting of four replicates, compared to seeds treated only with the chemical base.

TABLE 10

| | Cells from BT013A-pBCnam212 | Exosporium Fragment Preparation from BT013AexsYKO-pBC212 |
|---|---|---|
| Average ± Bu/acre | 0.28 | 2.64 |
| Average Percent Yield over Chemical Base-Treated Control | 0.49% | 4.55% |

Example 7. Use of a Recombinant *Bacillus cereus* Family Member Displaying a Serine Protease Variant to Control Soybean Cyst Nematodes, Root Knot Nematodes and Lesion Nematodes—Field Trials

*Heterodera glyciens* (SCN) Experiment

Seed were treated with a commercial insecticide/fungicide base alone or with one of three test treatments including two commercial seed applied nematicides and exosporium fragments from BT013AexsYKO-pBC212, referred to as the "Serine Protease Construct" in the tables below. Application rates for the exosporium fragments are provided in terms of CFU/seed and volume/100 kg seed. This is because when the exosporium fragment preparation is separated from the whole broth from which it was derived, very little liquid is lost during the centrifugation and filtration processes that are used to separate exosporium fragments from cells, so the CFU/seed provides another application rate that is useful when comparing results to other experiments. A total of 140 seed per treatment (Table 1) were hand planted in small strip micro-plots. Four reps (35 seed each) per treatment were arranged in a randomized complete block design. Just prior to planting, five soil core samples (30 cm deep each discarding the top 10 cm) were taken and utilized to create a composite sample for each micro-plot and analyzed to determine the natural SCN population. The average number of SCN juveniles per micro-plot ranged from 402 to 556/100 cc of soil (Table 12). After emergence, each plant was inoculated with a mixture containing 6,200 SCN eggs and juveniles and plants were latter thinned to exactly 30 per micro-plot at the V2 development stage. At 10 weeks (70 DAP), five plants were dug up per plot. Soil was collected and composited from around the root zone of each of the plants and used to determine a count of nematodes/100 $cm^3$ of soil. The harvested roots were processed (cysts collected, roots dried and weighed) to determine cysts/gram of root. Finally, cysts were crushed and eggs were collected to compare the total eggs recovered/plot. As shown in Table 12, the assessment of the average initial natural population of SCN was similar across all four treatments and the serine protease construct performed similarly (slightly better numerically) to the two commercial nematicides with regards to reducing nematode counts on the roots and in the surrounding soil.

TABLE 11

| Seed Treatment Application Rates | | | |
|---|---|---|---|
| BASE | Soybean | Corn | |
| Prothioconazole | 0.012 | 0.021 | MG A/SEED |
| Fluoxastrobin | 0.012 | 0.021 | MG A/SEED |
| Metalaxyl | 0.025 | 0.006 | MG A/SEED |
| Imidacloprod | 0.12 | n/a | MG A/SEED |
| Clothianadin | n/a | 0.05 | MG A/SEED |
| Coating | 65 | 326 | ML/100 KG |
| Colorant | 65 | 32.6 | ML/100 KG |
| Serine Protease | $1.36 \times 10^4$ | $2.76 \times 10^4$ | CFU equivalent/SEED |
| Construct | 234 | 323 | ML/100 KG |
| Commercial Nematicide #1 | 0.15 | 0.25 | MG A/SEED |
| Commercial Nematicide #2 | 0.25 | 0.5 | MG A/SEED |

TABLE 12

| | Average Nematodes/100 $cm^3$ of soil (at planting) | Average Cysts/ gram of root | Average SCN eggs recovered | Average Nematodes/ 100 $cm^3$ of soil |
|---|---|---|---|---|
| BASE | 513 | 173 | 13,230 | 9,632 |
| Serine Protease Construct | 556 | 15 | 669 | 309 |
| Commercial Nematicide #1 | 532 | 43 | 2,442 | 1,559 |
| Commercial Nematicide #2 | 402 | 32 | 1,303 | 410 |

*Meloidogyne incognita* (RKN)/*Heterodera glyciens* (SCN) Experiments

Micro-plots were created in buried containers (16" diameter) with fumigated confirmed nematode free soil at planting. Two separate experiments were conducted, one with RKN (Table 13) and one with a combination of RKN and SCN (Table 14). Seed of a different variety but with the same treatment list from the previous experiment (Table 11) were hand planted (two per micro-plot) with eight micro-plots/reps per treatment for each trial arranged in a randomized complete block design. Half of micro-plots (32) were inoculated with RKN eggs and the other half with a mix of RKN and SCN eggs between the VC and VE development stages. Thirty days after inoculation, four mico-plots per treatment/per experiment were taken down and the two plants recovered were given a composite qualitative gall rating (0-best to 6-worst). Soil samples were also collected from around the harvested plants to create 4 individual composite samples which were analyzed for nematodes per 100 $cm^3$ of soil. The remaining micro-plots were then harvested 30 days later (60 days after inoculation). The same procedures were used to perform gall ratings on all remaining plants and finally the dug roots were composited and analyzed to determine RKN per gram of root in the first experiment and RKN and SCN per gram of root in the co-inoculate experiment. As shown in Table 13 and Table 14, the serine protease construct performed as good (or better) than the two commercial nematicides with regards to reducing both RKN and SCN populations in both the soil and on the roots of treated plants.

TABLE 13

| | 30 Days After Emergence | | 60 Days After Emergence | | |
|---|---|---|---|---|---|
| | Average RKNs/100 $cm^3$ of soil | Average Gall Rating | Average RKN/100 $cm^3$ of soil | Average Gall Rating | Average RKN/g of Root |
| BASE | 94.0 | 3.3 | 325.3 | 4.9 | 74.0 |
| Serine Protease Construct | 33.8 | 0.1 | 215.3 | 1.5 | 33.0 |
| Commercial Nematicide #1 | 83.5 | 2.9 | 252.0 | 3.3 | 45.8 |
| Commercial Nematicide #2 | 59.0 | 0.8 | 241.8 | 1.6 | 43.8 |

TABLE 14

| | 30 Days After Emergence | | 60-Day | | | 60-Day | | |
|---|---|---|---|---|---|---|---|---|
| | Average RKNs/ 100 cm$^3$ of soil | Average Gall Rating | Average RKN/ 100 cm$^3$ of soil | Average Gall Rating | Average RKN/g of Root | Average SCN/ 100 cm$^3$ of soil | Average SCN Damage Rating | Average SCN/g of Root |
| BASE | 163.75 | 3.5 | 44.3 | 5.5 | 106.0 | 166.0 | 6.5 | 10.8 |
| Serine Protease Construct | 89.3 | 0.9 | 26.5 | 4.3 | 55.3 | 85.5 | 4.5 | 4.3 |
| Commercial Nematicide #1 | 123.5 | 1.5 | 23.5 | 4.5 | 98.8 | 91.5 | 5.1 | 9.3 |
| Commercial Nematicide #2 | 279.3 | 3.5 | 33.5 | 3.0 | 46.5 | 148.0 | 4.3 | 4.0 |

*Pratylenchus*—Lesion Nematode Experiments

Seed were treated with a commercial insecticide/fungicide base alone or with one of three test treatments including two commercial seed applied nematicides and exosporium fragments from BT013AexsYKO-pBC212, referred to as the "Serine Protease Construct" in the tables below. Seeds treated as described in Table 8 were hand planted and germinated in small pots in a greenhouse and at the VI development stage eight plants per treatment were inoculated with 100 Lesion (*Pratylenchus*) juveniles. Inoculated plants (and the surrounding soil) were transplanted to a field (which was tested and showed no natural lesion population) in a randomized complete block design. Eight weeks later core soil samples were taken from around each test plant to determine the number of nematodes per 100 cm$^3$ of soil. After soil sampling the individual plants were dug up and 25 g of root tissue was collected from the root tips of each plant. Root tissue was then individually analyzed using a Baermann Funnel procedure to determine the number of Lesion nematodes per gram of root (Table 15). As shown in Table 15, the two commercial nematicides and the serine protease construct had a similar impact on *Pratylenchus* (root lesion) nematodes both in the roots and in the soil surrounding treated plants as compared to the control.

TABLE 15

| | Average Lesion/ 100 cm$^3$ of soil | Average Lesion/ g of Root |
|---|---|---|
| BASE | 115.0 | 95.6 |
| Serine Protease Construct | 21.9 | 40.0 |
| Commercial Nematicide #1 | 35.0 | 23.6 |
| Commercial Nematicide #2 | 38.6 | 66.1 |

Example 8. Protease Assays

To determine and compare activities of the full length (SEQ ID NOs: 210 and 211) and variant (SEQ ID NO: 212) serine protease enzymes expressed on the exosporium of *Bacillus* spores, a protease assay was performed using a commercial protease kit (Sigma-Aldrich PF0100), which detects a diverse range of proteases, such as serine, cysteine, metallo and aspartic proteases.

1 mL of sporulated cultures of BT013A wildtype (7.90×10$^7$ CFU/mL), BT013A-pBC210, BT013A-pBC211 (each at 4.34×10$^7$ CFU/mL) and BT013A-pSuper212 (3.40×10$^7$ CFU/mL) were spun at 8,000×g for 10 min and the supernatant removed.

Cells were washed with 1 mL Butterfield's phosphate buffer, spun again at 8,000×g for 10 minutes, and the supernatant removed. Cell pellets were resuspended in 50 μL (20× concentration) Butterfield's phosphate buffer. 10 μL of each sample was used for the assay.

The assay was performed according to manufacturer's instructions. Briefly, 10 μL of the three cultures or 10 μL of various concentrations of trypsin, the positive control, were mixed with 20 μL incubation buffer and 20 μL of FITC casein substrate. Each assay was performed in triplicate using the same starting concentrated cell culture. A blank was also prepared by substituting Butterfield's phosphate buffer as the sample. Samples were incubated in the dark at 37° C. for 4 hr, then 150 μL of 0.6N TCA was added to stop the reaction. Samples were incubated in the dark at 37° C. for an additional 30 min. Samples were centrifuged at 10,000×g for 10 min to pellet precipitate. 10 μL of supernatant was mixed with 1 mL assay buffer and 200 μL was transferred in duplicate to a 96-well black flat bottom assay plate. Fluorescence was measured with excitation at 485 nm and emission at 535 nm. Duplicate values from the plate were averaged and those values used to calculate the average and standard deviation of the triplicate samples. The average of the blank samples was subtracted from the average of the samples containing spores. FIG. 2 shows the average of triplicate samples with error bars representing the standard deviation. This assay shows that the tested whole broth cultures have protease activity, with additional activity derived from the expressed serine protease of SEQ ID NO: 210 and SEQ ID NO: 212, given the differences in activity between the whole broth from the recombinant *Bacillus cereus* family members expressing the serine protease of SEQ ID NO: 210 and the variant serine protease of SEQ ID NO: 212 and the whole broth from wildtype BT013A.

Example 9. Stability of Free and Bound Protein as Measured in Serine Protease Assays Experiments were conducted to compare the stability of serine protease variant enzymes bound to the exosporium of BT013A and of free enzymes. Enzyme solutions were prepared by growing the strains of interest to sporulation (24 hr 30° C. 250 rpm colony inoculated BHI; 48 hr 30° C. 250 rpm 2% seed culture inoculated yeast extract-based media), followed by multiple filtration steps of this whole broth. Strains of interest are BT013AexsYKO-pBC212 (a strain expressing variant serine protease on exosporium fragments) and BT013AexsYKO (a mutant strain without a plasmid that results in exosporium fragments). Whole broth contains the cells of the above two strains and both chromosomally generated endogenous proteins that are secreted and also displayed on the exosporium and plasmid generated serine protease enzymes that are only displayed on the exosporium. The plasmid generated protein in most cases stays on the exosporium, which we refer to as bound protein, and some fall off the exosporium, which we refer to as free. In order to test the stability of the protein in the bound versus free forms, filtration steps were used to separate bound protein versus free.

Cells of the strains of interest shed their exosporium layer (due to the ExsY knock-out), resulting in a whole broth that contained exosporium fragments. Whole broth samples were pelleted at 8000×g 10 mins 25° C., pellet discarded, and supernatant flowed through a 0.22 μm filter to remove all cells. The cell free supernatant represents both exosporium bound and free proteins and is referred to as "processed strip". The processed strip was then filtered through a 50 kd filter, retentate saved, representing the bound protein on strips of the exosporium. The 50 kd filtrate was then filtered through a 3 kd filter, retentate saved, representing the free protein. In order to represent the bound protein stability and the free protein stability as these would occur in the supernatant from a whole broth culture of BT013AexsYKO-pBC212, the background proteins that would be present prior to the filtration were added back to the filtered free and bound protein fractions. To accomplish this, to the exosporium-bound protein (i.e., the 50 kd protein retentate) from the culture of BT013AexsYKO-pBC212 was added a 3 kd retentate from a culture of BT013AexsYKO, normalized to the CFU concentration of the starting whole broth culture for the BT013AexsYKO. Conversely, to the 3kd protein retentate from the culture of BT013AexsYKO-pBC212 was added a 50kd retentate from a culture of BT013AexsYKO, normalized to the CFU concentration of the starting whole broth culture for the BT013AexsYKO. The "Bound" enzymes solutions in the following studies contained 50kd BT013AexsYKO-pBC212+3kd BT013AexsYKO. The "Free" enzyme solutions in the following studies contained 3kd BT013AexsYKO-pBC212+50kd BT013AexsYKO.

The temperature stability of Bound and Free enzyme solutions was determined by incubating the crude enzyme solutions described above at different temperatures. The Bound and Free enzyme solutions (50 ml) in test tubes were incubated at specified temperatures (22° C.-80° C.) for 2 hours and stored at 4° C. until used. Protease activities were measured as described below and the percent residual activity was calculated by comparing protease activity of enzymes incubated in different temperature to the activity at 22° C. This experiment was done in triplicate.

Figure 3:
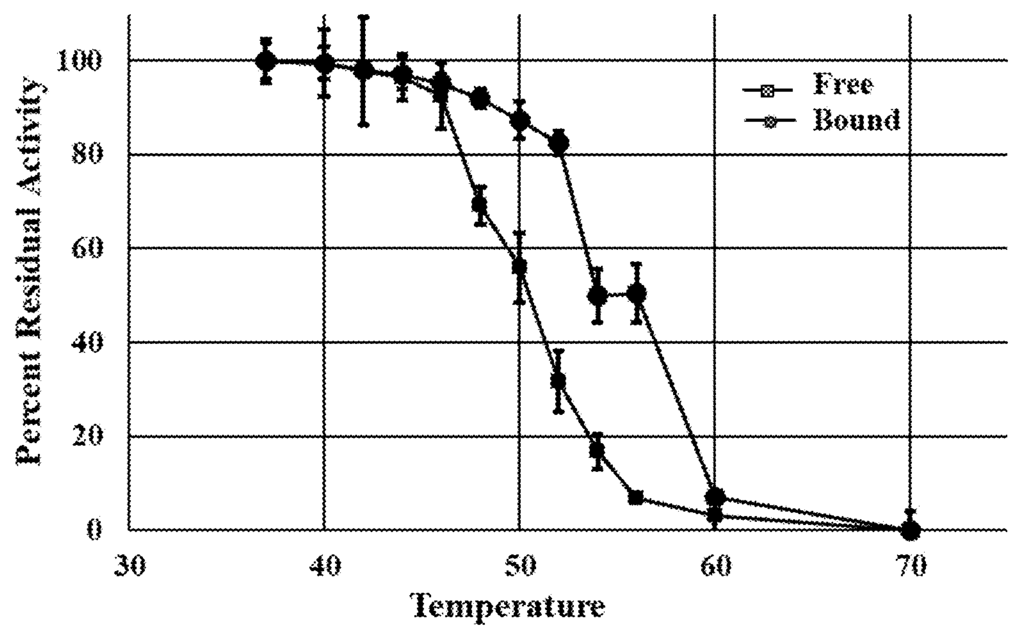
FIG. 3 depicts the results of an enzyme assay comparing the stability of the serine protein variant enzyme bound to the exosporium of *Bacillus thuringiensis* BT013A to the free serine protease variant enzyme.

Sep1 protease activity was determine using synthetic peptide substrate (Ala-Ala-Pro-Phe). The peptide substrate is fused with nitro phenyl at the C-terminus and succinyl group at the N-terminus. The peptide shows absorbance maxima at 320 nm before protease cleavage and shifts to 390 nm following the cleavage. The assay mixture consisted of 10 μl of 2.5 mg/mL peptide substrate in 240 μl of 50 mM Hepes buffer pH 7.5, containing 5 mM $CaCl_2$. The substrate and the buffer were pre-incubated at room temperature, followed by the addition of 25 μl of the enzyme solution. The rate of enzymatic activity was monitored in the spectrophotometer as continuous increase of OD at 390 nm. The rate of the enzymatic activity was determined by measuring the initial slope of the curve. Results are shown in FIG. 3. This data shows that the bound serine protease enzyme is more stable than the free enzyme.

Figure 4:
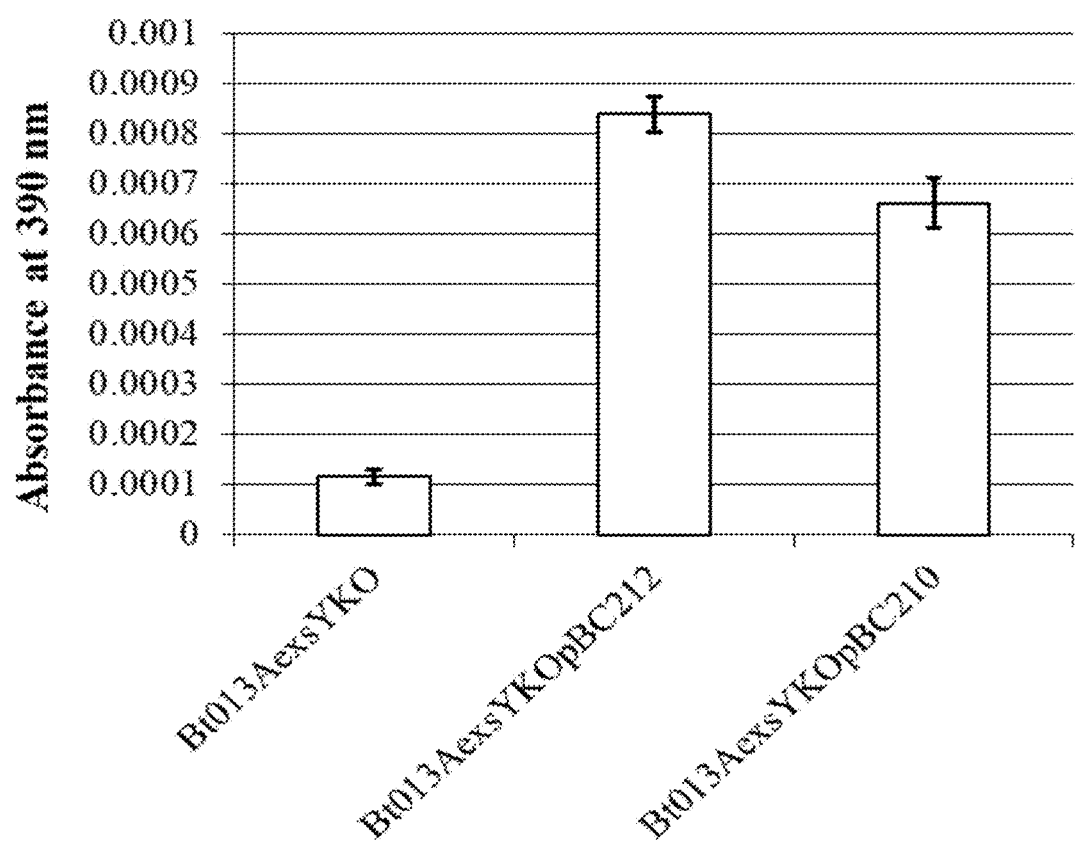
FIG. 4 depicts the enzymatic activity of exosporium fragments bearing full-length serine protease or serine protease variant.

Example 10. Comparison of Activity of Exosporium Fragments in Serine Protease Assays Whole broth cultures of BT013AExsYKO ($9.79\times10^7$ CFU/ml), BT013AExsYKO-pBC210 ($7.06\times10^7$ CFU/ml) and BT013AExsYKO-pBC212 ($7.06\times10^7$ CFU/ml) were grown as described in Example 2 to the CFU concentrations designated after each strain. Exosporium fragment filtrates were generated as described in Example 2, and equal volumes of each were tested as follows. Enzyme activity was determine using synthetic peptide substrate (Ala-Ala-Pro-Phe). The peptide substrate is fused with nitro phenyl at the C-terminus and succinyl group at the N-terminus. The peptide shows absorbance maxima at 320 nm before protease cleavage and shifts to 390 nm following the cleavage. The assay mixture consisted of L of 2.5 mg/mL peptide substrate in 240 μL of 50 mM Hepes buffer pH 7.5, containing 5 mM $CaCl_2$. The substrate and the buffer were pre-incubated at room temperature, followed by the addition of 25 μL of the enzyme solution. Results are shown in FIG. 4. This data shows that both whole broth cultures have enzymatic activity and BT013AExsYKO-pBC212 has slightly higher activity than does BT013AExsYKO-pBC210. Without wishing to be bound by any theory, Applicant hypothesizes that the recombinant *Bacillus cereus* family member with the variant serine protease (SEQ ID NO: 212) has greater biological activity than the recombinant *Bacillus cereus* family member with the full-length serine protease (SEQ ID NO: 210).

Example 11—Use of a Recombinant *Bacillus cereus* Family Member Displaying a Serine Protease or a Serine Protease Variant to Control Soybean Cyst Nematodes All seeds were treated with (i) an insecticide/fungicide base, as shown in Table 16, (ii) the base shown in Table 16 with a commercial nematicide (applied at 0.25 mg ai/seed), or (iii) the base shown in Table 16 and whole broth cultures or exosporium fragment preparations prepared as described in Examples 1 and 2, as listed in Table 17. All biological treatments were applied at 234.8 mL/100 kg of soybean seed. CFU concentrations (CFU/mL) provided in Table 17 below represent CFU of whole broth cultures that were applied to seed or of whole broth cultures from which exosporium fragments were prepared, as described in Example 2.

Figure 5:
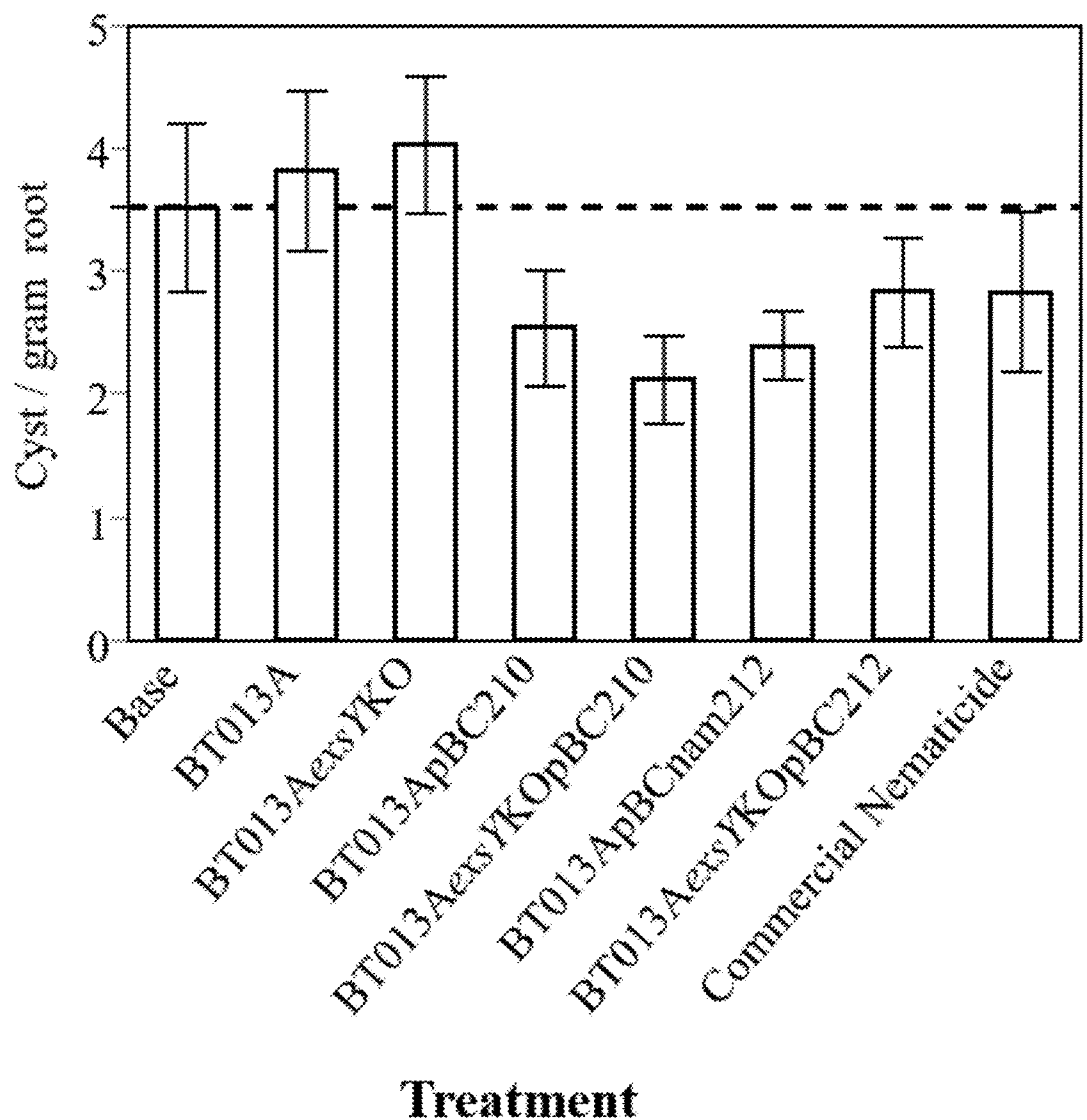
FIG. 5 depicts nematode control activity in trials with soybean seeds treated with whole broth cultures or exosporium fragments of recombinant *Bacillus cereus* family members displaying full-length serine protease or the serine protease variant.

Single seeds from each treatment were planted into individual pots of a sandy loam soil and inoculated with ~1,500 vermiform *Heterodera glycines* (SCN) eggs seven days after planting. Four weeks later plants and cysts were harvested and utilized to compare the relative cysts/gram of root. The two biological treatments not transformed with a serine protease construct, whole broth culture of BT013A and exosporium fragment preparation of a culture of BT013AexsYKO, had a similar number of cysts as the base treatment, while the four biological treatments containing a serine protease construct had a reduction in cysts similar to the commercial nematicide (FIG. 5).

TABLE 16

| Active Ingredient | Application Rate | |
|---|---|---|
| Imidacloprid | 0.127 | mg ai/seed |
| Fluoxastrobin | 0.012 | mg ai/seed |
| Prothioconazole | 0.012 | mg ai/seed |
| Metalaxyl | 0.025 | mg ai/seed |
| Color Coat Red | 0.8 | fl oz/cwt |

TABLE 17

| Biological Treatment | CFU/mL | CFU/Seed |
|---|---|---|
| BT013A (whole broth culture) | $5.00 \times 10^7$ | $2.06 \times 10^4$ |
| BT013AexsYKO (exosporium fragments) | $7.05 \times 10^7$ | $2.91 \times 10^4$ |
| BT013A-pBC210 (whole broth culture) | $6.30 \times 10^7$ | $2.60 \times 10^4$ |
| BT013AexsYKO-pBC210 (exosporium fragments) | $9.20 \times 10^7$ | $3.80 \times 10^4$ |
| BT013A-pBCnam212 (whole broth culture) | $4.95 \times 10^7$ | $2.04 \times 10^4$ |
| BT013AexsYKO-pBC212 (exosporium fragments) | $6.30 \times 10^7$ | $2.60 \times 10^4$ |

In view of the above, it will be seen that the several objects of the invention are achieved and other advantageous results attained. As various changes could be made in the above products, formulations, and methods without departing from the scope of the invention, it is intended that all matter contained in the above description shall be interpreted as illustrative and not in a limiting sense.

Embodiments

For further illustration, additional non-limiting embodiments of the present disclosure are set forth below.

Embodiment 1 is a fusion protein comprising the targeting sequence, exosporium protein or exosporium protein fragment described in Column 2 and the enzyme described in Column 1 of Table 18, below.

TABLE 18

| Fusion Proteins | |
|---|---|
| Column 1 - Enzyme | Column 2 - Targeting Sequence, Exosporium Protein or Exosporium Protein Fragment |
| SEQ ID NO: 210 | One of the targeting sequences, exosporium proteins or exosporium protein fragments numbered as 1-487 in paragraph [0188] or one of the targeting sequences, exosporium proteins or exosporium protein fragments disclosed in paragraphs [0189]-[0223]. |
| SEQ ID NO: 211 | One of the targeting sequences, exosporium proteins or exosporium protein fragments numbered as 1-487 in paragraph [0188] or one of the targeting sequences, exosporium proteins or exosporium protein fragments disclosed in paragraphs [0189]-[0223]. |
| SEQ ID NO: 212 | One of the targeting sequences, exosporium proteins or exosporium protein fragments numbered as 1-487 in paragraph [0188] or one of the targeting sequences, exosporium proteins or exosporium protein fragments disclosed in paragraphs [0189]-[0223]. |
| An amino acid sequence having at least 95% identity to SEQ ID NO: 212 | One of the targeting sequences, exosporium proteins or exosporium protein fragments numbered as 1-487 in paragraph [0188] or one of the targeting sequences, exosporium proteins or exosporium protein fragments disclosed in paragraphs [0189]-[0223]. |
| An amino acid sequence having at least 95% identity to SEQ ID NO: 212 | One of the targeting sequences, exosporium proteins or exosporium protein fragments numbered as 1-487 in paragraph [0188] or one of the targeting sequences, exosporium proteins or exosporium protein fragments disclosed in paragraphs [0189]-[0223]. |
| An amino acid sequence having at least 95% identity to SEQ ID NO: 212 | One of the targeting sequences, exosporium proteins or exosporium protein fragments numbered as 1-487 in paragraph [0188] or one of the targeting sequences, exosporium proteins or exosporium protein fragments disclosed in paragraphs [0189]-[0223]. |

Embodiment 2 is any of the fusion proteins of Embodiment 1 with an amino acid linker between the targeting sequence, the exosporium protein, or the exosporium protein fragment and the enzyme.

Embodiment 3 is any of the fusion proteins of Embodiment 2, where the linker comprises a polyalanine linker, a polyglycine linker, or a linker comprising a mixture of both alanine and glycine residues.

Embodiment 4 is a recombinant *Bacillus cereus* family member that expresses any of the fusion proteins of Embodiments 1-3.

Embodiment 5 is the recombinant *Bacillus cereus* family member of Embodiment 4 where the recombinant *Bacillus cereus* family member comprises *Bacillus thuringiensis* BT013A.

Embodiment 6 is the recombinant *Bacillus cereus* family member of Embodiment 4 having a mutation that results in *Bacillus cereus* family member spores having an exosporium that is easier to remove from the spore as compared to the exosproium of a wild-type spore. Specifically, the recombinant *Bacillus cereus* family member with the mutation can have one of the following mutations:

(i) a mutation in a CotE gene;

(ii) expresses an ExsY protein, wherein the expression of the ExsY protein is increased as compared to the expression of the ExsY protein in a wild-type *Bacillus cereus* family member under the same conditions, and wherein the ExsY protein comprises a carboxy-terminal tag comprising a globular protein;

(iii) expresses a BclB protein, wherein the expression of the BclB protein is increased as compared to the expression of the BclB protein in a wild-type *Bacillus cereus* family member under the same conditions;

(iv) expresses a YjcB protein, wherein the expression of the YjcB protein is increased as compared to the expression of the YjcB protein in a wild-type *Bacillus cereus* family member under the same conditions;

(v) comprises a mutation in an ExsY gene;

(vi) comprises a mutation in a CotY gene;

(vii) comprises a mutation in an ExsA gene; or (viii) comprises a mutation in a CotO gene.

Embodiment 7 comprises the recombinant *Bacillus cereus* family member of Embodiment 6, having a mutation in an ExsY or CotY gene.

Embodiment 8 comprises exosporium fragments from the recombinant *Bacillus cereus* family member of any one of Embodiments 6 and 7.

Embodiment 9 comprises the recombinant *Bacillus cereus* family member of any one of Embodiments 4 and 5 and an agriculturally acceptable carrier.

Embodiment 10 comprises the exosporium fragments of Embodiment 8 and an agriculturally acceptable carrier.

Embodiment 11 comprises a nucleic acid molecule comprising a nucleotide sequence encoding an amino acid sequence for a serine protease variant having nematode control activity. In one aspect of this embodiment, the nucleotide sequence is (i) the nucleotide sequence of SEQ ID NO: 213; (ii) a nucleotide sequence that encodes a peptide comprising the amino acid sequence of SEQ ID NO: 212; or (iii) a nucleotide sequence that encodes a peptide comprising an amino acid sequence having at least 95% sequence identity to the amino acid sequence of SEQ ID NO: 212.

Embodiment 12 comprises the nucleic acid molecule of Embodiment 11 wherein the nucleotide sequence is operably linked to a promoter capable of directing expression of the nucleotide sequence in a host cell. In one aspect of the embodiment the promoter is heterologous or foreign to the nucleotide sequence and is not the native or naturally occurring promoter for the nucleotide sequence.

Embodiment 13 comprises a vector containing the nucleic acid molecule of Embodiment 11 or 12. In one aspect, the vector is an expression vector.

Embodiment 14 comprises a host cell comprising the vector of Embodiment 13. In one particular embodiment, the host cell is a bacterial cell, such as a *Bacillus* cell or an *E. coli* cell.

Embodiment 15 comprises a serine protease variant having pest control activity comprising (i) a peptide comprising the amino acid sequence of SEQ ID NO: 212; (ii) a peptide comprising an amino acid sequence having at least 90% sequence identity to the amino acid sequence of SEQ ID NO: 212; or (iii) a peptide that is encoded by SEQ ID NO: 213. In one aspect, the peptide further comprises heterologous amino acid sequences. In one aspect the pest control activity is nematode control activity.

Embodiment 16 comprises a composition comprising the serine protease variant of Embodiment 15.

Embodiment 17 comprises the composition of Embodiment 16 comprising from about 1% to about 99% by weight of the serine protease variant.

Embodiment 18 comprises a method for producing the serine protease variant of Embodiment 15 comprising culturing the host cell of Embodiment 14 under conditions in which the nucleic acid molecule encoding the serine protease variant is expressed.

Embodiment 19 comprises a method for controlling a pest comprising applying the serine protease variant of Embodiment 15 or the composition of Embodiment 16 to a plant growth medium, a plant, a plant seed, or an area surrounding a plant or a plant seed or to a pest, such as a nematode. In one aspect of Embodiment 19 the serine protease variant is provided as a whole broth culture or fermentation product of the host cell of Embodiment 14.

What is claimed is:

1. A fusion protein comprising:

a targeting sequence, exosporium protein, or exosporium protein fragment that targets the fusion protein to the exosporium of a recombinant *Bacillus cereus* family member; and an enzyme having serine protease activity, wherein the enzyme comprises or consists of SEQ ID NO: 211 or SEQ ID NO: 212;

or a combination of any thereof.

2. The fusion protein of claim 1, wherein the targeting sequence comprises or consists of:

(a) an amino acid sequence having at least about 43% identity with amino acids 20-35 of SEQ ID NO: 1, wherein the identity with amino acids 25-35 is at least about 54%;

(b) amino acids 1-35 of SEQ ID NO: 1;

(c) amino acids 20-35 of SEQ ID NO: 1;

(d) SEQ ID NO: 1;

(e) SEQ ID NO: 96; or (f) SEQ ID NO: 120.

3. The fusion protein of claim 1, wherein the targeting sequence comprises the sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$, wherein:

$X_1$ is any amino acid or absent;

$X_2$ is phenylalanine (F), leucine (L), isoleucine (I), or methionine (M);

$X_3$ is any amino acid;

$X_4$ is proline (P) or serine (S);

$X_5$ is any amino acid;

$X_6$ is leucine (L), asparagine (N), serine (S), or isoleucine (I);

$X_7$ is valine (V) or isoleucine (I);

$X_8$ is glycine (G);

$X_9$ is proline (P);

$X_{10}$ is threonine (T) or proline (P);

$X_{11}$ is leucine (L) or phenylalanine (F);

$X_{12}$ is proline (P);

$X_{13}$ is any amino acid;

$X_{14}$ is any amino acid;

$X_{15}$ is proline (P), glutamine (Q), or threonine (T); and $X_{16}$ is proline (P), threonine (T), or serine (S).

4. The fusion protein of claim 2, wherein the targeting sequence, exosporium protein, or exosporium protein fragment further comprises a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

5. The fusion protein of claim 1, wherein the fusion protein further comprises an amino acid linker between the targeting sequence, the exosporium protein, or the exosporium protein fragment and the enzyme having serine protease activity.

6. A recombinant *Bacillus cereus* family member that expresses a fusion protein of claim 1.

7. The recombinant *Bacillus cereus* family member of claim 6, wherein the recombinant *Bacillus cereus* family member comprises a mutation that results in the *Bacillus cereus* family member spores having an exosporium that is easier to remove from the spore as compared to the exosporium of a wild-type spore.

8. The recombinant *Bacillus cereus* family member of claim 7, wherein the recombinant *Bacillus cereus* family member comprises:

(i) a mutation in a CotE gene;

(ii) a mutation in an ExsY gene;

(iii) a mutation in a CotY gene;

(iv) a mutation in a ExsA gene;

(v) a mutation in a CotO gene.

9. A fermentation product of the recombinant *Bacilus cereus* family member claim 6.

10. Exosporium fragments derived from the recombinant *Bacillus cereus* family member of claim 7, wherein the exosporium fragments comprise or consist of SEQ ID NO: 211 or SEQ ID NO: 212.

11. A formulation comprising the fermentation product of claim 9 and an agriculturally acceptable carrier.

12. A formulation comprising the exosporium fragments of claim 10 and an agriculturally acceptable carrier.

13. A plant seed treated with the formulation of claim 11 or claim 12.

14. A method for stimulating plant growth and/or promoting plant health and/or controlling nematodes, comprising applying a recombinant *Bacillus cereus* family member of claim 6 to a plant growth medium, a plant, a plant seed, or an area surrounding a plant or a plant seed.

15. A method for stimulating plant growth and/or promoting plant health and/or controlling nematodes, comprising applying exosporium fragments of claim 7 to a plant growth medium, a plant, a plant seed, or an area surrounding a plant or a plant seed.

* * * * *

UNITED STATES PATENT AND TRADEMARK OFFICE

CERTIFICATE OF CORRECTION

PATENT NO. : 11,793,196 B2
APPLICATION NO. : 16/822279
DATED : October 24, 2023
INVENTOR(S) : Curtis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 418 days.

Signed and Sealed this
Eighth Day of July, 2025

Coke Morgan Stewart
*Acting Director of the United States Patent and Trademark Office*